US008545839B2

(12) United States Patent
Goetsch et al.

(10) Patent No.: US 8,545,839 B2
(45) Date of Patent: Oct. 1, 2013

(54) ANTI-C-MET ANTIBODY

(75) Inventors: Liliane Goetsch, Ayze (FR); Thierry Wurch, Machilly (FR); Cédric Bes, Villevieille (FR)

(73) Assignee: Pierre Fabre Medicament, Boulogne Billancourt (FR)

( * ) Notice: Subject to any disclaimer, the term of this patent is extended or adjusted under 35 U.S.C. 154(b) by 382 days.

(21) Appl. No.: 12/791,681

(22) Filed: Jun. 1, 2010

(65) Prior Publication Data
US 2011/0097262 A1    Apr. 28, 2011

(51) Int. Cl.
*A61K 39/395* (2006.01)
(52) U.S. Cl.
USPC .................................... 424/130.1; 530/387.1
(58) Field of Classification Search
None
See application file for complete search history.

(56) References Cited

U.S. PATENT DOCUMENTS

| | | | |
|---|---|---|---|
| 4,424,200 | A | 1/1984 | Crockford et al. |
| 4,479,930 | A | 10/1984 | Hnatowich |
| 4,816,567 | A | 3/1989 | Cabilly et al. |
| 4,831,175 | A | 5/1989 | Gansow et al. |
| 5,530,101 | A | 6/1996 | Queen et al. |
| 5,585,089 | A | 12/1996 | Queen et al. |
| 5,639,641 | A | 6/1997 | Pedersen et al. |
| 5,693,761 | A | 12/1997 | Queen et al. |
| 5,877,293 | A | 3/1999 | Adair et al. |
| 5,886,152 | A | 3/1999 | Nakatani et al. |
| 6,054,297 | A | 4/2000 | Carter et al. |
| 6,180,370 | B1 | 1/2001 | Queen et al. |
| 6,207,152 | B1 | 3/2001 | Schwall et al. |
| 2005/0233960 | A1 | 10/2005 | Kong-Beltran et al. |
| 2010/0115639 | A1 | 5/2010 | Goetsch et al. |

FOREIGN PATENT DOCUMENTS

| | | |
|---|---|---|
| EP | 0 451216 | 10/1991 |
| EP | 0 566 647 | 10/1993 |
| EP | 0 682 040 | 11/1995 |
| EP | 0 939127 | 9/1999 |
| WO | WO 96/38557 | 12/1996 |
| WO | WO 2005/016382 | 2/2005 |
| WO | WO 2006/015371 | 2/2006 |
| WO | WO 2006/116260 | 11/2006 |
| WO | WO 2007/011941 | 1/2007 |
| WO | WO 2007/016285 | 2/2007 |
| WO | WO 2007/126799 A2 | 11/2007 |
| WO | WO 2009/007427 | 1/2009 |
| WO | WO 2010/064089 A1 | 6/2010 |
| WO | WO 2010/069765 A1 | 6/2010 |

OTHER PUBLICATIONS

Apantaku et al. (Breast cancer diagnosis and screening, American Family Physician 2000).*
Martin et al (Journal of the National Cancer Institute, vol. 92, No. 14: pp. 1126-1135, Jul. 19, 2000).*

Aapro, M. S., et al., "Developments in cytotoxic chemotherapy: advances in treatment utilising vinorelbine," *Crit. Rev. Oncol. Hematol.*, 40:251-263 (2001).
Angers, S., et al., "Detection of $\beta_2$-adrenergic receptor dimerization in living cells using bioluminescence resonance energy transfer (BRET)," *Proc. Natl. Acad. Sci. USA*, 97:3684-3689 (2000).
Bebbington, C. R., et al., "High-level expression of a recombinant antibody from myeloma cells using a glutamine synthetase gene as an amplifiable selectable marker," *Bio/Technology*, 10:169-175 (1992).
Bes, C., et al., "Efficient CD4 binding and immunosuppressive properties of the 13B8.2 monoclonal antibody are displayed by its CDR-HI-derived peptide CB1," *FEBS letters*, 508:67-74 (2001).
Bes, C., et al., "PIN-bodies: A new class of antibody-like proteins with CD4 specificity derived from the protein inhibitor of neuronal nitric oxide synthase," *BBRC*, 343:334-344 (2006).
Birchmeier, C., et al., "Met, metastasis, motility, and more," *Nat. Rev. Mol. Cell Biol.*, 4:915-925 (2003).
Bladt, F., et al., "Essential role for the *c-met* receptor in the migration of myogenic precursor cells into the limb bud," *Nature*, 376:768-771 (1995).
Bottaro, D. P., et al., "Identification of the Hepatocyte Growth Factor Receptor as the *c-met* Proto-Oncogene Product," *Science*, 251:802-804 (1991).
Brechbiel, M. W., et al., "Backbone-substituted DTPA ligands for 90Y radioimm.," *Bioconjug Che*, 2(3):187-194 (1991).
Burgess, T., et al., "Fully human monoclonal antibodies to hepatocyte growth factor with therapeutic potential against hepatocyte growth factor/c-Met-dependent human tumors," *Cancer Res*, 66(3):1721-1729 (2006).
Bussolino, F., et al., "Hepatocyte Growth Factor Is a Potent Angiogenic Factor Which Stimulates Endothelial Cell Motility and Growth," *J. Cell Biol.*, 119:629-641 (1992).
Cao, B., et al., "Neutralizing monoclonal antibodies to hepatocyte growth factor/scatter factor (HGF/SF) display antitumor activity in animal models," *Proc Natl Acad Sci U S A*, 98(13):7443-8 (2001).
Christensen, J. G., et al., "A Selective Small Molecule Inhibitor of c-Met Kinase Inhibits c-Met-Dependent Phenotypes in Vitro and Exhibits Cytoreductive Antitumor Activity in Vivo," *Cancer Res.*, 63:7345-55 (2003).
Christensen, J. G., et al., "c-Met as a target for human cancer and characterization of inhibitors for therapeutic intervention," *Cancer Letters*, 226:1-26 (2005).
Conrotto, P., et al., "Interplay between scatter factor receptors and B plexins controls invasive growth," *Oncogene*, 23:5131-7 (2004).
Conrotto, P., et al., "Sema4D induces angiogenesis through Met recruitment by Plexin B1," *Blood*, 105(11):4321-9 (2005).
Curran, M. P., et al., "Vinorelbine: A Review of its Use in Elderly Patients with Advanced Non-Small Cell Lung Cancer," *Drugs Aging*, 19:695-697 (2002).

(Continued)

*Primary Examiner* — Laura B Goddard
*Assistant Examiner* — Meera Natarajan
(74) *Attorney, Agent, or Firm* — Finnegan

(57) ABSTRACT

The invention relates to a novel antibody capable of binding specifically to the human c-Met receptor and/or capable of specifically inhibiting the tyrosine kinase activity of said receptor both in a ligand-dependent and in a ligand-independent manner, with an improved antagonistic activity, said antibody comprising a modified hinge region.
The invention also relates to a composition comprising such an antibody antagonist to c-Met and its use as a medicament for treating cancer.

33 Claims, 39 Drawing Sheets

(56) References Cited

OTHER PUBLICATIONS

Figure 1:
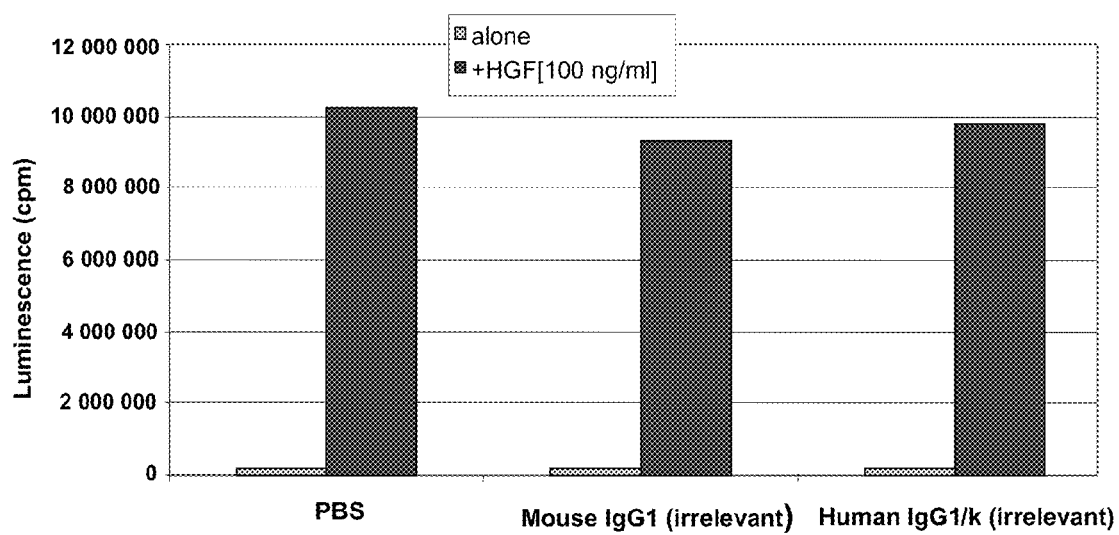

Di Renzo, M. F., et al., "Expression of the Met/HGF receptor in normal neoplastic human tissues," *Oncogene*, 6:1997-2003 (1991).
Engelman, J. A., et al., "MET Amplification Leads to Gefitinib Resistance in Lung Cancer by Activating ERBB3 Signaljng," *Science*, 316:1039-43 (2007).
Fan, S., et al., "The cytokine hepatocyte growth factor/scatter factor inhibits apoptosis and enhances DNA repair by a common mechanism involving signaling through phosphatidyl inositol 3' kinase," *Oncogene*, 19(18):2212-23 (2000).
Furge, K. A., et al., "Met receptor tyrosine kinase: enhanced signaling through adapter proteins," *Oncogene*, 19(49):5582-9 (2000).
Gansow, O. A., et al., "Chelates and antibodies: current methods and new directions.," *Cancer Treat Res.*, 51:153-171 (1990).
Gansow, O. A., et al., "Newer Approaches to the Radiolabeling of Monoclonal Antibodies by Use of Metal Chelates," *Int J Rad Appl Instr B Nucl Med Biol*, 18(4):369-381 (1991).
Gao, C. F., et al., "HGF/SF-Met signaling in tumor progression," *Cell Res.*, 15(I):49-51 (2005).
Giordano, S., et al., "The Semaphorin 4D receptor controls invasive growth by coupling with Met," *Nat Cell Biol.*, 4(9):720-4 (2002).
Green, L. L., et al., "Antigen-specific human monoclonal antibodies from mice engineered with human Ig heavy and light chain YACs," *Nature Genetics*, 7:13-21 (1994).
Green, L., et al., "Regulation of B Cell Development by Variable Gene Complexity in Mice Reconstituted with Human Immunoglobulin Yeast Artificial Chromosomes," *J. Exp. Med.*, 188:483-495 (1998).
Gu, H., et al., "The 'Gab' in signal transduction," *Trends Cell Biol.*, 13(3):122-30 (2003).
Harlow, E., et al., "Antibodies: A Laboratory Manual, Cold Spring Harbor Laboratory," *Cold Spring Harbor Laboratory*, pp. 726-727 (1988).
Hays, J. L., et al., "Watowich S.J., Oligomerization-Dependent Changes in the Thermodynamic Properties of the TPR-MET Receptor Tyrosine Kinase," *Biochemistry*, 43:10570-8 (2004).
Hunter, W. M., et al., "Preparation of iodine-131 labelled human growth hormone of high specific activity," *Nature*, 194:495 (1962).
Jones, P. T., et al., "Replacing the complementarity-determining regions in a human antibody with those from a mouse," *Nature*, 321:522-525 (1986).
Kaas, Q., et al., "IMGT Colliers de Perles: Standardized Sequence-Structure Representations of the IgSF and MhcSF Superfamily Domains," *Current Bioinformatics*, 2:21-30 (2007).
Kaas, Q., et al., "IMGT/3Dstructure-DB and IMGT/StructuralQuery, a database and a tool for immunoglobulin, T cell receptor and MHC structural data," *Nucl. Acids. Res.*, 32:D208-D210 (2004).
Kohl, A., et al., "Designed to be stable: Crystal structure of a consensus ankyrin repeat protein," *PNAS*, 100:1700-1705 (2003).
Kohler, G., et al., "Continuous cultures of fused cells secreting antibody of predefined specificity," *Nature*, 256:495-497 (1975).
Kraus-Berthier, L., et al., "Histology and Sensitivity to Anticancer Drugs of Two Human Non-Small Cell Lung Carcinomas Implanted in the Pleural Cavity of Nude Mice," *Clin. Cancer Res.*, 6:297-304 (2000).
Krejcarek, G. E., et al., "Covalent Attachment of Chelating Groups to Macromolecules," *BBRC*, 77(2):581-585 (1977).
Kuba, K., et al., "HGF/NK4, a Four-Kringle Antagonist of Hepatocyte Growth Factor, Is an Angiogenesis Inhibitor that Suppresses Tumor Growth and Metastasis in Mice," *Cancer Res.*, 60:6737-43 (2000).
Lefranc, M.-P., "The IMGT Unique Numbering for Immunoglobulins, T-Cell Receptors, and Ig-Like Domains," *The Immunologist*, 7:132-136 (1999).
Lefranc, M.-P., "Unique database numbering system for immunogenetic analysis," *Immunology Today*, 18:509 (1997).
Lefranc, M.-P., et al., "IMGT unique numbering for immunoglobulin and T cell receptor variable domains and Ig superfamily V-like domains," *Dev. Comp. Immunol.*, 27:55-77 (2003).

Maroun, C. R., et al., "The Gab1 PH Domain Is Required for Localization of Gab1 at Sites of Cell-Cell Contact and Epithelial Morphogenesis Downstream from the Met Receptor Tyrosine Kinase," *Mol. Cell. Biol.*, 19:1784-1799 (1999).
Martens, T., et al., "A Novel One-Armed Anti-c-Met Antibody Inhibits Glioblastoma Growth in vivo," *Clin Cancer Res.*, 12(20):6144-52 (2006).
Meares, C. F., et al., "Conjugation of Antibodies with Bifunctional Chelating Agents: Isothiocyanate and Bromoacetamide Reagents, Methods of Analysis, and Subsequent Addition of Metal Ions," *Anal-Biochem*, 142(1):68-78 (1984).
Morrison, S. L., et al., "Chimeric human antibody molecules: Mouse antigen-binding domains with human constant region domains," *Proc. Natl. Acad. Sci. USA*, 82:6851-6855 (1984).
Mountain, A., et al., "Engineering Antibodies for Therapy," *Biotechnol. Genet. Eng. Rev.*, 10:1-142 (1992).
Nagayama, T., et al., "Post-ischemic delayed expression of hepatocyte growth factor and c-Met in mouse brain following focal cerebral ischemia," *Brain Res.*, 5;999(2):155-66 (2004).
Nakamura, Y., et al., "Expression of Local Hepatocyte Growth Factor System in Vascular Tissues," *Biochem. Biophys. Res. Commun.*, 215:483-488 (1995).
Naldini, L., et al., "Scatter factor and hepatocyte growth factor are indistinguishable ligands for the MET Receptor," *Eur. Mol. Biol. Org. J.*, 10:2867-2878 (1991).
Needleman, S. B., et al., "A General Method Applicable to the Search for Similarities in the Amino Acid Sequence of Two Proteins," *J. Mol. Biol.*, 48:443 (1970).
Nicaise, M., et al., "Affinity transfer by CDR grafting on a nonimmunoglobulin scaffold," *Protein Sci.*, 13(7):1882-91 (2004).
Pearson, W. R., et al., "Improved tools for biological sequence comparison," *Proc. Natl. Acad. Sci. USA*, 85:2444 (1988).
Riechmann, L., et al., "Reshaping human antibodies for therapy," *Nature*, 332:323-327 (1988).
Rosen, E. M., et al., "Scatter factor stimulates migration of vascular endothelium and capillary-like tube formation," *Cell Motility Factors, Experientia Supplementum*, 59:76-88 (1991).
Ruiz, M., et al., "IMGT gene identification and Colliers de Perles of human immunoglobins with known 3D structures," *Immunogenetics*, 53, 857-883 (2002).
Schmidt, C., et al., "Scatter factor/hepatocyte growth factor is essential for liver development," *Nature*, 373:699-702 (1995).
Singer, I. I., et al., "Optimal Humanization of 1 84, an Anti-C018 Murine Monoclonal Antibody, Is Achieved by Correct Choice of Human V-Region Framework Sequences," *J. Immun.*, 150:2844-2857 (1993).
Skerra, A., "'Anticalins': a new class of engineered ligand-binding proteins with antibody-like properties," *Reviews in Molecular Biotechnology*, 74(4):257-75 (2001).
Skerra, A., "Engineered protein scaffolds for molecular recognition," *J. Mol. Recogn.*, 13:167-187 (2000).
Smith, T. F., et al., "Comparison of Biosequences," *Ad. App. Math.*, 2:482 (1981).
Smolen, G. A., et al., "Amplification of MET may identify a subset of cancers with extreme sensitivity to the selective tyrosine kinase inhibitor PHA-665752," *Proc. Natl. Acad. Sci. USA*, 103(7):2316-2321 (2006).
Sonnenberg, E., et al., "Scatter Factor/Hepatocyte Growth Factor and Its Receptor, the c-met Tyrosine Kinase, Can Mediate a Signal Exchange between Mesenchyme and Epithelia during Mouse Development," *J. Cell. Biol.*, 123:223-235 (1993).
Tahara, Y., et al., "Hepatocyte Growth Factor Facilitates Colonic Mucosal Repair in Experimental Ulcerative Colitis in Rats," *J Pharmacol Exp Ther.*, 307(1):146-51 (2003).
Tatusova, T. A., et al., "Blast 2 sequences—a new tool for comparing protein and nucleotide sequences", *FEMS Microbiol Lett.*, 174:247-250 (1999).
Trusolino, L., et al., "A Signaling Adapter Function for α6β4 Integrin in the Control of HGF-Dependent Invasive Growth," *Cell*, 107:643-54 (2001).
Trusolino, L., et al., "Scatter-factor and semaphorin receptors: cell signaling for invasive growth,"*Nat Rev. Cancer*, 2(4):289-300 (2002).

Tsarfaty, I., et al., "The Met Proto-Oncogene Mesenchymal to Epithelial Cell Conversion," *Science*, 263:98-101 (1994).

Van der Voort, R., et al., "Heparan Sulfate-modified CD44 Promotes Hepatocyte Growth Factor/Scatter Factor-induced Signal Transduction through the Receptor Tyrosine Kinase c-Met," *J Biol Chem.*, 274(10):6499-506 (1999).

Verhoeyen, M., et al., "Engineering of Antibodies," *BioEssays*, 8:74 (1988).

Verhoeyen, M., et al., "Reshaping Human Antibodies: Grafting an Antilysozyme Activity," *Science*, 239:1534-1536 (1988).

Zou, H. Y., et al., "An Orally Available Small-Molecule Inhibitor of c-Met, PF-2341 066, Exhibits Cytoreductive Antitumor Efficacy through Antiproliferative and Antiangiogenic Mechanisms," *Cancer Res.*, 67:4408-4417 (2007).

International Search Report for PCT/EP2008/059026, mailed Feb. 17, 2009.

International Search Report for PCT/EP2009/066201, mailed Mar. 4, 2010.

International Search Report for PCT/IB2008/055663, mailed Aug. 19, 2009.

Co-pending U.S. Appl. No. 12/440,571, published as US Publication No. 2010/0115639.

Apantaku et al., "Breast Cancer Diagnosis and Screening," *Am. Fam. Phys.*, 62:596 (2000).

Martin et al., "Genetic and Hormonal Risk Factors in Breast Cancer," *J. Natl. Can. Inst.*, 92:1126-1135 (2000).

Masayuki Kai, et al., "Switching Constant Domains Enhances Agonist Activities of Antibodies to a Thrombopoietin Receptor," *Nat. Bio.*, 26:209-211 (2008).

Phillips, M., et al., "Human/Mouse Chimeric Monoclonal Antibodies with Human IgG1, IgG2, IgG3 and IgG4 Constant Domains: Electron Microscopic and Hydrodynamic Characterization," *Mol. Imm.*, 31:1201-1210 (1994).

Shin, Su, et al., "Genetically-Engineered Antibodies: Tools for the Study of Diverse Properties of the Antibody Molecule," *Immuno. Re.*, 130:87-107 (1992).

International Search Report PCT/IB2008/055663, mailed Aug. 19, 2008.

International Search Report PCT/EP2009/066201, mailed Mar. 4, 2010.

SG Written Opinion 201103881-7, dated Jul. 19, 2012.

International Search Report for PCT/EP2011/059139, mailed Sep. 29, 2011.

\* cited by examiner

A

B

A

B

ELISA

SEQUENCE LISTING

<160> NUMBER OF SEQ IDS NOS: 117

<210> SEQ ID NO 1
<211> LENGTH: 8
<212> TYPE: PRT
<213> ORGANISM: Mus musculus

<400> SEQUENCE: 1

Gly Tyr Ile Phe Thr Ala Tyr Thr
1               5

<210> SEQ ID NO 2
<211> LENGTH: 8
<212> TYPE: PRT
<213> ORGANISM: Mus musculus

<400> SEQUENCE: 2

Ile Lys Pro Asn Asn Gly Leu Ala
1               5

<210> SEQ ID NO 3
<211> LENGTH: 11
<212> TYPE: PRT
<213> ORGANISM: Mus musculus

<400> SEQUENCE: 3

Ala Arg Ser Glu Ile Thr Thr Glu Phe Asp Tyr
1               5                   10

<210> SEQ ID NO 4
<211> LENGTH: 118
<212> TYPE: PRT
<213> ORGANISM: Mus musculus

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ala Tyr
            20                  25                  30

Thr Met His Trp Val Arg Gln Ala Pro Gly Gln Gly Leu Glu Trp Met
        35                  40                  45

Gly Trp Ile Lys Pro Asn Asn Gly Leu Ala Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Glu Ile Thr Thr Glu Phe Asp Tyr Trp Gly Gln Gly Thr
            100                 105                 110

Leu Val Thr Val Ser Ser
        115

<210> SEQ ID NO 5
<211> LENGTH: 10
<212> TYPE: PRT
<213> ORGANISM: Mus musculus

<400> SEQUENCE: 5

Glu Ser Val Asp Ser Tyr Ala Asn Ser Phe
1               5                   10

```
<210> SEQ ID NO 6
<211> LENGTH: 3
<212> TYPE: PRT
<213> ORGANISM: Mus musculus

<400> SEQUENCE: 6

Arg Ala Ser
1

<210> SEQ ID NO 7
<211> LENGTH: 9
<212> TYPE: PRT
<213> ORGANISM: Mus musculus

<400> SEQUENCE: 7

Gln Gln Ser Lys Glu Asp Pro Leu Thr
1               5

<210> SEQ ID NO 8
<211> LENGTH: 112
<212> TYPE: PRT
<213> ORGANISM: Mus musculus

<400> SEQUENCE: 8

Asp Ile Val Leu Thr Gln Ser Pro Asp Ser Leu Ala Val Ser Leu Gly
1               5                   10                  15

Glu Arg Ala Thr Ile Asn Cys Lys Ser Ser Glu Ser Val Asp Ser Tyr
            20                  25                  30

Ala Asn Ser Phe Met His Trp Tyr Gln Gln Lys Pro Gly Gln Pro Pro
        35                  40                  45

Lys Leu Leu Ile Tyr Arg Ala Ser Thr Arg Glu Ser Gly Val Pro Asp
    50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Glu Asp Pro Leu Thr Phe Gly Gly Gly Thr Lys Val Glu Ile Lys Arg
            100                 105                 110

<210> SEQ ID NO 9
<211> LENGTH: 112
<212> TYPE: PRT
<213> ORGANISM: Mus musculus

<400> SEQUENCE: 9

Asp Ile Val Met Thr Gln Ser Pro Asp Ser Leu Ala Val Ser Leu Gly
1               5                   10                  15

Glu Arg Ala Thr Ile Asn Cys Lys Ser Ser Glu Ser Val Asp Ser Tyr
            20                  25                  30

Ala Asn Ser Phe Met His Trp Tyr Gln Gln Lys Pro Gly Gln Pro Pro
        35                  40                  45

Lys Leu Leu Ile Tyr Arg Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Glu Asp Pro Leu Thr Phe Gly Gly Gly Thr Lys Val Glu Ile Lys Arg
            100                 105                 110
```

<210> SEQ ID NO 10
<211> LENGTH: 112
<212> TYPE: PRT
<213> ORGANISM: Mus musculus

<400> SEQUENCE: 10

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Asp Ser Tyr
            20                  25                  30

Ala Asn Ser Phe Leu His Trp Tyr Gln Gln Lys Pro Gly Gln Pro Pro
        35                  40                  45

Lys Leu Leu Ile Tyr Arg Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Glu Asp Pro Leu Thr Phe Gly Gly Gly Thr Lys Val Glu Ile Lys Arg
            100                 105                 110

<210> SEQ ID NO 11
<211> LENGTH: 24
<212> TYPE: DNA
<213> ORGANISM: Mus musculus

<400> SEQUENCE: 11
ggctacatct tcacagcata cacc                                              24

<210> SEQ ID NO 12
<211> LENGTH: 24
<212> TYPE: DNA
<213> ORGANISM: Mus musculus

<400> SEQUENCE: 12
attaaaccca acaatgggct ggcc                                              24

<210> SEQ ID NO 13
<211> LENGTH: 33
<212> TYPE: DNA
<213> ORGANISM: Mus musculus

<400> SEQUENCE: 13
gccaggagcg aaattacaac agaattcgat tac                                    33

<210> SEQ ID NO 14
<211> LENGTH: 354
<212> TYPE: DNA
<213> ORGANISM: Mus musculus

<400> SEQUENCE: 14
caggtccagc tggtgcaatc cggcgcagag gtgaagaagc caggcgcttc cgtgaaggtg        60
agctgtaagg cctctggcta catcttcaca gcatacacca tgcactgggt gaggcaagct       120
cctgggcagg gactggagtg gatgggatgg attaaaccca acaatgggct ggccaactac       180
gcccagaaat tccagggtag ggtcactatg acaaggqgata ccagcatcag caccgcatat       240
atggagctga gcaggctgag gtctgacgac actgctgtct attattgcgc caggagcgaa       300
attacaacag aattcgatta ctgggggcag ggcacccctgg tgaccgtgtc ctct             354

```
<210> SEQ ID NO 15
<211> LENGTH: 30
<212> TYPE: DNA
<213> ORGANISM: Mus musculus

<400> SEQUENCE: 15
gaatctgtgg actcttacgc aaacagcttt                                        30

<210> SEQ ID NO 16
<211> LENGTH: 9
<212> TYPE: DNA
<213> ORGANISM: Mus musculus

<400> SEQUENCE: 16 agggcttct                                                                9

<210> SEQ ID NO 17
<211> LENGTH: 27
<212> TYPE: DNA
<213> ORGANISM: Mus musculus

<400> SEQUENCE: 17
cagcagtcca aggaggaccc cctgact                                           27

<210> SEQ ID NO 18
<211> LENGTH: 333
<212> TYPE: DNA
<213> ORGANISM: Mus musculus

<400> SEQUENCE: 18
gacattgtgc tgacccagtc tcccgatagc ctggccgtgt ccctgggcga gagggctacc       60
atcaactgta aaagctccga atctgtggac tcttacgcaa acagctttat gcactggtat      120
cagcaaaagc caggccaacc tccaaagctg ctgatttaca gggcttctac cagggagagc      180
ggcgtgcccg ataggttcag cggatctggc agcaggaccg actttacact gaccatctcc      240
agcctgcagg ccgaagatgt ggcagtctat tactgccagc agtccaagga ggaccccctg      300
actttcgggg gtggtactaa agtggagatc aag                                    333

<210> SEQ ID NO 19
<211> LENGTH: 333
<212> TYPE: DNA
<213> ORGANISM: Mus musculus

<400> SEQUENCE: 19
gacattgtga tgacccagtc tcccgatagc ctggccgtgt ccctgggcga gagggctacc       60
atcaactgta aaagctccga atctgtggac tcttacgcaa acagctttat gcactggtat      120
cagcaaaagc caggccaacc tccaaagctg ctgatttaca gggcttctac cagggagagc      180
ggcgtgcccg ataggttcag cggatctggc agcggcaccg actttacact gaccatctcc      240
agcctgcagg ccgaagatgt ggcagtctat tactgccagc agtccaagga ggaccccctg      300
actttcgggg gtggtactaa agtggagatc aag                                    333

<210> SEQ ID NO 20
<211> LENGTH: 333
<212> TYPE: DNA
<213> ORGANISM: Mus musculus

<400> SEQUENCE: 20
gacattgtga tgacccagtc tcccgatagc ctggccgtgt ccctgggcga gagggctacc       60
atcaactgta aaagctccga atctgtggac tcttacgcaa acagctttct gcactggtat      120
```

```
cagcaaaagc caggccaacc tccaaagctg ctgatttaca gggcttctac cagggagagc    180
ggcgtgcccg ataggttcag cggatctggc agcggcaccg actttacact gaccatctcc    240
agcctgcagg ccgaagatgt ggcagtctat tactgccagc agtccaagga ggaccccctg    300
actttcgggg gtggtactaa agtggagatc aag                                 333
```

```
<210> SEQ ID NO 21
<211> LENGTH: 13
<212> TYPE: PRT
<213> ORGANISM: artificial sequence
<220> FEATURE:
<223> OTHER INFORMATION: consensus artificial hinge proteic sequence
<220> FEATURE:
<221> NAME/KEY: MUTAGEN
<222> LOCATION: (1)..(1)
<223> OTHER INFORMATION: Xaa is P or R
<220> FEATURE:
<221> NAME/KEY: MUTAGEN
<222> LOCATION: (2)..(2)
<223> OTHER INFORMATION: Xaa is K or R
<220> FEATURE:
<221> NAME/KEY: MUTAGEN
<222> LOCATION: (3)..(3)
<223> OTHER INFORMATION: Xaa is S, D or missing
<220> FEATURE:
<221> NAME/KEY: MUTAGEN
<222> LOCATION: (5)..(5)
<223> OTHER INFORMATION: Xaa is G, D or missing
<220> FEATURE:
<221> NAME/KEY: MUTAGEN
<222> LOCATION: (7)..(7)
<223> OTHER INFORMATION: Xaa is K, H or V
<220> FEATURE:
<221> NAME/KEY: MUTAGEN
<222> LOCATION: (8)..(8)
<223> OTHER INFORMATION: Xaa isE, P, T or missing
<220> FEATURE:
<221> NAME/KEY: MUTAGEN
<222> LOCATION: (10)..(10)
<223> OTHER INFORMATION: Xaa is P or I
<220> FEATURE:
<221> NAME/KEY: MUTAGEN
<222> LOCATION: (11)..(11)
<223> OTHER INFORMATION: Xaa is P or missing
<220> FEATURE:
<221> NAME/KEY: MUTAGEN
<222> LOCATION: (13)..(13)
<223> OTHER INFORMATION: Xaa is P or T

<400> SEQUENCE: 21

Xaa Xaa Xaa Cys Xaa Cys Xaa Xaa Cys Xaa Xaa Cys Xaa
1               5                   10

<210> SEQ ID NO 22
<211> LENGTH: 11
<212> TYPE: PRT
<213> ORGANISM: artificial sequence
<220> FEATURE:
<223> OTHER INFORMATION: artificial hinge derived from IgG2

<400> SEQUENCE: 22

Arg Lys Cys Cys Val Glu Cys Pro Pro Cys Pro
1               5                   10

<210> SEQ ID NO 23
<211> LENGTH: 12
<212> TYPE: PRT
<213> ORGANISM: artificial sequence
<220> FEATURE:
<223> OTHER INFORMATION: artificial hinge derived from IgG1

<400> SEQUENCE: 23
```

```
Pro Arg Asp Cys Gly Cys Lys Pro Cys Ile Cys Thr
1               5                   10
```

<210> SEQ ID NO 24
<211> LENGTH: 12
<212> TYPE: PRT
<213> ORGANISM: artificial sequence
<220> FEATURE:
<223> OTHER INFORMATION: artificial hinge derived from IgG1

<400> SEQUENCE: 24

```
Pro Lys Ser Cys Gly Cys Lys Pro Cys Ile Cys Thr
1               5                   10
```

<210> SEQ ID NO 25
<211> LENGTH: 12
<212> TYPE: PRT
<213> ORGANISM: artificial sequence
<220> FEATURE:
<223> OTHER INFORMATION: artificial hinge derived from IgG1

<400> SEQUENCE: 25

```
Pro Lys Ser Cys Gly Cys Lys Pro Cys Ile Cys Pro
1               5                   10
```

<210> SEQ ID NO 26
<211> LENGTH: 13
<212> TYPE: PRT
<213> ORGANISM: artificial sequence
<220> FEATURE:
<223> OTHER INFORMATION: artificial hinge derived from IgG1

<400> SEQUENCE: 26

```
Pro Arg Asp Cys Gly Cys Lys Pro Cys Pro Pro Cys Pro
1               5                   10
```

<210> SEQ ID NO 27
<211> LENGTH: 13
<212> TYPE: PRT
<213> ORGANISM: artificial sequence
<220> FEATURE:
<223> OTHER INFORMATION: artificial hinge derived from IgG1

<400> SEQUENCE: 27

```
Pro Arg Asp Cys Gly Cys His Thr Cys Pro Pro Cys Pro
1               5                   10
```

<210> SEQ ID NO 28
<211> LENGTH: 12
<212> TYPE: PRT
<213> ORGANISM: artificial sequence
<220> FEATURE:
<223> OTHER INFORMATION: artificial hinge derived from IgG1

<400> SEQUENCE: 28

```
Pro Lys Ser Cys Asp Cys His Cys Pro Pro Cys Pro
1               5                   10
```

<210> SEQ ID NO 29
<211> LENGTH: 33
<212> TYPE: DNA
<213> ORGANISM: artificial sequence
<220> FEATURE:
<223> OTHER INFORMATION: artificial hinge derived from IgG2

<400> SEQUENCE: 29

```
aggaagtgct gtgtggagtg ccccccctgc cca                           33
```

<210> SEQ ID NO 30
<211> LENGTH: 36
<212> TYPE: DNA
<213> ORGANISM: artificial sequence
<220> FEATURE:
<223> OTHER INFORMATION: artificial sequence derived from IgG1

<400> SEQUENCE: 30
ccccgggact gtgggtgcaa gccttgcatt tgtacc                                  36

<210> SEQ ID NO 31
<211> LENGTH: 36
<212> TYPE: DNA
<213> ORGANISM: artificial sequence
<220> FEATURE:
<223> OTHER INFORMATION: artificial hinge derived from IgG1

<400> SEQUENCE: 31
cccaagagct gtgggtgcaa gccttgcatt tgtacc                                  36

<210> SEQ ID NO 32
<211> LENGTH: 36
<212> TYPE: DNA
<213> ORGANISM: artificial sequence
<220> FEATURE:
<223> OTHER INFORMATION: artificial hinge derived from IgG1

<400> SEQUENCE: 32
ccaaagagct gcggctgcaa gccttgtatc tgtccc                                  36

<210> SEQ ID NO 33
<211> LENGTH: 39
<212> TYPE: DNA
<213> ORGANISM: artificial sequence
<220> FEATURE:
<223> OTHER INFORMATION: artificial hinge derived from IgG1

<400> SEQUENCE: 33
ccacgggact gtggctgcaa gccctgccct ccgtgtcca                               39

<210> SEQ ID NO 34
<211> LENGTH: 39
<212> TYPE: DNA
<213> ORGANISM: artificial sequence
<220> FEATURE:
<223> OTHER INFORMATION: artificial hinge derived from IgG1

<400> SEQUENCE: 34
cccagagact gtgggtgtca cacctgccct ccttgtcct                               39

<210> SEQ ID NO 35
<211> LENGTH: 36
<212> TYPE: DNA
<213> ORGANISM: artificial sequence
<220> FEATURE:
<223> OTHER INFORMATION: artificial hinge derived from IgG1

<400> SEQUENCE: 35
cccaaaagct gcgattgcca ctgtcctcca tgtcca                                  36

<210> SEQ ID NO 36
<211> LENGTH: 443
<212> TYPE: PRT
<213> ORGANISM: Mus musculus

<400> SEQUENCE: 36

```
Gln Val Gln Leu Val Gln Ser Gly Ala Glu Lys Lys Pro Gly Ala
1               5                   10                  15

Ser Val Lys Val Ser Cys Lys Ala Ser Gly Tyr Ile Phe Thr Ala Tyr
            20                  25                  30

Thr Met His Trp Val Arg Gln Ala Pro Gly Gln Gly Leu Glu Trp Met
        35                  40                  45

Gly Trp Ile Lys Pro Asn Asn Gly Leu Ala Asn Tyr Ala Gln Lys Phe
    50                  55                  60

Gln Gly Arg Val Thr Met Thr Arg Asp Thr Ser Ile Ser Thr Ala Tyr
65              70                  75                  80

Met Glu Leu Ser Arg Leu Arg Ser Asp Asp Thr Ala Val Tyr Tyr Cys
                85                  90                  95

Ala Arg Ser Glu Ile Thr Thr Glu Phe Asp Tyr Trp Gly Gln Gly Thr
                100                 105                 110

Leu Val Thr Val Ser Ser Ala Ser Thr Lys Gly Pro Ser Val Phe Pro
                115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
                260                 265                 270

Asn Trp Tyr Val Asp Gly Val Glu Val His Asn Ala Lys Thr Lys Pro
            275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
```

```
                420             425             430
Tyr Thr Gln Lys Ser Leu Ser Leu Ser Pro Gly
            435             440

<210> SEQ ID NO 37
<211> LENGTH: 445
<212> TYPE: PRT
<213> ORGANISM: Mus musculus

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ala Tyr
            20                  25                  30

Thr Met His Trp Val Arg Gln Ala Pro Gly Gln Gly Leu Glu Trp Met
        35                  40                  45

Gly Trp Ile Lys Pro Asn Asn Gly Leu Ala Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Glu Ile Thr Thr Glu Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Cys His Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
```

```
                355                 360                 365
Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 38
<211> LENGTH: 218
<212> TYPE: PRT
<213> ORGANISM: Mus musculus

<400> SEQUENCE: 38

Asp Ile Val Leu Thr Gln Ser Pro Asp Ser Leu Ala Val Ser Leu Gly
1               5                   10                  15

Glu Arg Ala Thr Ile Asn Cys Lys Ser Ser Glu Ser Val Asp Ser Tyr
            20                  25                  30

Ala Asn Ser Phe Met His Trp Tyr Gln Gln Lys Pro Gly Gln Pro Pro
        35                  40                  45

Lys Leu Leu Ile Tyr Arg Ala Ser Thr Arg Glu Ser Gly Val Pro Asp
    50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Glu Asp Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 39
<211> LENGTH: 218
<212> TYPE: PRT
<213> ORGANISM: Mus musculus

<400> SEQUENCE: 39

Asp Ile Val Met Thr Gln Ser Pro Asp Ser Leu Ala Val Ser Leu Gly
1               5                   10                  15

Glu Arg Ala Thr Ile Asn Cys Lys Ser Ser Glu Ser Val Asp Ser Tyr
            20                  25                  30
```

Ala Asn Ser Phe Met His Trp Tyr Gln Gln Lys Pro Gly Gln Pro Pro
            35                  40                  45

Lys Leu Leu Ile Tyr Arg Ala Ser Thr Arg Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Lys
                 85                  90                  95

Glu Asp Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
            210                 215

<210> SEQ ID NO 40
<211> LENGTH: 218
<212> TYPE: PRT
<213> ORGANISM: Mus musculus

<400> SEQUENCE: 40

Asp Ile Val Met Thr Gln Ser Pro Asp Ser Leu Ala Val Ser Leu Gly
1               5                   10                  15

Glu Arg Ala Thr Ile Asn Cys Lys Ser Ser Glu Ser Val Asp Ser Tyr
            20                  25                  30

Ala Asn Ser Phe Leu His Trp Tyr Gln Gln Lys Pro Gly Gln Pro Pro
            35                  40                  45

Lys Leu Leu Ile Tyr Arg Ala Ser Thr Arg Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Lys
                 85                  90                  95

Glu Asp Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205
Val Thr Lys Ser Phe Asn Arg Gly Glu Cys
            210                 215

<210> SEQ ID NO 41
<211> LENGTH: 1332
<212> TYPE: DNA
<213> ORGANISM: Mus musculus

<400> SEQUENCE: 41

| | | |
|---|---|---|
| caggtccagc tggtgcaatc cggcgcagag gtgaagaagc caggcgcttc cgtgaaggtg | 60 |
| agctgtaagg cctctggcta catcttcaca gcatacacca tgcactgggt gaggcaagct | 120 |
| cctgggcagg gactggagtg gatgggatgg attaaaccca caatgggct ggccaactac | 180 |
| gcccagaaat tccagggtag ggtcactatg acaagggata ccagcatcag caccgcatat | 240 |
| atggagctga gcaggctgag gtctgacgac actgctgtct attattgcgc caggagcgaa | 300 |
| attacaacag aattcgatta ctgggggcag ggcaccctgg tgaccgtgtc ctctgccagc | 360 |
| accaagggcc caagcgtgtt cccgctagcg ccctgctcca gaagcaccag cgagagcaca | 420 |
| gccgccctgg gctgcctggt gaaggactac ttccccgagc ccgtgaccgt gcctggaac | 480 |
| agcggagccc tgaccagcgg cgtgcacacc ttccccgccg tgctgcagag cagcggcctg | 540 |
| tacagcctga gcagcgtggt gaccgtgcca agcagcaact tcggcaccca gacctacacc | 600 |
| tgtaacgtgg accacaagcc cagcaacacc aaggtggaca gaccgtgga ggaagtgc | 660 |
| tgtgtggagt ccccccctg cccagccccc ccagtggccg acccagcgt gttcctgttc | 720 |
| cccccaagc caaggacac cctgatgatc agcagaaccc ccgaggtgac ctgtgtggtg | 780 |
| gtggacgtgt cccacgagga ccccgaggtg cagttcaact ggtacgtgga cggcgtggag | 840 |
| gtgcacaacg ccaagaccaa gcccagagag gagcagttta cagcaccctt ccgggtggtg | 900 |
| tccgtgctga ccgtggtgca ccaggactgg ctgaacggca aggagtacaa gtgtaaggtc | 960 |
| tccaacaagg gcctgccagc ccccatcgaa aagaccatca gcaagaccaa gggacagcca | 1020 |
| agagagccac aggtctacac cctgccccc agcagggagg agatgaccaa gaaccaggtg | 1080 |
| tccctgacct gtctggtgaa gggcttctac ccaagcgaca tcgccgtgga gtgggagagc | 1140 |
| aacggccagc ccgagaacaa ctacaagacc accccccccaa tgctggacag cgacggcagc | 1200 |
| ttcttcctgt acagcaagct gacagtggac aagagcagat ggcagcaggg caacgtgttc | 1260 |
| agctgctccg tgatgcacga ggccctgcac aaccactaca cccagaagag cctgagcctg | 1320 |
| tccccaggct ga | 1332 |

<210> SEQ ID NO 42
<211> LENGTH: 1341
<212> TYPE: DNA
<213> ORGANISM: Mus musculus

<400> SEQUENCE: 42

| | | |
|---|---|---|
| caggtccagc tggtgcaatc cggcgcagag gtgaagaagc caggcgcttc cgtgaaggtg | 60 |
| agctgtaagg cctctggcta catcttcaca gcatacacca tgcactgggt gaggcaagct | 120 |
| cctgggcagg gactggagtg gatgggatgg attaaaccca caatgggct ggccaactac | 180 |
| gcccagaaat tccagggtag ggtcactatg acaagggata ccagcatcag caccgcatat | 240 |
| atggagctga gcaggctgag gtctgacgac actgctgtct attattgcgc caggagcgaa | 300 |
| attacaacag aattcgatta ctgggggcag ggcaccctgg tgaccgtgtc ctctgccagc | 360 |

-continued

```
accaagggcc caagcgtgtt cccgctagcc ccgtcttcaa agagtacctc aggcggaact      420
gccgctcttg gttgccttgt gaaggactat tttcctgagc ccgtgacggt cagctggaac      480
tctggcgcac tgactagcgg cgtacacaca ttccctgcgg tgctccaaag ttccgggctg      540
tactcactgt cctccgttgt gaccgttcca tctagttccc tcgggacaca gacatacatc      600
tgtaatgtga atcataagcc ttcaaacacc aaggtcgaca aacgggtcga gcccaaaagc      660
tgcgattgcc actgtcctcc atgtccagcc cccgaactgt gggcggacc gagcgtgttc       720 ttgtttccac ccaagcccaa agataccctc atgatcagca gaaccccga ggtgacctgt        780 gtggtggtgg acgtgtccca cgaggaccca gaggtgaagt tcaactggta cgtggacggc      840
gtggaggtgc acaacgccaa gaccaagccc agagaggagc agtacaacag cacctacagg      900
gtggtgtccg tgctgaccgt gctgcaccag gactggctga acggcaagga gtacaagtgt      960
aaggtgtcca acaaggccct gccagcccca atcgaaaaga ccatcagcaa ggccaagggc     1020
cagccaagag agcccaggt gtacaccctg ccacccagca gggaggagat gaccaagaac      1080
caggtgtccc tgacctgtct ggtgaagggc ttctacccaa gcgacatcgc cgtggagtgg     1140
gagagcaacg gccagcccga gaacaactac aagaccaccc cccagtgct ggacagcgac       1200 ggcagcttct tcctgtacag caagctgacc gtggacaaga gcagatggca gcagggcaac     1260
gtgttcagct gctccgtgat gcacgaggcc ctgcacaacc actacaccca gaagagcctg     1320
agcctgtccc caggcaagtg a                                               1341
```

<210> SEQ ID NO 43
<211> LENGTH: 657
<212> TYPE: DNA
<213> ORGANISM: Mus musculus

<400> SEQUENCE: 43

```
gacattgtgc tgacccagtc tcccgatagc ctggccgtgt ccctgggcga gagggctacc       60
atcaactgta aaagctccga atctgtggac tcttacgcaa acagctttat gcactggtat      120
cagcaaaagc caggccaacc tccaaagctg ctgatttaca gggcttctac cagggagagc      180
ggcgtgcccg ataggttcag cggatctggc agcaggaccg actttacact gaccatctcc      240
agcctgcagg ccgaagatgt ggcagtctat tactgccagc agtccaagga ggaccccctg      300
actttcgggg gtggtactaa agtggagatc aagcgtacgg tggccgctcc cagcgtgttc      360
atcttccccc caagcgacga gcagctgaag agcggcaccg ccagcgtggt gtgtctgctg      420
aacaacttct accccaggga ggccaaggtg cagtggaagg tggacaacgc cctgcagagc      480
ggcaacagcc aggagagcgt caccgagcag gacagcaagg actccaccta cagcctgagc      540
agcaccctga ccctgagcaa ggccgactac gagaagcaca aggtgtacgc ctgtgaggtg      600
acccaccagg gcctgtccag ccccgtgacc aagagcttca caggggcga gtgctga         657
```

<210> SEQ ID NO 44
<211> LENGTH: 657
<212> TYPE: DNA
<213> ORGANISM: Mus musculus

<400> SEQUENCE: 44

```
gacattgtga tgacccagtc tcccgatagc ctggccgtgt ccctgggcga gagggctacc       60
atcaactgta aaagctccga atctgtggac tcttacgcaa acagctttat gcactggtat      120
cagcaaaagc caggccaacc tccaaagctg ctgatttaca gggcttctac cagggagagc      180
ggcgtgcccg ataggttcag cggatctggc agcggcaccg actttacact gaccatctcc      240
```

```
agcctgcagg ccgaagatgt ggcagtctat tactgccagc agtccaagga ggaccccctg    300
actttcgggg gtggtactaa agtggagatc aagcgtacgg tggccgctcc cagcgtgttc    360
atcttccccc caagcgacga gcagctgaag agcggcaccg ccagcgtggt gtgtctgctg    420
aacaacttct accccaggga ggccaaggtg cagtggaagg tggacaacgc cctgcagagc    480
ggcaacagcc aggagagcgt caccgagcag gacagcaagg actccaccta cagcctgagc    540
agcaccctga ccctgagcaa ggccgactac gagaagcaca aggtgtacgc ctgtgaggtg    600
acccaccagg gcctgtccag ccccgtgacc aagagcttca caggggcga gtgctga       657
```

```
<210> SEQ ID NO 45
<211> LENGTH: 657
<212> TYPE: DNA
<213> ORGANISM: Mus musculus

<400> SEQUENCE: 45
gacattgtga tgacccagtc tcccgatagc ctggccgtgt ccctgggcga gagggctacc    60
atcaactgta aagctccga atctgtggac tcttacgcaa acagctttct gcactggtat    120
cagcaaaagc caggccaacc tccaaagctg ctgatttaca gggcttctac cagggagagc    180
ggcgtgcccg ataggttcag cggatctggc agcggcaccg actttacact gaccatctcc    240
agcctgcagg ccgaagatgt ggcagtctat tactgccagc agtccaagga ggaccccctg    300
actttcgggg gtggtactaa agtggagatc aagcgtacgg tggccgctcc cagcgtgttc    360
atcttccccc caagcgacga gcagctgaag agcggcaccg ccagcgtggt gtgtctgctg    420
aacaacttct accccaggga ggccaaggtg cagtggaagg tggacaacgc cctgcagagc    480
ggcaacagcc aggagagcgt caccgagcag gacagcaagg actccaccta cagcctgagc    540
agcaccctga ccctgagcaa ggccgactac gagaagcaca aggtgtacgc ctgtgaggtg    600
acccaccagg gcctgtccag ccccgtgacc aagagcttca caggggcga gtgctga       657
```

```
<210> SEQ ID NO 46
<211> LENGTH: 118
<212> TYPE: PRT
<213> ORGANISM: Mus musculus

<400> SEQUENCE: 46

Glu Val Gln Leu Gln Gln Ser Gly Pro Glu Leu Val Lys Pro Gly Ala
1               5                  10                  15

Ser Val Lys Ile Ser Cys Lys Thr Ser Gly Tyr Ile Phe Thr Ala Tyr
            20                  25                  30

Thr Met His Trp Val Arg Gln Ser Leu Gly Glu Ser Leu Asp Trp Ile
        35                  40                  45

Gly Gly Ile Lys Pro Asn Asn Gly Leu Ala Asn Tyr Asn Gln Lys Phe
    50                  55                  60

Lys Gly Lys Ala Thr Leu Thr Val Asp Lys Ser Ser Thr Ala Tyr
65                  70                  75                  80

Met Asp Leu Arg Ser Leu Thr Ser Glu Asp Ser Ala Val Tyr Tyr Cys
                85                  90                  95

Ala Arg Ser Glu Ile Thr Thr Glu Phe Asp Tyr Trp Gly Gln Gly Thr
            100                 105                 110

Ala Leu Thr Val Ser Ser
        115
```

```
<210> SEQ ID NO 47
<211> LENGTH: 112
```

-continued

<212> TYPE: PRT
<213> ORGANISM: Mus musculus

<400> SEQUENCE: 47

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Ala Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Lys
                85                  90                  95

Glu Asp Pro Leu Thr Phe Gly Ser Gly Thr Lys Leu Glu Met Lys Arg
            100                 105                 110

<210> SEQ ID NO 48
<211> LENGTH: 354
<212> TYPE: DNA
<213> ORGANISM: Mus musculus

<400> SEQUENCE: 48
gaggtccagc tgcagcagag cgggccagaa ctggttaaac ctggcgccag cgtgaagatt      60
agctgtaaga ccagcggtta catctttaca gcatatacca tgcactgggt gaggcagagt     120
ctgggggaat ctctggactg gatcggaggt attaagccca caatggcct ggctaactat      180
aatcaaaaat tcaagggcaa agccacactg accgtcgata agtcctcttc cacagcttac     240
atggatctga aagcctgac atccgaggac agtgcagtgt actactgcgc ccggtctgag      300
atcactaccg agttcgacta ttggggacag ggcactgcac tgaccgtctc ctcc           354

<210> SEQ ID NO 49
<211> LENGTH: 333
<212> TYPE: DNA
<213> ORGANISM: Mus musculus

<400> SEQUENCE: 49
gatattgtgc tgacacagtc tcccgcaagc ctcgctgtta gcctgggtca acgggccaca      60
attagttgtc gcgcctctga atccgtcgac tcttatgcta acagctttat gcactggtat     120
caacagaagc ccgggcagcc acctaaactg ctgatctaca gggccagcaa tctggagagt     180
ggcatcccag ctagatttag cggttccggg tccaggaccg acttcactct gaccatcaac     240
cccgtggagg cagacgacgt ggccacttac tactgccagc agtctaaaga ggatcccctc     300
acattcggct ccggaacaaa gctggaaatg aag                                  333

<210> SEQ ID NO 50
<211> LENGTH: 443
<212> TYPE: PRT
<213> ORGANISM: Mus musculus

<400> SEQUENCE: 50

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Ile Phe Thr Ala Tyr
            20                  25                  30

Thr Met His Trp Val Arg Gln Ser Leu Gly Glu Ser Leu Asp Trp Ile
         35                  40                  45

Gly Gly Ile Lys Pro Asn Asn Gly Leu Ala Asn Tyr Asn Gln Lys Phe
 50                  55                  60

Lys Gly Lys Ala Thr Leu Thr Val Asp Lys Ser Ser Thr Ala Tyr
 65                  70                  75                  80

Met Asp Leu Arg Ser Leu Thr Ser Glu Asp Ser Ala Val Tyr Tyr Cys
                 85                  90                  95

Ala Arg Ser Glu Ile Thr Thr Glu Phe Asp Tyr Trp Gly Gln Gly Thr
                100                 105                 110

Ala Leu Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
        435                 440

<210> SEQ ID NO 51

<211> LENGTH: 446
<212> TYPE: PRT
<213> ORGANISM: Mus musculus

<400> SEQUENCE: 51

```
Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Ile Phe Thr Ala Tyr
            20                  25                  30

Thr Met His Trp Val Arg Gln Ser Leu Gly Glu Ser Leu Asp Trp Ile
        35                  40                  45

Gly Gly Ile Lys Pro Asn Asn Gly Leu Ala Asn Tyr Asn Gln Lys Phe
    50                  55                  60

Lys Gly Lys Ala Thr Leu Thr Val Asp Lys Ser Ser Thr Ala Tyr
65                  70                  75                  80

Met Asp Leu Arg Ser Leu Thr Ser Glu Asp Ser Ala Val Tyr Tyr Cys
                85                  90                  95

Ala Arg Ser Glu Ile Thr Thr Glu Phe Asp Tyr Trp Gly Gln Gly Thr
            100                 105                 110

Ala Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Cys His
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400
```

```
Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 52
<211> LENGTH: 218
<212> TYPE: PRT
<213> ORGANISM: Mus musculus

<400> SEQUENCE: 52

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Ala Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Lys
                85                  90                  95

Glu Asp Pro Leu Thr Phe Gly Ser Gly Thr Lys Leu Glu Met Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 53
<211> LENGTH: 1332
<212> TYPE: DNA
<213> ORGANISM: Mus musculus

<400> SEQUENCE: 53
gaggtccagc tgcagcagag cgggccagaa ctggttaaac ctggcgccag cgtgaagatt      60
agctgtaaga ccagcggtta catctttaca gcatatacca tgcactgggt gaggcagagt     120
ctgggggaat ctctggactg gatcggaggt attaagccca acaatggcct ggctaactat     180
aatcaaaaat tcaagggcaa agccacactg accgtcgata gtcctcttc cacagcttac     240 atggatctga aagcctgac atccgaggac agtgcagtgt actactgcgc ccggtctgag     300
atcactaccg agttcgacta ttggggacag ggcactgcac tgaccgtctc ctccgccagc     360
```

| | |
|---|---|
| accaagggcc caagcgtgtt cccgctagcg ccctgctcca gaagcaccag cgagagcaca | 420 |
| gccgccctgg gctgcctggt gaaggactac ttccccgagc ccgtgaccgt gtcctggaac | 480 |
| agcggagccc tgaccagcgg cgtgcacacc ttccccgccg tgctgcagag cagcggcctg | 540 |
| tacagcctga gcagcgtggt gaccgtgcca agcagcaact tcggcaccca gacctacacc | 600 |
| tgtaacgtgg accacaagcc cagcaacacc aaggtggaca gaccgtgga gaggaagtgc | 660 |
| tgtgtggagt gccccccctg cccagccccc cagtggccg acccagcgt gttcctgttc | 720 |
| ccccccaagc ccaaggacac cctgatgatc agcagaaccc ccgaggtgac ctgtgtggtg | 780 |
| gtggacgtgt cccacgagga ccccgaggtg cagttcaact ggtacgtgga cggcgtggag | 840 |
| gtgcacaacg ccaagaccaa gcccagagag gagcagttta cagcaccttt ccgggtggtg | 900 |
| tccgtgctga ccgtggtgca ccaggactgg ctgaacggca aggagtacaa gtgtaaggtc | 960 |
| tccaacaagg gcctgccagc ccccatcgaa aagaccatca gcaagaccaa gggacagcca | 1020 |
| agagagccac aggtctacac cctgccccc agcaggagg atgaccaa gaaccaggtg | 1080 |
| tccctgacct gtctggtgaa gggcttctac ccaagcgaca tcgccgtgga gtgggagagc | 1140 |
| aacggccagc ccgagaacaa ctacaagacc accccccaa tgctggacag cgacggcagc | 1200 |
| ttcttcctgt acagcaagct gacagtggac aagagcagat ggcagcaggg caacgtgttc | 1260 |
| agctgctccg tgatgcacga ggccctgcac aaccactaca cccagaagag cctgagcctg | 1320 |
| tccccaggct ga | 1332 |

<210> SEQ ID NO 54
<211> LENGTH: 1341
<212> TYPE: DNA
<213> ORGANISM: Mus musculus

<400> SEQUENCE: 54

| | |
|---|---|
| gaggtccagc tgcagcagag cgggccagaa ctggttaaac ctggcgccag cgtgaagatt | 60 |
| agctgtaaga ccagcggtta catctttaca gcatatacca tgcactgggt gaggcagagt | 120 |
| ctggggaat ctctggactg gatcggaggt attaagccca caatggcct ggctaactat | 180 |
| aatcaaaaat tcaagggcaa agccacactg accgtcgata gtcctcttc cacagcttac | 240 |
| atggatctga aagcctgac atccgaggac agtgcagtgt actactgcgc ccggtctgag | 300 |
| atcactaccg agttcgacta ttggggacag ggcactgcac tgaccgtctc ctccgccagc | 360 |
| accaagggcc caagcgtgtt cccgctagcc ccgtcttcaa agagtacctc aggcggaact | 420 |
| gccgctcttg gttgccttgt gaaggactat tttcctgagc ccgtgacggt cagctggaac | 480 |
| tctggcgcac tgactagcgg cgtacacaca ttccctgcgg tgctccaaag ttccgggctg | 540 |
| tactcactgt cctccgttgt gaccgttcca tctagttccc tcgggacaca gacatacatc | 600 |
| tgtaatgtga atcataagcc ttcaaacacc aaggtcgaca acgggtcga gcccaaaagc | 660 |
| tgcgattgcc actgtcctcc atgtccagcc ccgaactgt gggcggacc gagcgtgttc | 720 |
| ttgtttccac ccaagcccaa agataccctc atgatcagca gaaccccgga ggtgacctgt | 780 |
| gtggtggtgg acgtgtccca cgaggaccca gaggtgaagt tcaactggta cgtggacggc | 840 |
| gtggaggtgc acaacgccaa gaccaagccc agagaggagc agtacaacag cacctacagg | 900 |
| gtggtgtccg tgctgaccgt gctgcaccag gactggctga acggcaagga gtacaagtgt | 960 |
| aaggtgtcca acaaggccct gccagcccca tcgaaaaga ccatcagcaa ggccaagggc | 1020 |
| cagccaagag agcccaggt gtacccctg ccacccagca gggaggagat gaccaagaac | 1080 |
| caggtgtccc tgacctgtct ggtgaagggc ttctacccaa gcgacatcgc cgtggagtgg | 1140 |

-continued

```
gagagcaacg gccagcccga gaacaactac aagaccaccc ccccagtgct ggacagcgac    1200
ggcagcttct tcctgtacag caagctgacc gtggacaaga gcagatggca gcagggcaac    1260
gtgttcagct gctccgtgat gcacgaggcc ctgcacaacc actacaccca gaagagcctg    1320
agcctgtccc caggcaagtg a                                              1341
```

<210> SEQ ID NO 55
<211> LENGTH: 657
<212> TYPE: DNA
<213> ORGANISM: Mus musculus

<400> SEQUENCE: 55

```
gatattgtgc tgacacagtc tcccgcaagc ctcgctgtta gcctgggtca acgggccaca     60
attagttgtc gcgcctctga atccgtcgac tcttatgcta acagctttat gcactggtat    120
caacagaagc ccgggcagcc acctaaactg ctgatctaca gggccagcaa tctggagagt    180
ggcatcccag ctagatttag cggttccggg tccaggaccg acttcactct gaccatcaac    240
cccgtggagg cagacgacgt ggccacttac tactgccagc agtctaaaga ggatcccctc    300
acattcggct ccggaacaaa gctggaaatg aagcgtacgg tggccgctcc cagcgtgttc    360
atcttccccc caagcgacga gcagctgaag agcggcaccg ccagcgtggt gtgtctgctg    420
aacaacttct accccaggga ggccaaggtg cagtggaagg tggacaacgc cctgcagagc    480
ggcaacagcc aggagagcgt caccgagcag gacagcaagg actccaccta cagcctgagc    540
agcaccctga ccctgagcaa ggccgactac gagaagcaca aggtgtacgc ctgtgaggtg    600
acccaccagg gcctgtccag ccccgtgacc aagagcttca caggggcga gtgctga       657
```

<210> SEQ ID NO 56
<211> LENGTH: 14
<212> TYPE: PRT
<213> ORGANISM: artificial
<220> FEATURE:
<223> OTHER INFORMATION: consensus artificial hinge proteic sequence
<220> FEATURE:
<221> NAME/KEY: mutagen
<222> LOCATION: (1)..(1)
<223> OTHER INFORMATION: X is P, R, C or missing
<220> FEATURE:
<221> NAME/KEY: mutagen
<222> LOCATION: (2)..(2)
<223> OTHER INFORMATION: X is K, C, R or missing
<220> FEATURE:
<221> NAME/KEY: mutagen
<222> LOCATION: (3)..(3)
<223> OTHER INFORMATION: X is S, C, D or missing
<220> FEATURE:
<221> NAME/KEY: mutagen
<222> LOCATION: (5)..(5)
<223> OTHER INFORMATION: X is D, C, G or missing
<220> FEATURE:
<221> NAME/KEY: mutagen
<222> LOCATION: (6)..(6)
<223> OTHER INFORMATION: X is K, C or missing
<220> FEATURE:
<221> NAME/KEY: mutagen
<222> LOCATION: (7)..(7)
<223> OTHER INFORMATION: X is T, C or missing
<220> FEATURE:
<221> NAME/KEY: mutagen
<222> LOCATION: (8)..(8)
<223> OTHER INFORMATION: X is H, V, K or missing
<220> FEATURE:
<221> NAME/KEY: mutagen
<222> LOCATION: (9)..(9)
<223> OTHER INFORMATION: X is T, C, E, P or missing
<220> FEATURE:
<221> NAME/KEY: mutagen
<222> LOCATION: (11)..(11)

```
<223> OTHER INFORMATION: X is P or I
<220> FEATURE:
<221> NAME/KEY: mutagen
<222> LOCATION: (12)..(12)
<223> OTHER INFORMATION: X is P or missing
<220> FEATURE:
<221> NAME/KEY: mutagen
<222> LOCATION: (14)..(14)
<223> OTHER INFORMATION: X is P or T

<400> SEQUENCE: 56

Xaa Xaa Xaa Cys Xaa Xaa Xaa Xaa Xaa Cys Xaa Xaa Cys Xaa
1               5                   10

<210> SEQ ID NO 57
<211> LENGTH: 14
<212> TYPE: PRT
<213> ORGANISM: artificial
<220> FEATURE:
<223> OTHER INFORMATION: consensus artificial hinge proteic sequence
<220> FEATURE:
<221> NAME/KEY: mutagen
<222> LOCATION: (1)..(1)
<223> OTHER INFORMATION: X is P, R, C or missing
<220> FEATURE:
<221> NAME/KEY: mutagen
<222> LOCATION: (2)..(2)
<223> OTHER INFORMATION: X is K, C, R or missing
<220> FEATURE:
<221> NAME/KEY: mutagen
<222> LOCATION: (3)..(3)
<223> OTHER INFORMATION: X is S, C, D or missing
<220> FEATURE:
<221> NAME/KEY: mutagen
<222> LOCATION: (5)..(5)
<223> OTHER INFORMATION: X is D, C, G or missing
<220> FEATURE:
<221> NAME/KEY: mutagen
<222> LOCATION: (6)..(6)
<223> OTHER INFORMATION: X is K, C or missing
<220> FEATURE:
<221> NAME/KEY: mutagen
<222> LOCATION: (7)..(7)
<223> OTHER INFORMATION: X is T, C or missing
<220> FEATURE:
<221> NAME/KEY: mutagen
<222> LOCATION: (8)..(8)
<223> OTHER INFORMATION: X is H, V, K or missing
<220> FEATURE:
<221> NAME/KEY: mutagen
<222> LOCATION: (9)..(9)
<223> OTHER INFORMATION: X is T, C, E, P or missing

<400> SEQUENCE: 57

Xaa Xaa Xaa Cys Xaa Xaa Xaa Xaa Xaa Cys Pro Pro Cys Pro
1               5                   10

<210> SEQ ID NO 58
<211> LENGTH: 14
<212> TYPE: PRT
<213> ORGANISM: artificial
<220> FEATURE:
<223> OTHER INFORMATION: artificial hinge region

<400> SEQUENCE: 58

Cys Lys Ser Cys Asp Lys Thr His Thr Cys Pro Pro Cys Pro
1               5                   10

<210> SEQ ID NO 59
<211> LENGTH: 14
<212> TYPE: PRT
<213> ORGANISM: artificial
<220> FEATURE:
<223> OTHER INFORMATION: artificial hinge region
```

<400> SEQUENCE: 59

Pro Cys Ser Cys Asp Lys Thr His Thr Cys Pro Pro Cys Pro
1               5                   10

<210> SEQ ID NO 60
<211> LENGTH: 14
<212> TYPE: PRT
<213> ORGANISM: artificial
<220> FEATURE:
<223> OTHER INFORMATION: artificial hinge region

<400> SEQUENCE: 60

Pro Lys Cys Cys Asp Lys Thr His Thr Cys Pro Pro Cys Pro
1               5                   10

<210> SEQ ID NO 61
<211> LENGTH: 14
<212> TYPE: PRT
<213> ORGANISM: artificial
<220> FEATURE:
<223> OTHER INFORMATION: artificial hinge region

<400> SEQUENCE: 61

Pro Lys Ser Cys Cys Lys Thr His Thr Cys Pro Pro Cys Pro
1               5                   10

<210> SEQ ID NO 62
<211> LENGTH: 14
<212> TYPE: PRT
<213> ORGANISM: artificial
<220> FEATURE:
<223> OTHER INFORMATION: artificial hinge region

<400> SEQUENCE: 62

Pro Lys Ser Cys Asp Cys Thr His Thr Cys Pro Pro Cys Pro
1               5                   10

<210> SEQ ID NO 63
<211> LENGTH: 14
<212> TYPE: PRT
<213> ORGANISM: artificial
<220> FEATURE:
<223> OTHER INFORMATION: artificial hinge region

<400> SEQUENCE: 63

Pro Lys Ser Cys Asp Lys Cys His Thr Cys Pro Pro Cys Pro
1               5                   10

<210> SEQ ID NO 64
<211> LENGTH: 14
<212> TYPE: PRT
<213> ORGANISM: artificial
<220> FEATURE:
<223> OTHER INFORMATION: artificial hinge region

<400> SEQUENCE: 64

Pro Lys Ser Cys Asp Lys Thr His Cys Cys Pro Pro Cys Pro
1               5                   10

<210> SEQ ID NO 65
<211> LENGTH: 12
<212> TYPE: PRT
<213> ORGANISM: artificial
<220> FEATURE:
<223> OTHER INFORMATION: artificial hinge region

<400> SEQUENCE: 65

Lys Cys Asp Lys Thr His Thr Cys Pro Pro Cys Pro
1               5                   10

<210> SEQ ID NO 66
<211> LENGTH: 13
<212> TYPE: PRT
<213> ORGANISM: artificial
<220> FEATURE:
<223> OTHER INFORMATION: artificial hinge region

<400> SEQUENCE: 66

Pro Lys Ser Cys Asp Cys His Thr Cys Pro Pro Cys Pro
1               5                   10

<210> SEQ ID NO 67
<211> LENGTH: 13
<212> TYPE: PRT
<213> ORGANISM: artificial
<220> FEATURE:
<223> OTHER INFORMATION: artificial hinge region

<400> SEQUENCE: 67

Pro Lys Ser Cys Asp Cys Thr His Cys Pro Pro Cys Pro
1               5                   10

<210> SEQ ID NO 68
<211> LENGTH: 12
<212> TYPE: PRT
<213> ORGANISM: artificial
<220> FEATURE:
<223> OTHER INFORMATION: artificial hinge region

<400> SEQUENCE: 68

Pro Cys Ser Cys Lys His Thr Cys Pro Pro Cys Pro
1               5                   10

<210> SEQ ID NO 69
<211> LENGTH: 12
<212> TYPE: PRT
<213> ORGANISM: artificial
<220> FEATURE:
<223> OTHER INFORMATION: artificial hinge region

<400> SEQUENCE: 69

Pro Ser Cys Cys Thr His Thr Cys Pro Pro Cys Pro
1               5                   10

<210> SEQ ID NO 70
<211> LENGTH: 12
<212> TYPE: PRT
<213> ORGANISM: artificial
<220> FEATURE:
<223> OTHER INFORMATION: artificial hinge region

<400> SEQUENCE: 70

Pro Ser Cys Asp Lys His Cys Cys Pro Pro Cys Pro
1               5                   10

<210> SEQ ID NO 71
<211> LENGTH: 10
<212> TYPE: PRT
<213> ORGANISM: artificial
<220> FEATURE:
<223> OTHER INFORMATION: artificial hinge region

<400> SEQUENCE: 71

Pro Lys Ser Cys Thr Cys Pro Pro Cys Pro

```
<210> SEQ ID NO 72
<211> LENGTH: 14
<212> TYPE: PRT
<213> ORGANISM: artificial
<220> FEATURE:
<223> OTHER INFORMATION: artificial hinge region

<400> SEQUENCE: 72

Pro Lys Ser Cys Asp Lys Cys Val Glu Cys Pro Pro Cys Pro
1               5                   10

<210> SEQ ID NO 73
<211> LENGTH: 42
<212> TYPE: DNA
<213> ORGANISM: artificial
<220> FEATURE:
<223> OTHER INFORMATION: artificial hinge region

<400> SEQUENCE: 73
tgcaagagct gcgacaagac ccacacctgt cccccctgcc ct                    42

<210> SEQ ID NO 74
<211> LENGTH: 42
<212> TYPE: DNA
<213> ORGANISM: artificial
<220> FEATURE:
<223> OTHER INFORMATION: artificial hinge region

<400> SEQUENCE: 74
ccctgcagct gcgacaagac ccacacctgt cccccctgcc ct                    42

<210> SEQ ID NO 75
<211> LENGTH: 42
<212> TYPE: DNA
<213> ORGANISM: artificial
<220> FEATURE:
<223> OTHER INFORMATION: artificial hinge region

<400> SEQUENCE: 75
cccaagtgct gcgacaagac ccacacctgt cccccctgcc ct                    42

<210> SEQ ID NO 76
<211> LENGTH: 42
<212> TYPE: DNA
<213> ORGANISM: artificial
<220> FEATURE:
<223> OTHER INFORMATION: artificial hinge region

<400> SEQUENCE: 76
cctaagagct gttgcaagac ccacacctgt cccccctgcc ct                    42

<210> SEQ ID NO 77
<211> LENGTH: 42
<212> TYPE: DNA
<213> ORGANISM: artificial
<220> FEATURE:
<223> OTHER INFORMATION: artificial hinge region

<400> SEQUENCE: 77
cccaagagct gcgactgcac ccacacctgt cccccctgcc ct                    42

<210> SEQ ID NO 78
<211> LENGTH: 42
<212> TYPE: DNA
<213> ORGANISM: artificial
```

```
<220> FEATURE:
<223> OTHER INFORMATION: artificial hinge region

<400> SEQUENCE: 78
cccaagagct gcgacaagtg ccacacctgt cccccctgcc ct                    42

<210> SEQ ID NO 79
<211> LENGTH: 42
<212> TYPE: DNA
<213> ORGANISM: artificial
<220> FEATURE:
<223> OTHER INFORMATION: artificial hinge region

<400> SEQUENCE: 79
cccaagagct gcgacaagac ccactgctgt cccccctgcc ct                    42

<210> SEQ ID NO 80
<211> LENGTH: 36
<212> TYPE: DNA
<213> ORGANISM: artificial
<220> FEATURE:
<223> OTHER INFORMATION: artificial hinge region

<400> SEQUENCE: 80
aagtgcgaca agacccacac ctgtcccccc tgccct                           36

<210> SEQ ID NO 81
<211> LENGTH: 39
<212> TYPE: DNA
<213> ORGANISM: artificial
<220> FEATURE:
<223> OTHER INFORMATION: artificial hinge region

<400> SEQUENCE: 81
cccaagagct gcgactgcca cacctgtccc cctgccct                         39

<210> SEQ ID NO 82
<211> LENGTH: 39
<212> TYPE: DNA
<213> ORGANISM: artificial
<220> FEATURE:
<223> OTHER INFORMATION: artificial hinge region

<400> SEQUENCE: 82
cccaagagct gcgactgcac ccactgcccc cctgccct                         39

<210> SEQ ID NO 83
<211> LENGTH: 36
<212> TYPE: DNA
<213> ORGANISM: artificial
<220> FEATURE:
<223> OTHER INFORMATION: artificial hinge domain

<400> SEQUENCE: 83
ccctgcagct gcaagcacac ctgtcccccc tgccct                           36

<210> SEQ ID NO 84
<211> LENGTH: 36
<212> TYPE: DNA
<213> ORGANISM: artificial
<220> FEATURE:
<223> OTHER INFORMATION: artificial hinge region

<400> SEQUENCE: 84
cctagctgct gcacccacac ctgtcccccc tgccct                           36
```

```
<210> SEQ ID NO 85
<211> LENGTH: 36
<212> TYPE: DNA
<213> ORGANISM: artificial
<220> FEATURE:
<223> OTHER INFORMATION: artificial hinge region

<400> SEQUENCE: 85
cccagctgcg acaagcactg ctgcccccccc tgccct                           36

<210> SEQ ID NO 86
<211> LENGTH: 30
<212> TYPE: DNA
<213> ORGANISM: artificial
<220> FEATURE:
<223> OTHER INFORMATION: artificial hinge region

<400> SEQUENCE: 86
cccaagagct gcacctgtcc ccttgtcct                                    30

<210> SEQ ID NO 87
<211> LENGTH: 42
<212> TYPE: DNA
<213> ORGANISM: artificial
<220> FEATURE:
<223> OTHER INFORMATION: artificial hinge region

<400> SEQUENCE: 87
cccaagagct gcgataagtg cgtggagtgc ccccttgtc ct                      42

<210> SEQ ID NO 88
<211> LENGTH: 448
<212> TYPE: PRT
<213> ORGANISM: Mus musculus

<400> SEQUENCE: 88
```

| | | | | | | | | | | | | | | |
|---|---|---|---|---|---|---|---|---|---|---|---|---|---|---|
| Glu | Val | Gln | Leu | Gln | Gln | Ser | Gly | Pro | Glu | Leu | Val | Lys | Pro | Gly | Ala |
| 1 | | | | 5 | | | | | 10 | | | | | 15 | |
| Ser | Val | Lys | Ile | Ser | Cys | Lys | Thr | Ser | Gly | Tyr | Ile | Phe | Thr | Ala | Tyr |
| | | | 20 | | | | | 25 | | | | | 30 | | |
| Thr | Met | His | Trp | Val | Arg | Gln | Ser | Leu | Gly | Glu | Ser | Leu | Asp | Trp | Ile |
| | | 35 | | | | | 40 | | | | | 45 | | | |
| Gly | Gly | Ile | Lys | Pro | Asn | Asn | Gly | Leu | Ala | Asn | Tyr | Asn | Gln | Lys | Phe |
| | 50 | | | | | 55 | | | | | 60 | | | | |
| Lys | Gly | Lys | Ala | Thr | Leu | Thr | Val | Asp | Lys | Ser | Ser | Ser | Thr | Ala | Tyr |
| 65 | | | | | 70 | | | | | 75 | | | | | 80 |
| Met | Asp | Leu | Arg | Ser | Leu | Thr | Ser | Glu | Asp | Ser | Ala | Val | Tyr | Tyr | Cys |
| | | | | 85 | | | | | 90 | | | | | 95 | |
| Ala | Arg | Ser | Glu | Ile | Thr | Thr | Glu | Phe | Asp | Tyr | Trp | Gly | Gln | Gly | Thr |
| | | | 100 | | | | | 105 | | | | | 110 | | |
| Ala | Leu | Thr | Val | Ser | Ser | Ala | Ser | Thr | Lys | Gly | Pro | Ser | Val | Phe | Pro |
| | | 115 | | | | | 120 | | | | | 125 | | | |
| Leu | Ala | Pro | Ser | Ser | Lys | Ser | Thr | Ser | Gly | Gly | Thr | Ala | Ala | Leu | Gly |
| | 130 | | | | | 135 | | | | | 140 | | | | |
| Cys | Leu | Val | Lys | Asp | Tyr | Phe | Pro | Glu | Pro | Val | Thr | Val | Ser | Trp | Asn |
| 145 | | | | | 150 | | | | | 155 | | | | | 160 |
| Ser | Gly | Ala | Leu | Thr | Ser | Gly | Val | His | Thr | Phe | Pro | Ala | Val | Leu | Gln |
| | | | | 165 | | | | | 170 | | | | | 175 | |
| Ser | Ser | Gly | Leu | Tyr | Ser | Leu | Ser | Ser | Val | Val | Thr | Val | Pro | Ser | Ser |
| | | | 180 | | | | | 185 | | | | | 190 | | |
| Ser | Leu | Gly | Thr | Gln | Thr | Tyr | Ile | Cys | Asn | Val | Asn | His | Lys | Pro | Ser |

```
                  195                 200                 205
Asn Thr Lys Val Asp Lys Arg Val Glu Cys Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 89
<211> LENGTH: 448
<212> TYPE: PRT
<213> ORGANISM: Mus musculus

<400> SEQUENCE: 89

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Ile Phe Thr Ala Tyr
            20                  25                  30

Thr Met His Trp Val Arg Gln Ser Leu Gly Glu Ser Leu Asp Trp Ile
        35                  40                  45

Gly Gly Ile Lys Pro Asn Asn Gly Leu Ala Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Asp Leu Arg Ser Leu Thr Ser Glu Asp Ser Ala Val Tyr Tyr Cys
                85                  90                  95

Ala Arg Ser Glu Ile Thr Thr Glu Phe Asp Tyr Trp Gly Gln Gly Thr
            100                 105                 110

Ala Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
```

```
                130             135             140
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Cys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 90
<211> LENGTH: 448
<212> TYPE: PRT
<213> ORGANISM: Mus musculus

<400> SEQUENCE: 90

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Ile Phe Thr Ala Tyr
                20                  25                  30

Thr Met His Trp Val Arg Gln Ser Leu Gly Glu Ser Leu Asp Trp Ile
            35                  40                  45

Gly Gly Ile Lys Pro Asn Asn Gly Leu Ala Asn Tyr Asn Gln Lys Phe
        50                  55                  60

Lys Gly Lys Ala Thr Leu Thr Val Asp Lys Ser Ser Ser Thr Ala Tyr
```

```
                65                  70                  75                  80
Met Asp Leu Arg Ser Leu Thr Ser Glu Asp Ser Ala Val Tyr Tyr Cys
                        85                  90                  95

Ala Arg Ser Glu Ile Thr Thr Glu Phe Asp Tyr Trp Gly Gln Gly Thr
                100                 105                 110

Ala Leu Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Cys Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 91
<211> LENGTH: 448
<212> TYPE: PRT
<213> ORGANISM: Mus musculus

<400> SEQUENCE: 91

Glu Val Gln Leu Gln Gln Ser Gly Pro Glu Leu Val Lys Pro Gly Ala
```

```
            1               5                  10                  15
          Ser Val Lys Ile Ser Cys Lys Thr Ser Gly Tyr Ile Phe Thr Ala Tyr
                          20                  25                  30

Thr Met His Trp Val Arg Gln Ser Leu Gly Glu Ser Leu Asp Trp Ile
                          35                  40                  45

Gly Gly Ile Lys Pro Asn Asn Gly Leu Ala Asn Tyr Asn Gln Lys Phe
                          50                  55                  60

Lys Gly Lys Ala Thr Leu Thr Val Asp Lys Ser Ser Thr Ala Tyr
          65                  70                  75                  80

Met Asp Leu Arg Ser Leu Thr Ser Glu Asp Ser Ala Val Tyr Tyr Cys
                          85                  90                  95

Ala Arg Ser Glu Ile Thr Thr Glu Phe Asp Tyr Trp Gly Gln Gly Thr
                          100                 105                 110

Ala Leu Thr Val Ser Ser Ala Ser Thr Lys Gly Pro Ser Val Phe Pro
                          115                 120                 125

Leu Ala Pro Ser Ser Lys Ser Thr Ser Gly Gly Thr Ala Ala Leu Gly
                          130                 135                 140

Cys Leu Val Lys Asp Tyr Phe Pro Glu Pro Val Thr Val Ser Trp Asn
          145                 150                 155                 160

Ser Gly Ala Leu Thr Ser Gly Val His Thr Phe Pro Ala Val Leu Gln
                          165                 170                 175

Ser Ser Gly Leu Tyr Ser Leu Ser Val Val Thr Val Pro Ser Ser
                          180                 185                 190

Ser Leu Gly Thr Gln Thr Tyr Ile Cys Asn Val Asn His Lys Pro Ser
                          195                 200                 205

Asn Thr Lys Val Asp Lys Arg Val Glu Pro Lys Ser Cys Cys Lys Thr
                          210                 215                 220

His Thr Cys Pro Pro Cys Pro Ala Pro Glu Leu Leu Gly Gly Pro Ser
          225                 230                 235                 240

Val Phe Leu Phe Pro Pro Lys Pro Lys Asp Thr Leu Met Ile Ser Arg
                          245                 250                 255

Thr Pro Glu Val Thr Cys Val Val Val Asp Val Ser His Glu Asp Pro
                          260                 265                 270

Glu Val Lys Phe Asn Trp Tyr Val Asp Gly Val Glu Val His Asn Ala
                          275                 280                 285

Lys Thr Lys Pro Arg Glu Glu Gln Tyr Asn Ser Thr Tyr Arg Val Val
                          290                 295                 300

Ser Val Leu Thr Val Leu His Gln Asp Trp Leu Asn Gly Lys Glu Tyr
          305                 310                 315                 320

Lys Cys Lys Val Ser Asn Lys Ala Leu Pro Ala Pro Ile Glu Lys Thr
                          325                 330                 335

Ile Ser Lys Ala Lys Gly Gln Pro Arg Glu Pro Gln Val Tyr Thr Leu
                          340                 345                 350

Pro Pro Ser Arg Glu Glu Met Thr Lys Asn Gln Val Ser Leu Thr Cys
                          355                 360                 365

Leu Val Lys Gly Phe Tyr Pro Ser Asp Ile Ala Val Glu Trp Glu Ser
                          370                 375                 380

Asn Gly Gln Pro Glu Asn Asn Tyr Lys Thr Thr Pro Pro Val Leu Asp
          385                 390                 395                 400

Ser Asp Gly Ser Phe Phe Leu Tyr Ser Lys Leu Thr Val Asp Lys Ser
                          405                 410                 415

Arg Trp Gln Gln Gly Asn Val Phe Ser Cys Ser Val Met His Glu Ala
                          420                 425                 430
```

Leu His Asn His Tyr Thr Gln Lys Ser Leu Ser Leu Ser Pro Gly Lys
            435                 440                 445

<210> SEQ ID NO 92
<211> LENGTH: 448
<212> TYPE: PRT
<213> ORGANISM: Mus musculus

<400> SEQUENCE: 92

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Ile Phe Thr Ala Tyr
            20                  25                  30

Thr Met His Trp Val Arg Gln Ser Leu Gly Glu Ser Leu Asp Trp Ile
        35                  40                  45

Gly Gly Ile Lys Pro Asn Asn Gly Leu Ala Asn Tyr Asn Gln Lys Phe
    50                  55                  60

Lys Gly Lys Ala Thr Leu Thr Val Asp Lys Ser Ser Thr Ala Tyr
65                  70                  75                  80

Met Asp Leu Arg Ser Leu Thr Ser Glu Asp Ser Ala Val Tyr Tyr Cys
                85                  90                  95

Ala Arg Ser Glu Ile Thr Thr Glu Phe Asp Tyr Trp Gly Gln Gly Thr
            100                 105                 110

Ala Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Cys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

-continued

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 93
<211> LENGTH: 448
<212> TYPE: PRT
<213> ORGANISM: Mus musculus

<400> SEQUENCE: 93

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Ile Phe Thr Ala Tyr
            20                  25                  30

Thr Met His Trp Val Arg Gln Ser Leu Gly Glu Ser Leu Asp Trp Ile
        35                  40                  45

Gly Gly Ile Lys Pro Asn Asn Gly Leu Ala Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Asp Leu Arg Ser Leu Thr Ser Glu Asp Ser Ala Val Tyr Tyr Cys
                85                  90                  95

Ala Arg Ser Glu Ile Thr Thr Glu Phe Asp Tyr Trp Gly Gln Gly Thr
            100                 105                 110

Ala Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Cys
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

```
Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 94
<211> LENGTH: 448
<212> TYPE: PRT
<213> ORGANISM: Mus musculus

<400> SEQUENCE: 94

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Ile Phe Thr Ala Tyr
                20                  25                  30

Thr Met His Trp Val Arg Gln Ser Leu Gly Glu Ser Leu Asp Trp Ile
            35                  40                  45

Gly Gly Ile Lys Pro Asn Asn Gly Leu Ala Asn Tyr Asn Gln Lys Phe
        50                  55                  60

Lys Gly Lys Ala Thr Leu Thr Val Asp Lys Ser Ser Ser Thr Ala Tyr
65                  70                  75                  80

Met Asp Leu Arg Ser Leu Thr Ser Glu Asp Ser Ala Val Tyr Tyr Cys
                85                  90                  95

Ala Arg Ser Glu Ile Thr Thr Glu Phe Asp Tyr Trp Gly Gln Gly Thr
            100                 105                 110

Ala Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
210                 215                 220

His Cys Cys Pro Pro Cys Pro Ala Pro Glu Leu Leu Gly Gly Pro Ser
225                 230                 235                 240
```

```
Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 95
<211> LENGTH: 446
<212> TYPE: PRT
<213> ORGANISM: Mus musculus

<400> SEQUENCE: 95

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Ile Phe Thr Ala Tyr
            20                  25                  30

Thr Met His Trp Val Arg Gln Ser Leu Gly Glu Ser Leu Asp Trp Ile
        35                  40                  45

Gly Gly Ile Lys Pro Asn Asn Gly Leu Ala Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Asp Leu Arg Ser Leu Thr Ser Glu Asp Ser Ala Val Tyr Tyr Cys
                85                  90                  95

Ala Arg Ser Glu Ile Thr Thr Glu Phe Asp Tyr Trp Gly Gln Gly Thr
            100                 105                 110

Ala Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Lys Cys Asp Lys Thr His Thr
            210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 96
<211> LENGTH: 447
<212> TYPE: PRT
<213> ORGANISM: Mus musculus

<400> SEQUENCE: 96

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Ile Phe Thr Ala Tyr
            20                  25                  30

Thr Met His Trp Val Arg Gln Ser Leu Gly Glu Ser Leu Asp Trp Ile
            35                  40                  45

Gly Gly Ile Lys Pro Asn Asn Gly Leu Ala Asn Tyr Asn Gln Lys Phe
        50                  55                  60

Lys Gly Lys Ala Thr Leu Thr Val Asp Lys Ser Ser Ser Thr Ala Tyr
65                  70                  75                  80

Met Asp Leu Arg Ser Leu Thr Ser Glu Asp Ser Ala Val Tyr Tyr Cys
                85                  90                  95

Ala Arg Ser Glu Ile Thr Thr Glu Phe Asp Tyr Trp Gly Gln Gly Thr
            100                 105                 110
```

```
Ala Leu Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Cys His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 97
<211> LENGTH: 447
<212> TYPE: PRT
<213> ORGANISM: Mus musculus

<400> SEQUENCE: 97

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Ile Phe Thr Ala Tyr
            20                  25                  30

Thr Met His Trp Val Arg Gln Ser Leu Gly Glu Ser Leu Asp Trp Ile
        35                  40                  45
```

```
Gly Gly Ile Lys Pro Asn Asn Gly Leu Ala Asn Tyr Asn Gln Lys Phe
 50                  55                  60
Lys Gly Lys Ala Thr Leu Thr Val Asp Lys Ser Ser Thr Ala Tyr
 65                  70                  75                  80
Met Asp Leu Arg Ser Leu Thr Ser Glu Asp Ser Ala Val Tyr Tyr Cys
                     85                  90                  95
Ala Arg Ser Glu Ile Thr Thr Glu Phe Asp Tyr Trp Gly Gln Gly Thr
            100                 105                 110
Ala Leu Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
        130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Arg Val Glu Pro Lys Ser Cys Asp Cys Thr
210                 215                 220
His Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445

<210> SEQ ID NO 98
<211> LENGTH: 446
<212> TYPE: PRT
<213> ORGANISM: Mus musculus
```

<400> SEQUENCE: 98

```
Glu Val Gln Leu Gln Gln Ser Gly Pro Glu Leu Val Lys Pro Gly Ala
1               5                   10                  15
Ser Val Lys Ile Ser Cys Lys Thr Ser Gly Tyr Ile Phe Thr Ala Tyr
                20                  25                  30
Thr Met His Trp Val Arg Gln Ser Leu Gly Glu Ser Leu Asp Trp Ile
            35                  40                  45
Gly Gly Ile Lys Pro Asn Asn Gly Leu Ala Asn Tyr Asn Gln Lys Phe
        50                  55                  60
Lys Gly Lys Ala Thr Leu Thr Val Asp Lys Ser Ser Thr Ala Tyr
65                  70                  75                  80
Met Asp Leu Arg Ser Leu Thr Ser Glu Asp Ser Ala Val Tyr Tyr Cys
                85                  90                  95
Ala Arg Ser Glu Ile Thr Thr Glu Phe Asp Tyr Trp Gly Gln Gly Thr
            100                 105                 110
Ala Leu Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Arg Val Glu Pro Cys Ser Cys Lys His Thr
    210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
```

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 99
<211> LENGTH: 446
<212> TYPE: PRT
<213> ORGANISM: Mus musculus

<400> SEQUENCE: 99

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Ile Phe Thr Ala Tyr
            20                  25                  30

Thr Met His Trp Val Arg Gln Ser Leu Gly Glu Ser Leu Asp Trp Ile
        35                  40                  45

Gly Gly Ile Lys Pro Asn Asn Gly Leu Ala Asn Tyr Asn Gln Lys Phe
    50                  55                  60

Lys Gly Lys Ala Thr Leu Thr Val Asp Lys Ser Ser Thr Ala Tyr
65                  70                  75                  80

Met Asp Leu Arg Ser Leu Thr Ser Glu Asp Ser Ala Val Tyr Tyr Cys
                85                  90                  95

Ala Arg Ser Glu Ile Thr Thr Glu Phe Asp Tyr Trp Gly Gln Gly Thr
            100                 105                 110

Ala Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Ser Cys Cys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 100
<211> LENGTH: 446
<212> TYPE: PRT
<213> ORGANISM: Mus musculus

<400> SEQUENCE: 100

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Ile Phe Thr Ala Tyr
            20                  25                  30

Thr Met His Trp Val Arg Gln Ser Leu Gly Glu Ser Leu Asp Trp Ile
            35                  40                  45

Gly Gly Ile Lys Pro Asn Asn Gly Leu Ala Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Asp Leu Arg Ser Leu Thr Ser Glu Asp Ser Ala Val Tyr Tyr Cys
                85                  90                  95

Ala Arg Ser Glu Ile Thr Thr Glu Phe Asp Tyr Trp Gly Gln Gly Thr
            100                 105                 110

Ala Leu Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Ser Cys Asp Lys His Cys
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

```
Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 101
<211> LENGTH: 444
<212> TYPE: PRT
<213> ORGANISM: Mus musculus

<400> SEQUENCE: 101

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Ile Phe Thr Ala Tyr
            20                  25                  30

Thr Met His Trp Val Arg Gln Ser Leu Gly Glu Ser Leu Asp Trp Ile
        35                  40                  45

Gly Gly Ile Lys Pro Asn Asn Gly Leu Ala Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Asp Leu Arg Ser Leu Thr Ser Glu Asp Ser Ala Val Tyr Tyr Cys
                85                  90                  95

Ala Arg Ser Glu Ile Thr Thr Glu Phe Asp Tyr Trp Gly Gln Gly Thr
            100                 105                 110

Ala Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Thr Cys Pro
    210                 215                 220
```

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
            435                 440

<210> SEQ ID NO 102
<211> LENGTH: 448
<212> TYPE: PRT
<213> ORGANISM: Mus musculus

<400> SEQUENCE: 102

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Ile Phe Thr Ala Tyr
            20                  25                  30

Thr Met His Trp Val Arg Gln Ser Leu Gly Glu Ser Leu Asp Trp Ile
        35                  40                  45

Gly Gly Ile Lys Pro Asn Asn Gly Leu Ala Asn Tyr Asn Gln Lys Phe
    50                  55                  60

Lys Gly Lys Ala Thr Leu Thr Val Asp Lys Ser Ser Thr Ala Tyr
65                  70                  75                  80

Met Asp Leu Arg Ser Leu Thr Ser Glu Asp Ser Ala Val Tyr Tyr Cys
                85                  90                  95

Ala Arg Ser Glu Ile Thr Thr Glu Phe Asp Tyr Trp Gly Gln Gly Thr
            100                 105                 110

Ala Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

```
Ser Gly Ala Leu Thr Ser Gly Val His Thr Phe Pro Ala Val Leu Gln
            165                 170                 175
Ser Ser Gly Leu Tyr Ser Leu Ser Ser Val Val Thr Val Pro Ser Ser
        180                 185                 190
Ser Leu Gly Thr Gln Thr Tyr Ile Cys Asn Val Asn His Lys Pro Ser
    195                 200                 205
Asn Thr Lys Val Asp Lys Arg Val Glu Pro Lys Ser Cys Asp Lys Cys
210                 215                 220
Val Glu Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445

<210> SEQ ID NO 103
<211> LENGTH: 1347
<212> TYPE: DNA
<213> ORGANISM: Mus musculus

<400> SEQUENCE: 103
gaggtccagc tgcagcagag cgggccagaa ctggttaaac ctggcgccag cgtgaagatt      60
agctgtaaga ccagcggtta catctttaca gcatatacca tgcactgggt gaggcagagt     120
ctgggggaat ctctggactg gatcggaggt attaagccca acaatggcct ggctaactat     180
aatcaaaaat tcaagggcaa agccacactg accgtcgata gtcctcttc cacagcttac     240
atggatctga aagcctgac atccgaggac agtgcagtgt actactgcgc ccggtctgag     300
atcactaccg agttcgacta ttggggacag ggcactgcac tgaccgtctc ctccgccagc     360
accaagggcc caagcgtgtt cccgctagcc cccagcagca agagcaccag cggcggcaca     420
gccgccctgg gctgcctggt gaaggactac ttccccgagc ccgtgaccgt gtcctggaac     480
agcggagccc tgacctccgg cgtgcacaca ttccccgccg tgctgcagag cagcggcctg     540
```

```
tacagcctga gcagcgtggt gaccgtgcct agcagcagcc tgggcaccca gacctacatc    600
tgcaacgtga accacaagcc cagcaacacc aaggtggaca gcgggtgga gtgcaagagc     660 tgcgacaaga cccacacctg tccccccgtc cctgccctg aactgctggg cggacccagc     720
gtgttcctgt tcccccccaa gcccaaggac accctgatga tcagcagaac ccccgaggtg    780
acctgtgtgg tggtggacgt gtcccacgag gacccagagg tgaagttcaa ctggtacgtg    840
gacggcgtgg aggtgcacaa cgccaagacc aagcccagag aggagcagta caacagcacc    900
tacagggtgg tgtccgtgct gaccgtgctg caccaggact ggctgaacgg caaggagtac    960
aagtgtaagg tgtccaacaa ggccctgcca gccccaatcg aaaagaccat cagcaaggcc   1020
aagggccagc caagagagcc ccaggtgtac accctgccac ccagcaggga ggagatgacc   1080
aagaaccagg tgtccctgac ctgtctggtg aagggcttct acccaagcga catcgccgtg   1140
gagtgggaga gcaacggcca gcccgagaac aactacaaga ccaccccccc agtgctggac   1200
agcgacggca gcttcttcct gtacagcaag ctgaccgtgg acaagagcag atggcagcag   1260
ggcaacgtgt tcagctgctc cgtgatgcac gaggccctgc acaaccacta cacccagaag   1320
agcctgagcc tgtccccagg caagtga                                       1347

<210> SEQ ID NO 104
<211> LENGTH: 1347
<212> TYPE: DNA
<213> ORGANISM: Mus musculus

<400> SEQUENCE: 104
gaggtccagc tgcagcagag cgggccagaa ctggttaaac ctggcgccag cgtgaagatt     60
agctgtaaga ccagcggtta catctttaca gcatatacca tgcactgggt gaggcagagt    120
ctgggggaat ctctggactg gatcggaggt attaagccca caatggcct ggctaactat     180 aatcaaaaat tcaagggcaa agccacactg accgtcgata gtcctcttc cacagcttac    240 atggatctga gaagcctgac atccgaggac agtgcagtgt actactgcgc ccggtctgag    300
atcactaccg agttcgacta ttggggacag ggcactgcac tgaccgtctc ctccgccagc    360
accaagggcc caagcgtgtt cccgctagcc cccagcagca agagcaccag cggcggcaca    420
gccgccctgg gctgcctggt gaaggactac ttccccgagc ccgtgaccgt gtcctggaac    480
agcggagccc tgacctccgg cgtgcacaca ttccccgccg tgctgcagag cagcggcctg    540
tacagcctga gcagcgtggt gaccgtgcct agcagcagcc tgggcaccca gacctacatc    600
tgcaacgtga accacaagcc cagcaacacc aaggtggaca agagagtgga gccctgcagc    660
tgcgacaaga cccacacctg tccccccgtc cctgccctg aactgctggg cggacccagc     720
gtgttcctgt tcccccccaa gcccaaggac accctgatga tcagcagaac ccccgaggtg    780
acctgtgtgg tggtggacgt gtcccacgag gacccagagg tgaagttcaa ctggtacgtg    840
gacggcgtgg aggtgcacaa cgccaagacc aagcccagag aggagcagta caacagcacc    900
tacagggtgg tgtccgtgct gaccgtgctg caccaggact ggctgaacgg caaggagtac    960
aagtgtaagg tgtccaacaa ggccctgcca gccccaatcg aaaagaccat cagcaaggcc   1020
aagggccagc caagagagcc ccaggtgtac accctgccac ccagcaggga ggagatgacc   1080
aagaaccagg tgtccctgac ctgtctggtg aagggcttct acccaagcga catcgccgtg   1140
gagtgggaga gcaacggcca gcccgagaac aactacaaga ccaccccccc agtgctggac   1200
agcgacggca gcttcttcct gtacagcaag ctgaccgtgg acaagagcag atggcagcag   1260
ggcaacgtgt tcagctgctc cgtgatgcac gaggccctgc acaaccacta cacccagaag   1320
```
agcctgagcc tgtccccagg caagtga    1347

<210> SEQ ID NO 105
<211> LENGTH: 1347
<212> TYPE: DNA
<213> ORGANISM: Mus musculus

<400> SEQUENCE: 105

| | | |
|---|---|---|
| gaggtccagc tgcagcagag cgggccagaa ctggttaaac ctggcgccag cgtgaagatt | 60 |
| agctgtaaga ccagcggtta catctttaca gcatatacca tgcactgggt gaggcagagt | 120 |
| ctgggggaat ctctggactg gatcggaggt attaagccca acaatggcct ggctaactat | 180 |
| aatcaaaaat tcaagggcaa agccacactg accgtcgata gtcctcttc cacagcttac | 240 |
| atggatctga aagcctgac atccgaggac agtgcagtgt actactgcgc ccggtctgag | 300 |
| atcactaccg agttcgacta ttggggacag ggcactgcac tgaccgtctc ctccgccagc | 360 |
| accaagggcc caagcgtgtt cccgctagcc ccagcagca gagcaccag cggcggcaca | 420 |
| gccgccctgg gctgcctggt gaaggactac ttccccgagc ccgtgaccgt gtcctggaac | 480 |
| agcggagccc tgacctccgg cgtgcacaca ttccccgccg tgctgcagag cagcggcctg | 540 |
| tacagcctga gcagcgtggt gaccgtgcct agcagcagcc tgggcaccca gacctacatc | 600 |
| tgcaacgtga accacaagcc cagcaacacc aaggtggaca gcgcgtgga gcccaagtgc | 660 |
| tgcgacaaga cccacacctg tccccctgc cctgcccctg aactgctggg cggacccagc | 720 |
| gtgttcctgt tcccccccaa gcccaaggac accctgatga tcagcagaac ccccgaggtg | 780 |
| acctgtgtgg tggtggacgt gtcccacgag gacccagagg tgaagttcaa ctggtacgtg | 840 |
| gacggcgtga aggtgcacaa cgccaagacc aagcccagag aggagcagta caacagcacc | 900 |
| tacagggtgg tgtccgtgct gaccgtgctg caccaggact ggctgaacgg caaggagtac | 960 |
| aagtgtaagg tgtccaacaa ggccctgcca gccccaatcg aaaagaccat cagcaaggcc | 1020 |
| aagggccagc caagagagcc ccaggtgtac accctgccac ccagcaggga ggagatgacc | 1080 |
| aagaaccagg tgtccctgac ctgtctggtg aagggcttct acccaagcga catcgccgtg | 1140 |
| gagtgggaga gcaacggcca gcccgagaac aactacaaga ccaccccccc agtgctggac | 1200 |
| agcgacggca gcttcttcct gtacagcaag ctgaccgtgg acaagagcag atggcagcag | 1260 |
| ggcaacgtgt tcagctgctc cgtgatgcac gaggccctgc acaaccacta cacccagaag | 1320 |
| agcctgagcc tgtccccagg caagtga | 1347 |

<210> SEQ ID NO 106
<211> LENGTH: 1347
<212> TYPE: DNA
<213> ORGANISM: Mus musculus

<400> SEQUENCE: 106

| | | |
|---|---|---|
| gaggtccagc tgcagcagag cgggccagaa ctggttaaac ctggcgccag cgtgaagatt | 60 |
| agctgtaaga ccagcggtta catctttaca gcatatacca tgcactgggt gaggcagagt | 120 |
| ctgggggaat ctctggactg gatcggaggt attaagccca acaatggcct ggctaactat | 180 |
| aatcaaaaat tcaagggcaa agccacactg accgtcgata gtcctcttc cacagcttac | 240 |
| atggatctga aagcctgac atccgaggac agtgcagtgt actactgcgc ccggtctgag | 300 |
| atcactaccg agttcgacta ttggggacag ggcactgcac tgaccgtctc ctccgccagc | 360 |
| accaagggcc caagcgtgtt cccgctagcc ccagcagca gagcaccag cggcggcaca | 420 |
| gccgccctgg gctgcctggt gaaggactac ttccccgagc ccgtgaccgt gtcctggaac | 480 |

| | |
|---|---|
| agcggagccc tgacctccgg cgtgcacaca ttccccgccg tgctgcagag cagcggcctg | 540 |
| tacagcctga gcagcgtggt gaccgtgcct agcagcagcc tgggcaccca gacctacatc | 600 |
| tgcaacgtga accacaagcc cagcaacacc aaggtggaca agagagtgga gcctaagagc | 660 |
| tgttgcaaga cccacacctg tccccctgc cctgccctg aactgctggg cggacccagc | 720 |
| gtgttcctgt tccccccaa gcccaaggac accctgatga tcagcagaac ccccgaggtg | 780 |
| acctgtgtgg tggtggacgt gtcccacgag gacccagagg tgaagttcaa ctggtacgtg | 840 |
| gacggcgtgg aggtgcacaa cgccaagacc aagcccagag aggagcagta caacagcacc | 900 |
| tacagggtgg tgtccgtgct gaccgtgctg caccaggact ggctgaacgg caaggagtac | 960 |
| aagtgtaagg tgtccaacaa ggccctgcca gccccaatcg aaaagaccat cagcaaggcc | 1020 |
| aagggccagc caagagagcc ccaggtgtac accctgccac ccagcaggga ggagatgacc | 1080 |
| aagaaccagg tgtccctgac ctgtctggtg aagggcttct acccaagcga catcgccgtg | 1140 |
| gagtgggaga gcaacggcca gcccgagaac aactacaaga ccaccccccc agtgctggac | 1200 |
| agcgacggca gcttcttcct gtacagcaag ctgaccgtgg acaagagcag atggcagcag | 1260 |
| ggcaacgtgt tcagctgctc cgtgatgcac gaggccctgc acaaccacta cacccagaag | 1320 |
| agcctgagcc tgtccccagg caagtga | 1347 |

<210> SEQ ID NO 107
<211> LENGTH: 1346
<212> TYPE: DNA
<213> ORGANISM: Mus musculus

<400> SEQUENCE: 107

| | |
|---|---|
| gaggtccagc tgcagcagag cgggccagaa ctggttaaac ctggcgccag cgtgaagatt | 60 |
| agctgtaaga ccagcggtta catctttaca gcatatacca tgcactgggt gaggcagagt | 120 |
| ctggggaat ctctggactg gatcggaggt attaagccca acaatggcct ggctaactat | 180 |
| aatcaaaaat tcaagggcaa agccacactg accgtcgata gtcctcttc cacagcttac | 240 |
| atggatctga gaagcctgac atccgaggac agtgcagtgt actactgcgc ccggtctgag | 300 |
| atcactaccg agttcgacta ttggggacag ggcactgcac tgaccgtctc ctccgccagc | 360 |
| accaagggcc caagcgtgtt cccgctagcc cccagcagca gagcaccag cggcggcaca | 420 |
| gccgccctgg gctgcctggt gaaggactac ttccccgagc ccgtgaccgt gtcctggaac | 480 |
| agcggagccc tgacctccgg cgtgcacaca ttccccgccg tgctgcagag cagcggcctg | 540 |
| tacagcctga gcagcgtggt gaccgtgcct agcagcagcc tgggcaccca gacctacatc | 600 |
| tgcaacgtga accacaagcc cagcaacacc aaggtggaca agagagtgga gcccaagagc | 660 |
| tgcgactgca cccacacctg tccccctgc cctgccctg aactgctggg cggacccagc | 720 |
| gtgttcctgt tccccccaa gcccaaggac accctgatga tcagcagaac ccccgaggtg | 780 |
| acctgtgtgg tggtggacgt gtcccacgag gacccagagg tgaagttcaa ctggtacgtg | 840 |
| gacggcgtgg aggtgcacaa cgccaagacc aagcccagag aggagcagta caacagcacc | 900 |
| tacagggtgg tgtccgtgct gaccgtgctg caccaggact ggctgaacgg caaggagtac | 960 |
| aagtgtaagg tgtccaacaa ggccctgcca gccccaatcg aaaagaccat cagcaaggcc | 1020 |
| aagggccagc caagagagcc ccaggtgtac accctgccac ccagcaggga ggagatgacc | 1080 |
| aagaaccagg tgtccctgac ctgtctggtg aagggcttct acccaagcga catcgccgtg | 1140 |
| gagtgggaga gcaacggcca gcccgagaac aactacaaga ccaccccccc agtgctggac | 1200 |
| agcgacggca gcttcttcct gtacagcaag ctgaccgtgg acaagagcag atggcagcag | 1260 |

```
ggcaacgtgt tcagctgctc cgtgatgcac gaggccctgc acaaccacta cacccagaag    1320
agcctgagcc tgtccccagg caagtg                                         1346

<210> SEQ ID NO 108
<211> LENGTH: 1347
<212> TYPE: DNA
<213> ORGANISM: Mus musculus

<400> SEQUENCE: 108
gaggtccagc tgcagcagag cgggccagaa ctggttaaac ctggcgccag cgtgaagatt     60
agctgtaaga ccagcggtta catctttaca gcatatacca tgcactgggt gaggcagagt    120
ctgggggaat ctctggactg gatcggaggt attaagccca acaatggcct ggctaactat    180
aatcaaaaat tcaagggcaa agccacactg accgtcgata agtcctcttc cacagcttac    240
atggatctga aagcctgac atccgaggac agtgcagtgt actactgcgc ccggtctgag    300
atcactaccg agttcgacta ttggggacag ggcactgcac tgaccgtctc ctccgccagc    360
accaagggcc caagcgtgtt cccgctagcc cccagcagca agagcaccag cggcggcaca    420
gccgccctgg gctgcctggt gaaggactac ttccccgagc ccgtgaccgt gtcctggaac    480
agcggagccc tgacctccgg cgtgcacaca ttccccgccg tgctgcagag cagcggcctg    540
tacagcctga gcgcgtggt gaccgtgcct agcagcagcc tgggcaccca gacctacatc    600
tgcaacgtga accacaagcc cagcaacacc aaggtggaca gagagtgga gcccaagagc    660 tgcgacaagt gccacacctg tccccccgc cctgccctg aactgctggg cggacccagc    720
gtgttcctgt tccccccaa gcccaaggac accctgatga tcagcagaac cccgaggtg    780 acctgtgtgg tggtggacgt gtcccacgag gacccagagg tgaagttcaa ctggtacgtg    840
gacggcgtgg aggtgcacaa cgccaagacc aagcccagag aggagcagta caacagcacc    900
tacagggtgg tgtccgtgct gaccgtgctg caccaggact ggctgaacgg caaggagtac    960
aagtgtaagg tgtccaacaa ggccctgcca gccccaatcg aaaagaccat cagcaaggcc   1020
aagggccagc caagagagcc ccaggtgtac accctgccac ccagcaggga ggagatgacc   1080
aagaaccagg tgtccctgac ctgtctggtg aagggcttct acccaagcga catcgccgtg   1140
gagtgggaga gcaacggcca gcccgagaac aactacaaga ccacccccc agtgctggac   1200 agcgacggca gcttcttcct gtacagcaag ctgaccgtgg acaagagcag atggcagcag   1260
ggcaacgtgt tcagctgctc cgtgatgcac gaggccctgc acaaccacta cacccagaag   1320
agcctgagcc tgtccccagg caagtga                                       1347

<210> SEQ ID NO 109
<211> LENGTH: 1347
<212> TYPE: DNA
<213> ORGANISM: Mus musculus

<400> SEQUENCE: 109
gaggtccagc tgcagcagag cgggccagaa ctggttaaac ctggcgccag cgtgaagatt     60
agctgtaaga ccagcggtta catctttaca gcatatacca tgcactgggt gaggcagagt    120
ctgggggaat ctctggactg gatcggaggt attaagccca acaatggcct ggctaactat    180
aatcaaaaat tcaagggcaa agccacactg accgtcgata agtcctcttc cacagcttac    240
atggatctga aagcctgac atccgaggac agtgcagtgt actactgcgc ccggtctgag    300
atcactaccg agttcgacta ttggggacag ggcactgcac tgaccgtctc ctccgccagc    360
accaagggcc caagcgtgtt cccgctagcc cccagcagca agagcaccag cggcggcaca    420
```

```
gccgccctgg gctgcctggt gaaggactac ttccccgagc ccgtgaccgt gtcctggaac    480
agcggagccc tgacctccgg cgtgcacacc ttccccgccg tgctgcagag cagcggcctg    540
tacagcctga gcagcgtggt gaccgtgcct agcagcagcc tgggcaccca gacctacatc    600
tgcaacgtga accacaagcc cagcaacacc aaggtggaca agagagtgga gcccaagagc    660
tgcgacaaga cccactgctg tccccccctgc cctgccctg aactgctggg cggacccagc    720
gtgttcctgt tccccccaa gcccaaggac accctgatga tcagcagaac ccccgaggtg    780
acctgtgtgg tggtggacgt gtcccacgag acccgagagg tgaagttcaa ctggtacgtg    840
gacggcgtgg aggtgcacaa cgccaagacc aagcccagag aggagcagta caacagcacc    900
tacagggtgg tgtccgtgct gaccgtgctg caccaggact ggctgaacgg caaggagtac    960
aagtgtaagg tgtccaacaa ggccctgcca gccccaatcg aaaagaccat cagcaaggcc   1020
aagggccagc caagagagcc ccaggtgtac accctgccac ccagcaggga ggagatgacc   1080
aagaaccagg tgtccctgac ctgtctggtg aagggcttct acccaagcga catcgccgtg   1140
gagtgggaga gcaacggcca gcccgagaac aactacaaga ccaccccccc agtgctggac   1200
agcgacggca gcttcttcct gtacagcaag ctgaccgtgg acaagagcag atggcagcag   1260
ggcaacgtgt tcagctgctc cgtgatgcac gaggccctgc acaaccacta cacccagaag   1320
agcctgagcc tgtccccagg caagtga                                       1347

<210> SEQ ID NO 110
<211> LENGTH: 1341
<212> TYPE: DNA
<213> ORGANISM: Mus musculus

<400> SEQUENCE: 110
gaggtccagc tgcagcagag cgggccagaa ctggttaaac ctggcgccag cgtgaagatt     60
agctgtaaga ccagcggtta catctttaca gcatatacca tgcactgggt gaggcagagt    120
ctgggggaat ctctggactg gatcggaggt attaagccca caatggcct ggctaactat    180 aatcaaaaat tcaagggcaa agccacactg accgtcgata gtcctcttc cacagcttac    240 atggatctga gaagcctgac atccgaggac agtgcagtgt actactgcgc ccggtctgag    300
atcactaccg agttcgacta ttggggacag ggcactgcac tgaccgtctc ctccgccagc    360
accaagggcc caagcgtgtt cccgctagcc cccagcagca agagcaccag cggcggcaca    420
gccgccctgg gctgcctggt gaaggactac ttccccgagc ccgtgaccgt gtcctggaac    480
agcggagccc tgacctccgg cgtgcacaca ttccccgccg tgctgcagag cagcggcctg    540
tacagcctga gcagcgtggt gaccgtgcct agcagcagcc tgggcaccca gacctacatc    600
tgcaacgtga accacaagcc cagcaacacc aaggtggaca gcgggtgga gaagtgcgac    660 aagacccaca cctgtccccc ctgccctgcc cctgaactgc tgggcggacc cagcgtgttc    720
ctgttccccc ccaagcccaa ggacaccctg atgatcagca gaacccccga ggtgacctgt    780
gtggtggtgg acgtgtccca cgaggaccca gaggtgaagt tcaactggta cgtggacggc    840
gtggaggtgc acaacgccaa gaccaagccc agagaggagc agtacaacag cacctacagg    900
gtggtgtccg tgctgaccgt gctgcaccag gactggctga acggcaagga gtacaagtgt    960
aaggtgtcca acaaggccct gccagcccca atcgaaaaga ccatcagcaa ggccaagggc   1020
cagccaagag agcccaggt gtacaccctg ccacccagca gggaggagat gaccaagaac   1080
caggtgtccc tgacctgtct ggtgaagggc ttctacccaa gcgacatcgc cgtggagtgg   1140
gagagcaacg ccagcccga gaacaactac aagaccaccc ccccagtgct ggacagcgac   1200
```

| | |
|---|---:|
| ggcagcttct tcctgtacag caagctgacc gtggacaaga gcagatggca gcagggcaac | 1260 |
| gtgttcagct gctccgtgat gcacgaggcc ctgcacaacc actacaccca agagagcctg | 1320 |
| agcctgtccc caggcaagtg a | 1341 |

<210> SEQ ID NO 111
<211> LENGTH: 1344
<212> TYPE: DNA
<213> ORGANISM: Mus musculus

<400> SEQUENCE: 111

| | |
|---|---:|
| gaggtccagc tgcagcagag cgggccagaa ctggttaaac ctggcgccag cgtgaagatt | 60 |
| agctgtaaga ccagcggtta catctttaca gcatatacca tgcactgggt gaggcagagt | 120 |
| ctgggggaat ctctggactg gatcggaggt attaagccca caatggcct ggctaactat | 180 |
| aatcaaaaat tcaagggcaa agccacactg accgtcgata gtcctcttc cacagcttac | 240 |
| atggatctga agcctgac atccgaggac agtgcagtgt actactgcgc ccggtctgag | 300 |
| atcactaccg agttcgacta ttggggacag ggcactgcac tgaccgtctc ctccgccagc | 360 |
| accaagggcc caagcgtgtt cccgctagcc cccagcagca gagcaccag cggcggcaca | 420 |
| gccgccctgg gctgcctggt gaaggactac ttccccgagc ccgtgaccgt gtcctggaac | 480 |
| agcggagccc tgacctccgg cgtgcacaca ttccccgccg tgctgcagag cagcggcctg | 540 |
| tacagcctga gcagcgtggt gaccgtgcct agcagcagcc tgggcaccca gacctacatc | 600 |
| tgcaacgtga accacaagcc cagcaacacc aaggtggaca gagagtgga gcccaagagc | 660 |
| tgcgactgcc acacctgtcc cccctgccct gcccctgaac tgctgggcgg acccagcgtg | 720 |
| ttcctgttcc cccccaagcc caaggacacc ctgatgatca gcagaacccc cgaggtgacc | 780 |
| tgtgtggtgg tggacgtgtc ccacgaggac ccagaggtga agttcaactg gtacgtggac | 840 |
| ggcgtggagg tgcacaacgc caagaccaag cccagagagg agcagtacaa cagcacctac | 900 |
| agggtggtgt ccgtgctgac cgtgctgcac caggactggc tgaacggcaa ggagtacaag | 960 |
| tgtaaggtgt ccaacaaggc cctgccagcc ccaatcgaaa agaccatcag caaggccaag | 1020 |
| ggccagccaa gagagcccca ggtgtacacc ctgccaccca gcagggagga gatgaccaag | 1080 |
| aaccaggtgt ccctgacctg tctggtgaag ggcttctacc caagcgacat cgccgtggag | 1140 |
| tgggagagca acggccagcc cgagaacaac tacaagacca cccccccagt gctggacagc | 1200 |
| gacggcagct tcttcctgta cagcaagctg accgtggaca gagcagatg gcagcagggc | 1260 |
| aacgtgttca gctgctccgt gatgcacgag gccctgcaca accactacac ccagaagagc | 1320 |
| ctgagcctgt ccccaggcaa gtga | 1344 |

<210> SEQ ID NO 112
<211> LENGTH: 1344
<212> TYPE: DNA
<213> ORGANISM: Mus musculus

<400> SEQUENCE: 112

| | |
|---|---:|
| gaggtccagc tgcagcagag cgggccagaa ctggttaaac ctggcgccag cgtgaagatt | 60 |
| agctgtaaga ccagcggtta catctttaca gcatatacca tgcactgggt gaggcagagt | 120 |
| ctgggggaat ctctggactg gatcggaggt attaagccca caatggcct ggctaactat | 180 |
| aatcaaaaat tcaagggcaa agccacactg accgtcgata gtcctcttc cacagcttac | 240 |
| atggatctga agcctgac atccgaggac agtgcagtgt actactgcgc ccggtctgag | 300 |
| atcactaccg agttcgacta ttggggacag ggcactgcac tgaccgtctc ctccgccagc | 360 |

```
accaagggcc caagcgtgtt cccgctagcc cccagcagca agagcaccag cggcggcaca      420
gccgccctgg gctgcctggt gaaggactac ttccccgagc ccgtgaccgt gtcctggaac      480
agcggagccc tgacctccgg cgtgcacacc ttccccgccg tgctgcagag cagcggcctg      540
tacagcctga gcagcgtggt gaccgtgcct agcagcagcc tgggcaccca gacctacatc      600
tgcaacgtga accacaagcc cagcaacacc aaggtggaca agagagtgga gcccaagagc      660
tgcgactgca cccactgccc ccctgccct gccctgaac tgctgggcgg acccagcgtg      720
ttcctgttcc cccccaagcc caaggacacc ctgatgatca gcagaacccc cgaggtgacc      780
tgtgtggtgg tggacgtgtc ccacgaggac ccagaggtga agttcaactg gtacgtggac      840
ggcgtggagg tgcacaacgc caagaccaag cccagagagg agcagtacaa cagcacctac      900
agggtggtgt ccgtgctgac cgtgctgcac caggactggc tgaacggcaa ggagtacaag      960
tgtaaggtgt ccaacaaggc cctgccagcc ccaatcgaaa agaccatcag caaggccaag     1020
ggccagccaa gagagcccca ggtgtacacc ctgccaccca gcagggagga tgaccaagaa     1080
aaccaggtgt ccctgacctg tctggtgaag ggcttctacc caagcgacat cgccgtggag     1140
tgggagagca cggccagcc cgagaacaac tacaagacca cccccccagt gctggacagc     1200
gacggcagct tcttcctgta cagcaagctg accgtggaca gagcagatg gcagcagggc     1260 aacgtgttca gctgctccgt gatgcacgag gccctgcaca ccactacac ccagaagagc     1320 ctgagcctgt ccccaggcaa gtga                                           1344

<210> SEQ ID NO 113
<211> LENGTH: 1341
<212> TYPE: DNA
<213> ORGANISM: Mus musculus

<400> SEQUENCE: 113
gaggtccagc tgcagcagag cgggccagaa ctggttaaac ctggcgccag cgtgaagatt       60
agctgtaaga ccagcggtta catctttaca gcatatacca tgcactgggt gaggcagagt      120 ctggggaat ctctggactg gatcggaggt attaagccca acaatggcct ggctaactat      180
aatcaaaaat tcaagggcaa agccacactg accgtcgata gtcctcttc cacagcttac      240 atggatctga aagcctgac atccgaggac agtgcagtgt actactgcgc ccggtctgag      300
atcactaccg agttcgacta ttggggacag ggcactgcac tgaccgtctc ctccgccagc      360
accaagggcc aagcgtgtt cccgctagcc cccagcagca agagcaccag cggcggcaca      420
gccgccctgg gctgcctggt gaaggactac ttccccgagc ccgtgaccgt gtcctggaac      480
agcggagccc tgacctccgg cgtgcacaca ttccccgccg tgctgcagag cagcggcctg      540
tacagcctga gcagcgtggt gaccgtgcct agcagcagcc tgggcaccca gacctacatc      600
tgcaacgtga accacaagcc cagcaacacc aaggtggaca agagagtgga gcccgcagc      660 tgcaagcaca cctgtccccc ctgccctgcc cctgaactgc tgggcggacc cagcgtgttc      720
ctgttccccc ccaagcccaa ggacaccctg atgatcagca gaaccccga ggtgacctgt      780 gtggtggtgg acgtgtccca cgaggaccca gaggtgaagt tcaactggta cgtggacggc      840
gtggaggtgc acaacgccaa gaccaagccc agagaggagc agtacaacag cacctacagg      900
gtggtgtccg tgctgaccgt gctgcaccag gactggctga acggcaagga gtacaagtgt      960
aaggtgtcca acaaggccct gccagcccca atcgaaaaga ccatcagcaa ggccaagggc     1020
cagccaagag agcccaggt gtacaccctg ccacccagca gggaggagat gaccaagaac     1080
caggtgtccc tgacctgtct ggtgaagggc ttctacccaa gcgacatcgc cgtggagtgg     1140
```

```
gagagcaacg gccagcccga gaacaactac aagaccaccc ccccagtgct ggacagcgac   1200
ggcagcttct tcctgtacag caagctgacc gtggacaaga gcagatggca gcagggcaac   1260
gtgttcagct gctccgtgat gcacgaggcc ctgcacaacc actacaccca gaagagcctg   1320
agcctgtccc caggcaagtg a                                             1341
```

<210> SEQ ID NO 114
<211> LENGTH: 1341
<212> TYPE: DNA
<213> ORGANISM: Mus musculus

<400> SEQUENCE: 114

```
gaggtccagc tgcagcagag cgggccagaa ctggttaaac ctggcgccag cgtgaagatt    60
agctgtaaga ccagcggtta catctttaca gcatatacca tgcactgggt gaggcagagt   120
ctgggggaat ctctggactg gatcggaggt attaagccca acaatggcct ggctaactat   180
aatcaaaaat tcaagggcaa agccacactg accgtcgata gtcctcttc cacagcttac    240 atggatctga aagcctgac atccgaggac agtgcagtgt actactgcgc ccggtctgag    300
atcactaccg agttcgacta ttggggacag ggcactgcac tgaccgtctc ctccgccagc   360
accaagggcc caagcgtgtt cccgctagcc cccagcagca agagcaccag cggcggcaca   420
gccgccctgg gctgcctggt gaaggactac ttccccgagc ccgtgaccgt gtcctggaac   480
agcggagccc tgacctccgg cgtgcacaca ttccccgccg tgctgcagag cagcggcctg   540
tacagcctga gcagcgtggt gaccgtgcct agcagcagcc tgggcaccca gacctacatc   600
tgcaacgtga accacaagcc cagcaacacc aaggtggaca agagagtgga gcctagctgc   660
tgcacccaca cctgtccccc ctgccctgcc cctgaactgc tgggcggacc cagcgtgttc   720
ctgttccccc ccaagcccaa ggacaccctg atgatcagca gaacccccga ggtgacctgt   780
gtggtggtgg acgtgtccca cgaggaccca gaggtgaagt tcaactggta cgtggacggc   840
gtggaggtgc acaacgccaa gaccaagccc agagaggagc agtacaacag cacctacagg   900
gtggtgtccg tgctgaccgt gctgcaccag gactggctga acggcaagga gtacaagtgt   960
aaggtgtcca acaaggccct gccagcccca atcgaaaaga ccatcagcaa ggccaagggc  1020
cagccaagag agccccaggt gtacaccctg ccacccagca gggaggagat gaccaagaac  1080
caggtgtccc tgacctgtct ggtgaagggc ttctacccaa gcgacatcgc cgtggagtgg  1140
gagagcaacg gccagcccga gaacaactac aagaccaccc ccccagtgct ggacagcgac  1200
ggcagcttct tcctgtacag caagctgacc gtggacaaga gcagatggca gcagggcaac  1260
gtgttcagct gctccgtgat gcacgaggcc ctgcacaacc actacaccca gaagagcctg  1320
agcctgtccc caggcaagtg a                                            1341
```

<210> SEQ ID NO 115
<211> LENGTH: 1341
<212> TYPE: DNA
<213> ORGANISM: Mus musculus

<400> SEQUENCE: 115

```
gaggtccagc tgcagcagag cgggccagaa ctggttaaac ctggcgccag cgtgaagatt    60
agctgtaaga ccagcggtta catctttaca gcatatacca tgcactgggt gaggcagagt   120
ctgggggaat ctctggactg gatcggaggt attaagccca acaatggcct ggctaactat   180
aatcaaaaat tcaagggcaa agccacactg accgtcgata gtcctcttc cacagcttac    240 atggatctga aagcctgac atccgaggac agtgcagtgt actactgcgc ccggtctgag    300
```

```
atcactaccg agttcgacta ttggggacag ggcactgcac tgaccgtctc ctccgccagc    360
accaagggcc caagcgtgtt cccgctagcc cccagcagca agagcaccag cggcggcaca    420
gccgccctgg gctgcctggt gaaggactac ttccccgagc ccgtgaccgt gtcctggaac    480
agcggagccc tgacctccgg cgtgcacacc ttccccgccg tgctgcagag cagcggcctg    540
tacagcctga gcagcgtggt gaccgtgcct agcagcagcc tgggcaccca gacctacatc    600
tgcaacgtga accacaagcc cagcaacacc aaggtggaca agagagtgga gcccagctgc    660
gacaagcact gctgcccccc ctgccctgcc cctgaactgc tgggcggacc cagcgtgttc    720
ctgttccccc ccaagcccaa ggacaccctg atgatcagca gaacccccga ggtgacctgt    780
gtggtggtgg acgtgtccca cgaggaccca gaggtgaagt tcaactggta cgtggacggc    840
gtggaggtgc acaacgccaa gaccaagccc agagaggagc agtacaacag cacctacagg    900
gtggtgtccg tgctgaccgt gctgcaccag gactggctga acggcaagga gtacaagtgt    960
aaggtgtcca acaaggccct gccagcccca atcgaaaaga ccatcagcaa ggccaagggc   1020
cagccaagag agccccaggt gtacaccctg ccacccagca gggaggagat gaccaagaac   1080
caggtgtccc tgacctgtct ggtgaagggc ttctacccaa gcgacatcgc cgtggagtgg   1140
gagagcaacg gccagcccga gaacaactac aagaccaccc ccccagtgct ggacagcgac   1200
ggcagcttct tcctgtacag caagctgacc gtggacaaga gcagatggca gcagggcaac   1260
gtgttcagct gctccgtgat gcacgaggcc ctgcacaacc actacaccca gaagagcctg   1320
agcctgtccc caggcaagtg a                                             1341

<210> SEQ ID NO 116
<211> LENGTH: 1335
<212> TYPE: DNA
<213> ORGANISM: Mus musculus

<400> SEQUENCE: 116
gaggtccagc tgcagcagag cgggccagaa ctggttaaac ctggcgccag cgtgaagatt     60
agctgtaaga ccagcggtta catctttaca gcatatacca tgcactgggt gaggcagagt    120
ctgggggaat ctctggactg gatcggaggt attaagccca caatggcct ggctaactat     180 aatcaaaaat tcaagggcaa agccacactg accgtcgata gtcctcttc cacagcttac    240 atggatctga agcctgac atccgaggac agtgcagtgt actactgcgc ccggtctgag    300
atcactaccg agttcgacta ttggggacag ggcactgcac tgaccgtctc ctccgccagc    360
accaagggcc caagcgtgtt cccgctagcc cccagcagca agagcacaag cggcggaaca    420
gccgccctgg gctgcctggt gaaggactac ttccccgagc ccgtgaccgt gtcttggaac    480
agcggagccc tgaccagcgg cgtgcacacc tttccagccg tgctgcagag cagcggcctg    540
tacagcctga gcagcgtggt gaccgtgcct agcagcagcc tgggcaccca gacctacatc    600
tgcaacgtga accacaagcc cagcaacacc aaggtggaca agagagtgga gcccaagagc    660
tgcacctgtc cccttgtcc tgcccctgag ctgctgggcg gacccagcgt gttcctgttc     720
ccccccaagc caaggacac cctgatgatc agcagaaccc ccgaggtgac ctgtgtggtg     780
gtggacgtgt cccacgagga cccagaggtg aagttcaact ggtacgtgga cggcgtggag    840
gtgcacaacg ccaagaccaa gcccagagag agcagtaca acagcaccta cagggtggtg    900
tccgtgctga ccgtgctgca ccaggactgg ctgaacggca aggagtacaa gtgtaaggtg    960
tccaacaagg ccctgccagc cccaatcgaa aagaccatca gcaaggccaa ggccagcca   1020 agagagcccc aggtgtacac cctgccaccc agcagggagg agatgaccaa gaaccaggtg   1080
```

-continued

```
tccctgacct gtctggtgaa gggcttctac ccaagcgaca tcgccgtgga gtgggagagc    1140
aacggccagc ccgagaacaa ctacaagacc acccccccag tgctggacag cgacggcagc    1200
ttcttcctgt acagcaagct gaccgtggac aagagcagat ggcagcaggg caacgtgttc    1260
agctgctccg tgatgcacga ggccctgcac aaccactaca cccagaagag cctgagcctg    1320
tccccaggca agtga                                                     1335
```

<210> SEQ ID NO 117
<211> LENGTH: 1347
<212> TYPE: DNA
<213> ORGANISM: Mus musculus

<400> SEQUENCE: 117

```
gaggtccagc tgcagcagag cgggccagaa ctggttaaac ctggcgccag cgtgaagatt    60
agctgtaaga ccagcggtta catctttaca gcatatacca tgcactgggt gaggcagagt    120
ctgggggaat ctctggactg gatcggaggt attaagccca acaatggcct ggctaactat    180
aatcaaaaat tcaagggcaa agccacactg accgtcgata gtcctcttc cacagcttac     240 atggatctga aagcctgac atccgaggac agtgcagtgt actactgcgc ccggtctgag     300
atcactaccg agttcgacta ttggggacag ggcactgcac tgaccgtctc ctccgccagc    360
accaagggcc caagcgtgtt cccgctagcc ccagcagca agagcacaag cggcggaaca    420
gccgccctgg gctgcctggt gaaggactac ttccccgagc ccgtgaccgt gtcttggaac    480
agcggagccc tgaccagcgg cgtgcacacc tttccagccg tgctgcagag cagcggcctg    540
tacagcctga gcagcgtggt gaccgtgcct agcagcagcc tgggcaccca gacctacatc    600
tgcaacgtga accacaagcc cagcaacacc aaggtggaca gagagtgga gcccaagagc    660 tgcgataagt gcgtggagtg cccccccttgt cctgcccctg agctgctggg cggacccagc    720
gtgttcctgt tccccccaa gcccaaggac accctgatga tcagcagaac ccccgaggtg    780
acctgtgtgg tggtggacgt gtcccacgag gacccagagg tgaagttcaa ctggtacgtg    840
gacggcgtga aggtgcacaa cgccaagacc aagcccagag aggagcagta caacagcacc    900
tacagggtgg tgtccgtgct gaccgtgctg caccaggact ggctgaacgg caaggagtac    960
aagtgtaagg tgtccaacaa ggccctgcca gccccaatcg aaaagaccat cagcaaggcc    1020
aagggccagc caagagagcc ccaggtgtac accctgccac cagcaggga ggagatgacc    1080 aagaaccagg tgtccctgac ctgtctggtg aagggcttct acccaagcga catcgccgtg    1140
gagtgggaga gcaacggcca gcccgagaac aactacaaga ccaccccccc agtgctggac    1200
agcgacggca gcttcttcct gtacagcaag ctgaccgtgg acaagagcag atggcagcag    1260
ggcaacgtgt tcagctgctc cgtgatgcac gaggccctgc acaaccacta cacccagaag    1320
agcctgagcc tgtccccagg caagtga                                        1347
```

ANTI-C-MET ANTIBODY

REFERENCE TO SEQUENCE LISTING SUBMITTED ELECTRONICALLY

The official copy of the sequence listing is submitted electronically via EFS-Web as an ASCII formatted sequence listing with a file named "SequenceListing.txt", created on Jun. 1, 2010, and having a size of 138 kilobytes and is filed concurrently with the specification. The sequence listing contained in this ASCII formatted document is part of the specification and is herein incorporated by reference in its entirety.

The present invention relates to a novel divalent antibody capable of binding specifically to the human c-Met receptor and/or capable of specifically inhibiting the tyrosine kinase activity of said receptor, as well as the amino acid and nucleic acid sequences coding for said antibody. More particularly, the antibody according to the invention is capable of inhibiting the c-Met dimerization. The invention likewise comprises the use of said antibody as a medicament for the prophylactic and/or therapeutic treatment of cancers or any pathology connected with the overexpression of said receptor as well as in processes or kits for diagnosis of illnesses connected with the over-expression of c-Met. The invention finally comprises products and/or compositions comprising such an antibody in combination with other antibodies and/or chemical compounds directed against other growth factors involved in tumor progression or metastasis and/or compounds and/or anti-cancer agents or agents conjugated with toxins and their use for the prevention and/or the treatment of certain cancers.

Receptor tyrosine kinase (RTK) targeted agents such as trastuzumab, cetuximab, bevacizumab, imatinib and gefitinib inhibitors have illustrated the interest of targeting this protein class for treatment of selected cancers.

c-Met, is the prototypic member of a sub-family of RTKs which also includes RON and SEA. The c-Met RTK family is structurally different from other RTK families and is the only known high-affinity receptor for hepatocyte growth factor (HGF), also called scatter factor (SF) [D. P. Bottaro et al., Science 1991, 251:802-804; L. Naldini et al., Eur. Mol. Biol. Org. J. 1991, 10:2867-2878]. c-Met and HGF are widely expressed in a variety of tissue and their expression is normally restricted to cells of epithelial and mesenchymal origin respectively [M. F. Di Renzo et al., Oncogene 1991, 6:1997-2003; E. Sonnenberg et al., J. Cell. Biol. 1993, 123:223-235]. They are both required for normal mammalian development and have been shown to be particularly important in cell migration, morphogenic differentiation, and organization of the three-dimensional tubular structures as well as growth and angiogenesis [F. Baldt et al., Nature 1995, 376:768-771; C. Schmidt et al., Nature. 1995:373:699-702; Tsarfaty et al., Science 1994, 263:98-101]. While the controlled regulation of c-Met and HGF have been shown to be important in mammalian development, tissue maintenance and repair [Nagayama T., Nagayama M., Kohara S., Kamiguchi H., Shibuya M., Katoh Y., Itoh J., Shinohara Y., Brain Res. 2004, 5; 999 (2):155-66; Tahara Y., Ido A., Yamamoto S., Miyata Y., Uto H., Hori T., Hayashi K., Tsubouchi H., J Pharmacol Exp Ther. 2003, 307(1):146-51], their dysregulation is implicated in the progression of cancers.

Aberrant signalling driven by inappropriate activation of c-Met is one of the most frequent alteration observed in human cancers and plays a crucial role in tumorigenesis and metastasis [Birchmeier et al., Nat. Rev. Mol. Cell. Biol. 2003, 4:915-925; L. Trusolino and Comoglio P. M., Nat. Rev. Cancer. 2002, 2(4):289-300].

Inappropriate c-Met activation can arise by ligand-dependent and independent mechanisms, which include overexpression of c-Met, and/or paracrine or autocrine activation, or through gain in function mutation [J. G. Christensen, Burrows J. and Salgia R., Cancer Latters. 2005, 226:1-26]. However an oligomerization of c-Met receptor, in presence or in absence of the ligand, is required to regulate the binding affinity and binding kinetics of the kinase toward ATP and tyrosine-containing peptide substrates [Hays J L, Watowich S J, Biochemistry, 2004 Aug. 17, 43:10570-8]. Activated c-Met recruits signalling effectors to its multidocking site located in the cytoplasm domain, resulting in the activation of several key signalling pathways, including Ras-MAPK, PI3K, Src and Stat3 [Gao C F, Vande Woude G F, Cell Res. 2005, 15(1):49-51; Furge K A, Zhang Y W, Vande Woude G F, Oncogene. 2000, 19(49):5582-9]. These pathways are essential for tumour cell proliferation, invasion and angiogenesis and for evading apoptosis [Furge K A, Zhang Y W, Vande Woude G F, Oncogene, 2000, 19(49):5582-9; Gu H., Neel B G, Trends Cell Biol. 2003 March, 13(3):122-30; Fan S., Ma Y X, Wang J A, Yuan R Q, Meng Q., Cao Y., Laterra J J, Goldberg I D, Rosen E M, Oncogene. 2000 Apr. 27, 19(18): 2212-23]. In addition, a unique facet of the c-Met signalling relative to other RTK is its reported interaction with focal adhesion complexes and non kinase binding partners such as α6β4 integrins [Trusolino L., Bertotti A., Comoglio P M, Cell. 2001, 107:643-54], CD44v6 [Van der Voort R., Taher T E, Wielenga V J, Spaargaren M., Prevo R., Smit L., David G., Hartmann G., Gherardi E., Pals S T, J. Biol. Chem. 1999, 274(10):6499-506], Plexin B1 or semaphorins [Giordano S., Corso S., Conrotto P., Artigiani S., Gilestro G., Barberis D., Tamagnone L., Comoglio P M, Nat Cell Biol. 2002, 4(9):720-4; Conrotto P., Valdembri D., Corso S., Serini G., Tamagnone L., Comoglio P M, Bussolino F., Giordano S., Blood. 2005, 105(11):4321-9; Conrotto P., Corso S., Gamberini S., Comoglio P M, Giordano S., Oncogene. 2004, 23:5131-7] which may further add to the complexity of regulation of cell function by this receptor. Finally recent data demonstrate that c-Met could be involved in tumor resistance to gefitinib or erlotinib suggesting that combination of compound targeting both EGFR and c-Met might be of significant interest [Engelman J A et al., Science, 2007, 316:1039-43].

In the past few years, many different strategies have been developed to attenuate c-Met signalling in cancer cell lines. These strategies include i) neutralizing antibodies against c-Met or HGF/SF [Cao B., Su Y., Oskarsson M., Zhao P., Kort E J, Fisher R J, Wang L M, Vande Woude G F, Proc Natl Acad Sci USA. 2001, 98(13):7443-8; Martens T., Schmidt N O, Eckerich C., Fillbrandt R., Merchant M., Schwall R., Westphal M., Lamszus K., Clin Cancer Res. 2006, 12(20):6144-52] or the use of HGF/SF antagonist NK4 to prevent ligand binding to c-Met [Kuba K., Matsumoto K., Date K., Shimura H., Tanaka M., Nakamura T., Cancer Res., 2000, 60:6737-43], ii) small ATP binding site inhibitors to c-Met that block kinase activity [Christensen J G, Schreck R., Burrows J., Kuruganti P., Chan E, Le P., Chen J., Wang X., Ruslim L., Blake R., Lipson K E, Ramphal J., Do S., Cui J J, Chemington J M, Mendel D B, Cancer Res. 2003, 63:7345-55], iii) engineered SH2 domain polypeptide that interferes with access to the multidocking site and RNAi or ribozyme that reduce receptor or ligand expression. Most of these approaches display a selective inhibition of c-Met resulting in tumor inhibition and showing that c-Met could be of interest for therapeutic intervention in cancer.

Within the molecules generated for c-Met targeting, some are antibodies. The most extensively described is the anti-c-Met 5D5 antibody generated by Genentech [WO 96/38557]

which behaves as a potent agonist when added alone in various models and as an antagonist when used as a Fab fragment. A monovalent engineered form of this antibody described as one armed 5D5 (OA5D5) and produced as a recombinant protein in *E. Coli* is also the subject of a patent application [WO 2006/015371] by Genentech. However, this molecule that could not be considered as an antibody because of its particular scaffold, displays also mutations that could be immunogenic in humans. In terms of activity, this unglycosylated molecule is devoided of effector functions and finally, no clear data demonstrate that OA5D5 inhibits dimerization of c-Met. Moreover, when tested in the G55 in vivo model, a glioblastoma cell line that expresses c-Met but not HGF mRNA and protein and that grows independently of the ligand, the one armed anti-c-Met had no significant effect on G55 tumor growth suggesting that OA5D5 acts primarily by blocking HGF binding and is not able to target tumors activated independently of HGF [Martens T. et al, Clin. Cancer Res., 2006, 12 (20): 6144-6152].

Another antibody targeting c-Met is described by Pfizer as an antibody acting "predominantly as c-Met antagonist, and in some instance as a c-Met agonist" [WO 2005/016382]. No data showing any effect of Pfizer antibodies on c-Met dimerization is described in this application.

One of the innovative aspects of the present invention is to generate a chimeric and/or humanized monoclonal antibody without intrinsic agonist activity and inhibiting c-Met dimerization. More particularly, an innovative aspect of the present invention is to generate a chimeric and/or humanized monoclonal antibody with antagonist activity and inhibiting c-Met dimerization.

In addition of targeting ligand-dependent tumors, this approach will also impair ligand-independent activations of c-Met due to its overexpression or mutations of the intra cellular domains which remained dependent to oligomerization for signalling. Another aspect of the activity of this antibody could be a steric hindrance for c-Met interaction with its partners that will result in impairment of c-Met functions. This antibody is humanized and engineered preferentially, but not limited, as human IgG1 to get effector functions such as ADCC and CDC in addition to functions linked to the specific blockade of the c-Met receptor.

Surprisingly, for the first time, inventors have managed to generate a chimeric and/or humanized monoclonal antagonist antibody capable of binding to c-Met but also capable of inhibiting the c-Met dimerization, said monoclonal antibody being divalent contrary to existing antagonist antibodies directed against c-Met. If it is true that, in the prior art, it is sometimes suggested that an antibody capable of inhibiting the dimerization of c-Met with its partners could be an interesting one, it has never been disclosed, or clearly suggested, an antibody capable of doing so. Moreover, regarding antibody specificity, it was not evident at all to succeed in the generation of such an active divalent antibody.

As it was explained before, the inhibition of the c-Met dimerization is a capital aspect of the invention as such antibodies will present a real interest for a larger population of patients. Not only ligand-dependent activated c-Met cancer, as it was the case until the present invention, but also ligand-independent activated c-Met cancer could be traited with antibodies generated by the process of the present invention.

Antibodies were evaluated by BRET analysis on cells expressing both c-Met-RLuc/c-Met-YFP and selected on their ability to inhibit at least 40%, preferably 45%, 50%, 55% and most preferably 60% of the BRET signal.

The BRET technology is known as being representative of the protein dimerization [Angers et al., PNAS, 2000, 97:3684-89].

The BRET technology is well known by the man skill in the art and will be detailed in the following examples. More particularly, BRET (Bioluminescence Resonance Energy Transfer) is a non-radiative energy transfer occurring between a bioluminescent donor (*Renilla* Luciferase (Rluc)) and a fluorescent acceptor, a mutant of GFP (Green Fluorescent Protein) or YFP (Yellow fluorescent protein). In the present case EYFP (Enhanced Yellow Fluorescent Protein) was used. The efficacy of transfer depends on the orientation and the distance between the donor and the acceptor. Then, the energy transfer can occur only if the two molecules are in close proximity (1-10 nm). This property is used to generate protein-protein interaction assays. Indeed, in order to study the interaction between two partners, the first one is genetically fused to the *Renilla* Luciferase and the second one to the yellow mutant of the GFP. Fusion proteins are generally, but not obligatory, expressed in mammalian cells. In presence of its membrane permeable substrate (coelenterazine), Rluc emits blue light. If the GFP mutant is closer than 10 nm from the Rluc, an energy transfer can occur and an additional yellow signal can be detected. The BRET signal is measured as the ratio between the light emitted by the acceptor and the light emitted by the donor. So the BRET signal will increase as the two fusion proteins are brought into proximity or if a conformational change brings Rluc and GFP mutant closer.

If the BRET analysis consists in a preferred embodiment, any method known by the man skilled in the art can be used to measure c-Met dimerization. Without limitation, the following technologies can be mentioned: FRET (Fluorescence Resonance Energy Transfer), HTRF (Homogenous Time resolved Fluorescence), FLIM (Fluorescence Lifetime Imaging Microscopy) or SW-FCCS single wavelength fluorescence cross-correlation spectroscopy).

Other classical technologies could also be used, such as Co-immunoprecipitation, Alpha screen, Chemical cross-linking, Double-Hybrid, Affinity Chromatography, ELISA or Far western blot.

The terms "antibody", "antibodies" or "immunoglobulin" are used interchangeably in the broadest sense and include monoclonal antibodies (e.g., full length or intact monoclonal antibodies), polyclonal antibodies, multivalent antibodies or multispecific antibodies (e.g., bispecific antibodies so long as they exhibit the desired biological activity).

More particularly, such molecule consists in a glycoprotein comprising at least two heavy (H) chains and two light (L) chains inter-connected by disulfide bonds. Each heavy chain is comprised of a heavy chain variable region (or domain) (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g. effector cells) and the first component (Clq) of the classical complement system.

The heavy chains of immunoglobulins can be divided into three functional regions: the Fd region, the hinge region, and the Fc region (fragment crystallizable). The Fd region comprises the VH and CH1 domains and, in combination with the light chain, forms Fab—the antigen-binding fragment. The Fc fragment is responsible for the immunoglobulin effector functions, which includes, for example, complement fixation and binding to cognate Fc receptors of effector cells. The hinge region, found in IgG, IgA, and IgD immunoglobulin classes, acts as a flexible spacer that allows the Fab portion to move freely in space relative to the Fc region. The hinge domains are structurally diverse, varying in both sequence and length among immunoglobulin classes and subclasses.

According to crystallographic studies, the immunoglobulin hinge region can be further subdivided structurally and functionally into three regions: the upper hinge, the core, and the lower hinge (Shin et al., Immunological Reviews 130:87, 1992). The upper hinge includes amino acids from the carboxyl end of CH1 to the first residue in the hinge that restricts motion, generally the first cysteine residue that forms an interchain disulfide bond between the two heavy chains. The length of the upper hinge region correlates with the segmental flexibility of the antibody. The core hinge region contains the inter-heavy chain disulfide bridges. The lower hinge region joins the amino terminal end of, and includes residues in the CH2 domain. The core hinge region of human IgG1 contains the sequence Cys-Pro-Pro-Cys that, when dimerized by disulfide bond formation, results in a cyclic octapeptide believed to act as a pivot, thus conferring flexibility. Conformational changes permitted by the structure and flexibility of the immunoglobulin hinge region polypeptide sequence may affect the effector functions of the Fc portion of the antibody.

The term <<Monoclonal Antibody>> is used in accordance with its ordinary meaning to denote an antibody obtained from a population of substantially homogeneous antibodies, i.e. the individual antibodies comprising the population are identical except for possible naturally occurring mutations that may be present in minor amounts. In other words, a monoclonal antibody consists in a homogenous antibody resulting from the proliferation of a single clone of cells (e.g., hybridoma cells, eukaryotic host cells transfected with DNA encoding the homogenous antibody, prokaryotic host cells transformed with DNA encoding the homogenous antibody, etc.), and which is generally characterized by heavy chains of a single class and subclass, and light chains of a single type. Monoclonal antibodies are highly specific, being directed against a single antigen. Furthermore, in contrast to polyclonal antibodies preparations that typically include different antibodies directed against different determinants, or epitope, each monoclonal antibody is directed against a single determinant on the antigen.

In the present description, the terms polypeptides, polypeptide sequences, amino acid sequences, peptides and proteins attached to antibody compounds or to their sequence are interchangeable.

The invention relates to a monoclonal antibody, or a divalent functional fragment or derivative thereof, capable to inhibit the c-Met dimerization and comprising a heavy chain comprising CDR-H1, CDR-H2 and CDR-H3 with respectively the amino acid sequences SEQ ID Nos. 1, 2 and 3 or a sequence having at least 80% identity after optimum alignment with sequences SEQ ID Nos. 1, 2 and 3; and a light chain comprising CDR-L1, CDR-L2 and CDR-L3 with respectively the amino acid sequences SEQ ID Nos. 5, 6 and 7 or a sequence having at least 80% identity after optimum alignment with sequences SEQ ID Nos. 5, 6 or 7, said antibody being further characterized in that it also comprises a hinge region comprising the amino acid sequence SEQ ID No. 56.

More particularly, the invention relates to a monoclonal antibody, or a divalent functional fragment or derivative thereof, as above described characterized in that it also comprises a hinge region comprising the amino acid sequence SEQ ID No. 57.

In other words, the invention relates to a monoclonal antibody, or a divalent functional fragment or derivative thereof, capable to inhibit the c-Met dimerization and comprising a heavy chain comprising CDR-H1, CDR-H2 and CDR-H3 with respectively the amino acid sequences SEQ ID Nos. 1, 2 and 3 or a sequence having at least 80% identity after optimum alignment with sequences SEQ ID Nos. 1, 2 and 3; and a light chain comprising CDR-L1, CDR-L2 and CDR-L3 with respectively the amino acid sequences SEQ ID Nos. 5, 6 and 7 or a sequence having at least 80% identity after optimum alignment with sequences SEQ ID Nos. 5, 6 or 7, said antibody being further characterized in that it also comprises a hinge region comprising the amino acid sequence SEQ ID No. 57.

More particularly, the invention relates to a monoclonal antibody, or a divalent functional fragment or derivative thereof, as above described characterized in that it also comprises a hinge region comprising the amino acid sequence SEQ ID No. 21.

In other words, the invention also relates to a monoclonal antibody, or a divalent functional fragment or derivative thereof, capable to inhibit the c-Met dimerization and comprising a heavy chain comprising CDR-H1, CDR-H2 and CDR-H3 with respectively the amino acid sequences SEQ ID Nos. 1, 2 and 3 or a sequence having at least 80% identity after optimum alignment with sequences SEQ ID Nos. 1, 2 and 3; and a light chain comprising CDR-L1, CDR-L2 and CDR-L3 with respectively the amino acid sequences SEQ ID Nos. 5, 6 and 7 or a sequence having at least 80% identity after optimum alignment with sequences SEQ ID Nos. 5, 6 or 7, said antibody being further characterized in that it also comprises a hinge region comprising the amino acid sequence SEQ ID No. 21.

As it will be apparent for the man skilled in the art, the consensus sequences SEQ ID Nos. 57 and 21 are comprised in the consensus sequence SEQ ID No. 56.

TABLE 1

|  | #01 | #02 | #03 | #04 | #05 | #06 | #07 | #08 | #09 | #10 | #11 | #12 | #13 | #14 |
|---|---|---|---|---|---|---|---|---|---|---|---|---|---|---|
| SEQ ID NO 56 | X1 | X2 | X3 | C | X5 | X6 | X7 | X8 | X9 | C | X11 | X12 | C | X14 |
| SEQ ID NO 57 | X1 | X2 | X3 | C | X5 | X6 | X7 | X8 | X9 | C | P | P | C | P |

TABLE 1-continued

| | #01 | #02 | #03 | #04 | #05 | #06 | #07 | #08 | #09 | #10 | #11 | #12 | #13 | #14 |
|---|---|---|---|---|---|---|---|---|---|---|---|---|---|---|
| SEQ ID NO 21 | X1 | X2 | X3 | C | X5 | — | C | X8 | X9 | C | X11 | X12 | C | X14 |

For SEQ ID No. 56:
X1: P, R, C, —
X2: K, C, R, —
X3: S, C, D, —
X5: D, C, G, —
X6: K, C, —
X7: T, C, —
X8: H, V, K, —
X9: T, C, E, P, —
X11: P, I
X12: P, —
X14: P, T

The expression "functional fragments and derivatives" will be defined in details later in the present specification.

By CDR regions or CDR(s), it is intended to indicate the hypervariable regions of the heavy and light chains of the immunoglobulins as defined by IMGT.

The IMGT unique numbering has been defined to compare the variable domains whatever the antigen receptor, the chain type, or the species [Lefranc M.-P., Immunology Today 18, 509 (1997); Lefranc M.-P., The Immunologist, 7, 132-136 (1999); Lefranc, M.-P., Pommié, C., Ruiz, M., Giudicelli, V., Foulquier, E., Truong, L., Thouvenin-Contet, V. and Lefranc, Dev. Comp. Immunol., 27, 55-77 (2003)]. In the IMGT unique numbering, the conserved amino acids always have the same position, for instance cysteine 23 (1 st-CYS), tryptophan 41 (CONSERVED-TRP), hydrophobic amino acid 89, cysteine 104 (2nd-CYS), phenylalanine or tryptophan 118 (J-PHE or J-TRP). The IMGT unique numbering provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. As gaps represent unoccupied positions, the CDR-IMGT lengths (shown between brackets and separated by dots, e.g. [8.8.13]) become crucial information. The IMGT unique numbering is used in 2D graphical representations, designated as IMGT Colliers de Perles [Ruiz, M. and Lefranc, M.-P., Immunogenetics, 53, 857-883 (2002); Kaas, Q. and Lefranc, M.-P., Current Bioinformatics, 2, 21-30 (2007)], and in 3D structures in IMGT/3Dstructure-DB [Kaas, Q., Ruiz, M. and Lefranc, M.-P., T cell receptor and MHC structural data. Nucl. Acids. Res., 32, D208-D210 (2004)].

Three heavy chain CDRs and 3 light chain CDRs exist. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

By "percentage of identity" between two nucleic acid or amino acid sequences in the sense of the present invention, it is intended to indicate a percentage of nucleotides or of identical amino acid residues between the two sequences to be compared, obtained after the best alignment (optimum alignment), this percentage being purely statistical and the differences between the two sequences being distributed randomly and over their entire length. The comparisons of sequences between two nucleic acid or amino acid sequences are traditionally carried out by comparing these sequences after having aligned them in an optimum manner, said comparison being able to be carried out by segment or by "comparison window". The optimum alignment of the sequences for the comparison can be carried out, in addition to manually, by means of the local homology algorithm of Smith and Waterman (1981) [Ad. App. Math. 2:482], by means of the local homology algorithm of Neddleman and Wunsch (1970) [J. Mol. Biol. 48: 443], by means of the similarity search method of Pearson and Lipman (1988) [Proc. Natl. Acad. Sci. USA 85:2444), by means of computer software using these algorithms (GAP, BESTFIT, FASTA and TFASTA in the Wisconsin Genetics Software Package, Genetics Computer Group, 575 Science Dr., Madison, Wis., or else by BLAST N or BLAST P comparison software).

The percentage of identity between two nucleic acid or amino acid sequences is determined by comparing these two sequences aligned in an optimum manner and in which the nucleic acid or amino acid sequence to be compared can comprise additions or deletions with respect to the reference sequence for an optimum alignment between these two sequences. The percentage of identity is calculated by determining the number of identical positions for which the nucleotide or the amino acid residue is identical between the two sequences, by dividing this number of identical positions by the total number of positions in the comparison window and by multiplying the result obtained by 100 in order to obtain the percentage of identity between these two sequences.

For example, it is possible to use the BLAST program, "BLAST 2 sequences" (Tatusova et al., "Blast 2 sequences—a new tool for comparing protein and nucleotide sequences", FEMS Microbiol Lett. 174:247-250) available on the site http://www.ncbi.nlm.nih.gov/gorf/bl2.html, the parameters used being those given by default (in particular for the parameters "open gap penalty": 5, and "extension gap penalty": 2; the matrix chosen being, for example, the matrix "BLOSUM 62" proposed by the program), the percentage of identity between the two sequences to be compared being calculated directly by the program.

By amino acid sequence having at least 80%, preferably 85%, 90%, 95% and 98% identity with a reference amino acid sequence, those having, with respect to the reference sequence, certain modifications, in particular a deletion, addition or substitution of at least one amino acid, a truncation or an elongation are preferred. In the case of a substitution of one or more consecutive or nonconsecutive amino acid(s), the substitutions are preferred in which the substituted amino acids are replaced by "equivalent" amino acids. The expression "equivalent amino acids" is aimed here at indicating any amino acid capable of being substituted with one of the amino acids of the base structure without, however, essentially modifying the biological activities of the corresponding antibodies and such as will be defined later, especially in the examples. These equivalent amino acids can be determined either by relying on their structural homology with the amino acids which they replace, or on results of comparative trials of biological activity between the different antibodies capable of being carried out.

By way of example, mention is made of the possibilities of substitution capable of being carried out without resulting in a profound modification of the biological activity of the corresponding modified antibody.

As non limitative example, the following table 2 is giving substitution possibilities conceivable with a conservation of the biological activity of the modified antibody. The reverse substitutions are also, of course, possible in the same conditions.

TABLE 2

| Original residue | Substitution(s) |
|---|---|
| Ala (A) | Val, Gly, Pro |
| Arg (R) | Lys, His |
| Asn (N) | Gln |
| Asp (D) | Glu |
| Cys (C) | Ser |
| Gln (Q) | Asn |
| Glu (G) | Asp |
| Gly (G) | Ala |
| His (H) | Arg |
| Ile (I) | Leu |
| Leu (L) | Ile, Val, Met |
| Lys (K) | Arg |
| Met (M) | Leu |
| Phe (F) | Tyr |
| Pro (P) | Ala |
| Ser (S) | Thr, Cys |
| Thr (T) | Ser |
| Trp (W) | Tyr |
| Tyr (Y) | Phe, Trp |
| Val (V) | Leu, Ala |

It must be understood here that the invention does not relate to the antibodies in natural form, that is to say they are not in their natural environment but that they have been able to be isolated or obtained by purification from natural sources, or else obtained by genetic recombination, or by chemical synthesis, and that they can then contain unnatural amino acids as will be described further on.

It must also be understood, as previously mentioned, that the invention concerns more particularly a chimeric and/or a humanized divalent antibody, or any divalent functional fragment or derivative, with an antagonistic activity. Divalent antibodies of the prior art are agonists or partial agonists. The monoclonal antibody of the invention, including a modified hinge as previously described, i.e. including a hinge region comprising the amino acid sequence SEQ ID No. 56, 57 or 21, is novel and presents the particularity to have a improved antagonistic activity compared to the chimeric or humanized antibody 224G11 without such a modified hinge as it will appear from the following examples.

Contrary to the prior art, inventors have obtained an improved antagonistic activity without modifying the format of the antibody. Actually, in the closest prior art represented by the antibody 5D5, it has been necessary to develop a monovalent fragment of the antibody to generate an antagonistic activity. In the present application, by the use of the hinge of the invention, it is possible for the first time to obtain a full divalent antibody with increased antagonistic activity, and this contrary to the general knowledge.

In a preferred embodiment, the antibody of the invention comprises a hinge region comprising an amino acid sequence selected from the group consisting of SEQ ID Nos. 22 to 28 and 58 to 72, or a sequence having at least 80% identity after optimum alignment with sequences SEQ ID Nos. 22 to 28 and 58 to 72.

For more clarity, the following tables 3 and 4 regroup the amino acids and nucleotides sequences of the different preferred hinges of the invention.

TABLE 3

| SEQ ID No. | Amino acids | SEQ ID No. | Nucleotides |
|---|---|---|---|
| 22 | RKCCVECPPCP | 29 | AGGAAGTGCTGTGTGGAGTGCCCCCCCTGCCCA |
| 23 | PRDCGCKPCICT | 30 | CCCCGGGACTGTGGGTGCAAGCCTTGCATTTGTACC |
| 24 | PKSCGCKPCICT | 31 | CCCAAGAGCTGTGGGTGCAAGCCTTGCATTTGTACC |
| 25 | PKSCGCKPCICP | 32 | CCAAAGAGCTGCGGCTGCAAGCCTTGTATCTGTCCC |
| 26 | PRDCGCKPCPPCP | 33 | CCACGGGACTGTGGCTGCAAGCCCTGCCCTCCGTGTCCA |
| 27 | PRDCGCHTCPPCP | 34 | CCCAGAGACTGTGGGTGTCACACCTGCCCTCCTTGTCCT |
| 28 | PKSCDCHCPPCP | 35 | CCCAAAAGCTGCGATTGCCACTGTCCTCCATGTCCA |

TABLE 4

| SEQ ID No. | Amino acids | SEQ ID No. | Nucleotides |
|---|---|---|---|
| 58 | CKSCDKTHTCPPCP | 73 | TGCAAGAGCTGCGACAAGACCCACACCTGTCCCCCCTGCCCT |
| 59 | PCSCDKTHTCPPCP | 74 | CCCTGCAGCTGCGACAAGACCCACACCTGTCCCCCCTGCCCT |
| 60 | PKCCDKTHTCPPCP | 75 | CCCAAGTGCTGCGACAAGACCCACACCTGTCCCCCCTGCCCT |
| 61 | PKSCCKTHTCPPCP | 76 | CCTAAGAGCTGTTGCAAGACCCACACCTGTCCCCCCTGCCCT |
| 62 | PKSCDCTHTCPPCP | 77 | CCCAAGAGCTGCGACTGCACCCACACCTGTCCCCCCTGCCCT |
| 63 | PKSCDKCHTCPPCP | 78 | CCCAAGAGCTGCGACAAGTGCCACACCTGTCCCCCCTGCCCT |
| 64 | PKSCDKTHCCPPCP | 79 | CCCAAGAGCTGCGACAAGACCCACTGCTGTCCCCCCTGCCCT |
| 65 | KCDKTHTCPPCP | 80 | AAGTGCGACAAGACCCACACCTGTCCCCCCTGCCCT |
| 66 | PKSCDCHTCPPCP | 81 | CCCAAGAGCTGCGACTGCCACACCTGTCCCCCCTGCCCT |
| 67 | PKSCDCTHCCPPCP | 82 | CCCAAGAGCTGCGACTGCACCCACTGCCCCCCTGCCCT |
| 68 | PCSCKHTCPPCP | 83 | CCCTGCAGCTGCAAGCACACCTGTCCCCCCTGCCCT |
| 69 | PSCCTHTCPPCP | 84 | CCTAGCTGCTGCACCCACACCTGTCCCCCCTGCCCT |
| 70 | PSCDKHCCPPCP | 85 | CCCAGCTGCGACAAGCACTGCTGCCCCCCTGCCCT |

TABLE 4-continued

| SEQ ID No. | Amino acids | SEQ ID No. | Nucleotides |
|---|---|---|---|
| 71 | PKSCTCPPCP | 86 | CCCAAGAGCTGCACCTGTCCC CCTTGTCCT |
| 72 | PKSCDKCVECPPCP | 87 | CCCAAGAGCTGCGATAAGTGC GTGGAGTGCCCCCCTTGTCCT |

According a first approach, the antibody will be defined by its heavy chain sequence. More particularly, the antibody of the invention, or one of its functional fragments or derivatives, is characterized in that it comprises a heavy chain comprising at least one CDR chosen from CDRs comprising the amino acid sequences SEQ ID Nos. 1 to 3.

The mentioned sequences are the following ones:

SEQ ID No. 1:        GYIFTAYT

SEQ ID No. 2:        IKPNNGLA

SEQ ID No. 3:        ARSEITTEFDY

According to a preferred aspect, the antibody of the invention, or one of its functional fragments or derivatives, comprises a heavy chain comprising at least one, preferably two, and most preferably three, CDR(s) chosen from CDR-H1, CDR-H2 and CDR-H3, wherein:

CDR-H1 comprises the amino acid sequence SEQ ID No. 1,

CDR-H2 comprises the amino acid sequence SEQ ID No. 2,

CDR-H3 comprises the amino acid sequence SEQ ID No. 3.

In a second approach, the antibody will be now defined by its light chain sequence. More particularly, according to a second particular aspect of the invention, the antibody, or one of its functional fragments or derivatives, is characterized in that it comprises a light chain comprising at least one CDR chosen from CDRs comprising the amino acid sequence SEQ ID Nos. 5 to 7.

The mentioned sequences are the following ones:

SEQ ID No. 5:        ESVDSYANSF

SEQ ID No. 6:        RAS

SEQ ID No. 7:        QQSKEDPLT

According to another preferred aspect, the antibody of the invention, or one of its functional fragments or derivatives, comprises a light chain comprising at least one, preferably two, and most preferably three, CDR(s) chosen from CDR-L1, CDR-L2 and CDR-L3, wherein:

CDR-L1 comprises the amino acid sequence SEQ ID No. 5,

CDR-L2 comprises the amino acid sequence SEQ ID No. 6,

CDR-L3 comprises the amino acid sequence SEQ ID No. 7.

The murine hybridoma capable of secreting monoclonal antibodies according to the present invention, especially hybridoma of murine origin, was deposited at the CNCM (Institut Pasteur, Paris, France) on Mar. 14, 2007 under the number CNCM I-3731.

In the present application, IgG1 are preferred to get effector functions, and most preferably ADCC and CDC.

The skilled artisan will recognize that effector functions include, for example, C1q binding; complement dependent cytotoxicity (CDC); Fc receptor binding; antibody-dependent cell-mediated cytotoxicity (ADCC); phagocytosis; and down regulation of cell surface receptors (e.g. B cell receptor; BCR).

The antibodies according to the present invention, are preferably specific monoclonal antibodies, especially of murine, chimeric or humanized origin, which can be obtained according to the standard methods well known to the person skilled in the art.

In general, for the preparation of monoclonal antibodies or their functional fragments or derivatives, especially of murine origin, it is possible to refer to techniques which are described in particular in the manual "Antibodies" (Harlow and Lane, Antibodies: A Laboratory Manual, Cold Spring Harbor Laboratory, Cold Spring Harbor N.Y., pp. 726, 1988) or to the technique of preparation from hybridomas described by Kohler and Milstein (Nature, 256:495-497, 1975).

The monoclonal antibodies according to the invention can be obtained, for example, from an animal cell immunized against the c-Met, or one of its fragments containing the epitope specifically recognized by said monoclonal antibodies according to the invention. Said c-Met, or one of its said fragments, can especially be produced according to the usual working methods, by genetic recombination starting with a nucleic acid sequence contained in the cDNA sequence coding for the c-Met or by peptide synthesis starting from a sequence of amino acids comprised in the peptide sequence of the c-Met.

The monoclonal antibodies according to the invention can, for example, be purified on an affinity column on which the c-Met or one of its fragments containing the epitope specifically recognized by said monoclonal antibodies according to the invention has previously been immobilized. More particularly, said monoclonal antibodies can be purified by chromatography on protein A and/or G, followed or not followed by ion-exchange chromatography aimed at eliminating the residual protein contaminants as well as the DNA and the LPS, in itself followed or not followed by exclusion chromatography on Sepharose™ gel in order to eliminate the potential aggregates due to the presence of dimers or of other multimers. In an even more preferred manner, the whole of these techniques can be used simultaneously or successively.

The antibody of the invention, or a divalent functional fragment or derivative thereof, consists preferably of a chimeric antibody.

By chimeric antibody, it is intended to indicate an antibody which contains a natural variable (light chain and heavy chain) region derived from an antibody of a given species in combination with the light chain and heavy chain constant regions of an antibody of a species heterologous to said given species (e.g. mouse, horse, rabbit, dog, cow, chicken, etc.).

The antibodies or their fragments of chimeric type according to the invention can be prepared by using the techniques of genetic recombination. For example, the chimeric antibody can be produced by cloning a recombinant DNA containing a promoter and a sequence coding for the variable region of a non-human, especially murine, monoclonal antibody according to the invention and a sequence coding for the constant region of human antibody. A chimeric antibody of the invention encoded by such a recombinant gene will be, for example, a mouse-man chimera, the specificity of this antibody being determined by the variable region derived from the murine DNA and its isotype determined by the constant region derived from the human DNA. For the methods of preparation of chimeric antibodies, it is possible, for example, to refer to the documents Verhoeyn et al. (BioEssays, 8:74, 1988), Morrison et al. (Proc. Natl. Acad. Sci. USA 82:6851-6855, 1984) or U.S. Pat. No. 4,816,567.

More particularly, said antibody, or a functional fragment or derivative thereof, comprises a chimeric heavy chain variable domain of sequence comprising the amino acid sequence SEQ ID No. 46 or a sequence having at least 80% identity after optimum alignment with the sequence SEQ ID No. 46.

```
SEQ ID No. 46:
EVQLQQSGPELVKPGASVKISCKTSGYIFTAYTMHWVRQSLGESLD

WIGGIKPNNGLANYNQKFKGKATLTVDKSSSTAYMDLRSLTSEDSA

VYYCARSEITTEFDYWGQGTALTVSS
```

More particularly, said antibody, or a functional fragment or derivative thereof, comprises a chimeric light chain variable domain of sequence comprising the amino acid sequence SEQ ID No. 47 or a sequence having at least 80% identity after optimum alignment with the sequence SEQ ID No. 47.

```
SEQ ID No. 47:
DIVLTQSPASLAVSLGQRATISCRASESVDSYANSFMHWYQQKPGQ

PPKLLIYRASNLESGIPARFSGSGSRTDFTLTINPVEADDVATYYC

QQSKEDPLTFGSGTKLEMKR
```

More particularly, a preferred antibody, or a divalent functional fragment or derivative thereof, according to the invention and named [224G11] [IgG2chim], comprises a heavy chain variable domain comprising the amino acid sequence SEQ ID No. 46, a light chain variable domain comprising the amino acid sequence SEQ ID No. 47, and a hinge region comprising the amino acid sequence SEQ ID No. 22.

In the present application, the use of square brackets is not necessary and, as en example, the reference [224G11] [IgG2chim] must be considered as identical to 224G11IgG2chim. In a same way, to indicate that the antibody is a murine one, the expression murine or the letter m can be added; to indicate that the antibody is a chimeric one, the expression chim or the letter c can be added and; to indicate that the antibody is a humanized one, the expression hum, hz, Hz or the letter h can be added. As an example, the chimeric antibody 224G1IgG2 can be referred as c224G11IgG2, c224G11[IgG2], c[224G11]IgG2, c[224G11][IgG2], 224G11IgG2chim, 224G11[IgG2chim], [224G11]IgG2chim or [224G11][IgG2chim].

In another aspect, a preferred antibody, or a divalent functional fragment or derivative thereof, according to the invention and named [224G11][TH7chim], comprises a heavy chain variable domain comprising the amino acid sequence SEQ ID No. 46, a light chain variable domain comprising the amino acid sequence SEQ ID No. 47, and a hinge region comprising the amino acid sequence SEQ ID No. 28.

In the present application, the reference TH7 must be considered as identical to C7Δ6-9 or TH7C7Δ6-9. The symbol Δ means deletion.

In another aspect, a preferred antibody, or a divalent functional fragment or derivative thereof, according to the invention and named [224G11] [MHchim], comprises a heavy chain variable domain comprising the amino acid sequence SEQ ID No. 46, a light chain variable domain comprising the amino acid sequence SEQ ID No. 47, and a hinge region comprising the amino acid sequence SEQ ID No. 23.

In another aspect, a preferred antibody, or a divalent functional fragment or derivative thereof, according to the invention and named [224G11] [MUP9Hchim], comprises a heavy chain variable domain comprising the amino acid sequence SEQ ID No. 46, a light chain variable domain comprising the amino acid sequence SEQ ID No. 47, and a hinge region comprising the amino acid sequence SEQ ID No. 26.

In another aspect, a preferred antibody, or a divalent functional fragment or derivative thereof, according to the invention and named [224G11] [MMCHchim], comprises a heavy chain variable domain comprising the amino acid sequence SEQ ID No. 46, a light chain variable domain comprising the amino acid sequence SEQ ID No. 47, and a hinge region comprising the amino acid sequence SEQ ID No. 24.

In another aspect, a preferred antibody, or a divalent functional fragment or derivative thereof, according to the invention and named [224G11] [C1], comprises a heavy chain variable domain comprising the amino acid sequence SEQ ID No. 46, a light chain variable domain comprising the amino acid sequence SEQ ID No. 47, and a hinge region comprising the amino acid sequence SEQ ID No. 58.

In another aspect, a preferred antibody, or a divalent functional fragment or derivative thereof, according to the invention and named [224G11] [C2], comprises a heavy chain variable domain comprising the amino acid sequence SEQ ID No. 46, a light chain variable domain comprising the amino acid sequence SEQ ID No. 47, and a hinge region comprising the amino acid sequence SEQ ID No. 59.

In another aspect, a preferred antibody, or a divalent functional fragment or derivative thereof, according to the invention and named [224G11] [C3], comprises a heavy chain variable domain comprising the amino acid sequence SEQ ID No. 46, a light chain variable domain comprising the amino acid sequence SEQ ID No. 47, and a hinge region comprising the amino acid sequence SEQ ID No. 60.

In another aspect, a preferred antibody, or a divalent functional fragment or derivative thereof, according to the invention and named [224G11] [C5], comprises a heavy chain variable domain comprising the amino acid sequence SEQ ID No. 46, a light chain variable domain comprising the amino acid sequence SEQ ID No. 47, and a hinge region comprising the amino acid sequence SEQ ID No. 61.

In another aspect, a preferred antibody, or a divalent functional fragment or derivative thereof, according to the invention and named [224G11] [C6], comprises a heavy chain variable domain comprising the amino acid sequence SEQ ID No. 46, a light chain variable domain comprising the amino acid sequence SEQ ID No. 47, and a hinge region comprising the amino acid sequence SEQ ID No. 62.

In another aspect, a preferred antibody, or a divalent functional fragment or derivative thereof, according to the invention and named [224G11] [C7], comprises a heavy chain variable domain comprising the amino acid sequence SEQ ID No. 46, a light chain variable domain comprising the amino acid sequence SEQ ID No. 47, and a hinge region comprising the amino acid sequence SEQ ID No. 63.

In another aspect, a preferred antibody, or a divalent functional fragment or derivative thereof, according to the invention and named [224G11] [C9], comprises a heavy chain variable domain comprising the amino acid sequence SEQ ID No. 46, a light chain variable domain comprising the amino acid sequence SEQ ID No. 47, and a hinge region comprising the amino acid sequence SEQ ID No. 64.

In another aspect, a preferred antibody, or a divalent functional fragment or derivative thereof, according to the invention and named [224G11] [Δ1-3], comprises a heavy chain variable domain comprising the amino acid sequence SEQ ID No. 46, a light chain variable domain comprising the amino acid sequence SEQ ID No. 47, and a hinge region comprising the amino acid sequence SEQ ID No. 65.

In another aspect, a preferred antibody, or a divalent functional fragment or derivative thereof, according to the invention and named [224G11] [C7Δ6], comprises a heavy chain variable domain comprising the amino acid sequence SEQ ID No. 46, a light chain variable domain comprising the amino acid sequence SEQ ID No. 47, and a hinge region comprising the amino acid sequence SEQ ID No. 66.

In another aspect, a preferred antibody, or a divalent functional fragment or derivative thereof, according to the invention and named [224G11] [C6Δ9], comprises a heavy chain variable domain comprising the amino acid sequence SEQ ID No. 46, a light chain variable domain comprising the amino acid sequence SEQ ID No. 47, and a hinge region comprising the amino acid sequence SEQ ID No. 67.

In another aspect, a preferred antibody, or a divalent functional fragment or derivative thereof, according to the invention and named [224G11] [C2Δ5-7], comprises a heavy chain variable domain comprising the amino acid sequence SEQ ID No. 46, a light chain variable domain comprising the amino acid sequence SEQ ID No. 47, and a hinge region comprising the amino acid sequence SEQ ID No. 68.

In another aspect, a preferred antibody, or a divalent functional fragment or derivative thereof, according to the invention and named [224G11] [C5Δ2-6], comprises a heavy chain variable domain comprising the amino acid sequence SEQ ID No. 46, a light chain variable domain comprising the amino acid sequence SEQ ID No. 47, and a hinge region comprising the amino acid sequence SEQ ID No. 69.

In another aspect, a preferred antibody, or a divalent functional fragment or derivative thereof, according to the invention and named [224G11] [C9Δ2-7], comprises a heavy chain variable domain comprising the amino acid sequence SEQ ID No. 46, a light chain variable domain comprising the amino acid sequence SEQ ID No. 47, and a hinge region comprising the amino acid sequence SEQ ID No. 70.

In another aspect, a preferred antibody, or a divalent functional fragment or derivative thereof, according to the invention and named [224G11] [Δ5-6-7-8], comprises a heavy chain variable domain comprising the amino acid sequence SEQ ID No. 46, a light chain variable domain comprising the amino acid sequence SEQ ID No. 47, and a hinge region comprising the amino acid sequence SEQ ID No. 71.

In another aspect, a preferred antibody, or a divalent functional fragment or derivative thereof, according to the invention and named [224G11] [IgG1/IgG2], comprises a heavy chain variable domain comprising the amino acid sequence SEQ ID No. 46, a light chain variable domain comprising the amino acid sequence SEQ ID No. 47, and a hinge region comprising the amino acid sequence SEQ ID No. 72.

The antibody of the invention, or a divalent functional fragment or derivative thereof, consists preferably of a human antibody.

The term "human antibody" includes all antibodies that have one or more variable and constant region derived from human immunoglobulin sequences. In a preferred embodiment, all of the variable and constant domains (or regions) are derived from human immunoglobulin sequence (fully human antibody). In other words, it includes any antibody which have variable and constant regions (if present) derived from human germline immunoglobulin sequences, i.e. which possesses an amino acid sequence which corresponds to that of an antibody produced by a human and/or has been made using any techniques for making human antibodies known by the man skill in the art.

In one embodiment, the human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

As example for such transgenic mouse, it can be mentioned the XENOMOUSE™ which is an engineered mouse strain that comprises large fragments of the human immunoglobulin loci and is deficient in mouse antibody production (Green at al., 1994, Nature Genetics, 7:13-21). The XENOMOUSE™ produces an adult-like human repertoire of fully human antibodies, and generate antigen-specific human monoclonal antibodies. A second generation XENOMOUSE™ contains approximately 80% of the human antibody repertoire (Green & Jakobovits, 1998, J. Exp. Med., 188:483-495).

Any other technique known by the man skill in the art, such as phage display technique, can also be used for the generation of human antibody according to the invention.

The antibody of the invention, or a divalent functional fragment or derivative thereof, consists preferably of a humanized antibody.

By the expression "humanized antibody", it is intended to indicate an antibody which contains CDR regions derived from an antibody of nonhuman origin, the other parts of the antibody molecule being derived from one (or from several) human antibodies. Moreover, some of the residues of the segments of the skeleton (called FR) can be modified in order to conserve the affinity of the binding (Jones et al., Nature, 321:522-525, 1986; Verhoeyen et al., Science, 239:1534-1536, 1988; Riechmann et al., Nature, 332:323-327, 1988).

The humanized antibodies according to the invention or their fragments can be prepared by techniques known to the person skilled in the art (such as, for example, those described in the documents Singer et al., J. Immun. 150:2844-2857, 1992; Mountain et al., Biotechnol. Genet. Eng. Rev., 10:1-142, 1992; or Bebbington et al., Bio/Technology, 10:169-175, 1992).

Other humanization methods are known by the man skilled in the art as, for example, the "CDR Grafting" method described by Protein Design Labs (PDL) in the patent applications EP 0 451216, EP 0 682 040, EP 0 939127, EP 0 566 647 or U.S. Pat. No. 5,530,101, U.S. Pat. No. 6,180,370, U.S. Pat. No. 5,585,089 and U.S. Pat. No. 5,693,761. The following patent applications can also be mentioned: U.S. Pat. No. 5,639,641; U.S. Pat. No. 6,054,297; U.S. Pat. No. 5,886,152 and U.S. Pat. No. 5,877,293.

More particularly, said antibody, or a functional fragment or derivative thereof, comprises a humanized heavy chain variable domain of sequence comprising the amino acid sequence SEQ ID No. 4 or a sequence having at least 80% identity after optimum alignment with the sequence SEQ ID No. 4.

```
SEQ ID No. 4:
QVQLVQSGAEVKKPGASVKVSCKASGYIFTAYTMHWVRQAPGQGLE

WMGWIKPNNGLANYAQKFQGRVTMTRDTSISTAYMELSRLRSDDTA

VYYCARSEITTEFDYWGQGTLVTVSS
```

More particularly, said antibody, or a functional fragment or derivative thereof, comprises a humanized light chain variable domain selected from the group of sequences comprising the amino acid sequence SEQ ID No. 8, 9 or 10 or a sequence having at least 80% identity after optimum alignment with the sequence SEQ ID No. 8, 9 or 10.

```
SEQ ID No. 8:
DIVLTQSPDSLAVSLGERATINCKSSESVDSYANSFMHWYQQKPG
QPPKLLIYRASTRESGVPDRFSGSGSRTDFTLTISSLQAEDVAVY
YCQQSKEDPLTFGGGTKVEIKR

SEQ ID No. 9:
DIVMTQSPDSLAVSLGERATINCKSSESVDSYANSFMHWYQQKPG
QPPKLLIYRASTRESGVPDRFSGSGSGTDFTLTISSLQAEDVAVY
YCQQSKEDPLTFGGGTKVEIKR

SEQ ID No. 10:
DIVMTQSPDSLAVSLGERATINCKSSESVDSYANSFLHWYQQKPG
QPPKLLIYRASTRESGVPDRFSGSGSGTDFTLTISSLQAEDVAVY
YCQQSKEDPLTFGGGTKVEIKR
```

More particularly, a preferred antibody, or a divalent functional fragment or derivative thereof, according to the invention and named [224G11] [IgG2Hz1], comprises a heavy chain variable domain comprising the amino acid sequence SEQ ID No. 4, a light chain variable domain comprising the amino acid sequence SEQ ID No. 8, and a hinge region comprising the amino acid sequence SEQ ID No. 22.

In another aspect, a preferred antibody, or a divalent functional fragment or derivative thereof, according to the invention and named [224G11] [IgG2Hz2], comprises a heavy chain variable domain comprising the amino acid sequence SEQ ID No. 4, a light chain variable domain comprising the amino acid sequence SEQ ID No. 9, and a hinge region comprising the amino acid sequence SEQ ID No. 22.

In another aspect, a preferred antibody, or a divalent functional fragment or derivative thereof, according to the invention and named [224G11] [IgG2Hz3], comprises a heavy chain variable domain comprising the amino acid sequence SEQ ID No. 4, a light chain variable domain comprising the amino acid sequence SEQ ID No. 10, and a hinge region comprising the amino acid sequence SEQ ID No. 22.

In another aspect, a preferred antibody, or a divalent functional fragment or derivative thereof, according to the invention and named [224G11] [TH7Hz1], comprises a heavy chain variable domain comprising the amino acid sequence SEQ ID No. 4, a light chain variable domain comprising the amino acid sequence SEQ ID No. 8, and a hinge region comprising the amino acid sequence SEQ ID No. 28.

In another aspect, a preferred antibody, or a divalent functional fragment or derivative thereof, according to the invention and named [224G11] [TH7z2], comprises a heavy chain variable domain comprising the amino acid sequence SEQ ID No. 4, a light chain variable domain comprising the amino acid sequence SEQ ID No. 9, and a hinge region comprising the amino acid sequence SEQ ID No. 28.

In another aspect, a preferred antibody, or a divalent functional fragment or derivative thereof, according to the invention and named [224G11] [TH7Hz3], comprises a heavy chain variable domain comprising the amino acid sequence SEQ ID No. 4, a light chain variable domain comprising the amino acid sequence SEQ ID No. 10, and a hinge region comprising the amino acid sequence SEQ ID No. 28.

In another aspect, antibodies of the invention can be described by their total heavy and light chains, respectively.

As example, the antibody [224G11] [IgG2chim] of the invention comprises a complete heavy chain comprising the amino acid sequence SEQ ID No. 50, or a sequence having at least 80% identity after optimum alignment with the sequence SEQ ID No. 50, and a complete light chain comprising the amino acid sequence SEQ ID No. 52, or a sequence having at least 80% identity after optimum alignment with the sequence SEQ ID No. 52.

As another example, the antibody [224G11] [TH7chim] of the invention comprises a complete heavy chain comprising the amino acid sequence SEQ ID No. 51, or a sequence having at least 80% identity after optimum alignment with the sequence SEQ ID No. 51, and a complete light chain comprising the amino acid sequence SEQ ID No. 52, or a sequence having at least 80% identity after optimum alignment with the sequence SEQ ID No. 52.

As another example, the antibody [224G11] [C1] of the invention comprises a complete heavy chain comprising the amino acid sequence SEQ ID No. 88, or a sequence having at least 80% identity after optimum alignment with the sequence SEQ ID No. 88, and a complete light chain comprising the amino acid sequence SEQ ID No. 52, or a sequence having at least 80% identity after optimum alignment with the sequence SEQ ID No. 52.

As another example, the antibody [224G11] [C2] of the invention comprises a complete heavy chain comprising the amino acid sequence SEQ ID No. 89, or a sequence having at least 80% identity after optimum alignment with the sequence SEQ ID No. 89, and a complete light chain comprising the amino acid sequence SEQ ID No. 52, or a sequence having at least 80% identity after optimum alignment with the sequence SEQ ID No. 52.

As another example, the antibody [224G11] [C3] of the invention comprises a complete heavy chain comprising the amino acid sequence SEQ ID No. 90, or a sequence having at least 80% identity after optimum alignment with the sequence SEQ ID No. 90, and a complete light chain comprising the amino acid sequence SEQ ID No. 52, or a sequence having at least 80% identity after optimum alignment with the sequence SEQ ID No. 52.

As another example, the antibody [224G11] [C5] of the invention comprises a complete heavy chain comprising the amino acid sequence SEQ ID No. 91, or a sequence having at least 80% identity after optimum alignment with the sequence SEQ ID No. 91, and a complete light chain comprising the amino acid sequence SEQ ID No. 52, or a sequence having at least 80% identity after optimum alignment with the sequence SEQ ID No. 52.

As another example, the antibody [224G11] [C6] of the invention comprises a complete heavy chain comprising the amino acid sequence SEQ ID No. 92, or a sequence having at least 80% identity after optimum alignment with the sequence SEQ ID No. 92, and a complete light chain comprising the amino acid sequence SEQ ID No. 52, or a sequence having at least 80% identity after optimum alignment with the sequence SEQ ID No. 52.

As another example, the antibody [224G11] [C7] of the invention comprises a complete heavy chain comprising the amino acid sequence SEQ ID No. 93, or a sequence having at least 80% identity after optimum alignment with the sequence SEQ ID No. 93, and a complete light chain comprising the amino acid sequence SEQ ID No. 52, or a sequence having at least 80% identity after optimum alignment with the sequence SEQ ID No. 52.

As another example, the antibody [224G11] [C9] of the invention comprises a complete heavy chain comprising the amino acid sequence SEQ ID No. 94, or a sequence having at least 80% identity after optimum alignment with the sequence SEQ ID No. 94, and a complete light chain comprising the amino acid sequence SEQ ID No. 52, or a sequence having at least 80% identity after optimum alignment with the sequence SEQ ID No. 52.

As another example, the antibody [224G11] [Δ1-3] of the invention comprises a complete heavy chain comprising the amino acid sequence SEQ ID No. 95, or a sequence having at least 80% identity after optimum alignment with the sequence SEQ ID No. 95, and a complete light chain comprising the amino acid sequence SEQ ID No. 52, or a sequence having at least 80% identity after optimum alignment with the sequence SEQ ID No. 52.

As another example, the antibody [224G11] [C7Δ6] of the invention comprises a complete heavy chain comprising the amino acid sequence SEQ ID No. 96, or a sequence having at least 80% identity after optimum alignment with the sequence SEQ ID No. 96, and a complete light chain comprising the amino acid sequence SEQ ID No. 52, or a sequence having at least 80% identity after optimum alignment with the sequence SEQ ID No. 52.

As another example, the antibody [224G11] [C6Δ9] of the invention comprises a complete heavy chain comprising the amino acid sequence SEQ ID No. 97, or a sequence having at least 80% identity after optimum alignment with the sequence SEQ ID No. 97, and a complete light chain comprising the amino acid sequence SEQ ID No. 52, or a sequence having at least 80% identity after optimum alignment with the sequence SEQ ID No. 52.

As another example, the antibody [224G11] [C2Δ5-7] of the invention comprises a complete heavy chain comprising the amino acid sequence SEQ ID No. 98, or a sequence having at least 80% identity after optimum alignment with the sequence SEQ ID No. 98, and a complete light chain comprising the amino acid sequence SEQ ID No. 52, or a sequence having at least 80% identity after optimum alignment with the sequence SEQ ID No. 52.

As another example, the antibody [224G11] [C5Δ2-6] of the invention comprises a complete heavy chain comprising the amino acid sequence SEQ ID No. 99, or a sequence having at least 80% identity after optimum alignment with the sequence SEQ ID No. 99, and a complete light chain comprising the amino acid sequence SEQ ID No. 52, or a sequence having at least 80% identity after optimum alignment with the sequence SEQ ID No. 52.

As another example, the antibody [224G11] [C9Δ2-7] of the invention comprises a complete heavy chain comprising the amino acid sequence SEQ ID No. 100, or a sequence having at least 80% identity after optimum alignment with the sequence SEQ ID No. 100, and a complete light chain comprising the amino acid sequence SEQ ID No. 52, or a sequence having at least 80% identity after optimum alignment with the sequence SEQ ID No. 52.

As another example, the antibody [224G11] [Δ5-6-7-8] of the invention comprises a complete heavy chain comprising the amino acid sequence SEQ ID No. 101, or a sequence having at least 80% identity after optimum alignment with the sequence SEQ ID No. 101, and a complete light chain comprising the amino acid sequence SEQ ID No. 52, or a sequence having at least 80% identity after optimum alignment with the sequence SEQ ID No. 52.

As another example, the antibody [224G11] [IgG1/IgG2] of the invention comprises a complete heavy chain comprising the amino acid sequence SEQ ID No. 102, or a sequence having at least 80% identity after optimum alignment with the sequence SEQ ID No. 102, and a complete light chain comprising the amino acid sequence SEQ ID No. 52, or a sequence having at least 80% identity after optimum alignment with the sequence SEQ ID No. 52.

As another example, the antibody [224G11] [IgG2Hz1] of the invention comprises a complete heavy chain comprising the amino acid sequence SEQ ID No. 36, or a sequence having at least 80% identity after optimum alignment with the sequence SEQ ID No. 36 and a complete light chain comprising the amino acid sequence SEQ ID No. 38, or a sequence having at least 80% identity after optimum alignment with the sequence SEQ ID No. 38.

As another example, the antibody [224G11] [IgG2Hz2] of the invention comprises a complete heavy chain comprising the amino acid sequence SEQ ID No. 36, or a sequence having at least 80% identity after optimum alignment with the sequence SEQ ID No. 36 and a complete light chain comprising the amino acid sequence SEQ ID No. 39, or a sequence having at least 80% identity after optimum alignment with the sequence SEQ ID No. 39.

As another example, the antibody [224G11] [IgG2Hz3] of the invention comprises a complete heavy chain comprising the amino acid sequence SEQ ID No. 36, or a sequence having at least 80% identity after optimum alignment with the sequence SEQ ID No. 36 and a complete light chain comprising the amino acid sequence SEQ ID No. 40, or a sequence having at least 80% identity after optimum alignment with the sequence SEQ ID No. 40.

As another example, the antibody [224G11] [TH7Hz1] of the invention comprises a complete heavy chain comprising the amino acid sequence SEQ ID No. 37, or a sequence having at least 80% identity after optimum alignment with the sequence SEQ ID No. 37 and a complete light chain comprising the amino acid sequence SEQ ID No. 38, or a sequence having at least 80% identity after optimum alignment with the sequence SEQ ID No. 38.

As another example, the antibody [224G11] [TH7Hz2] of the invention comprises a complete heavy chain comprising the amino acid sequence SEQ ID No. 37, or a sequence having at least 80% identity after optimum alignment with the sequence SEQ ID No. 37 and a complete light chain comprising the amino acid sequence SEQ ID No. 39, or a sequence having at least 80% identity after optimum alignment with the sequence SEQ ID No. 39.

As another example, the antibody [224G11] [TH7Hz3] of the invention comprises a complete heavy chain comprising the amino acid sequence SEQ ID No. 37, or a sequence having at least 80% identity after optimum alignment with the sequence SEQ ID No. 37 and a complete light chain comprising the amino acid sequence SEQ ID No. 40, or a sequence having at least 80% identity after optimum alignment with the sequence SEQ ID No. 40.

Other examples of antibodies, or derivatives thereof, according to the invention comprises complete heavy chains comprising an amino acid sequence selected in the group consisting of SEQ ID Nos. 88 to 102 (corresponding nucleotide sequences are SEQ ID Nos. 103 to 117).

By "functional fragment" of an antibody according to the invention, it is intended to indicate in particular an antibody fragment, such as Fv, scFv (sc for single chain), Fab, F(ab')$_2$, Fab', scFv-Fc fragments or diabodies, or any fragment of which the half-life time would have been increased by chemical modification, such as the addition of poly(alkylene) glycol such as poly(ethylene) glycol ("PEGylation") (pegylated fragments called Fv-PEG, scFv-PEG, Fab-PEG, F(ab')$_2$-PEG or Fab'-PEG) ("PEG" for Poly(Ethylene) Glycol), or by incorporation in a liposome, said fragments having at least one of the characteristic CDRs of sequence SEQ ID Nos. 1 to 3 and 5 to 7 according to the invention, and, especially, in that it is capable of exerting in a general manner an even partial activity of the antibody from which it is descended, such as in particular the capacity to recognize and to bind to the c-Met, and, if necessary, to inhibit the activity of the c-Met.

Preferably, said functional fragments will be constituted or will comprise a partial sequence of the heavy or light variable chain of the antibody from which they are derived, said partial sequence being sufficient to retain the same specificity of binding as the antibody from which it is descended and a sufficient affinity, preferably at least equal to 1/100, in a more preferred manner to at least 1/10, of that of the antibody from which it is descended, with respect to the c-Met. Such a functional fragment will contain at the minimum 5 amino acids, preferably 6, 7, 8, 9, 10, 12, 15, 25, 50 and 100 consecutive amino acids of the sequence of the antibody from which it is descended.

Preferably, these functional fragments will be fragments of Fv, scFv, Fab, F(ab')$_2$, F(ab'), scFv-Fc type or diabodies, which generally have the same specificity of binding as the antibody from which they are descended. In a more preferred embodiment of the invention, these fragments are selected among divalent fragments such as F(ab')$_2$ fragments. According to the present invention, antibody fragments of the invention can be obtained starting from antibodies such as described above by methods such as digestion by enzymes, such as pepsin or papain and/or by cleavage of the disulfide bridges by chemical reduction. In another manner, the antibody fragments comprised in the present invention can be obtained by techniques of genetic recombination likewise well known to the person skilled in the art or else by peptide synthesis by means of, for example, automatic peptide synthesizers such as those supplied by the company Applied Biosystems, etc.

By "divalent fragment", it must be understood any antibody fragments comprising two arms and, more particularly, F(ab')$_2$ fragments.

By "derivatives" of an antibody according to the invention, it is meant a binding protein comprising a protein scaffold and at least on of the CDRs selected from the original antibody in order to maintain the binding capacity. Such compounds are well known by the man skilled in the art and will be described in more details in the following specification.

More particularly, the antibody, or one of its functional fragments or derivatives, according to the invention is characterized in that said derivative consists in a binding protein comprising a scaffold on which at least one CDR has been grafted for the conservation of the original antibody paratopic recognizing properties.

One or several sequences through the 6 CDR sequences described in the invention can be presented on a protein scaffold. In this case, the protein scaffold reproduces the protein backbone with appropriate folding of the grafted CDR(s), thus allowing it (or them) to maintain their antigen paratopic recognizing properties.

The man skilled in the art knows how to select the protein scaffold on which at least one CDR selected from the original antibody could be grafted. More particularly, it is known that, to be selected, such scaffold should display several features as follow (Skerra A., J. Mol. Recogn., 13, 2000, 167-187):
  phylogenetically good conservation,
  robust architecture with a well known three-dimensional molecular organization (such as, for example, crystallography or NMR),
  small size,
  no or only low degree of post-translational modifications, easy to produce, express and purify.

Such protein scaffold can be, but without limitation, structure selected from the group consisting in fibronectin and preferentially the tenth fibronectin type III domain (FNfn10), lipocalin, anticalin (Skerra A., J. Biotechnol., 2001, 74(4): 257-75), the protein Z derivative from the domain B of staphylococcal protein A, thioredoxin A or any protein with repeated domain such as "ankyrin repeat" (Kohl et al., PNAS, 2003, vol. 100, No. 4, 1700-1705), "armadillo repeat", "leucin-rich repeat" or "tetratricopeptide repeat".

It could also be mentioned scaffold derivative from toxins (such as, for example, scorpion, insect, plant or mollusc toxins) or protein inhibitors of neuronal nitric oxide synthase (PIN).

As non limitative example of such hybrid constructions, it can be mentioned the insertion of the CDR-H1 (heavy chain) of an anti-CD4 antibody, i.e. the 13B8.2 antibody, into one of the exposed loop of the PIN. The binding properties of the obtained binding protein remain similar to the original antibody (Bes et al., BBRC 343, 2006, 334-344). It can also be mentioned the grafting of the CDR-H3 (heavy chain) of an anti-lyzozyme VHH antibody on a loop of neocarzinostatine (Nicaise et al., 2004).

As above mentioned, such protein scaffold can comprise from 1 to 6 CDR(s) from the original antibody. In a preferred embodiment, but without any limitation, the man skilled in the art would select at least a CDR from the heavy chain, said heavy chain being known to be particularly implicated in the antibody specificity. The selection of the CDR(s) of interest will be evident for the man of the art with known method (BES et al., FEBS letters 508, 2001, 67-74).

As an evidence, these examples are not limitative and any other scaffold known or described must be included in the present specification.

According to a novel aspect, the present invention relates to an isolated nucleic acid, characterized in that it is chosen from the following nucleic acids:
  a) a nucleic acid, DNA or RNA, coding for an antibody, or one of its functional fragments or derivatives, according to the invention;
  b) a nucleic acid sequence comprising the sequences SEQ ID No. 11, SEQ ID No. 12, SEQ ID No. 13 and the sequences SEQ ID No. 15, SEQ ID No. 16 and SEQ ID No. 17;
  c) a nucleic acid sequence comprising the sequences SEQ ID No. 14 and SEQ ID No. 18, 19 or 20;
  d) the corresponding RNA nucleic acids of the nucleic acids as defined in b) or c);
  e) the complementary nucleic acids of the nucleic acids as defined in a), b) and c); and
  f) a nucleic acid of at least 18 nucleotides capable of hybridizing under conditions of high stringency with at least one of the CDRs of sequence SEQ ID Nos. 11 to 13 and 15 to 17.

According to still another aspect, the present invention relates to an isolated nucleic acid, characterized in that it is chosen from the following nucleic acids:
  a nucleic acid, DNA or RNA, coding for an antibody, or one of its functional fragments or derivatives, according to the present invention and wherein the nucleic sequence coding for the hinge region of said antibody comprises or has a sequence selected from the group consisting of the sequences SEQ ID Nos. 29 to 35 and SEQ ID Nos. 73 to 87.

By nucleic acid, nucleic or nucleic acid sequence, polynucleotide, oligonucleotide, polynucleotide sequence, nucleotide sequence, terms which will be employed indifferently in the present invention, it is intended to indicate a precise linkage of nucleotides, which are modified or unmodified, allowing a fragment or a region of a nucleic acid to be defined, containing or not containing unnatural nucleotides, and being able to correspond just as well to a double-stranded DNA, a single-stranded DNA as to the transcription products of said DNAs.

It must also be understood here that the present invention does not concern the nucleotide sequences in their natural chromosomal environment, that is to say in the natural state. It concerns sequences which have been isolated and/or purified, that is to say that they have been selected directly or indirectly, for example by copy, their environment having been at least partially modified. It is thus likewise intended to indicate here the isolated nucleic acids obtained by genetic recombination by means, for example, of host cells or obtained by chemical synthesis.

A hybridization under conditions of high stringency signifies that the temperature conditions and ionic strength conditions are chosen in such a way that they allow the maintenance of the hybridization between two fragments of complementary DNA. By way of illustration, conditions of high stringency of the hybridization step for the purposes of defining the polynucleotide fragments described above are advantageously the following.

The DNA-DNA or DNA-RNA hybridization is carried out in two steps: (1) prehybridization at 42° C. for 3 hours in phosphate buffer (20 mM, pH 7.5) containing 5×SSC (1×SSC corresponds to a 0.15 M NaCl+0.015 M sodium citrate solution), 50% of formamide, 7% of sodium dodecyl sulfate (SDS), 10×Denhardt's, 5% of dextran sulfate and 1% of salmon sperm DNA; (2) actual hybridization for 20 hours at a temperature dependent on the size of the probe (i.e.: 42° C., for a probe size >100 nucleotides) followed by 2 washes of 20 minutes at 20° C. in 2×SSC+2% of SDS, 1 wash of 20 minutes at 20° C. in 0.1×SSC+0.1% of SDS. The last wash is carried out in 0.1×SSC+0.1% of SDS for 30 minutes at 60° C. for a probe size >100 nucleotides. The hybridization conditions of high stringency described above for a polynucleotide of defined size can be adapted by the person skilled in the art for oligonucleotides of greater or smaller size, according to the teaching of Sambrook et al. (1989, Molecular cloning: a laboratory manual. 2nd Ed. Cold Spring Harbor).

The invention likewise relates to a vector comprising a nucleic acid according to the present invention.

The invention aims especially at cloning and/or expression vectors which contain a nucleotide sequence according to the invention.

The vectors according to the invention preferably contain elements which allow the expression and/or the secretion of the translated nucleotide sequences in a determined host cell. The vector must therefore contain a promoter, signals of initiation and termination of translation, as well as appropriate regions of regulation of transcription. It must be able to be maintained in a stable manner in the host cell and can optionally have particular signals which specify the secretion of the translated protein. These different elements are chosen and optimized by the person skilled in the art as a function of the host cell used. To this effect, the nucleotide sequences according to the invention can be inserted into autonomous replication vectors in the chosen host, or be integrative vectors of the chosen host.

Such vectors are prepared by methods currently used by the person skilled in the art, and the resulting clones can be introduced into an appropriate host by standard methods, such as lipofection, electroporation, thermal shock, or chemical methods.

The vectors according to the invention are, for example, vectors of plasmidic or viral origin. They are useful for transforming host cells in order to clone or to express the nucleotide sequences according to the invention.

The invention likewise comprises the host cells transformed by or comprising a vector according to the invention.

The host cell can be chosen from prokaryotic or eukaryotic systems, for example bacterial cells but likewise yeast cells or animal cells, in particular mammalian cells. It is likewise possible to use insect cells or plant cells.

The invention likewise concerns animals, except man, which comprise at least one cell transformed according to the invention.

According to another aspect, a subject of the invention is a process for production of an antibody, or one of its functional fragments according to the invention, characterized in that it comprises the following stages:

a) culture in a medium and appropriate culture conditions of a host cell according to the invention; and b) the recovery of said antibodies, or one of their functional fragments, thus produced starting from the culture medium or said cultured cells.

The cells transformed according to the invention can be used in processes for preparation of recombinant polypeptides according to the invention. The processes for preparation of a polypeptide according to the invention in recombinant form, characterized in that they employ a vector and/or a cell transformed by a vector according to the invention, are themselves comprised in the present invention. Preferably, a cell transformed by a vector according to the invention is cultured under conditions which allow the expression of said polypeptide and said recombinant peptide is recovered.

As has been said, the host cell can be chosen from prokaryotic or eukaryotic systems. In particular, it is possible to identify nucleotide sequences according to the invention, facilitating secretion in such a prokaryotic or eukaryotic system. A vector according to the invention carrying such a sequence can therefore advantageously be used for the production of recombinant proteins, intended to be secreted. In effect, the purification of these recombinant proteins of interest will be facilitated by the fact that they are present in the supernatant of the cell culture rather than in the interior of the host cells.

It is likewise possible to prepare the polypeptides according to the invention by chemical synthesis. Such a preparation process is likewise a subject of the invention. The person skilled in the art knows the processes of chemical synthesis, for example the techniques employing solid phases [Steward et al., 1984, Solid phase peptide synthesis, Pierce Chem. Company, Rockford, 111, 2nd ed., (1984)] or techniques using partial solid phases, by condensation of fragments or by a classical synthesis in solution. The polypeptides obtained by chemical synthesis and being able to contain corresponding unnatural amino acids are likewise comprised in the invention.

The antibodies, or one of their functional fragments or derivatives, capable of being obtained by a process according to the invention are likewise comprised in the present invention.

The invention also concerns the antibody of the invention as a medicament.

The invention likewise concerns a pharmaceutical composition comprising by way of active principle a compound consisting of an antibody, or one of its functional fragments according to the invention, preferably mixed with an excipient and/or a pharmaceutically acceptable vehicle.

Another complementary embodiment of the invention consists in a composition such as described above which comprises, moreover, as a combination product for simultaneous, separate or sequential use, an anti-tumoral antibody.

Most preferably, said second anti-tumoral antibody could be chosen through anti-IGF-IR, anti-EGFR, anti-HER2/neu, anti-VEGFR, anti-VEGF, etc., antibodies or any other anti-tumoral antibodies known by the man skilled in the art. It is evident that the use, as second antibody, of functional fragments or derivatives of above mentioned antibodies is part of the invention.

As a most preferred antibody, anti-EGFR antibodies are selected such as for example the antibody C225 (Erbitux).

"Simultaneous use" is understood as meaning the administration of the two compounds of the composition according to the invention in a single and identical pharmaceutical form.

"Separate use" is understood as meaning the administration, at the same time, of the two compounds of the composition according to the invention in distinct pharmaceutical forms.

"Sequential use" is understood as meaning the successive administration of the two compounds of the composition according to the invention, each in a distinct pharmaceutical form.

In a general fashion, the composition according to the invention considerably increases the efficacy of the treatment of cancer. In other words, the therapeutic effect of the anti-c-Met antibodies according to the invention is potentiated in an unexpected manner by the administration of a cytotoxic agent. Another major subsequent advantage produced by a composition according to the invention concerns the possibility of using lower efficacious doses of active principle, which allows the risks of appearance of secondary effects to be avoided or to be reduced, in particular the effects of the cytotoxic agent.

In addition, this composition according to the invention would allow the expected therapeutic effect to be attained more rapidly.

The composition of the invention can also be characterized in that it comprises, moreover, as a combination product for simultaneous, separate or sequential use, a cytotoxic/cytostatic agent.

By "anti-cancer therapeutic agents" or "cytotoxic/cytostatic agents", it is intended a substance which, when administered to a subject, treats or prevents the development of cancer in the subject's body. As non limitative example of such agents, it can be mentioned alkylating agents, anti-metabolites, anti-tumor antibiotics, mitotic inhibitors, chromatin function inhibitors, anti-angiogenesis agents, anti-estrogens, anti-androgens or immunomodulators.

Such agents are, for example, cited in the 2001 edition of VIDAL, on the page devoted to the compounds attached to the cancerology and hematology column "Cytotoxics", these cytotoxic compounds cited with reference to this document are cited here as preferred cytotoxic agents.

More particularly, the following agents are preferred according to the invention.

"Alkylating agent" refers to any substance which can cross-link or alkylate any molecule, preferably nucleic acid (e.g., DNA), within a cell. Examples of alkylating agents include nitrogen mustard such as mechlorethamine, chlorambucol, melphalen, chlorydrate, pipobromen, prednimustin, disodic-phosphate or estramustine; oxazophorins such as cyclophosphamide, altretamine, trofosfamide, sulfofosfamide or ifosfamide; aziridines or imine-ethylenes such as thiotepa, triethylenamine or altetramine; nitrosourea such as carmustine, streptozocin, fotemustin or lomustine; alkylesulfonates such as busulfan, treosulfan or improsulfan; triazenes such as dacarbazine; or platinum complexes such as cis-platinum, oxaliplatin and carboplatin.

"Anti-metabolites" refer to substances that block cell growth and/or metabolism by interfering with certain activities, usually DNA synthesis. Examples of anti-metabolites include methotrexate, 5-fluoruracil, floxuridine, 5-fluorodeoxyuridine, capecitabine, cytarabine, fludarabine, cytosine arabinoside, 6-mercaptopurine (6-MP), 6-thioguanine (6-TG), chlorodesoxyadenosine, 5-azacytidine, gemcitabine, cladribine, deoxycoformycin and pentostatin.

"Anti-tumor antibiotics" refer to compounds which may prevent or inhibit DNA, RNA and/or protein synthesis. Examples of anti-tumor antibiotics include doxorubicin, daunorubicin, idarubicin, valrubicin, mitoxantrone, dactinomycin, mithramycin, plicamycin, mitomycin C, bleomycin, and procarbazine.

"Mitotic inhibitors" prevent normal progression of the cell cycle and mitosis. In general, microtubule inhibitors or taxoides such as paclitaxel and docetaxel are capable of inhibiting mitosis. Vinca alkaloid such as vinblastine, vincristine, vindesine and vinorelbine are also capable of inhibiting mitosis.

"Chromatin function inhibitors" or "topoisomerase inhibitors" refer to substances which inhibit the normal function of chromatin modeling proteins such as topoisomerase I or topoisomerase II. Examples of chromatin function inhibitors include, for topoisomerase I, camptothecine and its derivatives such as topotecan or irinotecan, and, for topoisomerase II, etoposide, etoposide phosphate and teniposide.

"Anti-angiogenesis agent" refers to any drug, compound, substance or agent which inhibits growth of blood vessels. Exemplary anti-angiogenesis agents include, but are by no means limited to, razoxin, marimastat, batimastat, prinomastat, tanomastat, ilomastat, CGS-27023A, halofuginon, COL-3, neovastat, BMS-275291, thalidomide, CDC 501, DMXAA, L-651582, squalamine, endostatin, SU5416, SU6668, interferon-alpha,EMD121974, interleukin-12, IM862, angiostatin and vitaxin.

"Anti-estrogen" or "anti-estrogenic agent" refer to any substance which reduces, antagonizes or inhibits the action of estrogen. Examples of anti-estrogen agents are tamoxifen, toremifene, raloxifene, droloxifene, iodoxyfene, anastrozole, letrozole, and exemestane.

"Anti-androgens" or "anti-androgen agents" refer to any substance which reduces, antagonizes or inhibits the action of an androgen. Examples of anti-androgens are flutamide, nilutamide, bicalutamide, sprironolactone, cyproterone acetate, finasteride and cimitidine.

"Immunomodulators" are substances which stimulate the immune system.

Examples of immunomodulators include interferon, interleukin such as aldesleukine, OCT-43, denileukin diflitox and interleukin-2, tumoral necrose fators such as tasonermine or others immunomodulators such as lentinan, sizofuran, roquinimex, pidotimod, pegademase, thymopentine, poly I:C or levamisole in conjunction with 5-fluorouracil.

For more detail, the man skill in the art could refer to the manual edited by the "Association Française des Enseignants de Chimie Thérapeutique" and entitled "Traité de chimie thérapeutique", vol. 6, Médicaments antitumoraux et perspectives dans le traitement des cancers, edition TEC & DOC, 2003.

Can also be mentioned as chemical agents or cytotoxic agents, all kinase inhibitors such as, for example, gefitinib or erlotinib.

In a particularly preferred embodiment, said composition as a combination product according to the invention is characterized in that said cytotoxic agent is coupled chemically to said antibody for simultaneous use.

In order to facilitate the coupling between said cytotoxic agent and said antibody according to the invention, it is especially possible to introduce spacer molecules between the two compounds to be coupled, such as poly(alkylene) glycols like polyethylene glycol, or else amino acids, or, in another embodiment, to use active derivatives of said cytotoxic agents into which would have been introduced functions capable of reacting with said antibody according to the invention. These coupling techniques are well known to the person skilled in the art and will not be expanded upon in the present description.

The invention relates, in another aspect, to a composition characterized in that one, at least, of said antibodies, or one of their functional fragments or derivatives, is conjugated with a cell toxin and/or a radioelement.

Preferably, said toxin or said radioelement is capable of inhibiting at least one cell activity of cells expressing the c-Met, in a more preferred manner capable of preventing the growth or the proliferation of said cell, especially of totally inactivating said cell.

Preferably also, said toxin is an enterobacterial toxin, especially *Pseudomonas* exotoxin A.

The radioelements (or radioisotopes) preferably conjugated to the antibodies employed for the therapy are radioisotopes which emit gamma rays and preferably iodine$^{131}$, yttrium$^{90}$, gold$^{199}$, palladium$^{100}$, copper$^{67}$, bismuth$^{217}$ and antimony$^{211}$. The radioisotopes which emit beta and alpha rays can likewise be used for the therapy.

By toxin or radioelement conjugated to at least one antibody, or one of its functional fragments, according to the invention, it is intended to indicate any means allowing said toxin or said radioelement to bind to said at least one antibody, especially by covalent coupling between the two compounds, with or without introduction of a linking molecule.

Among the agents allowing binding in a chemical (covalent), electrostatic or noncovalent manner of all or part of the components of the conjugate, mention may particularly be made of benzoquinone, carbodiimide and more particularly EDC (1-ethyl-3-[3-dimethyl-aminopropyl]-carbodiimide hydrochloride), dimaleimide, dithiobis-nitrobenzoic acid (DTNB), N-succinimidyl S-acetyl thio-acetate (SATA), the bridging agents having one or more phenylazide groups reacting with the ultraviolets (U.V.) and preferably N-[-4-(azidosalicylamino)butyl]-3'-(2'-pyridyldithio)-propionamide (APDP), N-succinimid-yl 3-(2-pyridyldithio)propionate (SPDP), 6-hydrazino-nicotinamide (HYNIC).

Another form of coupling, especially for the radioelements, can consist in the use of a bifunctional ion chelator.

Among these chelates, it is possible to mention the chelates derived from EDTA (ethylenediaminetetraacetic acid) or from DTPA (diethylenetriaminepentaacetic acid) which have been developed for binding metals, especially radioactive metals, and immunoglobulins. Thus, DTPA and its derivatives can be substituted by different groups on the carbon chain in order to increase the stability and the rigidity of the ligand-metal complex (Krejcarek et al. (1977); Brechbiel et al. (1991); Gansow (1991); U.S. Pat. No. 4,831,175).

For example diethylenetriaminepentaacetic acid (DTPA) and its derivatives, which have been widely used in medicine and in biology for a long time either in their free form, or in the form of a complex with a metallic ion, have the remarkable characteristic of forming stable chelates with metallic ions and of being coupled with proteins of therapeutic or diagnostic interest such as antibodies for the development of radioimmunoconjugates in cancer therapy (Meases et al., 1984; Gansow et al., 1990).

Likewise preferably, said at least one antibody forming said conjugate according to the invention is chosen from its functional fragments, especially the fragments amputated of their Fc component such as the scFv fragments.

As already mentioned, in a preferred embodiment of the invention, said cytotoxic/cytostatic agent or said toxin and/or a radioelement is coupled chemically to at least one of the elements of said composition for simultaneous use.

The present invention comprises the described composition as a medicament.

The present invention moreover comprises the use of the composition according to the invention for the preparation of a medicament.

In another aspect, the invention deals with the use of an antibody, or one of its functional fragments or derivatives, and/or of a composition as above described for the preparation of a medicament intended to inhibit the growth and/or the proliferation of tumor cells.

Another aspect of the invention consists in the use of an antibody, or one of its functional fragments or derivatives and/or of a composition, as described above or the use above mentioned, for the preparation of a medicament intended for the prevention or for the treatment of cancer.

Is also comprised in the present invention a method intended to inhibit the growth and/or the proliferation of tumor cells in a patient comprising the administration to a patient in need thereof of an antibody, or one of its functional fragments or derivatives according to the invention, an antibody produced by an hybridoma according to the invention or a composition according to the invention.

The present invention further comprises a method for the prevention or the treatment of cancer in a patient in need thereof, comprising the administration to the patient of an antibody, or one of its functional fragments or derivatives according to the invention, an antibody produced by an hybridoma according to the invention or a composition according to the invention.

In a particular preferred aspect, said cancer is a cancer chosen from prostate cancer, osteosarcomas, lung cancer, breast cancer, endometrial cancer, glioblastoma or colon cancer.

As explained before, an advantage of the invention is to allow the treatment of HGF dependent and independent Met-activation related cancers.

In a particular aspect, the invention comprises the use of an antibody, or one of its functional fragments or derivatives and/or of a composition, as described above or the use above mentioned, for the preparation of a medicament intended for the prevention or for the treatment of a patient in need thereof having a cancer characterized by overexpression of c-Met (for example, due to a genic amplification of c-Met) resulting in a ligand-independent constitutive activation of said c-Met receptor.

Preferably, said cancer characterized by a genic amplification of c-Met resulting in a ligand-independent constitutive activation of said c-Met receptor is selected from the group consisting of renal cell carcinoma and gastric cancer.

The invention, in yet another aspect, encompasses a method of in vitro diagnosis of illnesses induced by an overexpression or an underexpression of the c-Met receptor starting from a biological sample in which the abnormal presence of c-Met receptor is suspected, said method being characterized in that it comprises a step wherein said biological sample is contacted with an antibody of the invention, it being possible for said antibody to be, if necessary, labeled.

Preferably, said illnesses connected with an abnormal presence of c-Met receptor in said diagnosis method will be cancers.

Said antibody, or one of its functional fragments, can be present in the form of an immunoconjugate or of a labelled antibody so as to obtain a detectable and/or quantifiable signal.

The antibodies labelled according to the invention or their functional fragments include, for example, antibodies called immunoconjugates which can be conjugated, for example, with enzymes such as peroxidase, alkaline phosphatase, beta-D-galactosidase, glucose oxydase, glucose amylase, carbonic anhydrase, acetylcholinesterase, lysozyme, malate dehydrogenase or glucose 6-phosphate dehydrogenase or by a molecule such as biotin, digoxygenin or 5-bromodeoxyuridine. Fluorescent labels can be likewise conjugated to the antibodies or to their functional fragments according to the invention and especially include fluorescein and its derivatives, fluorochrome, rhodamine and its derivatives, GFP (GFP for "Green Fluorescent Protein"), dansyl, umbelliferone etc. In such conjugates, the antibodies of the invention or their functional fragments can be prepared by methods known to the person skilled in the art. They can be coupled to the enzymes or to the fluorescent labels directly or by the intermediary of a spacer group or of a linking group such as a polyaldehyde, like glutaraldehyde, ethylenediaminetetraacetic acid (EDTA), diethylene-triaminepentaacetic acid (DPTA), or in the presence of coupling agents such as those mentioned above for the therapeutic conjugates. The conjugates containing labels of fluorescein type can be prepared by reaction with an isothiocyanate.

Other conjugates can likewise include chemoluminescent labels such as luminol and the dioxetanes, bio-luminescent labels such as luciferase and luciferin, or else radioactive labels such as iodine$^{123}$, iodine$^{125}$, iodine$^{126}$, iodine$^{133}$, bromine$^{77}$, technetium$^{99m}$, indium$^{111}$, indium$^{113m}$, gallium$^{67}$, gallium$^{68}$, ruthenium$^{95}$, ruthenium$^{97}$, ruthenium$^{103}$, ruthenium$^{105}$, mercury$^{107}$, mercury$^{203}$, rhenium$^{99m}$, rhenium$^{101}$, rhenium$^{105}$, scandium$^{47}$, tellurium$^{121m}$, tellurium$^{122m}$, tellurium$^{125m}$, thulium$^{165}$, thulium$^{167}$, thulium$^{168}$, fluorine$^{18}$, yttrium$^{199}$, iodine$^{131}$. The methods known to the person skilled in the art existing for coupling the therapeutic radioisotopes to the antibodies either directly or via a chelating agent such as EDTA, DTPA mentioned above can be used for the radioelements which can be used in diagnosis. It is likewise possible to mention labelling with Na[I$^{125}$] by the chloramine T method [Hunter W. M. and Greenwood F. C. (1962) Nature 194:495] or else with technetium$^{99m}$ by the technique of Crockford et al. (U.S. Pat. No. 4,424,200) or attached via DTPA as described by Hnatowich (U.S. Pat. No. 4,479,930).

Thus, the antibody, or a functional fragment or derivative thereof, according to the invention can be employed in a process for the detection and/or the quantification of an overexpression or of an underexpression, preferably an overexpression, of the c-Met receptor in a biological sample, characterized in that it comprises the following steps:

a) the contacting of the biological sample with an antibody, or a functional fragment or derivative thereof, according to the invention; and b) the demonstration of the c-Met/antibody complex possibly formed.

In a particular embodiment, the antibody, or a functional fragment or derivative thereof, according to the invention, can be employed in a process for the detection and/or the quantification of the c-Met receptor in a biological sample, for the monitoring of the efficacy of a prophylactic and/or therapeutic treatment of c-Met-dependent cancer.

More generally, the antibody or a functional fragment or derivative thereof, according to the invention can be advantageously employed in any situation where the expression of the c-Met-receptor must be observed in a qualitative and/or quantitative manner.

Preferably, the biological sample is formed by a biological fluid, such as serum, whole blood, cells, a tissue sample or biopsies of human origin.

Any procedure or conventional test can be employed in order to carry out such a detection and/or dosage. Said test can be a competition or sandwich test, or any test known to the person skilled in the art dependent on the formation of an immune complex of antibody-antigen type. Following the applications according to the invention, the antibody or a functional fragment or derivative thereof can be immobilized or labelled. This immobilization can be carried out on numerous supports known to the person skilled in the art. These supports can especially include glass, polystyrene, poly-propylene, polyethylene, dextran, nylon, or natural or modified cells. These supports can be either soluble or insoluble.

By way of example, a preferred method brings into play immunoenzymatic processes according to the ELISA technique, by immunofluorescence, or radio-immunoassay (RIA) technique or equivalent.

Thus, the present invention likewise comprises the kits or sets necessary for carrying out a method of diagnosis of illnesses induced by an overexpression or an underexpression of the c-Met receptor or for carrying out a process for the detection and/or the quantification of an overexpression or of an underexpression of the c-Met receptor in a biological sample, preferably an overexpression of said receptor, characterized in that said kit or set comprises the following elements:

a) an antibody, or a functional fragment or derivative thereof, according to the invention;

b) optionally, the reagents for the formation of the medium favorable to the immunological reaction;

c) optionally, the reagents allowing the demonstration of c-Met/antibody complexes produced by the immunological reaction.

A subject of the invention is likewise the use of an antibody or a composition according to the invention for the preparation of a medicament intended for the specific targeting of a biologically active compound to cells expressing or overexpressing the c-Met receptor.

It is intended here by biologically active compound to indicate any compound capable of modulating, especially of inhibiting, cell activity, in particular their growth, their proliferation, transcription or gene translation.

A subject of the invention is also an in vivo diagnostic reagent comprising an antibody according to the invention, or a functional fragment or derivative thereof, preferably labelled, especially radiolabelled, and its use in medical imaging, in particular for the detection of cancer connected with the expression or the overexpression by a cell of the c-Met receptor.

The invention likewise relates to a composition as a combination product or to an anti-c-Met/toxin conjugate or radioelement, according to the invention, as a medicament.

Preferably, said composition as a combination product or said conjugate according to the invention will be mixed with an excipient and/or a pharmaceutically acceptable vehicle.

In the present description, pharmaceutically acceptable vehicle is intended to indicate a compound or a combination of compounds entering into a pharmaceutical composition not provoking secondary reactions and which allows, for example, facilitation of the administration of the active compound(s), an increase in its lifespan and/or in its efficacy in the body, an increase in its solubility in solution or else an improvement in its conservation. These pharmaceutically acceptable vehicles are well known and will be adapted by the person skilled in the art as a function of the nature and of the mode of administration of the active compound(s) chosen.

Preferably, these compounds will be administered by the systemic route, in particular by the intravenous route, by the intramuscular, intradermal, intraperitoneal or subcutaneous route, or by the oral route. In a more preferred manner, the composition comprising the antibodies according to the invention will be administered several times, in a sequential manner.

Their modes of administration, dosages and optimum pharmaceutical forms can be determined according to the criteria generally taken into account in the establishment of a treatment adapted to a patient such as, for example, the age or the body weight of the patient, the seriousness of his/her general condition, the tolerance to the treatment and the secondary effects noted.

Other characteristics and advantages of the invention appear in the continuation of the description with the examples and the figures wherein:

FIG. 1: Effect of irrelevant IgG1 Mabs from mouse and human origin and PBS on c-Met receptor phosphorylation on A549 cells.

Figure 2A:
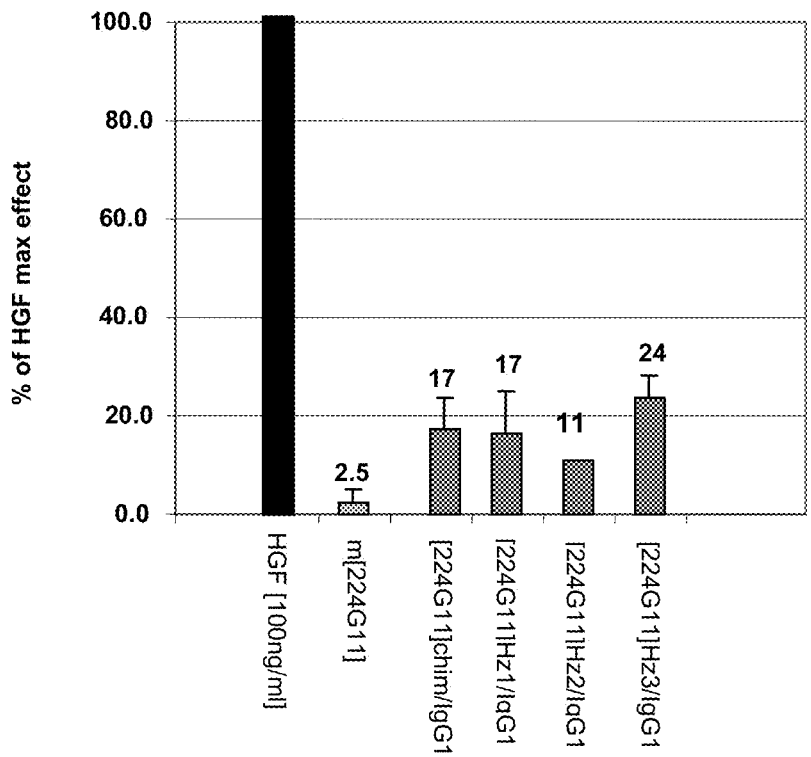
Figure 2B:
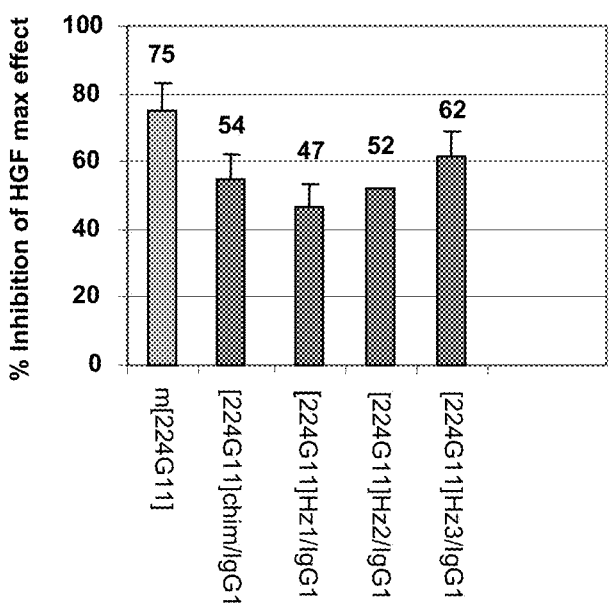

FIGS. 2A and 2B: Effect of murine and humanized 224G11 Mabs produced as a human IgG1/kappa isotype on c-Met receptor phosphorylation on A549 cells.

FIG. 2A: agonist effect calculated as percentage versus maximal stimulation of c-Met phosphorylation by HGF [100 ng/ml].

FIG. 2B: antagonist effect calculated as percentage of inhibition of the maximal stimulation of c-Met phosphorylation by HGF [100 ng/ml].

Figure 3A:
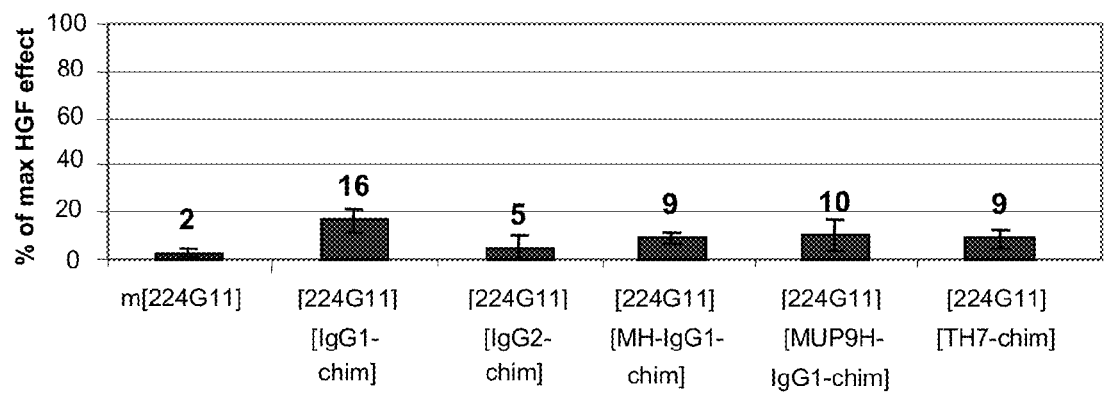
Figure 3B:
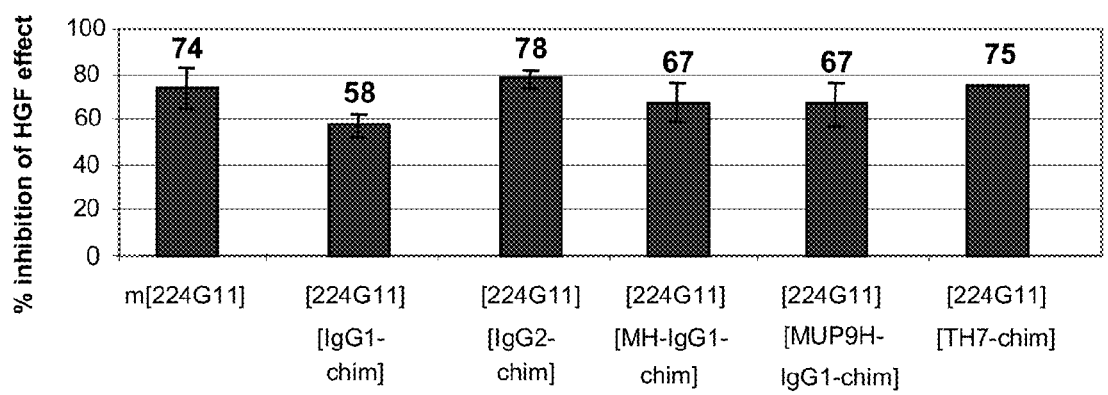

FIGS. 3A and 3B: Comparison between murine 224G11 Mab and chimeric 224G11 Mabs containing various engineered hinge regions, on c-Met receptor phosphorylation on A549 cells.

FIG. 3A: agonist effect calculated as percentage versus maximal stimulation of c-Met phosphorylation by HGF [100 ng/ml].

FIG. 3B: antagonist effect calculated as percentage of inhibition of the maximal stimulation of c-Met phosphorylation by HGF [100 ng/ml].

Figure 4A:
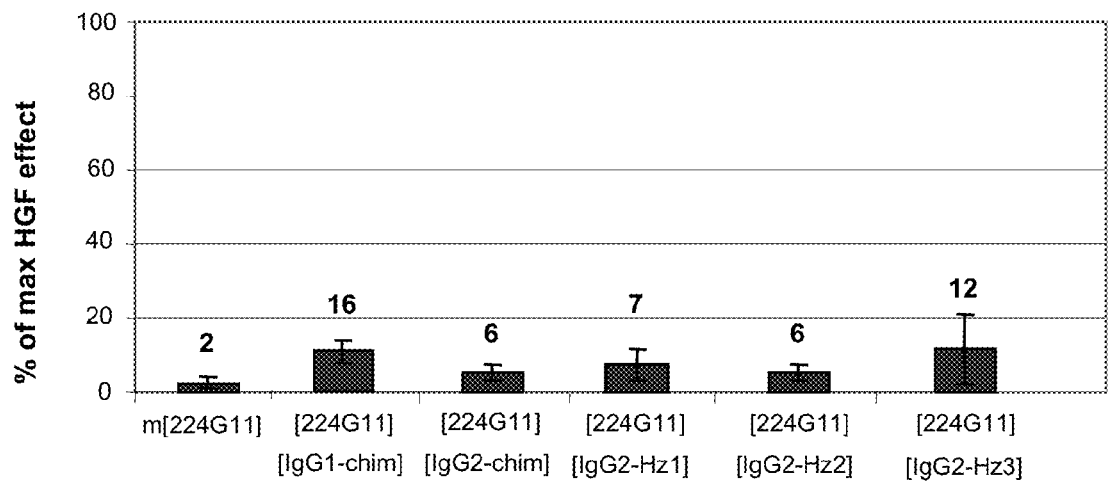
Figure 4B:
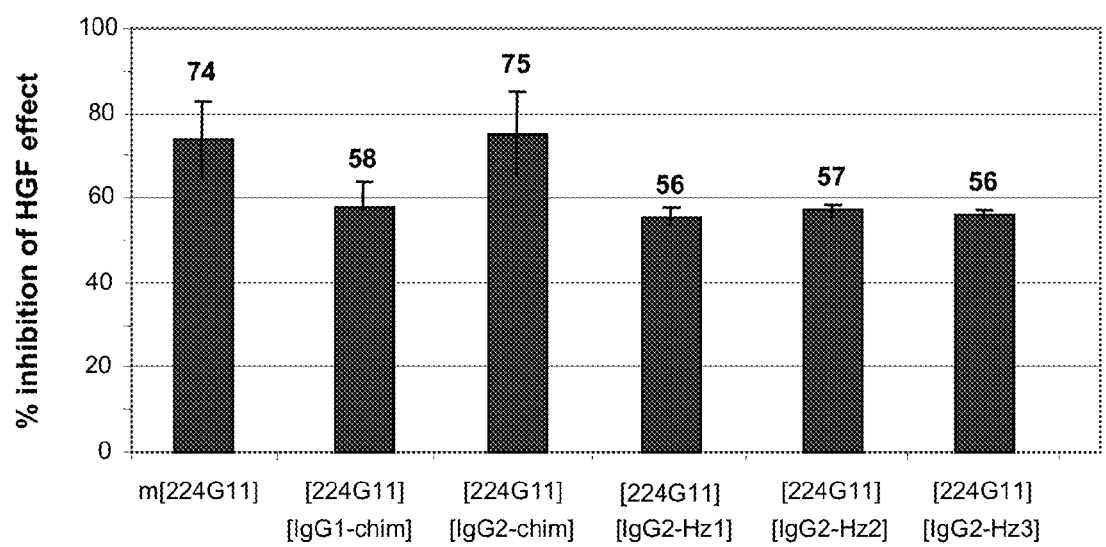

FIGS. 4A and 4B: Comparison between murine 224G11 Mab and chimeric and humanized 224G11 Mabs produced as a human IgG2/kappa isotype, on c-Met receptor phosphorylation on A549 cells.

FIG. 4A: agonist effect calculated as percentage versus maximal stimulation of c-Met phosphorylation by HGF [100 ng/ml].

FIG. 4B: antagonist effect calculated as percentage of inhibition of the maximal stimulation of c-Met phosphorylation by HGF [100 ng/ml].

Figure 5A:
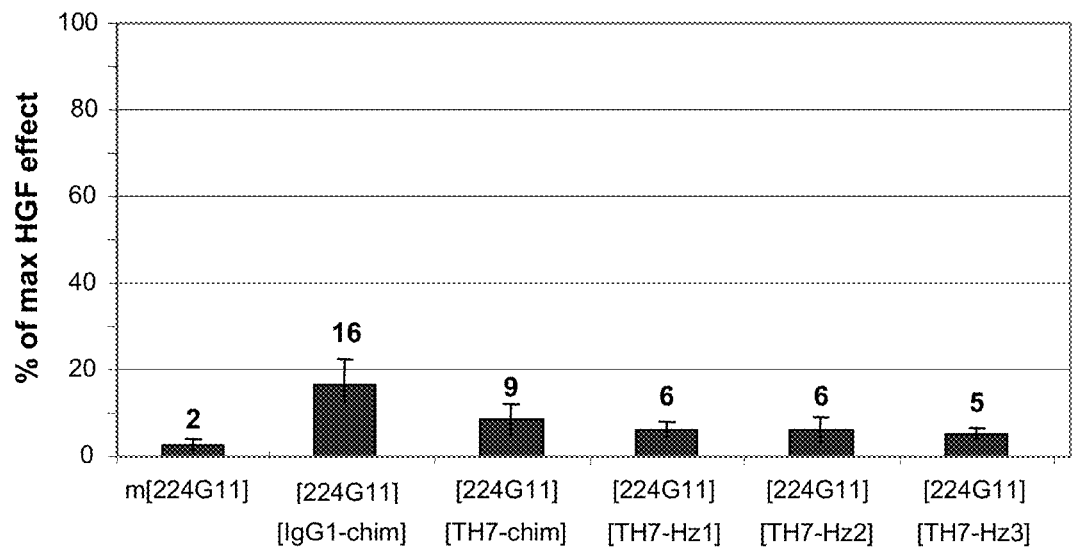
Figure 5B:
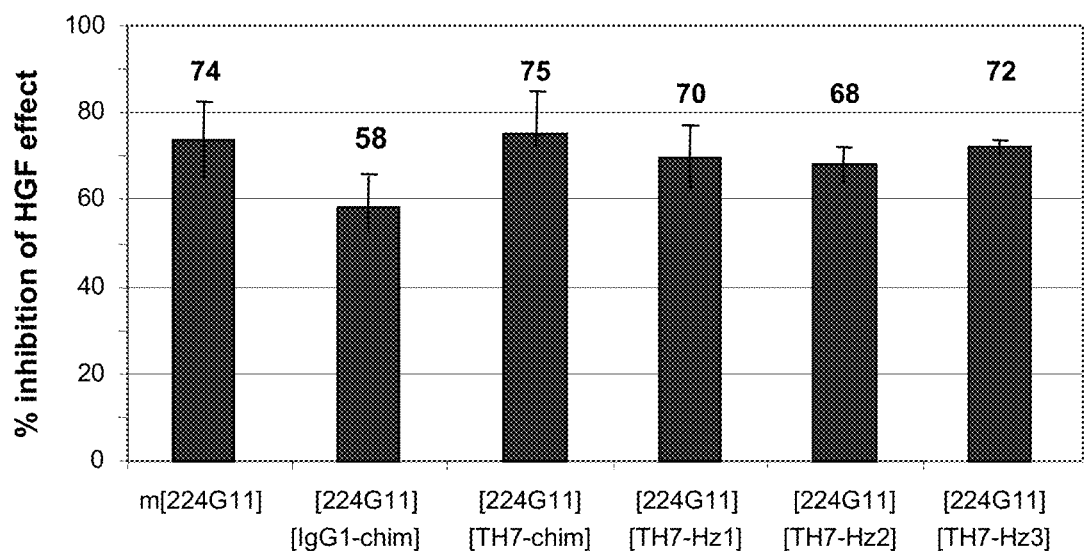
Figure 6A:
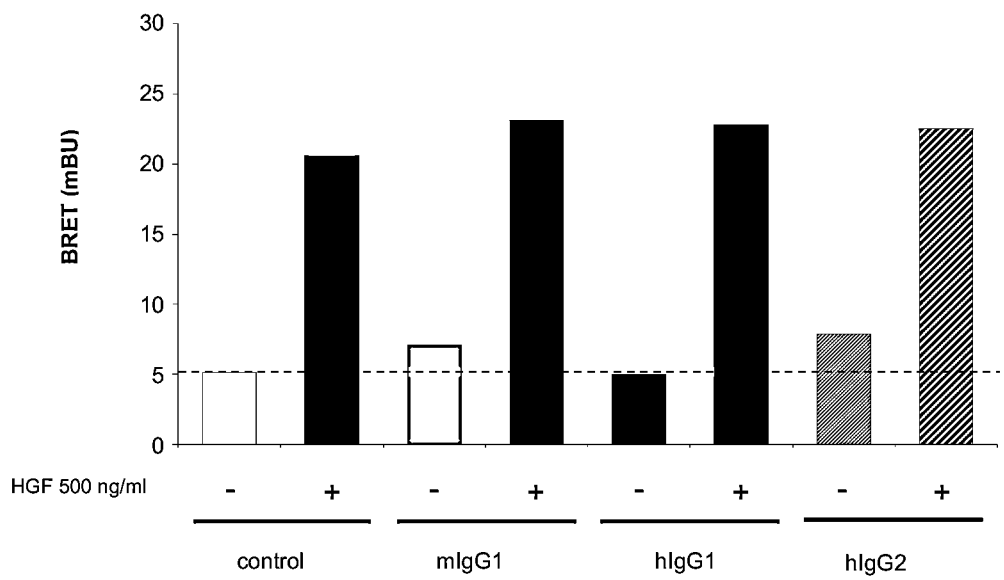
Figure 6B:
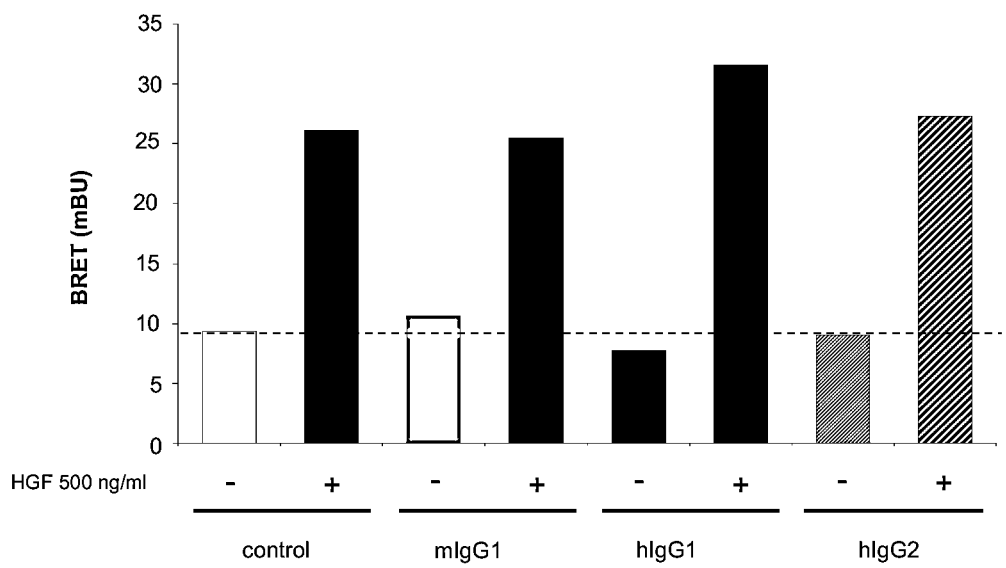

FIGS. 5A and 5B: Comparison between murine 224G11 Mab and chimeric and humanized 224G11 Mabs produced as an engineered hinge mutant TH7IgG1/kappa, on c-Met receptor phosphorylation on A549 cells.

FIG. 5A: agonist effect calculated as percentage versus maximal stimulation of c-Met phosphorylation by HGF [100 ng/ml].

FIG. 5B: antagonist effect calculated as percentage of inhibition of the maximal stimulation of c-Met phosphorylation by HGF [100 ng/ml].

FIGS. 6A and 6B, FIGS. 7A and 7B, FIGS. 8A and 8B, FIGS. 9A and 9B, FIGS. 10A and 10B: BRET models with Figures A: c-Met dimerization model; and Figures B: c-Met activation model.

Figure 11:
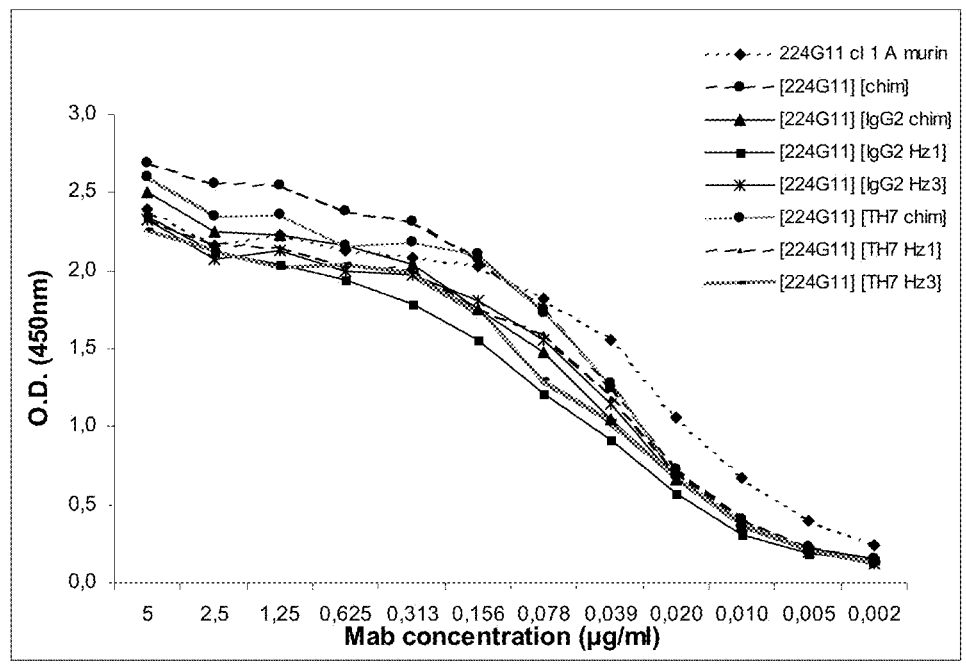
Figure 11:
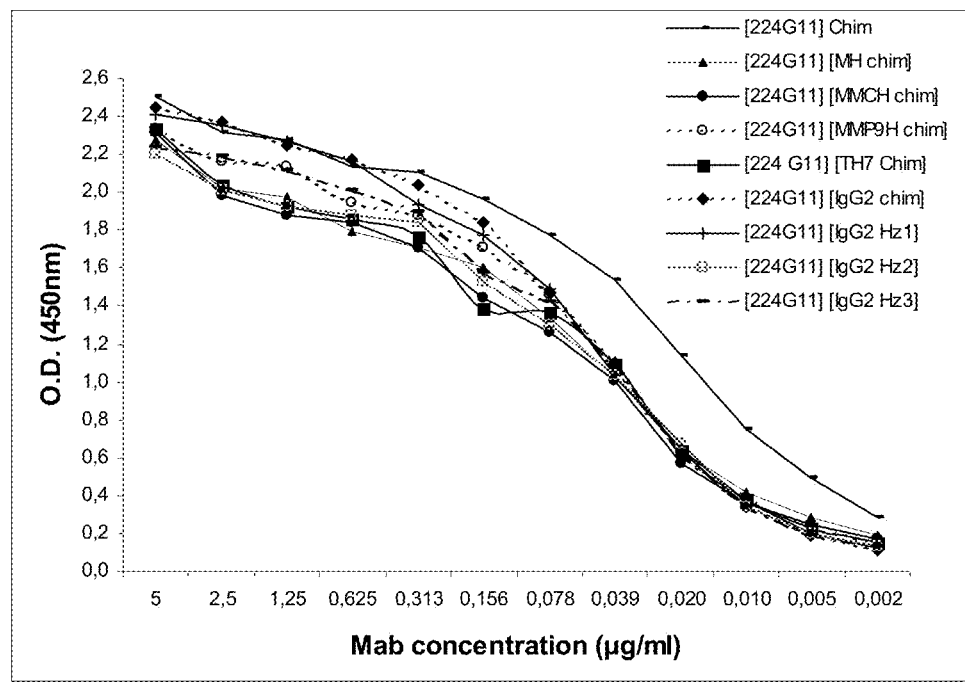

FIG. 11: c-Met recognition by chimeric and humanized 224G11 forms.

Figure 12:
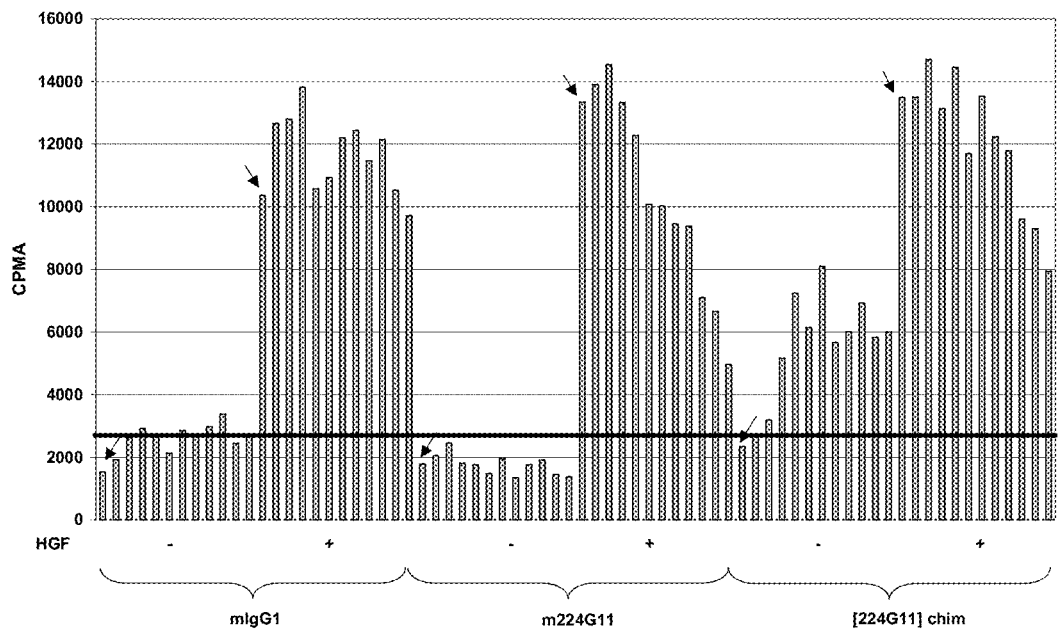

FIG. 12: Effect of murine and chimeric antibodies on HGF-induced proliferation of NCI-H441 cells in vitro. NCI-H441 cells were plated in serum-free medium. 24 hours after plating m224G11 and [224G11]chim were added either in absence or in presence of HGF. Black arrows indicate the wells plated with cells alone either in absence ⬈ or in presence ⬊ of HGF. A murine IgG1 (mIgG1) was introduced as an isotype control.

Figure 13:
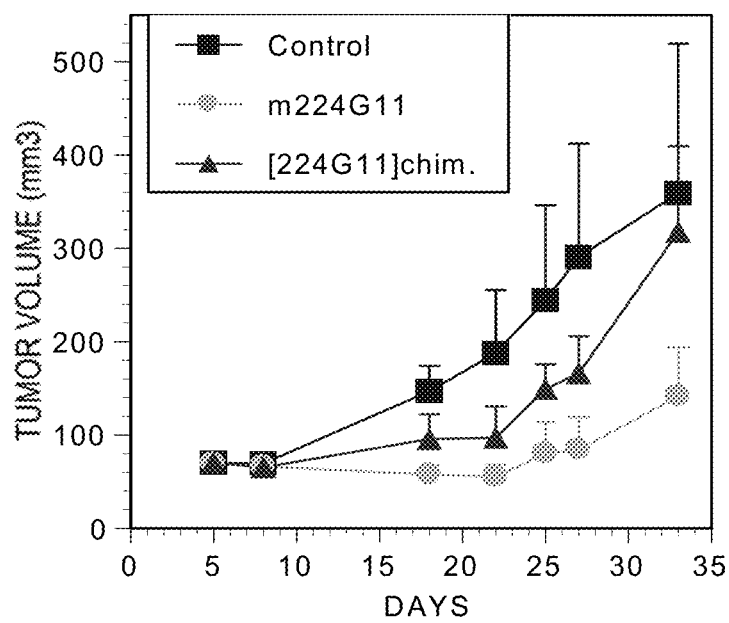

FIG. 13: In vivo comparison of murine and IgG1 chimeric 224G11 Mabs on the NCI-H441 xenograft model.

Figure 14A:
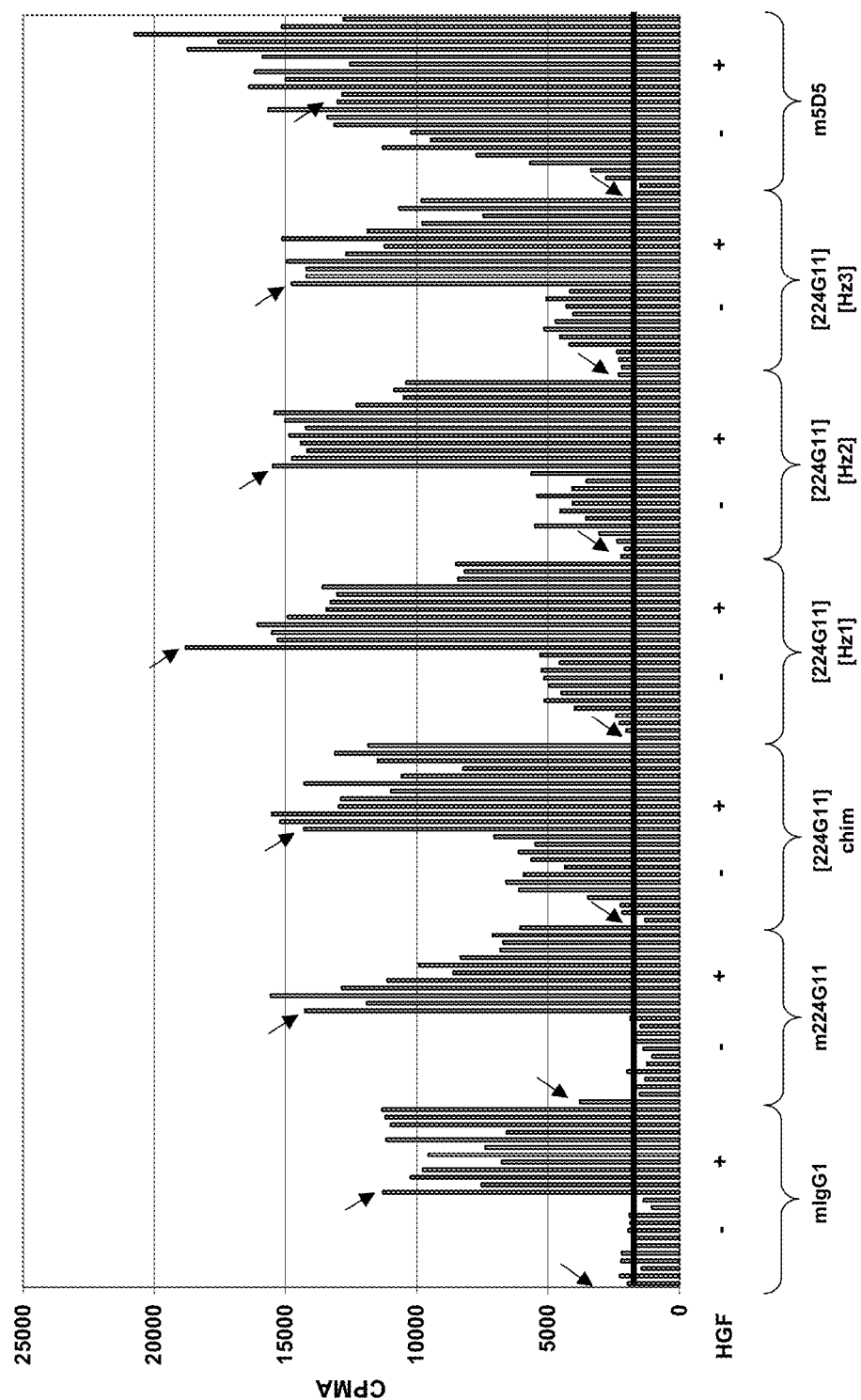
Figure 14B:
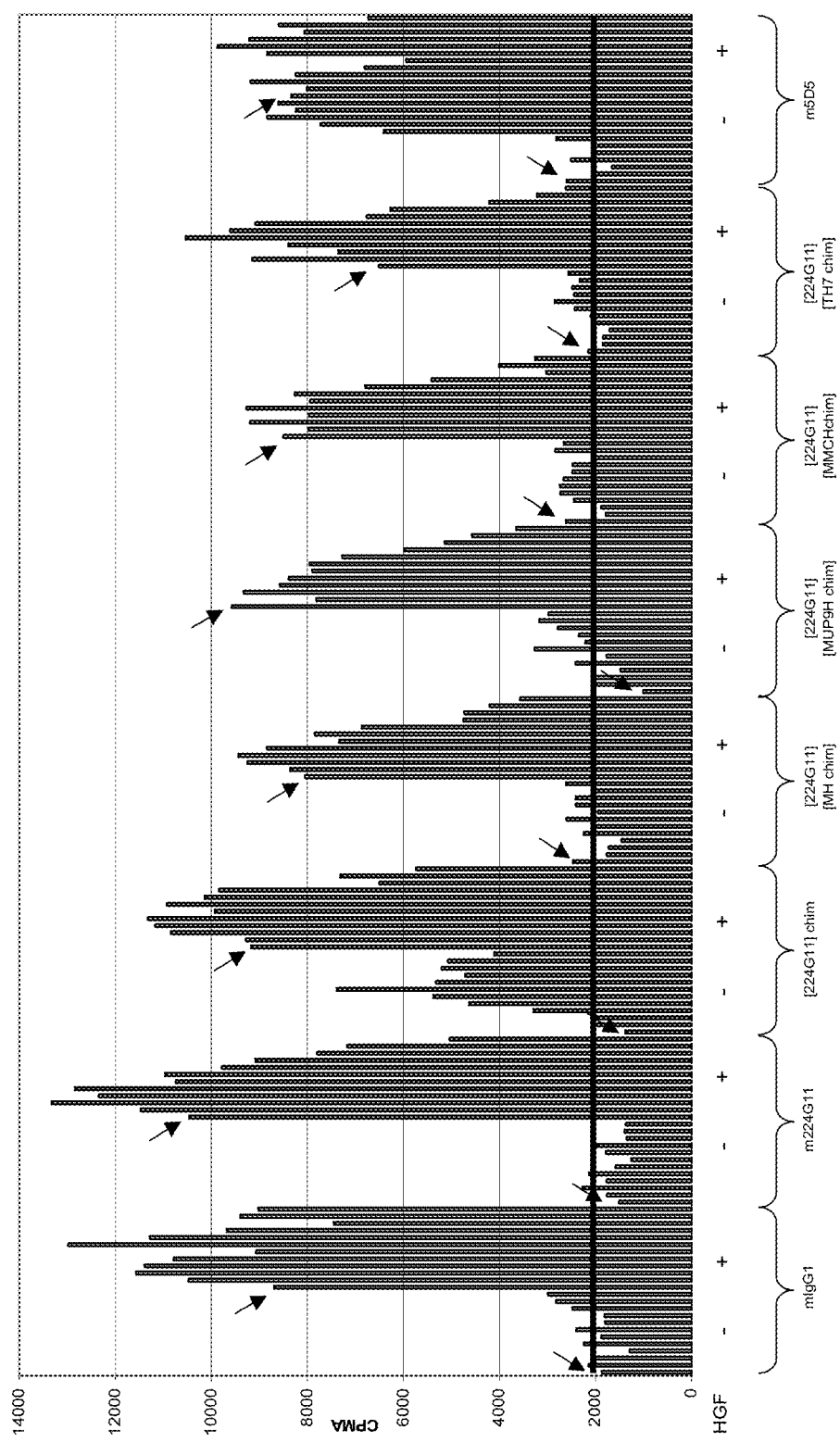

FIGS. 14A and 14B: Effect of the murine 224G11 Mab and of various chimeric and humanized versions of this antibody on HGF-induced proliferation of NCI-H441 cells in vitro. NCI-H441 cells were plated in serum-free medium. Twenty four hours after plating antibody to be tested were added either in absence or in presence of HGF. In panel (FIG. 14A), the murine m224G11, chimeric IgG1 [224G11]chim, humanized IgG1 [224G11] [Hz1], [224G11] [Hz2], [224G11] [Hz3] versions were shown. In panel (FIG. 14B), the murine m224G11 and various chimeric IgG1 forms ([224G11] chim, [224G11] [MH chim], [224G11] [MUP9H chim], [224G11] [MMCH chim], [224G11] [TH7 chim]) were presented. Black arrows indicate the wells plated with cells alone either in absence ⬈ or in presence ⬊ of HGF. A murine IgG1 was introduced as a negative control for agonist activity. The m5D5 was used as a dose-dependent full agonist control.

Figure 15:
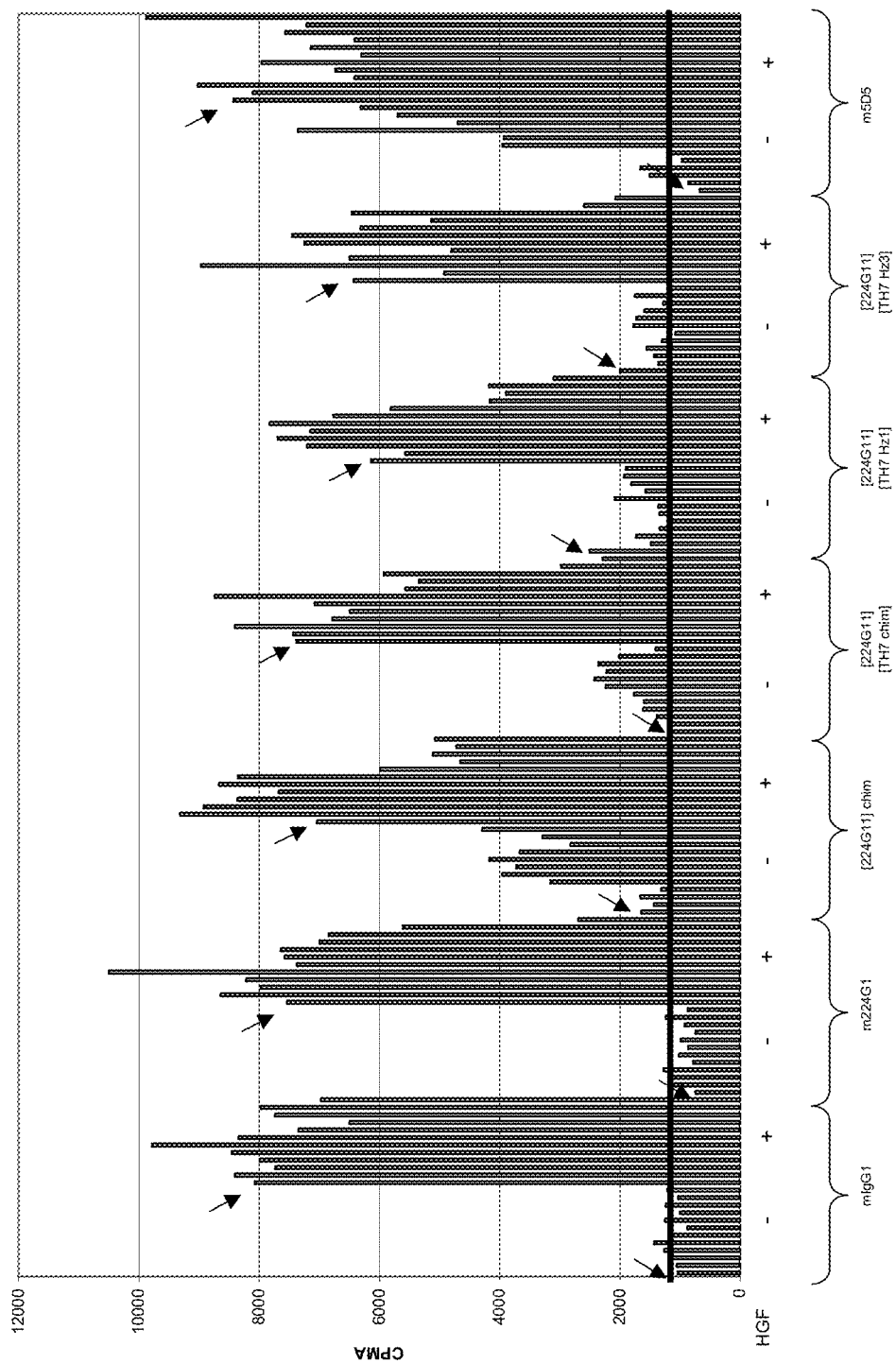

FIG. 15: Effect of the murine 224G11 Mab and of various chimeric and humanized versions of this antibody on HGF-induced proliferation of NCI-H441 cells in vitro. NCI-H441 cells were plated in serum-free medium. Twenty four hours after plating antibody to be tested were added either in absence or in presence of HGF. The murine m224G11, [224G11] chim, [224G11] [TH7 chim]) IgG1 chimeric forms and [224G11] [TH7 Hz1], [224G11] [TH7 Hz3],) were presented. Black arrows indicate the wells plated with cells alone either in absence ⬈ or in presence ⬊ of HGF. A murine IgG1 was introduced as a negative control for agonist activity. The m5D5 was used as a dose-dependent full agonist control.

Figure 16:
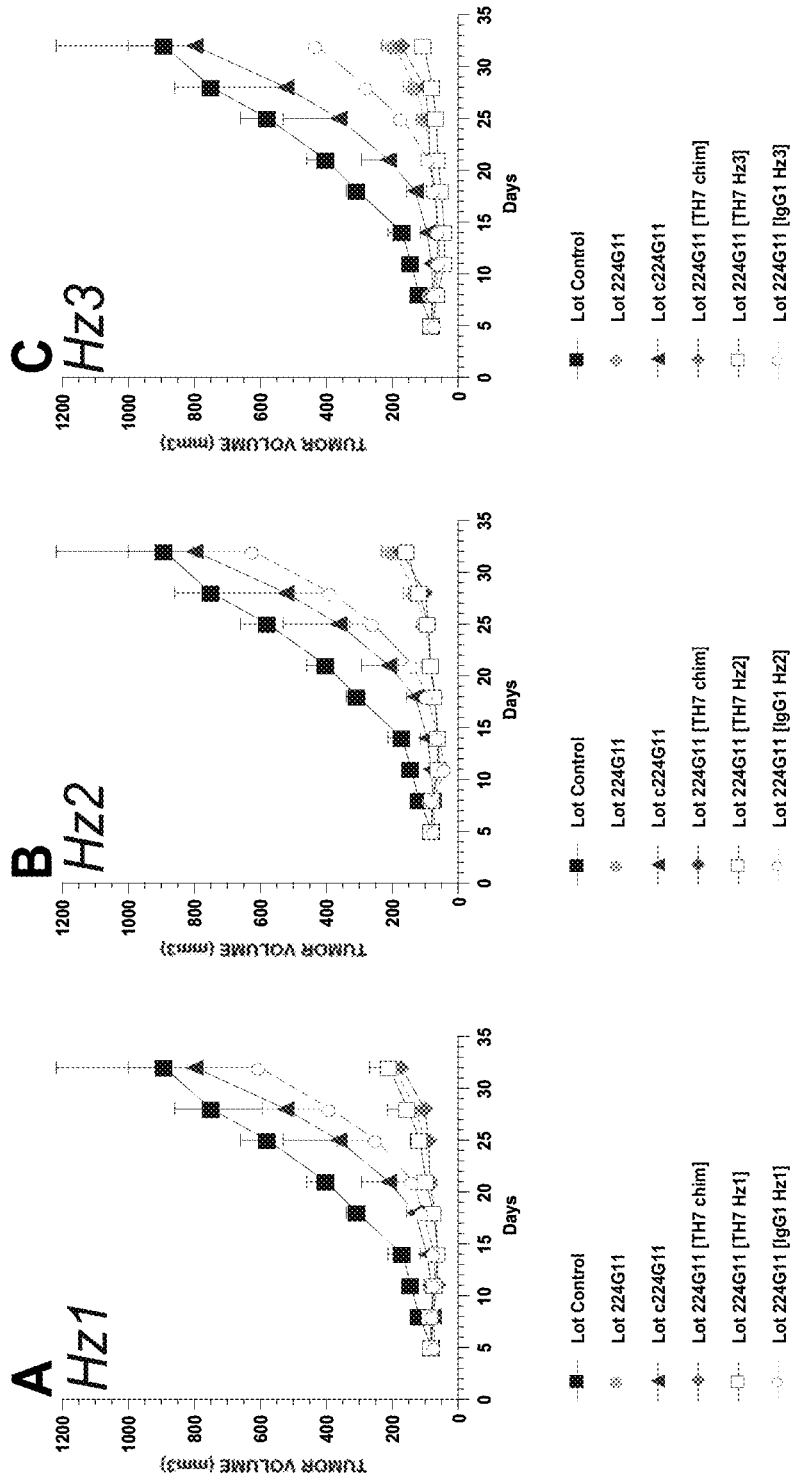

FIG. 16: In vivo comparison of murine, chimeric and humanized 224G11 Mabs on the NCI-H441 xenograft model.

Figure 17A:
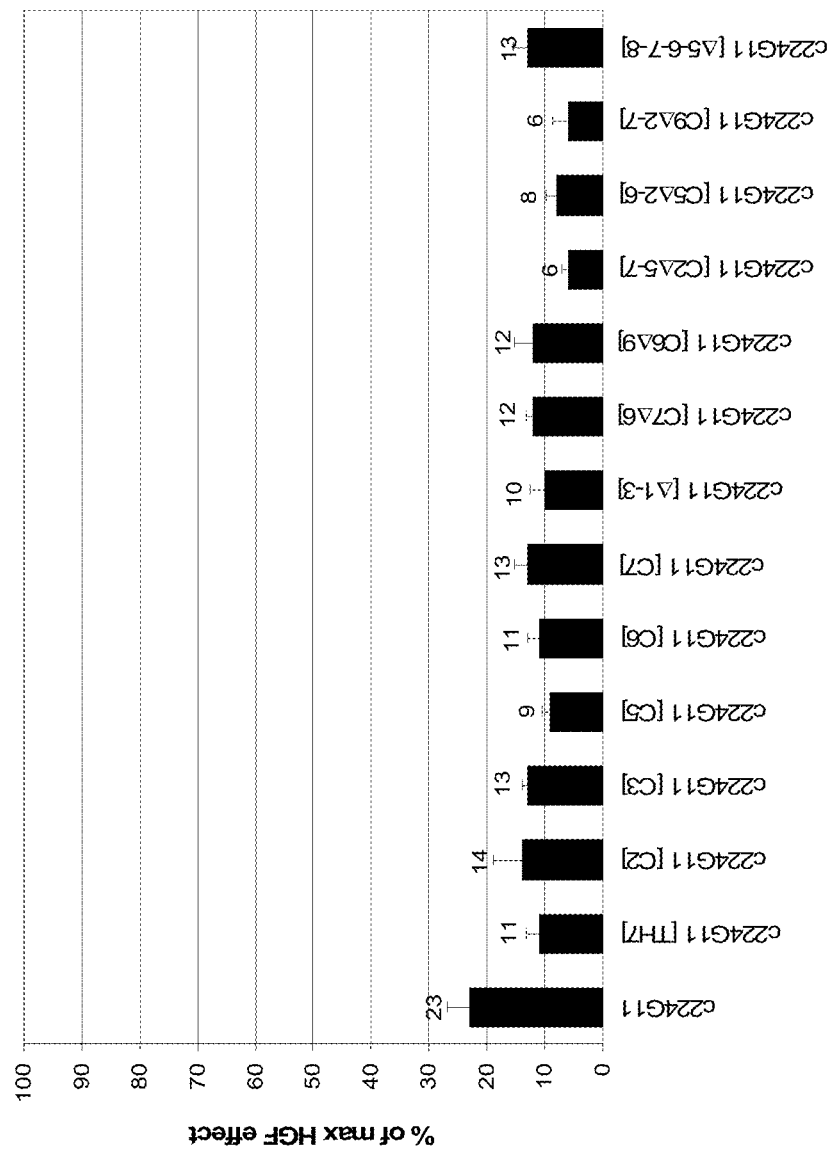

FIG. 17A: agonist effect calculated as percentage versus maximal stimulation of c-Met phosphorylation by HGF [100 ng/ml].

Figure 17B:
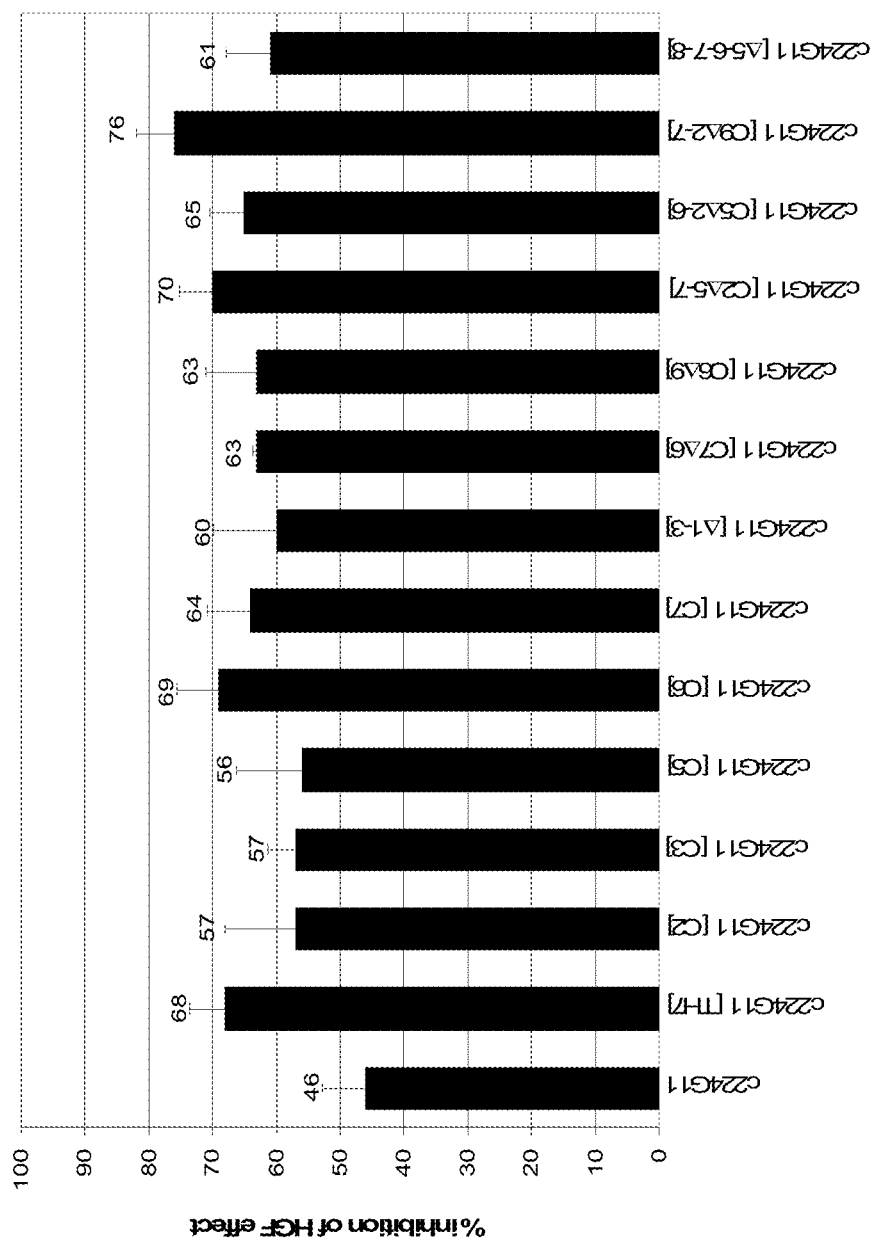

FIG. 17B: antagonist effect calculated as percentage of inhibition of the maximal stimulation of c-Met phosphorylation by HGF [100 ng/ml].

Figure 18:
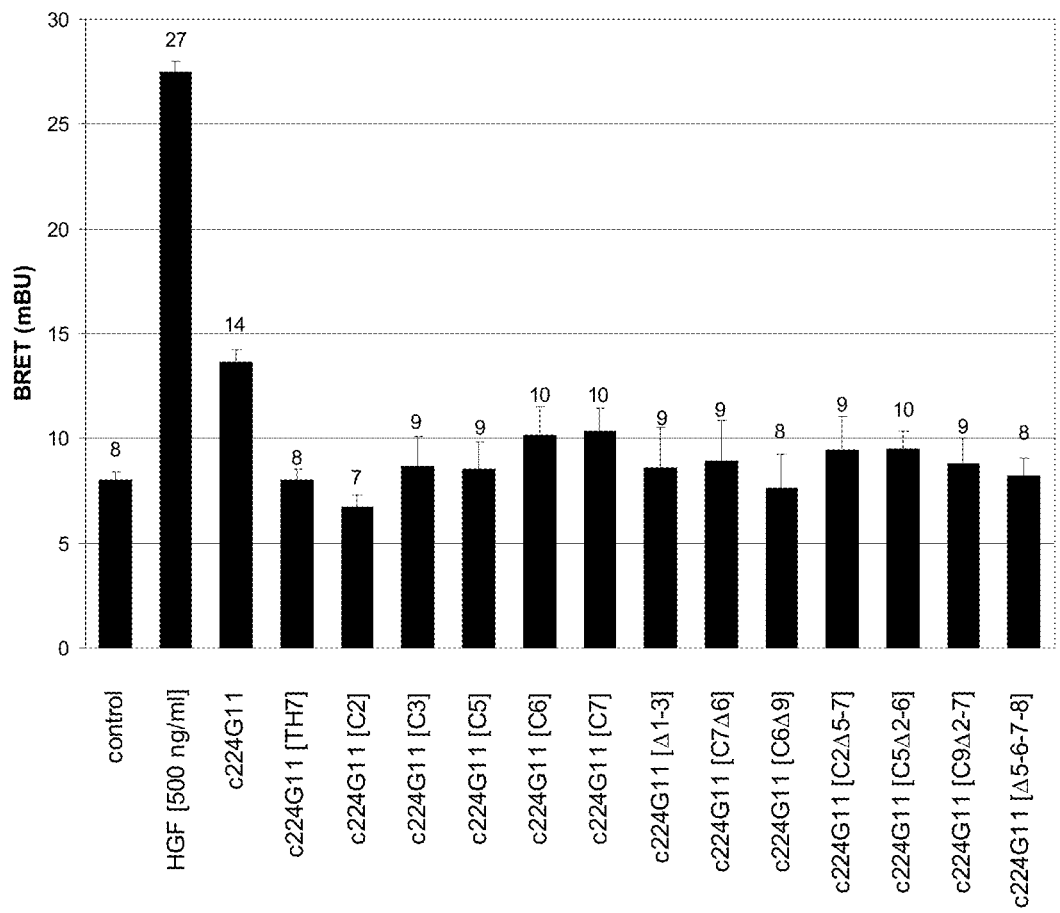

FIG. 18: BRET models with c-Met activation model.

Figure 19:
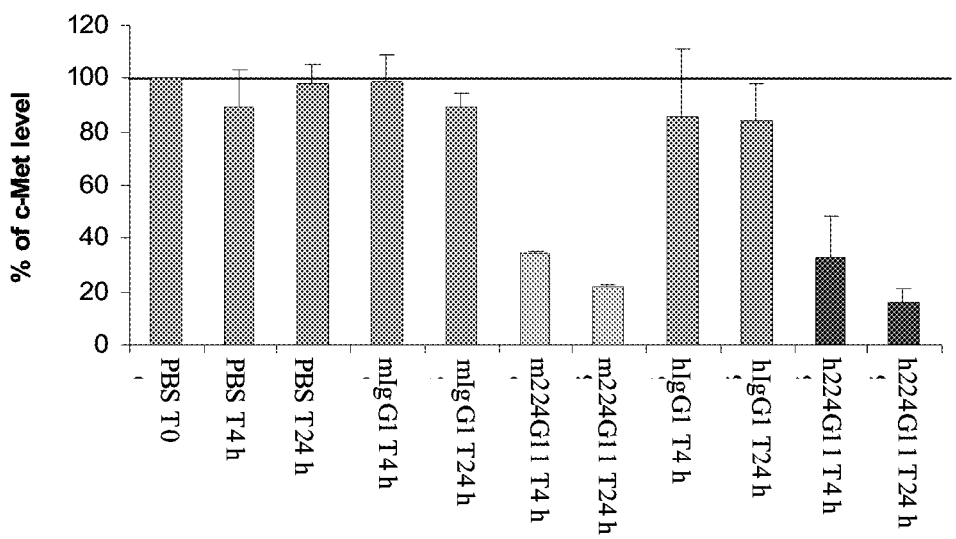
Figure 19:
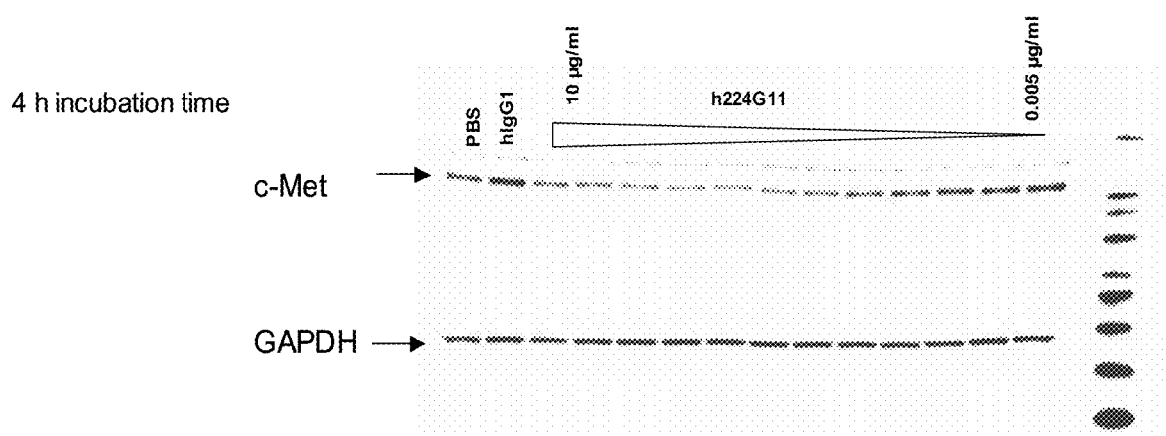

FIG. 19: Effect of m224G11 and h224G11 on c-Met degradation on A549 cells. A) Mean of 4 independent experiments+/−s.e.m. B) Western blot image representative of the 4 independent experiments performed.

Figure 20:
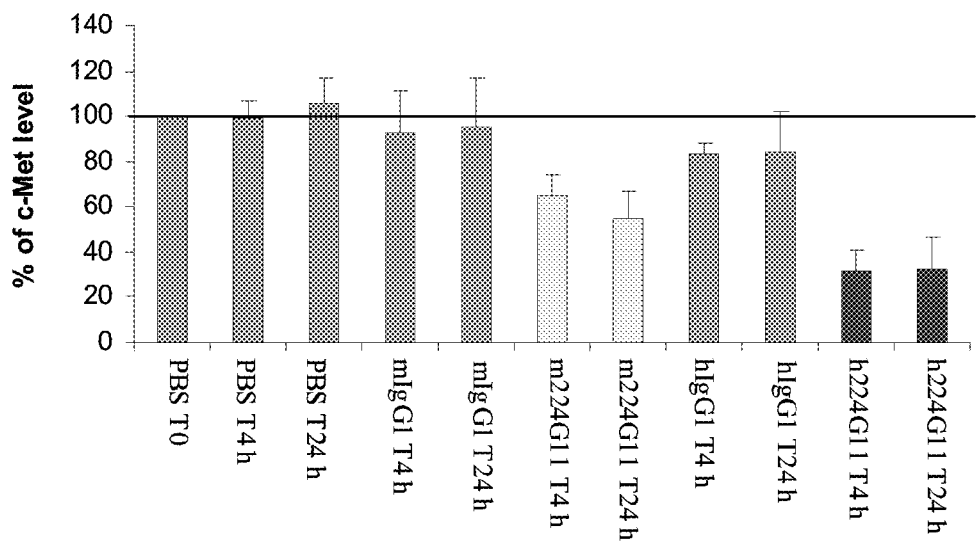
Figure 20:
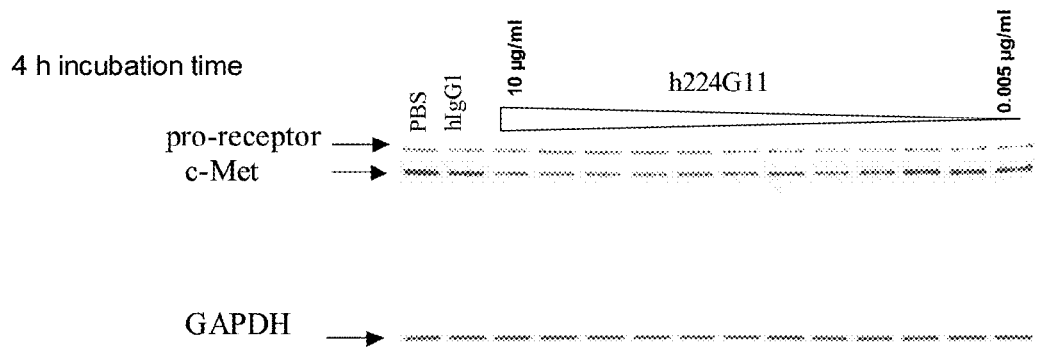

FIG. 20: Effect of m224G11 and h224G11 on c-Met degradation on NCI-H441 cells. A) Mean of 4 independent experiments+/−s.e.m. B) Western blot image representative of the 4 independent experiments performed.

Figure 21:
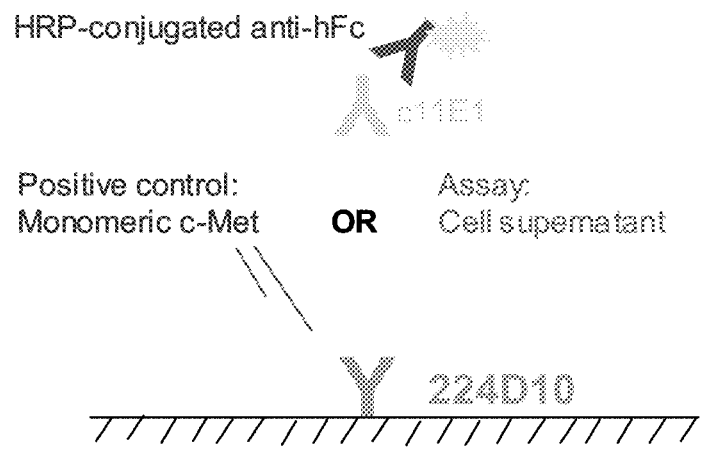

FIG. 21: Set up of an ELISA to evaluate c-Met shedding.

Figure 22:
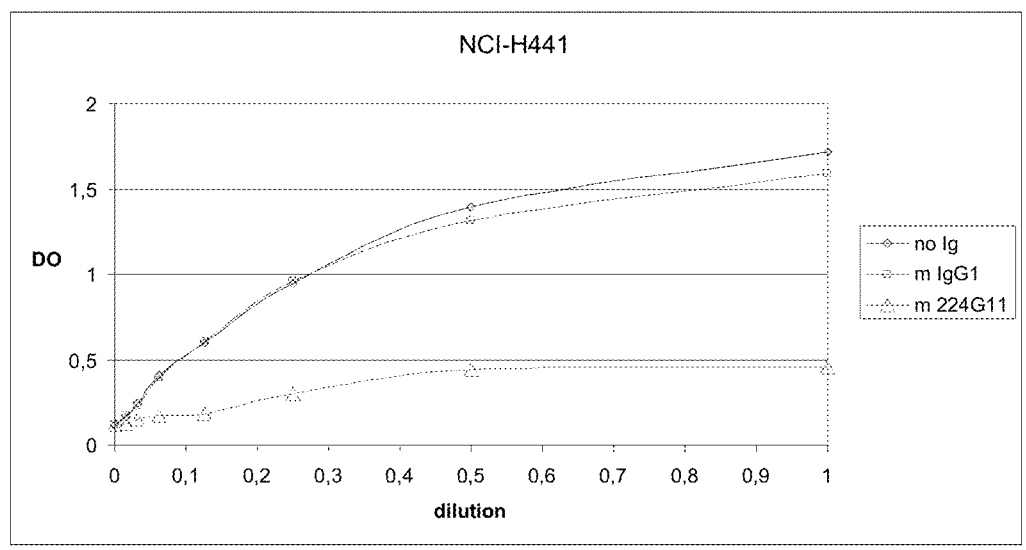

FIG. 22: In vitro evaluation of c-Met shedding on NCI-H441 cells treated for 5 days with m224G11. mIgG1 is an irrelevant antibody used as an isotype control.

Figure 23:
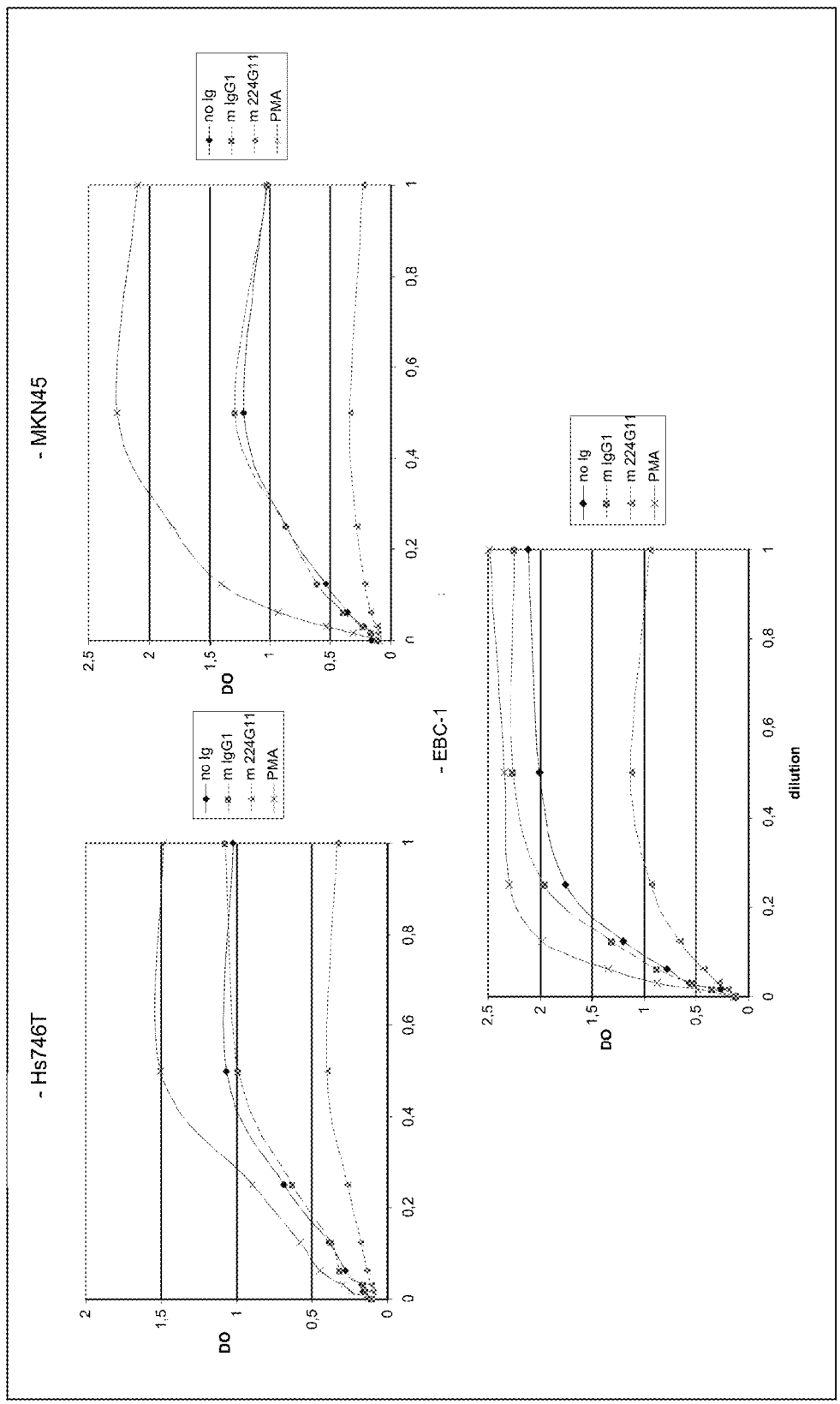

FIG. 23: In vitro evaluation of c-Met shedding on amplified Hs746T, MKN45 and EBC-1 cell lines treated for 5 days with m224G11. mIgG1 is an irrelevant antibody used as an isotype control. PMA is a shedding inducer used as a positive control.

Figure 24:
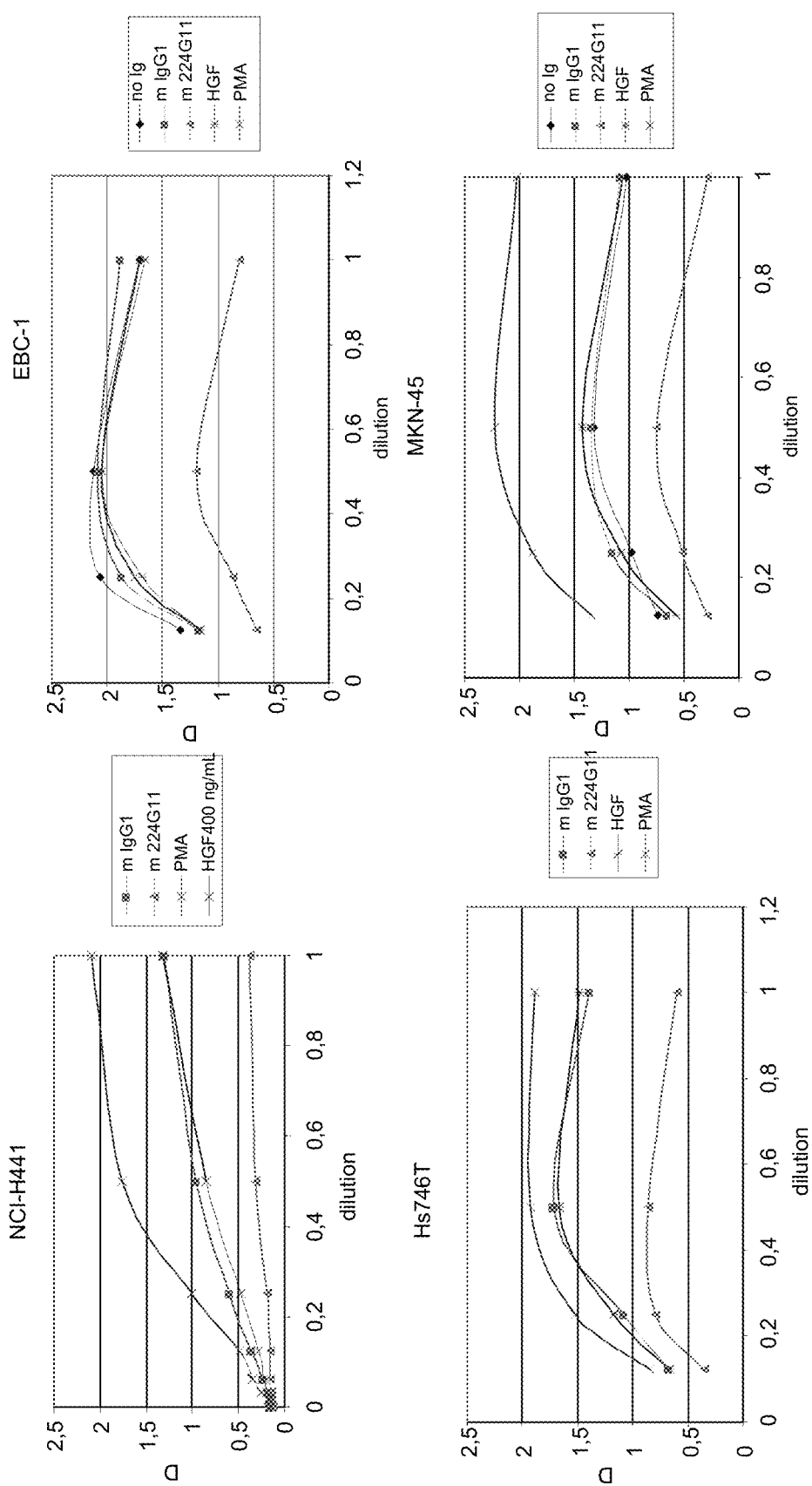

FIG. 24: In vitro evaluation of c-Met shedding on NCI-H441 and amplified Hs746T, MKN45 and EBC-1 cell lines treated for 5 days with m224G11. mIgG1 is an irrelevant antibody used as an isotype control. PMA is a shedding inducer used as a positive control.

Figure 25:
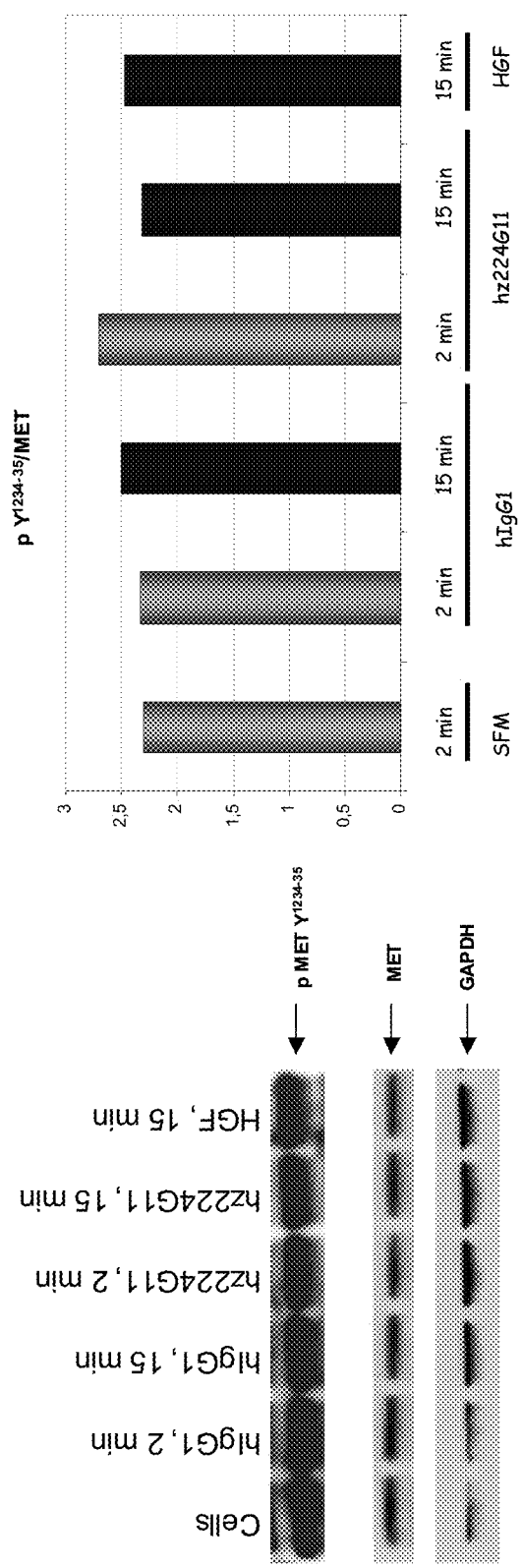

FIG. 25: Study of intrinsic phosphorylation of h224G11 on Hs746T cell line.

Figure 26:
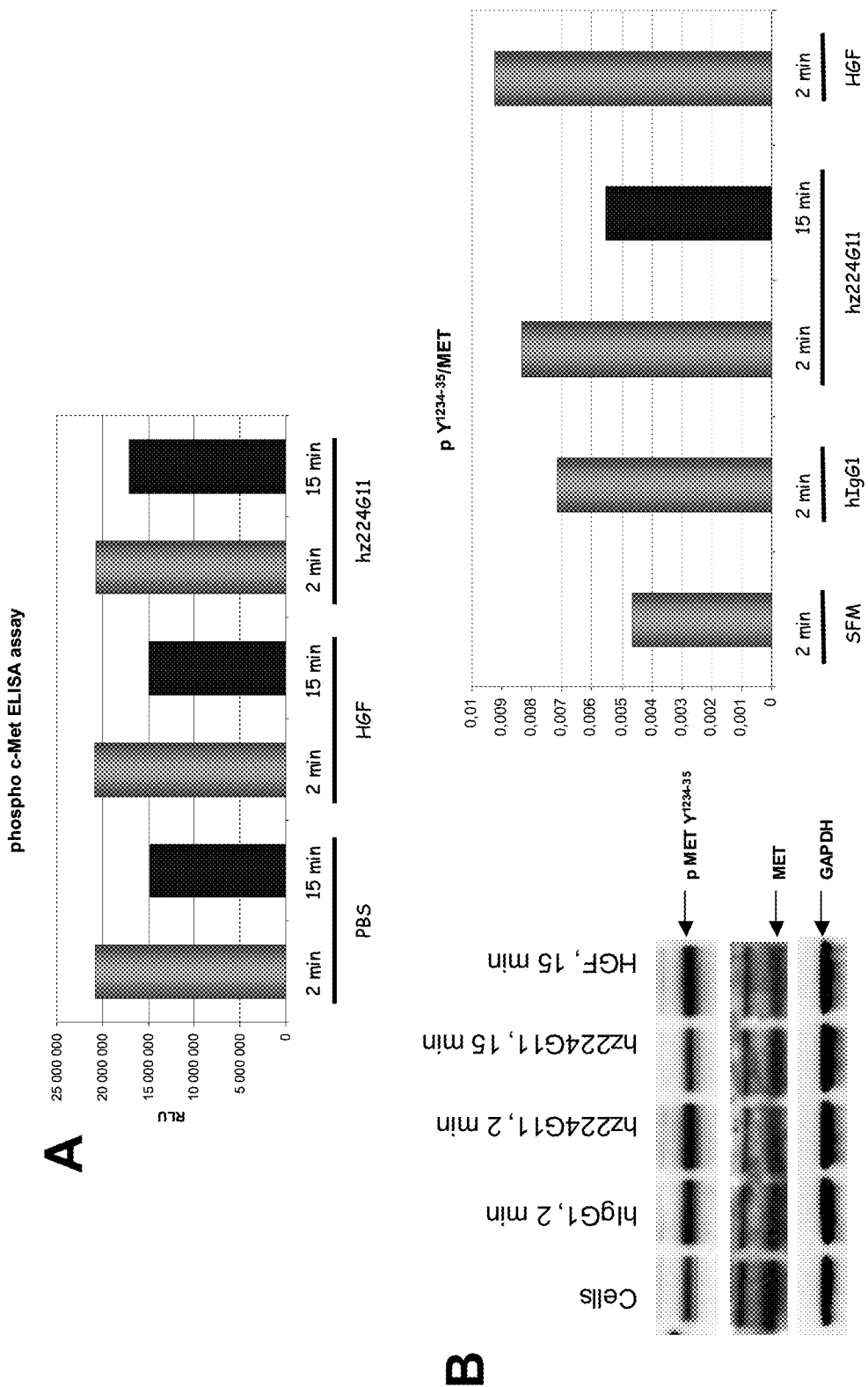

FIG. 26: Study of intrinsic phosphorylation of h224G11 on NCI-H441 cell line. A) phospho-ELISA and B) Western analysis.

Figure 27:
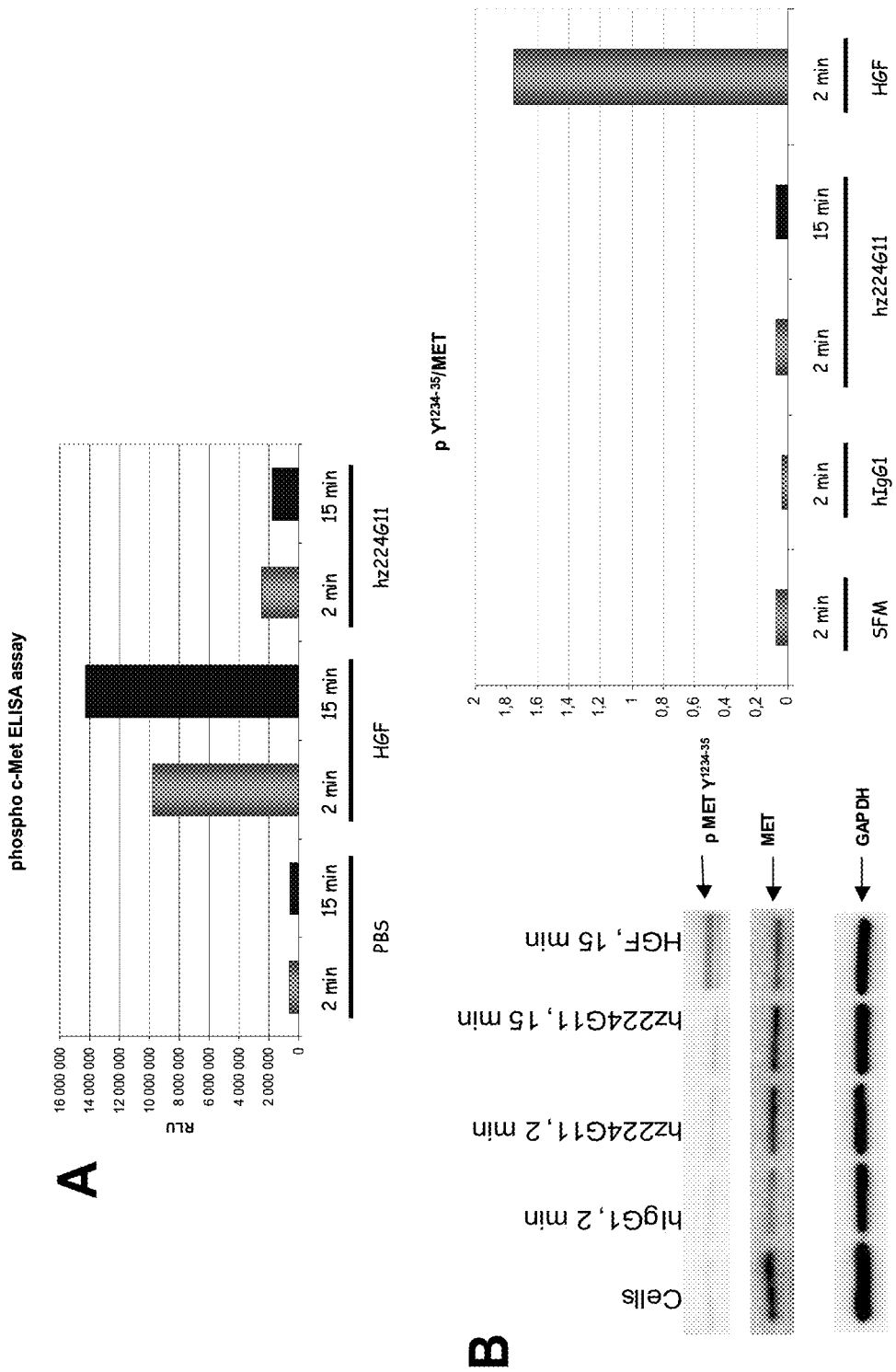

FIG. 27: Study of intrinsic phosphorylation of h224G11 on Hs578T cell line. A) phospho-ELISA and B) Western analysis.

Figure 28:
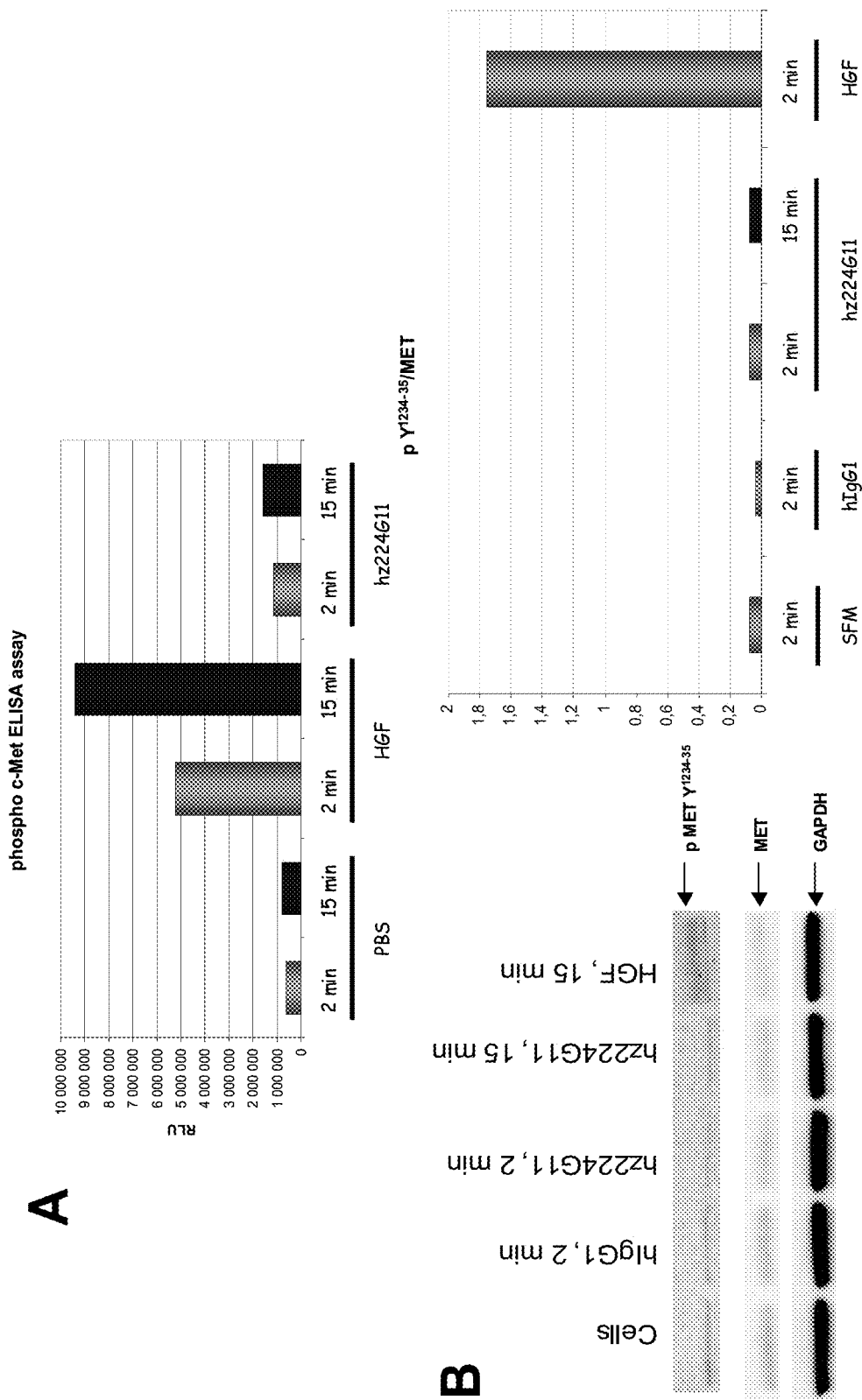

FIG. 28: Study of intrinsic phosphorylation of h224G11 on NCI-H125 cell line. A) phospho-ELISA and B) Western analysis.

Figure 29:
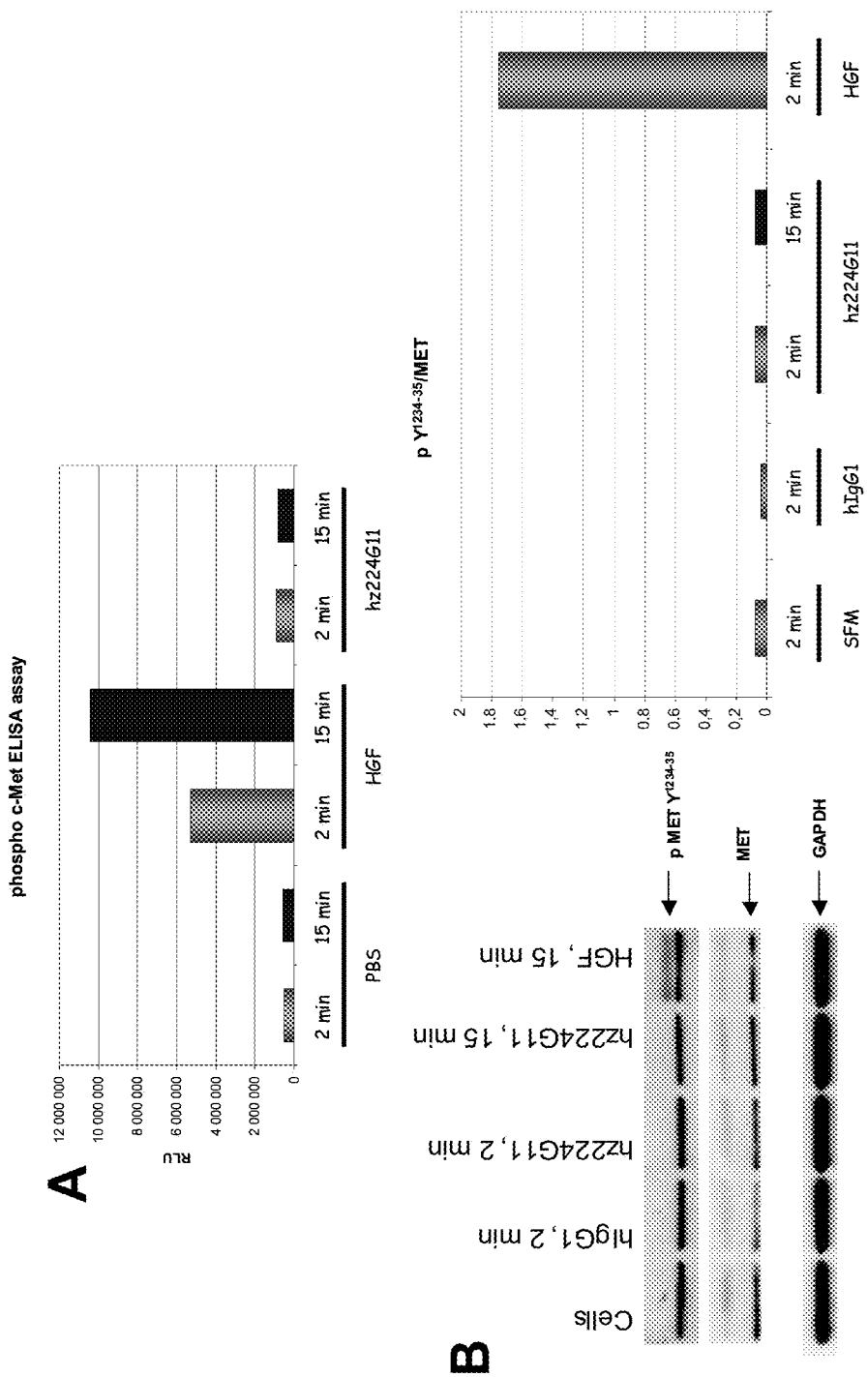

FIG. 29: Study of intrinsic phosphorylation of h224G11 on T98G cell line. A) phospho-ELISA and B) Western analysis.

Figure 30:
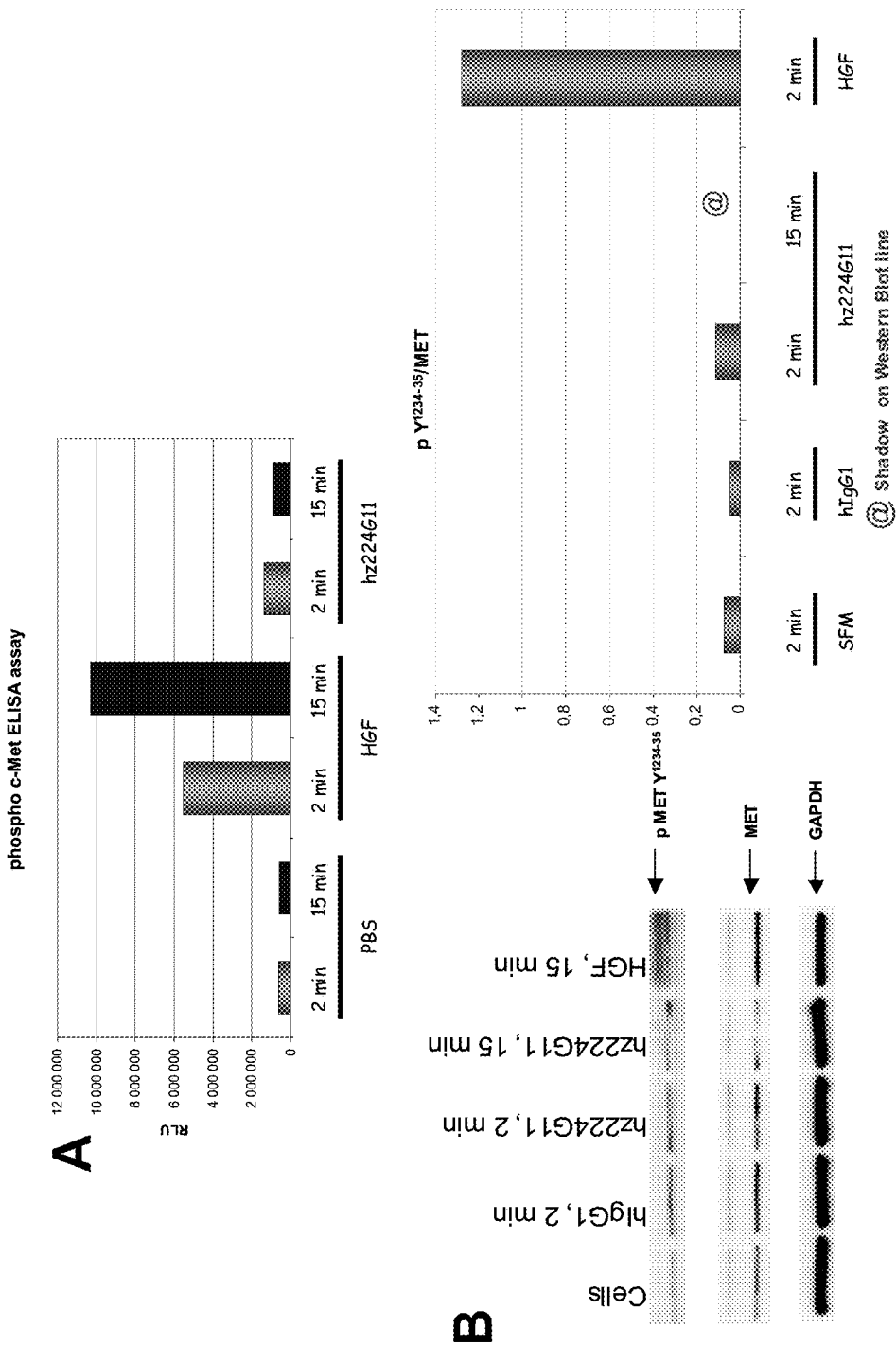

FIG. 30: Study of intrinsic phosphorylation of h224G11 on MDA-MB-231 cell line. A) phospho-ELISA and B) Western analysis.

Figure 31:
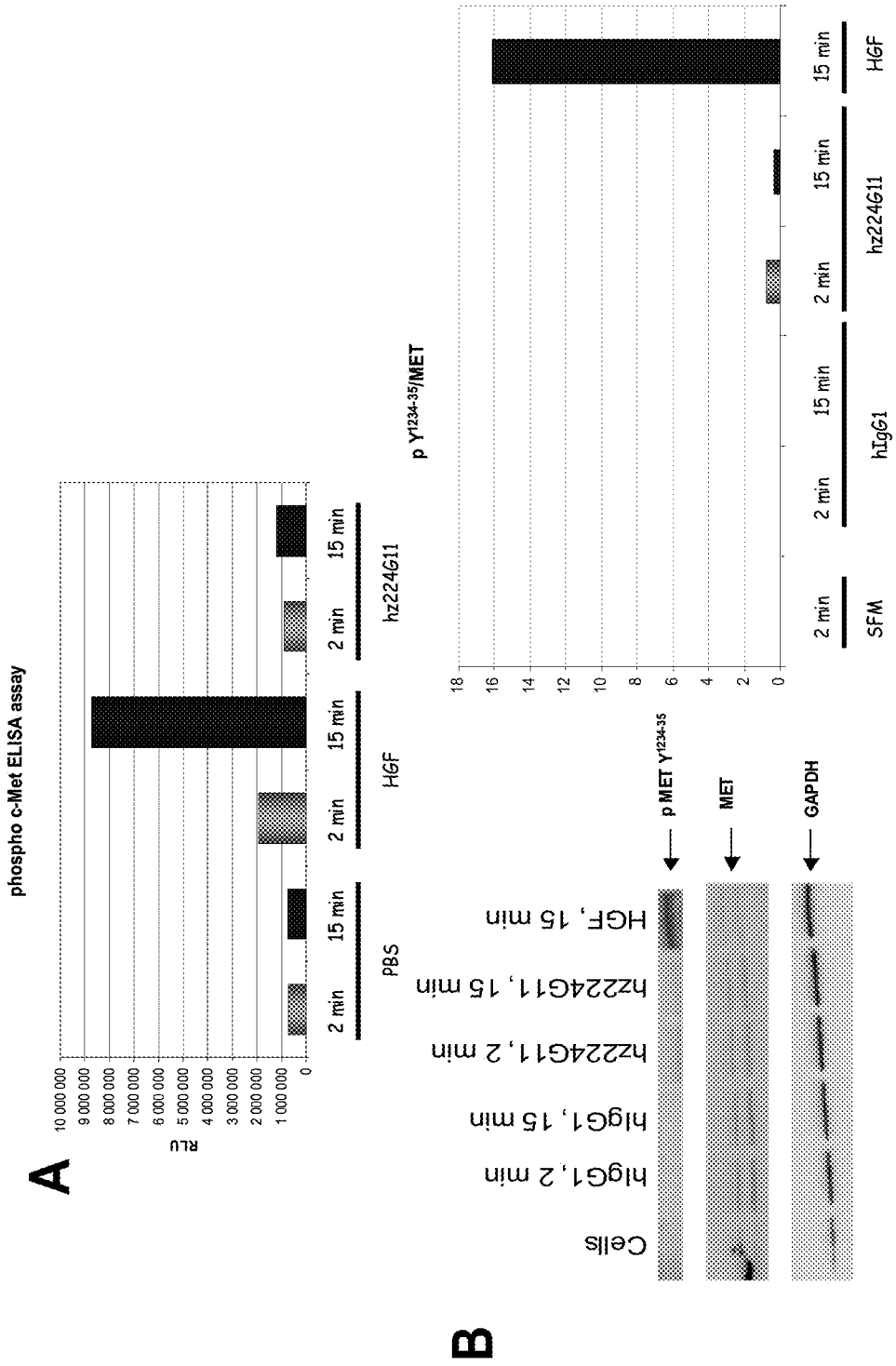

FIG. 31: Study of intrinsic phosphorylation of h224G11 on PC3 cell line. A) phospho-ELISA and B) Western analysis.

Figure 32:
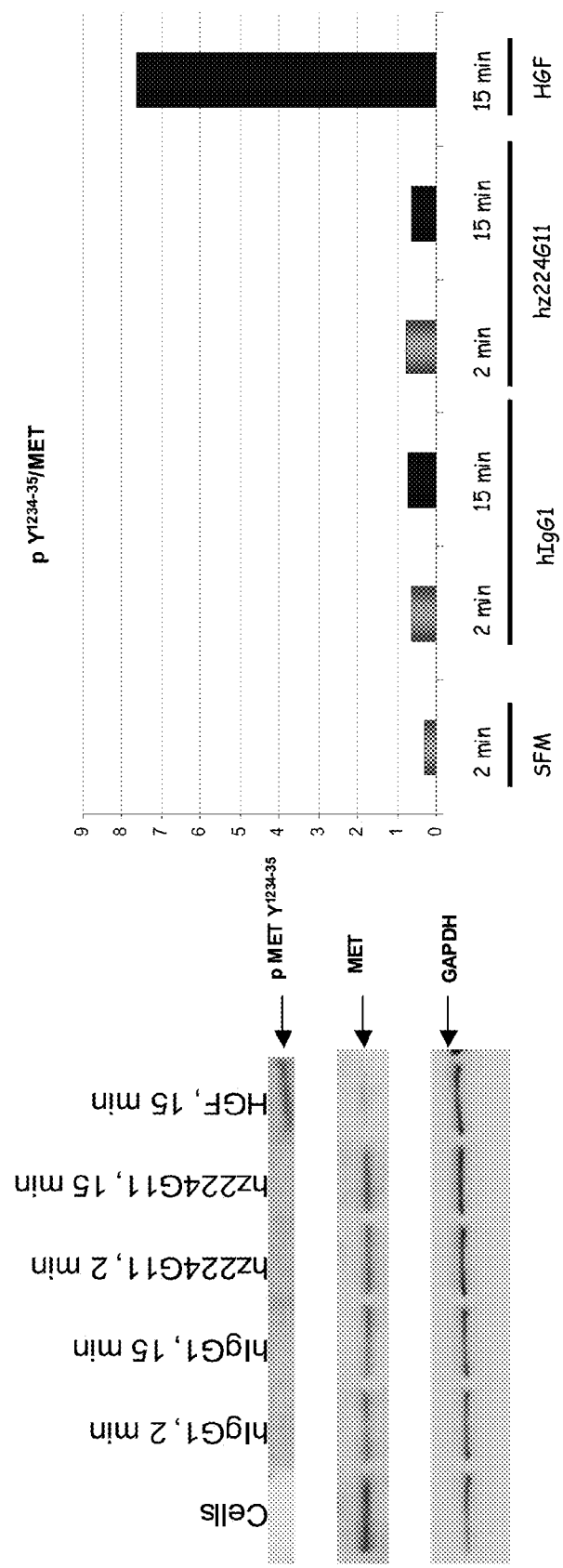

FIG. 32: Study of intrinsic phosphorylation of h224G11 on HUVEC cells.

Figure 33:
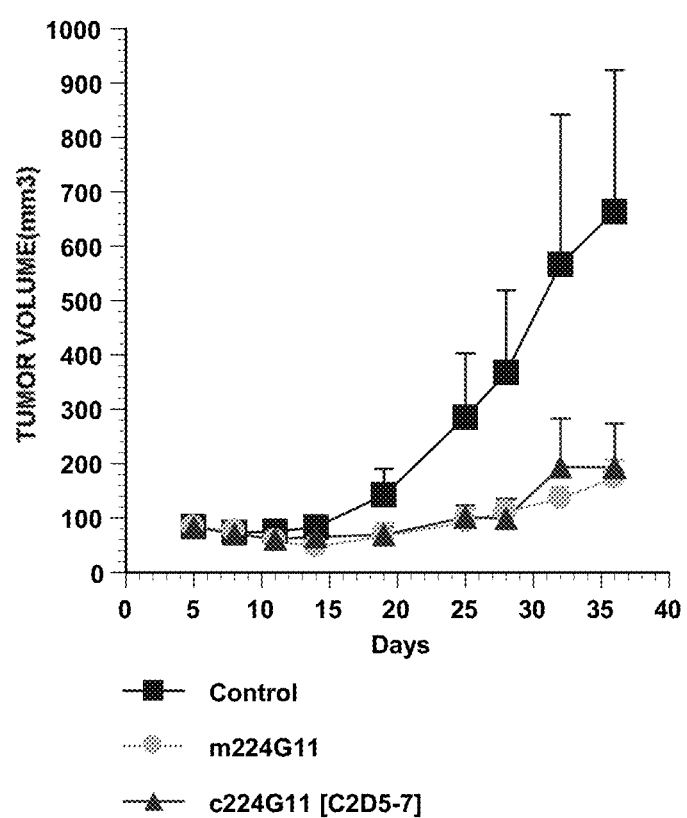

FIG. 33: In vivo comparison of the wild type murine 224G11 antibody with a chimeric hinge-engineered 224G11 [C2D5-7] Mabs on the NCI-H441 xenograft model.

Figure 34:
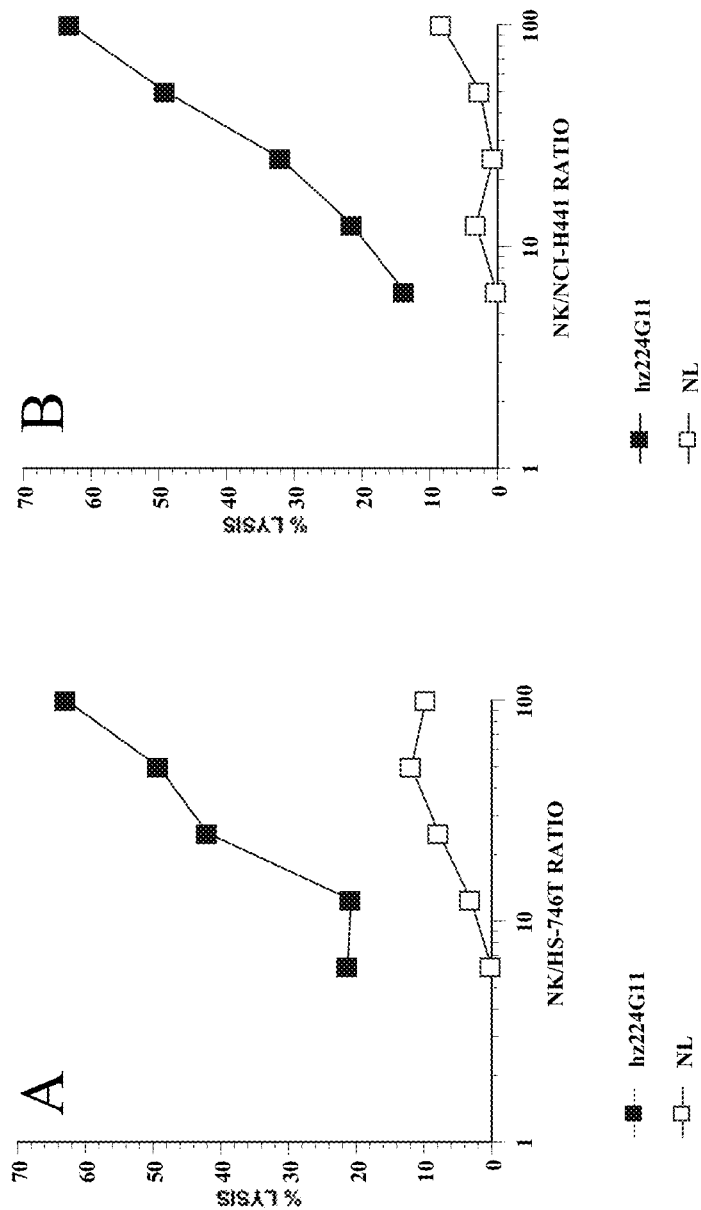

FIG. 34: ADCC induction by h224G11 on both Hs746T and NCI-H441 cells. $^{51}$Cr-labeled Hs746T (A) or NCI-H441 (B) cells loaded (bold squares) or not (empty squares) with h224G11 were mixed with different ratio of human NK cells and incubated for 4 hr. Cells were harvested and cpm of $^{51}$Cr released by lysis was counted. The results are plotted as percentage of lysis against the effector/target cell ratio. NL for non loaded cells.

Figure 35:
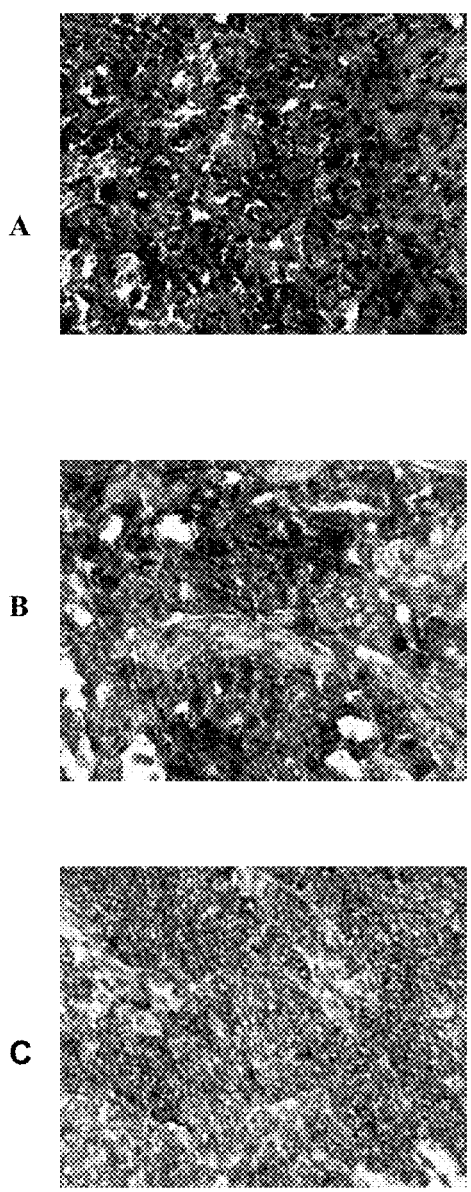

FIG. 35: h224G11 staining in tumor xenograft which expressed various level of c-Met (A: Hs746T amplified cell line for c-Met, B: NCI-H441 high level of c-Met expression and C: MCF-7 low level of c-Met).

Figure 36:
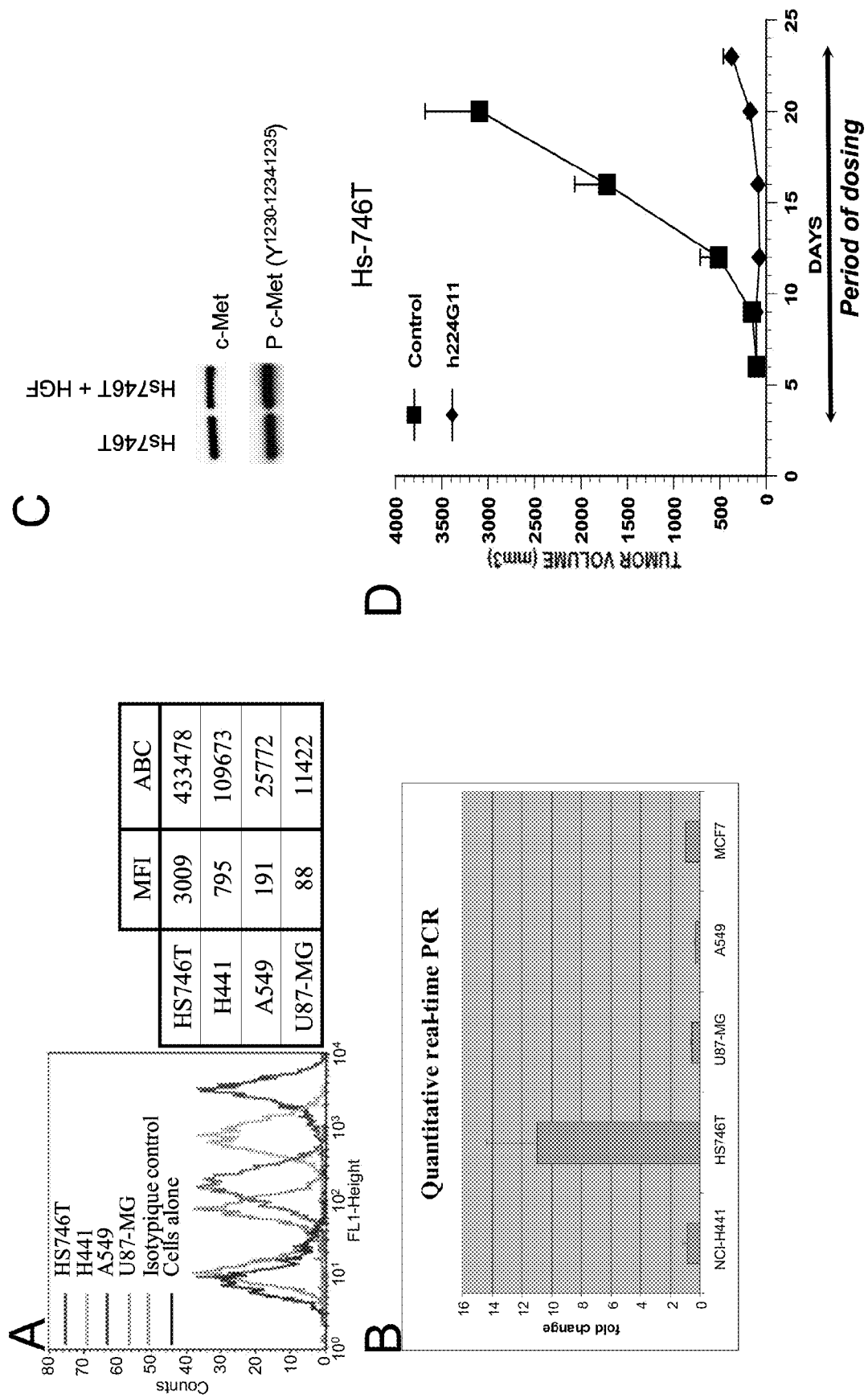

FIG. 36: In vivo activity of h224G11 on the Hs746T xenograft model. A) FACS analysis showing c-Met expression on Hs746T cells compared to other cell lines expressing c-Met. B) QRTPCR showing c-Met amplification. C) c-Met phosphorylation in absence or in presence of HGF. D) In vivo model.

Figure 37:
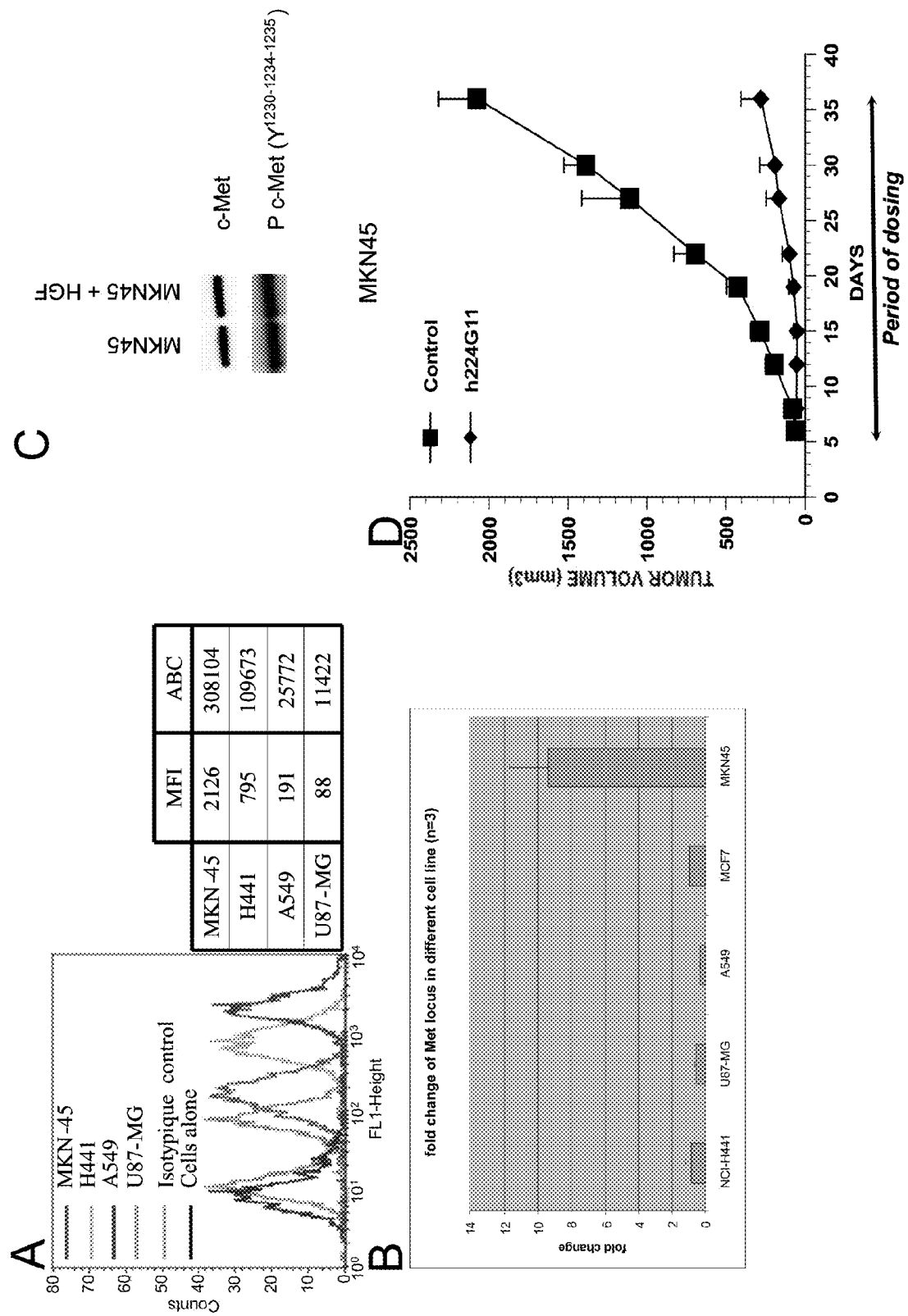

FIG. 37: In vivo activity of h224G11 on the MKN-45 xenograft model. A) FACS analysis showing c-Met expression on MKN45 cells compared to other cell lines expressing c-Met. B) QRTPCR showing c-Met amplification. C) c-Met phosphorylation in absence or in presence of HGF. D) In vivo model.

Figure 38:
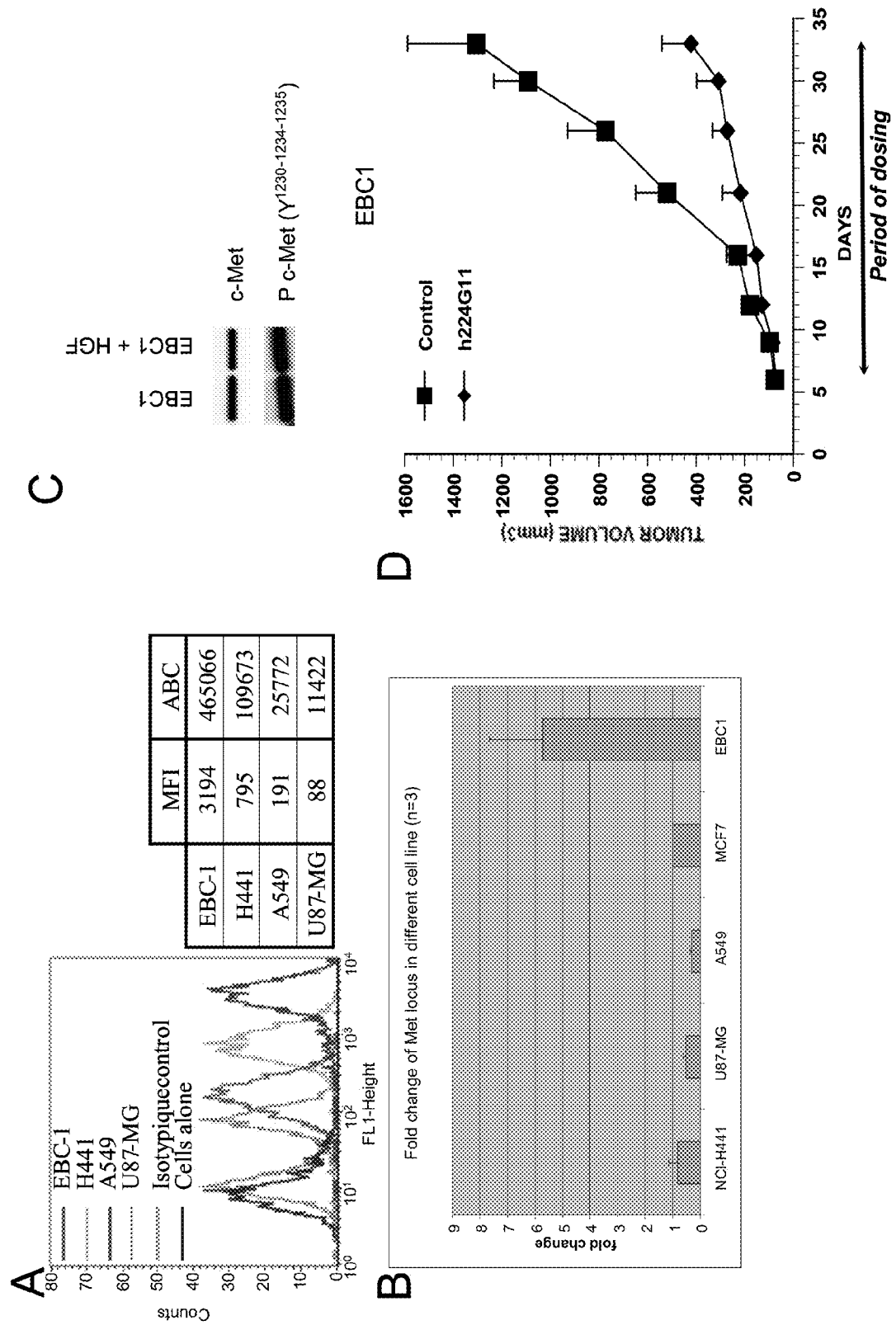

FIG. 38: In vivo activity of h224G11 on the EBC-1 xenograft model. A) FACS analysis showing c-Met expression on EBC-1 cells compared to other cell lines expressing c-Met. B) QRTPCR showing c-Met amplification. C) c-Met phosphorylation in absence or in presence of HGF. D) In vivo model.

Figure 39:
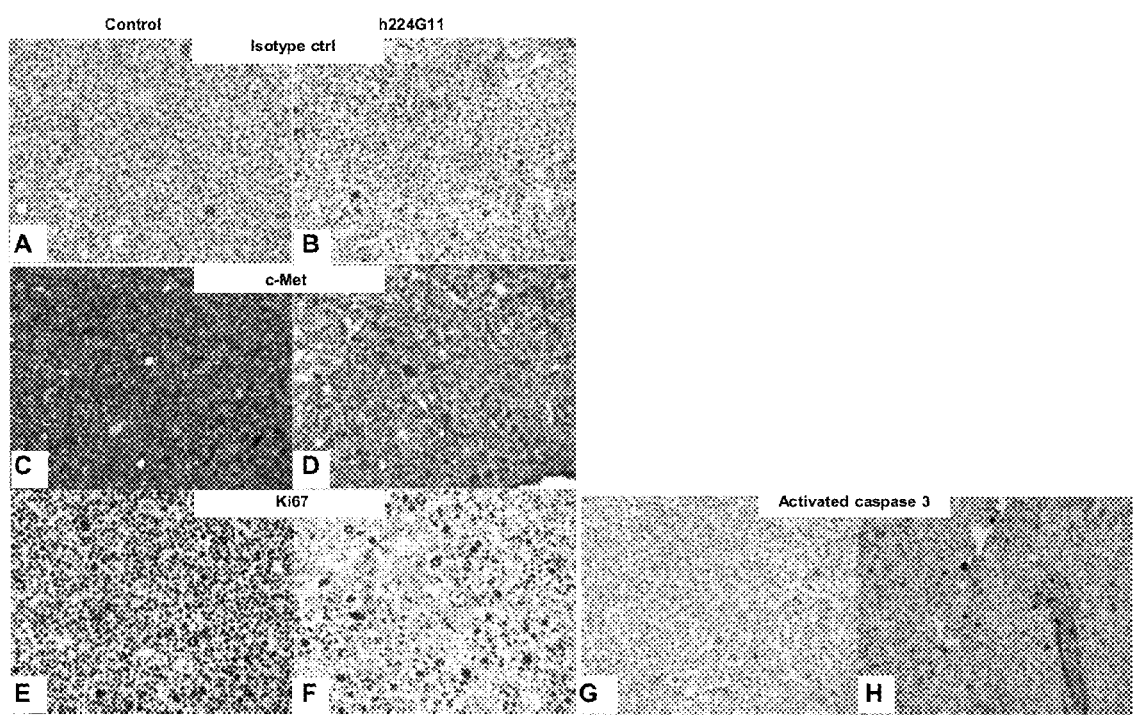

FIG. 39: IHC examination of Hs746T tumors in mice treated with the h224G11 Mab compared to control-treated tumors. (A) and (B) panels correspond to isotype control antibodies. (C) and (D) show the expression of c-Met on tumor sections from mice treated with PBS or h224G11 respectively demonstrating that a chronic treatment with h224G11 induced a dramatic down regulation of c-Met. Ki-67 staining is significantly decreased on treated tumors (F) compared to PBS control samples (E). A significant apoptosis was observed in tumor treated with h224G11 (H) while no apoptosis was noticed in control tumors (G).

EXAMPLE 1

Generation of Antibodies Against c-Met

To generate anti-c-Met antibodies 8 weeks old BALB/c mice were immunized either 3 to 5 times subcutaneously with a CHO transfected cell line that express c-Met on its plasma membrane ($20 \times 10^6$ cells/dose/mouse) or 2 to 3 times with a c-Met extracellular domain fusion protein (10-15 µg/dose/mouse) (R&D Systems, Catalog #358MT) or fragments of this recombinant protein mixed with complete Freund adjuvant for the first immunization and incomplete Freund adjuvant for the following ones. Mixed protocols in which mice received both CHO-cMet cells and recombinant proteins were also performed. Three days before cell fusion, mice were boosted i.p. or i.v. with the recombinant protein or fragments. Then spleens of mice were collected and fused to SP2/0-Ag14 myeloma cells (ATCC) and subjected to HAT selection. Four fusions were performed. In general, for the preparation of monoclonal antibodies or their functional fragments, especially of murine origin, it is possible to refer to techniques which are described in particular in the manual "Antibodies" (Harlow and Lane, Antibodies: A Laboratory Manual, Cold Spring Harbor Laboratory, Cold Spring Harbor N.Y., pp. 726, 1988) or to the technique of preparation of hybridomas described by Kohler and Milstein (Nature, 256: 495-497, 1975).

Obtained hybridomas were initially screened by ELISA on the c-Met recombinant protein and then by FACS analysis on A549 NSCLC, BxPC3 pancreatic, and U87-MG glioblastoma cell lines to be sure that the produced antibodies will be able to also recognize the native receptor on tumor cells. Positive reactors on these 2 tests were amplified, cloned and a set of hybridomas was recovered, purified and screened for its ability to inhibit in vitro cell proliferation in the BxPC3 model.

For that purpose 50 000 BxPC3 cells were plated in 96 well plates in RPMI medium, 2 mM L. Glutamine, without SVF. 24 hours after plating, antibodies to be tested were added at a final concentration ranging from 0.0097 to 40 ng/ml 60 min before addition of 100 ng/ml of hHGF. After 3 days, cells were pulsed with 0.5 µCi of [$^3$H]thymidine for 16 hours. The magnitude of [$^3$H]thymidine incorporated into trichloroacetic acid-insoluble DNA was quantified by liquid scintillation counting. Results were expressed as raw data to really evaluate the intrinsic agonistic effect of each Mab.

Then antibodies inhibiting at least 50% cell proliferation were evaluated for their activity on c-Met dimerization and activation BRET analysis on transfected cells. c-Met receptor activity was quantified by measuring the Gab 1 signalling molecule recruitment on activated c-Met. For that purpose, CHO stable cell lines expressing C-Met-Rluc or C-Met-Rluc and C-Met-K1100A-YFP for c-Met dimerization or C-Met-Rluc and a mutated form of Gab1 [Maroun et al., Mol. Cell. Biol., 1999, 19:1784-1799] fused to YFP for c-Met activation were generated. Cells were distributed in white 96 well microplates in DMEM-F12/FBS 5% culture medium one or two days before BRET experiments. Cells were first cultured at 37° C. with $CO_2$ 5% in order to allow cell attachment to the plate. Cells were then starved with 200 µl DMEM/well overnight. Immediately prior to the experiment, DMEM was removed and cells quickly washed with PBS. Cells were incubated in PBS in the presence or absence of antibodies to be tested or reference compounds, 10 min at 37° C. prior to the addition of coelenterazine with or without HGF in a final volume of 50 µl. After incubation for further 10 minutes at 37° C., light-emission acquisition at 485 nm and 530 nm was initiated using the Mithras luminometer (Berthold) (1s/wave length/well repeated 15 times).

BRET ratio has been defined previously [Angers et al., Proc. Natl. Acad. Sci. USA, 2000, 97:3684-3689] as: [(emission at 530 nm)−(emission at 485 nm)×Cf]/(emission at 485 nm), where Cf corresponds to (emission at 530 nm)/(emission at 485 nm) for cells expressing Rluc fusion protein alone in the same experimental conditions. Simplifying this equation shows that BRET ratio corresponds to the ratio 530/485 nm obtained when the two partners were present, corrected by the ratio 530/485 nm obtained under the same experimental conditions, when only the partner fused to *R. reniformis* luciferase was present in the assay. For the sake of readability, results are expressed in milliBRET units (mBU); mBU corresponds to the BRET ratio multiplied by 1000.

After this second in vitro test, the antibody 224G11 i) without intrinsic activity as a whole molecule in the functional test of proliferation, ii) inhibiting significantly BxPC3 proliferation and iii) inhibiting c-Met dimerization was selected. In the experiments, the 5D5 Mab, generated by Genentech, and available at the ATCC, was added as a control for the intrinsic agonistic activity.

EXAMPLE 2

Humanization Process of Mouse 224G11 Mab by CDR-Grafting

1°) Humanization of the Light Chain Variable Domain (VL)

As a preliminary step, the nucleotide sequence of 224G11 VL was compared to the murine germline gene sequences included in the IMGT database (http://imgt.cines.fr). Murine IGKV3-5*01 and IGKJ4*01 germline genes showing a sequence identity of 99.31% for the V region and 94.28% for the J region, respectively, have been identified. Regarding these high homologies, the 224G11VL nucleotide sequence has been used directly to search for human homologies, instead of corresponding mouse germlines.

In a second step, the human germline gene displaying the best identity with the 224G11VL has been searched to identify the best human candidate for the CDR grafting. For optimization of the selection, alignments between the amino acid sequences have been performed. The human IGKV4-1*01 germline gene yielded a sequence identity of 67.30%, but showed a different length for CDR1 (10 amino acids in 224G11 VL and 12 amino acids in IGKV4-1*01). For the J region, the human IGKJ4*02 germline gene (sequence identity of 77.14%) was selected.

In a next step, mouse 224G11 VL CDR regions were engrafted into the above selected human framework sequences. Each amino acid position was analyzed for several criteria such as participation in VH/VL interface, in antigen binding or in CDR structure, localization of the residue in the 3D structure of the variable domain, CDR anchors, residues belonging to the Vernier zone. Three humanized versions, corresponding to SEQ ID No. 8, SEQ ID No. 9 and SEQ ID No. 10 were constructed, and containing respectively four (4, 39, 40, 84), two (39, 40) or one (40) murine residues in their FR regions and the CDRs corresponding to mouse 224G11 VL.

2°) Humanization of the Heavy Chain Variable Domain (VH)

As a preliminary step, the nucleotidic sequence of the 224G11 VH was compared to the murine germline genes sequences included in the IMGT database (http://imgt.cines.fr).

Murine IGHV1-18*01, IGHD2-4*01 and IGHJ2*01 germline genes with a sequence identity of 92.70% for the V region, 75.00% for the D region and 89.36% for the J region, respectively, have been identified. Regarding these high homologies, it has been decided to use directly the 224G11VH nucleotide sequences to search for human homologies, instead of corresponding mouse germlines.

In a second step, the human germline gene displaying the best identity with the 224G11 VH has been searched to identify the best human candidate for the CDR grafting. To this end, the nucleotidic sequence of 224G11VH has been aligned with the human germline genes sequences belonging to the IMGT database. The human IGHV1-2*02 V sequence exhibited a sequence identity of 75.00% at the nucleotide level and 64.30% at the amino acid level. Looking for homologies for the J region led to the identification of the human IGHJ4*04 germline gene with a sequence identity of 78.72%.

In a next step, mouse 224G11 VH CDR regions were engrafted into the above selected human framework sequences. Each amino acid position was analyzed for several criteria such as participation in VH/VL interface, in antigen binding or in CDR structure, localization of the residue in the 3D structure of the variable domain, CDR anchors, residues belonging to the Vernier zone. One fully humanized form, corresponding to SEQ ID 4 was constructed; it contains exclusively human residues in its FR regions and the CDRs corresponding to mouse 224G11 VH.

EXAMPLE 3

Engineering of Improved Hinge Mutants

It is well known by the skilled artisan that the hinge region strongly participates in the flexibility of the variable domain of immunoglobulins (see Brekke et al., 1995; Roux et al., 1997). During the chimerization process of 224G11 Mab, the mouse constant domain IGHG1 was replaced by the equivalent IGHG1 portion of human origin. Since the amino acid sequence of the hinge region were highly divergent, "murinization" of the hinge region was performed in order to keep its length and rigidity. Since the human IGHG2 hinge region corresponds to the closest homologue of the mouse IGHG1 hinge, this sequence was as well considered. A series of 7 different hinge sequences were constructed (SEQ ID Nos. 22 to 28) by incorporating portions of the mouse IGHG1 and the human IGHG2 hinges into the human IGHG1 hinge portion.

Another series of hinge mutants was designed and constructed (SEQ ID Nos. 58 to 72) to evaluate the influence of either an additional cysteine and its position along the hinge domain, deletion of 1, 2, 3 or 4 amino acids along the hinge domain and a combination of these two parameters (cysteine addition and amino acid deletion).

EXAMPLE 4

Production of Humanized 224G11 Mab and Engineered Hinge Mab Formats

All above described Mab forms containing either chimeric, humanized and/or engineered hinge regions were produced upon transient transfection and by using the HEK293/EBNA system with a pCEP4 expression vector (InVitrogen, US).

The entire nucleotide sequences corresponding to the humanized versions of the variable domain of 224G11 Mab light (SEQ ID No. 18, SEQ ID No. 19 and SEQ ID No. 20) and heavy (SEQ ID No. 14) chains were synthesized by global gene synthesis (Genecust, Luxembourg). They were subcloned into a pCEP4 vector (InVitrogen, US) carrying the entire coding sequence of the constant domain [CH1-Hinge-CH2-CH3] of a human IgG1 or IgG2 immunoglobulin. Modification of the hinge region was performed by exchanging a {NheII-BclI} restriction fragment by the equivalent portion carrying the desired modifications, each respective {Nhe1-Bcl1} fragment being synthesized by global gene synthesis (Genecust, LU). All cloning steps were performed according to conventional molecular biology techniques as described in the Laboratory manual (Sambrook and Russel, 2001) or according to the supplier's instructions. Each genetic construct was fully validated by nucleotide sequencing using Big Dye terminator cycle sequencing kit (Applied Biosystems, US) and analyzed using a 3100 Genetic Analyzer (Applied Biosystems, US).

Suspension-adapted HEK293 EBNA cells (InVitrogen, US) were routinely grown in 250 ml flasks in 50 ml of serum-free medium Excell 293 (SAFC Biosciences) supplemented with 6 mM glutamine on an orbital shaker (110 rpm rotation speed). Transient transfection was performed with $2.10^6$ cells/ml using linear 25 kDa polyethyleneimine (PEI) (Polysciences) prepared in water at a final concentration of 1 mg/ml mixed and plasmid DNA (final concentration of 1.25 µg/ml for heavy to light chain plasmid ratio of 1:1). At 4 hours post-transfection, the culture was diluted with one volume of fresh culture medium to achieve a final cell density of $10^6$ cells/ml. Cultivation process was monitored on the basis of cell viability and Mab production. Typically, cultures were maintained for 4 to 5 days. Mabs were purified using a conventional chromatography approach on a Protein A resin (GE Healthcare, US).

All different forms of Mabs were produced at levels suitable with functional evaluations. Productivity levels are typically ranging between 15 and 30 mg/l of purified Mabs.

EXAMPLE 5

Evaluation of c-Met Phosphorylation Status by a Phospho-c-Met-Specific ELISA Assay This functional assay allows to monitor modulation c-Met phosphorylation status either by Mabs alone or in the co-presence of HGF.

A549 cells were seeded in a 12MW plate in complete growth medium [F12K+10% FCS]. Cells were starved for 16 hours before stimulation with HGF [100 ng/ml], and each Mab to be tested was added at its final concentration of 30 µg/ml 15 minutes prior to ligand stimulation. Ice-cold lysis buffer was added 15 minutes after the addition of HGF to stop the phosphorylation reaction. Cells were scaped mechanically and cell lysates were collected by centrifugation at 13000 rpm for 10 min. at 4° C. and correspond to the supernatant phase. Protein content was quantified using a BCA kit (Pierce) and stored at −20° C. until use. The phosphorylation status of c-Met was quantified by ELISA. A goat anti-c-Met Mab (R&D, ref AF276) was used as a capture antibody (overnight coating at 4° C.) and after a saturation step with a TBS-BSA 5% buffer (1 hour at room temperature (RT)), 25 µg of protein lysates were added to each well of the coated 96MW plate. After a 90 minutes incubation at RT, plates were washed four time and the detection antibody was added (anti-phospho-c-Met Mab, directed against the phopshorylated Tyr residues at position 1230, 1234 and 1235). After an additional 1 hour incubation and 4 washes, an anti-rabbit antibody coupled to HRP (Biosource) was added for 1 hour at RT, and the luminescence detection was performed by adding Luminol Luminescence readings were on a Mithras LB920 multi-mode plate reader (Berthold).

Both basal and HGF [100 ng/ml]-induced c-Met receptor phosphorylation level were unaffected neither by PBS treatment, nor by the addition of mouse or human Mabs which do not target human c-Met receptor (FIG. 1). On the other hand, mouse (m) 224G11 Mab strongly inhibited HGF [100 ng/ml]-induced c-Met phosphorylation (FIG. 2B) without altering by itself receptor phosphorylation (FIG. 2A). Surprisingly, the chimeric form of 224G11 Mab (224G11chim/IgG1), meaning variable domain (VH+VL) from m224G11 combined with human constant domain IgG1/kappa yielded strong (17% of maximal HGF effect, FIG. 2A) agonist activity associated with a reduced antagonist efficacy (54% inhibition of HGF maximal effect compared to the m224G11 that yields 75% inhibition of HGF maximum effect, FIG. 2B). Three humanized forms of 224G11 Mab, [224G11]Hz1/IgG1, [224G11]Hz2/IgG1 and [224G11]Hz3/IgG 1, also constructed on a human IgG1/kappa backbone, yielded also decreased antagonist efficacy and significant agonist activity (11 to 24% of maximal HGF level) as compared to mouse 224G11 (FIGS. 2A and 2B). A series of engineered versions of the heavy chain hinge domain were constructed and assayed in the c-Met receptor phosphorylation assay. As shown in FIG. 3A, an important reduction of the agonist effect associated with the hIgG1/kappa isotype was observed for both the IgG2-based construct and for engineered IgG1/kappa constructs [MH, MUP9H and TH7]. A concomitant increase in antagonist efficacy was as well obtained. The hIgG1/kappa-based TH7 hinge mutant, with the most human sequence, was selected to complete the humanization process. In a next step, three humanized versions of 224G11 Mab variable domain were generated by combination to either a human IgG2/kappa or an IgG1/kappa-based TH7 engineered hinge constant domain. For the hIgG2/kappa humanized constructs, the humanized version Hz3 yielded strong agonism (FIG. 4A), and for all three humanized versions, the antagonist efficacy was below that observed with murine 224G11 Mab and comparable to the chimeric hIgG1-based Mab (56-57% inhibition of HGF effect, FIG. 4B). On the other hand, combination of the three humanized versions Hz1, Hz2 or Hz3 to the engineered IgG1/TH7 mutant almost fully restored the properties of mouse 224G11 Mab in terms of weak agonist activity (5-6% of HGF effect) and strong antagonist efficacy (68 to 72% inhibition of HGF effect) of c-Met receptor phosphorylation (FIGS. 5A and 5B). These variants were highly improved as compared to chimeric IgG1-based 224G11 Mab but also to IgG2-based humanized forms.

A second series of engineered versions of the heavy chain hinge domain was constructed and assayed in the c-Met receptor phosphorylation assay. As shown in FIG. 17A, all those new versions (c224G11[C2], c224G11[C3], c224G11[C5], c224G11[C6], c224G11[C7], c224G11[Δ1-3], c224G11[C7Δ6], c224G11[C6Δ9], c224G11[C2Δ5-7], c224G11[C5Δ2-6], c224G11[C9Δ2-7] and c224G11[Δ5-6-7-8]) exhibited weaker agonist effect than c224G11 since their agonism activities are comprised between 6 and 14% of the HGF effect compared to 23% for c224G11. As c224G11 [TH7], all those new versions exhibited a concomitant increase in antagonist efficacy [FIG. 17B]. Those results showed that engineering of the heavy chain domain by point mutation and/or deletion could modify agonistic/antagonistic properties of an antibody.

EXAMPLE 6

BRET Analysis

In a first set of experiments, it had been control that irrelevant mouse IgG1, human IgG1 and human IgG2 had no effect of HGF induced BRET signal in both BRET models (representative experiment out of 12 independent experiments; FIG. 6). These Mabs are forthwith cited as controls.

Figure 7A:
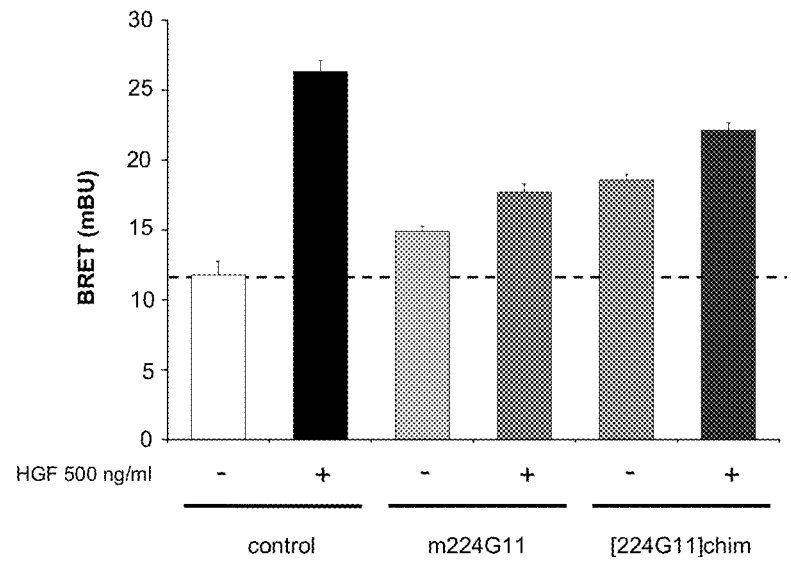
Figure 7B:
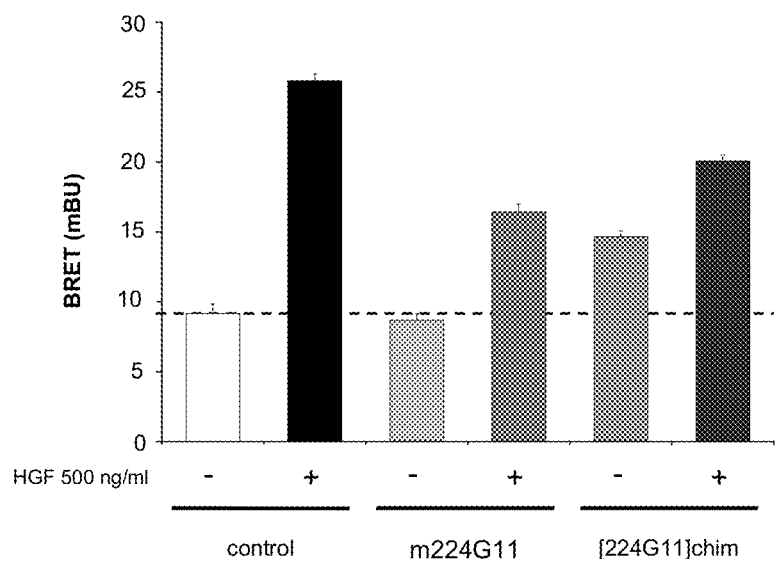

The effect of a IgG1 chimeric form of mouse 224G11 Mab ([224G11]chim) on both c-Met dimerization and c-met activation BRET model was evaluated. While mouse 224G11 Mab inhibited 59.4% of the HGF induced BRET signal on c-Met dimerization model, [224G11]chim Mab inhibited only 28.9% (FIG. 7A). [224G11]chim antibody was also less effective in inhibiting HGF induced c-Met activation since [224G11]chim and m224G11 antibodies inhibited respectively 34.5% and 56.4% of HGF induced BRET signal (FIG. 7B). Moreover, m224G11 alone had no effect on c-Met activation while [224G11]chim had a partial agonist effect on c-Met activation corresponding to 32.9% of the HGF induced signal. This partial agonist effect of the [224G11]chim was also seen on c-Met dimerization BRET model since [224G11]chim alone induced a BRET increase corresponding to 46.6% of HGF-induced signal versus 21.3% for m224G11 (FIG. 7A).

Figure 8A:
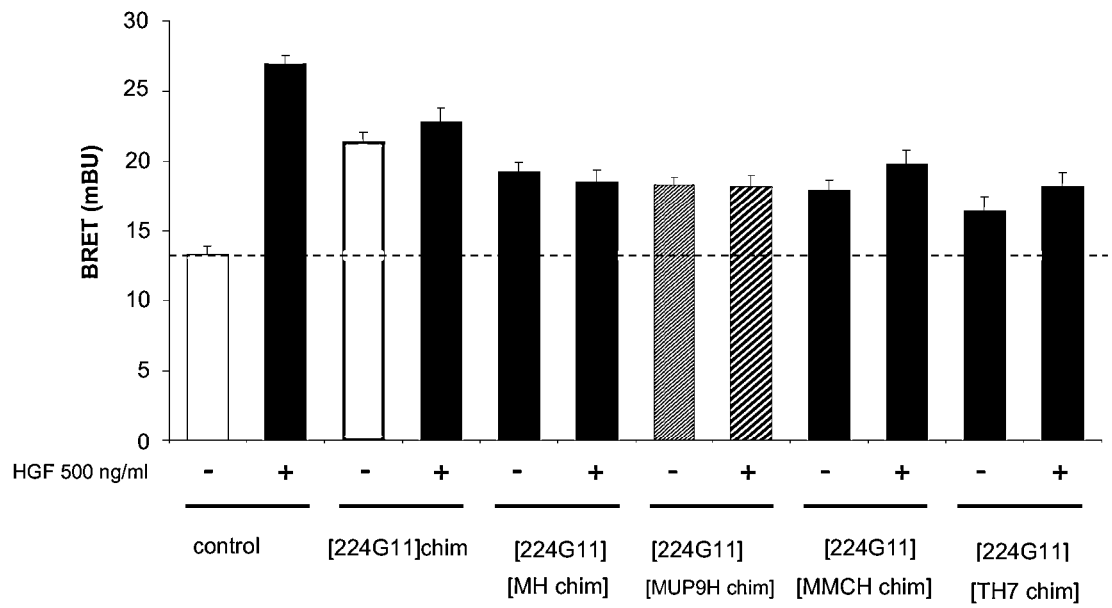
Figure 8B:
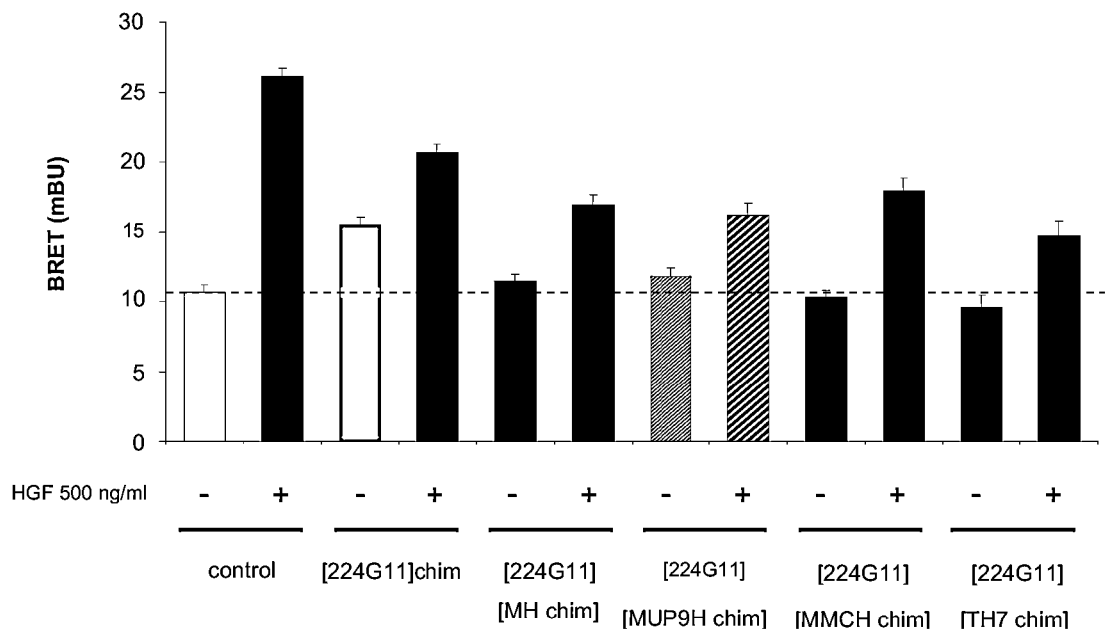

In FIGS. 8A and 8B, hinge mutated chimeric forms of 224G11 antibody showed a greater inhibitory effect on HGF induced BRET signal than [224G11]chim since they showed a 59.7%, 64.4%, 53.2% and 73.8% inhibition of the HGF induced activation BRET signal (FIG. 8B) and 61.8%, 64.4% 52.5% and 64.4% inhibition of the HGF induced c-Met dimerization BRET signal (FIG. 8A) for [224G11][MH chim], [224G11][MUP9H chim], [224G11][MMCH chim] and [224G11][TH7 chim] respectively. Contrary to [224G11] chim, which had a partial agonist effect on c-Met activation, hinge mutated chimerical forms of 224G11 antibody showed no significant effect on c-Met activation alone (5.1%, 7.6%, −2.0% and −6.9% respectively) as observed for m224G11.

Figure 9A:
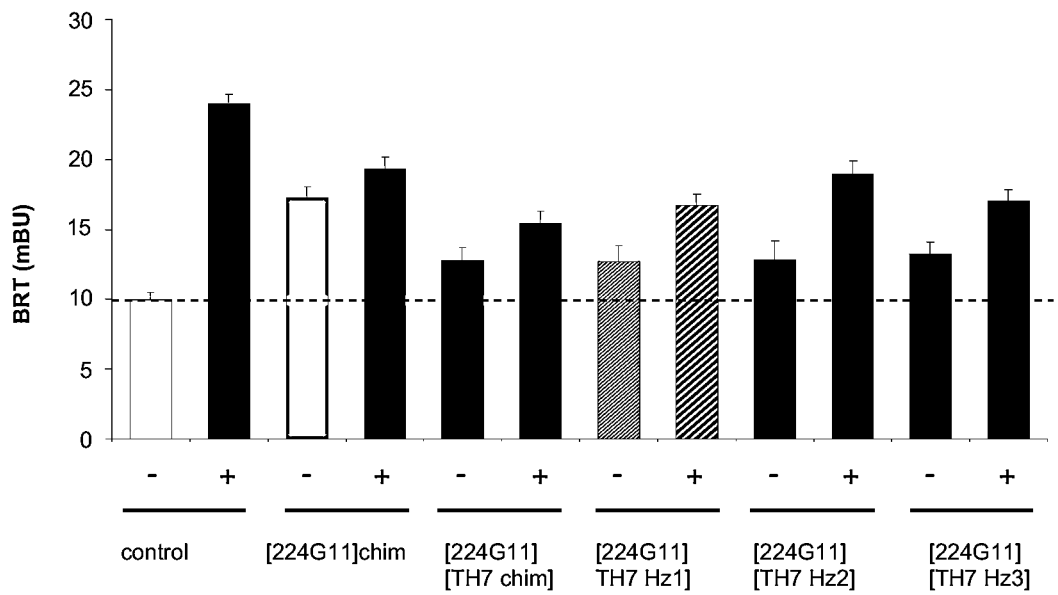
Figure 9B:
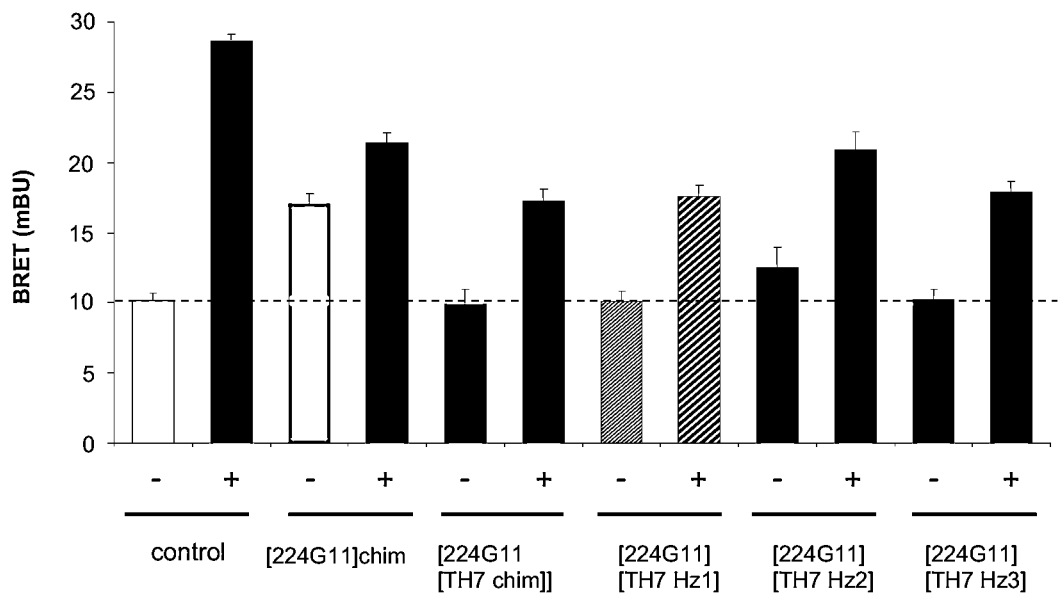

In FIG. 9B, like the [224G11] [TH7 chim], the 3 humanized versions of 224G11 IgG1 antibody with the TH7 hinge induced no significant increased of BRET signal in activation model when tested alone and showed a strong inhibition of HGF induced BRET signal: 59.9%, 41.8% and 57.9% for the Hz1, Hz2 and Hz3 forms respectively. Moreover, [224G11] [TH7 Hz1], [224G11] [TH7 Hz2] and [224G11][TH7 Hz3] inhibited HGF induced BRET signal on dimerization model of 52.2%, 35.8% and 49.4% respectively (FIG. 9A).

Figure 10A:
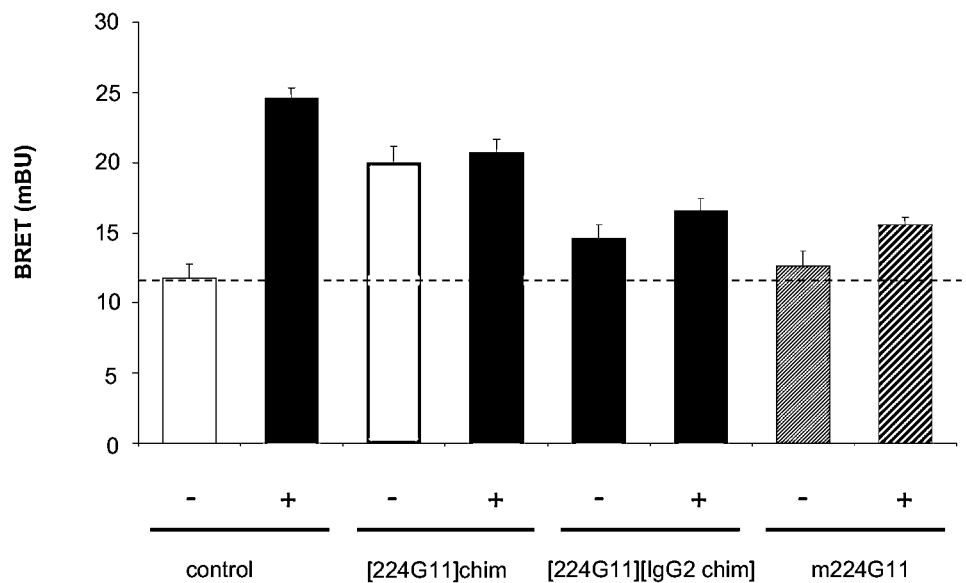
Figure 10B:
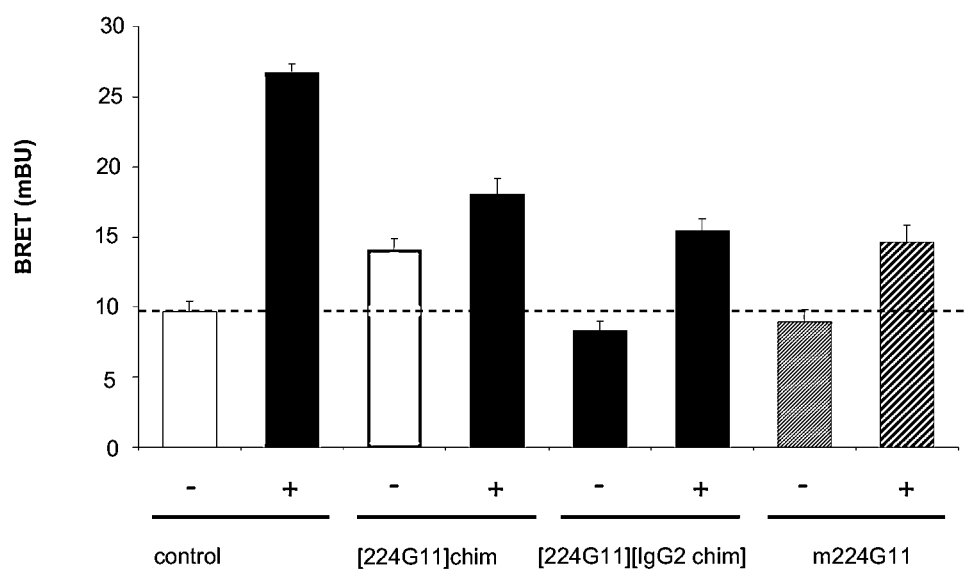

Contrary to [224G11]chim, the chimeric form of 224G11 IgG2 antibody ([224G11] [IgG2 chim]) showed no partial agonist effect alone and inhibited 66.3% of the HGF effect on c-Met activation model (FIG. 10B). On c-Met dimerization model, [224G11] [IgG2 chim] inhibited 62.4% of the HGF induced BRET signal (FIG. 10A).

The agonist efficacy of the second series of engineered versions of the heavy chain hinge domain was evaluated in c-Met activation BRET model (FIG. 18). In contrast to c224G11, which had a partial agonist effect on c-Met activation, c224G11[C2], c224G11[C3], c224G11[C5], c224G11 [C6], c224G11[C7], c224G11[Δ1-3], c224G11[C7Δ6], c224G11[C6Δ9], c224G11[C2Δ5-7], c224G11[C5Δ2-6], c224G11[C9Δ2-7] and c224G11[Δ5-6-7-8] hinge mutated chimeric forms of 224G11 antibody showed no significant effect on c-Met activation alone.

EXAMPLE 7 c-Met Recognition by Chimeric and Humanized 224G11 Forms

A direct ELISA has been set up to determine the binding ability of the various chimeric and humanized forms on the recombinant c-Met. Briefly recombinant dimeric c-Met from R&D Systems was coated at 1.25 µg/ml on 96-well Immunlon II plates. After an overnight incubation at 4° C., wells were saturated with a 0.5% gelatine/PBS solution. Plates were then incubated for 1 hour at 37° C. before addition of 2 fold dilutions of antibodies to be tested. Plates were incubated an additional hour before addition of a goat anti-mouse IgG HRP for detecting the murine antibody and a goat anti-human Kappa light chain HRP for chimeric and humanized antibody recognition. Plates were incubated for one hour and the peroxydase substrate TMB Uptima was added for 5 nm before neutralization with $H_2SO_4$ 1M. Results presented in FIG. 11 showed that all tested forms were comparable for c-Met recognition.

EXAMPLE 8

Effect of Murine and Chimeric 224G11 on HGF-Induced Proliferation of NCI-H441 Cells In Vitro NCI-H441 cells from ATCC were routinely cultured in RPMI 1640 medium (Invitrogen Corporation, Scotland, UK), 10% FCS (Invitrogen Corporation), 1% L-Glutamine (Invitrogen corporation). For proliferation assays, cells were split 3 days before use so that they were in the confluent phase of growth before plating. NCI-H441 cells were plated in 96-well tissue culture plates at a density of $3.75 \times 10^4$ cells/well in 200 µl of serum free medium (RPMI 1640 medium plus 1% L-Glutamine). Twenty four hours after plating, antibodies to be tested were added to NCI-H441 and incubated at 37° C. for thirty minutes before adding HGF at a final concentration of 400 ng/ml (5 nM) for 142 additional hours. The dose range tested for each antibody is from 10 to 0.0097 µg/ml (final concentration in each well). In this experiment, a murine IgG1 Mab was added as a murine isotype control and the tested antibodies were the following one: m224G11 and its human IgG1 chimeric form identified as [224G11]chim. Wells plated with cells alone −/+ HGF were also included. Then cells were pulsed with 0.25 µCi of [$^3$H]Thymidine (Amersham Biosciences AB, Uppsala, Sweden) for 7 hours and 30 minutes. The magnitude of [$^3$H]Thymidine incorporated in trichloroacetic acid-insoluble DNA was quantified by liquid scintillation counting. Results are expressed as non transformed cpm data to better evaluate the potential intrinsic agonist activity that could occur with anti-c-Met Mabs when added alone to tumour cell.

Results described in FIG. 12 demonstrated that, as expected, the murine antibody m224G11 displayed no agonist effect when added alone to cancer cells whatever the tested dose. No significant inhibition of the HGF-induced proliferation was observed with the isotype control regarding to the cpm variations observed for this compound in this experiment. When added alone, the m224G11 antibody did not show any agonist effect compared to the mIgG1 isotype control Mab or cells alone. A dose dependent anti-proliferative activities reaching 78% was observed for m224G11 (% inhibition calculation: 100−[(cpm cells+Mab to be tested−mean cpm background mIgG1)×100/(mean cpm cells+HGF−mean cpm cells alone)]). Surprisingly, the chimeric form of the 224G11 Mabs induced a significant, dose dependent agonist effect when added alone. This agonist effect had an impact on the in vitro inhibition of HGF-induced proliferation that shifted from 78% for the murine 224G11 to 50% for its chimeric form. To determine whether such "lower" in vitro intrinsic agonist activity was compatible with an unchanged in vivo effect, both m224G11 and [224G11]chim were produced for in vivo testing. As, in previous studies, the 30 µg/mice dose had demonstrated a significant in vivo activity, that dose was selected for in vivo evaluation.

EXAMPLE 9

In Vivo Comparison of Murine and Chimeric 224G11 Mabs on the NCI-H441 Xenograft Model NCI-H441 is derived from papillary lung adenocarcinoma, expresses high levels of c-Met, and demonstrates constitutive phosphorylation of c-Met RTK.

To evaluate the in vivo effect of antibodies on the NCI-H441 xenograft model, six to eight weeks old athymic mice were housed in sterilized filter-topped cages, maintained in sterile conditions and manipulated according to French and European guidelines. Mice were injected subcutaneously with $9 \times 10^6$ cells. Then, six days after cell implantation, tumors were measurable (approximately 100 mm$^3$), animals were divided into groups of 6 mice with comparable tumor size and treated first with a loading dose of 60 µg of antibody/mice and then twice a week with 30 µg/dose of each antibody to be tested. The mice were followed for the observation of xenograft growth rate. Tumor volume was calculated by the formula: π (Pi)/6×length×width×height. Results described in FIG. 13 demonstrate that the murine Mab devoided of agonist activity in vivo behave, as expected, as potent antagonist even at the low tested dose. In contrast to what observed with the murine Mab, the chimeric one displayed a very transient in vivo activity and tumor completely escaped to the treatment at D20 post cell injection. This experiment demonstrates clearly that the increase of in vitro agonist effect that resulted in a decrease of antagonist activity was also responsible for a significant in vivo loss of antagonist activity.

EXAMPLE 10

Effect of the Murine 224G11 Mab and of Various Chimeric and Humanized Versions of this Antibody on HGF-Induced Proliferation of NCI-H441 Cells In Vitro NCI-H441 cells from ATCC were routinely cultured in RPMI 1640 medium (Invitrogen Corporation, Scotland, UK), 10% FCS (Invitrogen Corporation), 1% L-Glutamine (Invitrogen Corporation). For proliferation assays, cells were split 3 days before use so that they were in the confluent phase of growth before plating. NCI-H441 cells were plated in 96-well tissue culture plates at a density of $3.75 \times 10^4$ cells/well in 200 µl of serum free medium (RPMI 1640 medium plus 1% L-Glutamine). Twenty four hours after plating, antibodies to be tested were added to NCI-H441 and incubated at 37° C. for thirty minutes before adding HGF at a final concentration of 400 ng/ml (5 nM) for 142 additional hours. The dose range tested for each antibody is from 10 to 0.0097 µg/ml (final concentration in each well). In this experiment, murine IgG1 Mab was added as a murine isotype control and as an agonist negative control. The tested antibodies were the following one: i) m224G11, ii) its human IgG1 chimeric forms respectively identified as [224G11] chim, [224G11] [MH chim], [224G11] [MUP9H chim], [224G11] [MMCH chim], [224G11] [TH7 chim] iii) its humanized IgG1 forms respectively described as [224G11] [Hz1], [224G11] [Hz2], [224G11] [Hz3]. Wells plated with cells alone −/+ HGF were also included. The 5D5 whole antibody from Genentech commercially available at the ATCC as an hybridoma cell line was introduced as a full agonist positive control and thereafter called m5D5. Then cells were pulsed with 0.25 µCi of [$^3$H] Thymidine (Amersham Biosciences AB, Uppsala, Sweden) for 7 hours and 30 minutes. The magnitude of [$^3$H]Thymidine incorporated in trichloroacetic acid-insoluble DNA was quantified by liquid scintillation counting. Results are expressed as non transformed cpm data to better evaluate the potential intrinsic agonist activity that could occur with anti-c-Met Mabs when added alone to tumour cell.

Results described in FIG. 14A demonstrated that as expected neither the isotype control nor the m224G11 displayed any agonist activity on NCI-H441 proliferation. The isotype control was without effect on HGF-induced cell proliferation whereas m224G11 showed a 66% inhibition when added at the final concentration of 10 µg/ml. The m5D5 used as an agonist control showed, as expected, a full dose dependent agonist effect when added alone to the cells. As already observed, the [224G11] chim Mab displayed a significant dose-dependent agonist effect and, a decreased inhibitory activity of this chimeric form was observed: 19% instead of 66% for the murine form. When added alone, the 3 IgG 1 humanized Mabs demonstrated dose dependent agonist effects compared to the m224G11 form. [224G11] [Hz1], [224G11] [Hz2] and [224G11] [Hz3] had comparable antagonist activities about 46, 30 and 35%. These activities are significantly lower than the one observed for m224G11. In FIG. 14B, various IgG1 chimeric forms were tested. Compared to [224G11] chim form which displayed a dose-dependent agonist effect when added alone to NCI-H441 cells, the [224G11] [MH chim], [224G11] [MUP9H chim], [224G11] [MMCH chim], [224G11] [TH7 chim] forms were without significant intrinsic agonist effect. Their antagonist activity was higher than the one observed for the m224G11 Mab (57%) with inhibitions reaching 79, 78, 84 and 93% respectively for [224G11] [MH chim], [224G11] [MUP9H chim], [224G11] [MMCH chim] and [224G11] [TH7 chim].

EXAMPLE 11

In Vitro Effect of Various IgG1 Humanized form of the 224G11 Mab

NCI-H441 cells from ATCC were routinely cultured in RPMI 1640 medium (Invitrogen Corporation, Scotland, UK), 10% FCS (Invitrogen Corporation), 1% L-Glutamine (Invitrogen Corporation). For proliferation assays, cells were split 3 days before use so that they were in the confluent phase of growth before plating. NCI-H441 cells were plated in 96-well tissue culture plates at a density of $3.75 \times 10^4$ cells/well in 200 nl of serum free medium (RPMI 1640 medium plus 1% L-Glutamine). Twenty four hours after plating, antibodies to be tested were added to NCI-H441 and incubated at 37° C. for thirty minutes before adding HGF at a final concentration of 400 ng/ml (5 nM) for 142 additional hours. The dose range tested for each antibody is from 10 to 0.0097 ng/ml (final concentration in each well). In this experiment, murine IgG1 Mab was added as a background negative control for agonist activity and the tested antibodies were the following one: i) m224G11, ii) its human IgG1 chimeric forms respectively identified as [224G11] chim, [224G11] [TH7 chim] iii) its humanized IgG1 forms respectively described as [224G11]

[TH7 Hz1], [224G11] [TH7 Hz3]. Wells plated with cells alone −/+ HGF were also included. The 5D5 whole antibody from Genentech commercially available at the ATCC as an hybridoma cell line was introduced as a full agonist positive control and thereafter called m5D5. Then cells were pulsed with 0.25 µCi of [$^3$H]Thymidine (Amersham Biosciences AB, Uppsala, Sweden) for 7 hours and 30 minutes. The magnitude of [$^3$H]Thymidine incorporated in trichloroacetic acid-insoluble DNA was quantified by liquid scintillation counting. Results are expressed as non transformed cpm data to better evaluate the potential intrinsic agonist activity that could occur with anti-c-Met Mabs when added alone to tumour cell.

FIG. 15 showed that the m224G11 Mab displayed the usual inhibitory effect (74% inhibition). The chimeric IgG1 form [224G11] chim had as expected a dose dependent intrinsic agonist effect and a lower antagonist effect compared to the murine form: 33% versus 74% inhibition. The [224G11] [TH7 chim] had a very weak agonist activity in this experiment. However it displayed a high inhibitory effect (81%) close to the one noticed for the murine Mab. The 2 humanized forms had no intrinsic agonist effect and had an antagonist activity close to the ones observed for the murine Mab or the [224G11] [TH7 chim] with respectively 67 and 76% inhibition for [224G11] [TH7 Hz1] and [224G11] [TH7 Hz3].

EXAMPLE 12

In Vivo Comparison of Murine, Chimeric and Humanized 224G11 Mabs Bearing Either the Wild Type or the TH7-Engineered Hinge (NCI-H441 Xenograft Model)

NCI-H441 is derived from papillary lung adenocarcinoma, expresses high levels of c-Met, and demonstrates constitutive phosphorylation of c-Met RTK.

To evaluate the necessity of hinge engineering to save in vivo activity of the 224G11 murine antibody, six to eight weeks old athymic mice were housed in sterilized filter-topped cages, maintained in sterile conditions and manipulated according to French and European guidelines. Mice were injected subcutaneously with 9×10$^6$ NCI-H441 cells. Then, six days after cell implantation, tumors were measurable (approximately 100 mm$^3$), animals were divided into groups of 6 mice with comparable tumor size and treated first with a loading dose of 2 mg of antibody/mice and then twice a week with a 1 mg/dose of each antibody to be tested. Ten antibodies were evaluated in this experiment including the m224G11, the chimeric form displaying the wild type hinge (c224G11), the TH7-engineered chimeric form (224G11 [TH7 chim]), three humanized form bearing the wild type hinge (224G11[IgG1 Hz1], 224G11[IgG1 Hz2] and 224G11 [IgG1 Hz3]) and the three corresponding TH7-engineered forms (224G11[TH7 Hz1], 224G11[TH7 Hz2] and 224G11 [TH7 Hz3]). Mice were followed for the observation of xenograft growth rate.

Tumor volume was calculated by the formula: π (Pi)/6× length×width×height.

Results described in FIG. 16 demonstrate that the murine Mab devoid of any agonist activity in vitro behave, as expected, as potent in vivo antagonist. In contrast to what observed with the murine Mab, both chimeric and humanized forms bearing the wild type hinge displayed only a very transient in vivo activity. In any cases the substitution of the wild type hinge by the TH7-engineered one resulted in a complete restoration of the in vivo activity observed with murine antibodies. This experiment demonstrates clearly that the increase of in vitro agonist effect that resulted in a decrease of antagonist activity was also responsible of a significant in vivo loss of antagonist activity. It also demonstrates that the use of a TH7-engineered region instead of the wild type one is needed for keeping the in vivo properties of the murine Mab.

EXAMPLE 13

Effect of m224G11 and Its Humanized Form h224G11 on c-Met Downregulation In Vitro In the following examples, for the avoidance of doubt, the expression h224G11 refers to the humanized form 224G11 [TH7 Hz3] of the antibody of the invention.

Two cell lines have been selected to address the activity of anti-c-Met antibodies on c-Met receptor degradation. A549 (#HTB-174) and NCI-H441 (#CCL-185) are two NSCLC cell lines from the ATCC collection. NCI-H441 cells were seeded in RPMI 1640+1% L-glutamine+10% heat-inactivated FBS, at 3×10$^4$ cells/cm$^2$ in six-well plates for 24 h at 37° C. in a 5% CO$_2$ atmosphere. A549 cells were seeded in F12K+ 10% heat-inactivated FBS, at 2×10$^4$ cells/cm$^2$ in six-well plates for 24 h at 37° C. in a 5% CO$_2$ atmosphere.

Then, cells were washed twice with phosphate buffer saline (PBS) before being serum-starved for 24 additional hours. Anti-c-Met antibodies (10 µg/ml), irrelevant mIgG1 (10 µg/ml), or HGF (400 ng/mL) were added in serum-free DMEM medium at 37° C. After either 4 hours or 24 hours of incubation, the medium was gently removed and cells washed twice with cold PBS. Cells were lysed with 500 µL of ice-cold lysis buffer [50 mM Tris-HCl (pH 7.5); 150 mM NaCl; 1% Nonidet P40; 0.5% deoxycholate; and 1 complete protease inhibitor cocktail tablet plus 1% antiphosphatases]. Cell lysates were shaken for 90 min at 4° C. and cleared at 15 000 rpm for 10 minutes. At this stage, cell lysates could be stored at −20° C. until needed for western blot analysis. Protein concentration was quantified using BCA. Whole cell lysates (5 µg in 20 µl) were separated by SDS-PAGE and transferred to nitrocellulose membrane. Membranes were saturated for 1 h at RT with TBS-Tween 20 0.1% (TBST); 5% non-fat dry milk and probed with anti-c-Met antibody (dilution 1/1000) overnight at 4° C. in TBST-5% non-fat dry milk. Antibodies were diluted in tris-buffered saline-0.1% tween 20 (v/v) (TBST) with 1% non-fat dry milk. Then, membranes were washed with TBST and incubated with peroxydase-conjugated secondary antibody (dilution 1:1000) for 1 h at RT. Immunoreactive proteins were visualized with ECL (Pierce #32209). After c-Met visualization, membranes were washed once again with TBST and incubated for 1 h at RT with mouse anti-GAPDH antibody (dilution 1/200 000) in TBST-5% non-fat dry milk. Then, membranes were washed in TBST and incubated with peroxydase-conjugated secondary antibodies, for 1 h at RT. Membranes were washed and GAPDH was revealed using ECL. Band intensity was quantified by densitometry.

Results presented in FIGS. 19A and 20A demonstrated that both m224G11 and h224G11 are able to significantly downregulate c-Met, in a dose-dependant way, in both A549 and NCI-H441 cell lines. The downregulation is already significant after a 4 hour incubation time and still increased at 24 hour. Histograms presented in FIGS. 19A and 20A corresponds to mean values or respectively 4 and 3 independent experiments. Western blot images corresponding to one significant experiment were included in FIGS. 19B and 20B.

EXAMPLE 14

Effect of m224G11 and Its Humanized Form h224G11 on c-Met Shedding In Vitro

Soluble shedded forms of the c-Met receptor occur naturally in the serum of mice xenografted with human tumor or in serum of human patient carrying tumors expressing c-Met. Moreover, antibodies directed against c-Met such as the DN30 Mab, are described as shedding inducers of c-Met in in vitro experiments. To determine whether the m224G11 as such a property, cells were seeded in six-well plates in 10% FCS medium. When they reached approximately 80% confluence, medium was removed and fresh complete culture medium +/− compounds to be tested was added. Cells were incubated 72 additional hours with either m224G11, an isotype control mIgG1 or PBS. PMA (phorbol meristate acetate) was introduced as a shedding inducer. HGF was also tested on cells to determine the impact of c-Met ligand on natural occurring shedding. Then supernatants were collected and filtered on 0.2 μm before use in an ELISA test which soluble forms of c-Met were captured with an anti-c-Met antibody that does not recognize the same epitope as either m224G11 or the c11E1 (FIG. 21). Moreover, cells from each well were washed once with PBS and lysed to determine protein concentration. For the ELISA, 224D10 was used as a capture antibody and after plate saturation, filtered supernatants from six well plates were added in the ELISA test. A monomeric c-Met form was used as a positive control. After supernatant incubation, plates were washed to remove the unbound c-Met and c11E1 was used to detect c-Met captured by the 224G11 Mab. The revelation of the test was finally performed by addition of an HRP-conjugated anti-hFc polyclonal antibody.

Results shown in FIG. 22 indicate that a natural shedding of c-Met occurred when cells were cultured for 72 hours in vitro. No effect of the mIgG1 was observed. However, the addition of m224G11 seemed to inhibit c-Met shedding. These results were confirmed for 3 other cells lines (Hs746T, EBC1 and MKN45) in FIG. 23. In that second experiment, the PMA, added as a positive shedding inducer, increased significantly, as expected, c-Met shedding at least in 2 cell lines (Hs746T and MKN45). Finally, in a third experiment (FIG. 24), HGF was introduced as a control. No additional shedding was induced by HGF compared as cells alone or cells+mIgG1. Once again, a significant inhibition of c-Met shedding was observed with m224G11.

EXAMPLE 15

Intrinsic Effect of h224G11 Ab on Various Cell Lines

In previous experiments described in this patent, it has been demonstrated that in contrast to what was observed with other antibodies such as 5D5, the m224G11 and its humanized form h224G11 do not display significant intrinsic activity tumor cell lines. To extend this property to other cell lines, western blot and phospho-ELISA experiments were performed with the antibody alone, added for various times, on a set of cancer cell lines, with variable levels of c-Met expression, including Hs746T, NCI-H441, Hs578T, NCI-H125, T98G, MDA-MB-231, PC3. The same test was also performed in a normal cell: HUVEC.

Method for the phospho cMet ELISA assay was already described in example 5 of the present patent application. For the western analysis, protein lysates were made from pelleted cells by incubation in lysis buffer with proteases and phosphatase inhibitors [10 nM Tris (pH 7.4), 150 mM NaCl, 1 mM EDTA, 1 mM EGTA, 0.5% Nonidet P40, 100 mM sodium fluoride, 10 mM sodium pyrophosphate, 2 mM sodium orthovanadate, 2 mM PMSF, 10 mg/ml leupeptin, 10 mg/ml aprotinin] at 4° C. Protein lysates were cleared of cellular debris by centrifugation, resolved by electrophoresis on 8% SDS-PAGE gels, and electrotransferred to a nitrocellulose membrane. For c-Met experiments, lysates were immunoprecipitated for specific protein of interest before electrophoresis and transfer.

Results presented in FIGS. 25 to 32 demonstrate once again that no intrinsic activity of the h224G11 antibody was observed in the tested cells.

EXAMPLE 16

In Vivo Comparison of the Murine Wild Type 224G11 with a Chimeric Hinge-Engineered 224G11 Form Described as 224G11[C2D5-7] (NCI-H441 Xenograft Model)

NCI-H441 is derived from papillary lung adenocarcinoma, expresses high levels of c-Met, and demonstrates constitutive phosphorylation of c-Met RTK.

To evaluate the necessity of hinge engineering to save in vivo activity of the 224G11 murine antibody, six to eight weeks old athymic mice were housed in sterilized filter-topped cages, maintained in sterile conditions and manipulated according to French and European guidelines. Mice were injected subcutaneously with $9 \times 10^6$ NCI-H441 cells. Then, six days after cell implantation, tumors were measurable (approximately 100 mm$^3$), animals were divided into groups of 6 mice with comparable tumor size and treated first with a loading dose of 2 mg of antibody/mice and then twice a week with a 1 mg/dose of each antibody to be tested. Mice were followed for the observation of xenograft growth rate. Tumor volume was calculated by the formula: $\pi$ (Pi)/6× length×width×height. Results described in FIG. 33 demonstrate that the murine Mab devoid of any agonist activity in vitro behave, as expected, as a potent in vivo antagonist. As suggested by the results obtained in vitro, in phosphorylation assays, the c224G11[C2D5-7] hinge-engineered antibody, that did not display a significant agonist effect, demonstrate a strong in vivo activity, comparable to the one of the m224G11 on the NCI-H441 xenograft model.

EXAMPLE 17

Evaluation of h224G11 in an ADCC Test

As h224G11 is of IgG1 isotype, ADCC could be part of its in vivo efficacy in human. An in vitro [$^{51}$Cr] release cytotoxicity assay was performed using either Hs746T or NCI-H441 cells as target cells and NK cells purified from human peripheral blood mononuclear lymphocytes.

Briefly, one million Hs746T or NCI-H441 target cells were incubated with or without 20 μg of h224G11 Ab in presence of 100 μCi of $^{51}$Chromium (Perkin Elmer) for 1 hr. Then, $4 \times 10^3$ cells were plated with an increasing number of human natural killer (NK) cells isolated from peripheral blood mononuclear cells (PBMC) using a negative selection (Stemcell Technologies). Cells were incubated together for 4 additional hours at 37° C. Percent of cell lysis was calculated following the formula: [(experimental $^{51}$Cr release–spontaneous $^{51}$Cr release)/(full $^{51}$Cr release–spontaneous $^{51}$Cr release)]×100. Spontaneous release represents the counts obtained when the target cells were cultured in absence of natural killer cells. Full release represents the counts obtained when the target cells were lysed with 1% Triton X-100. h224G11 significantly enhanced lysis of both Hs746T (FIG. 34a) and NCI-H441 (FIG. 34b) cells by 62.9% and 63.2%, respectively, at a ratio NK/Target cells of 100.

EXAMPLE 18

Immunohistochemical Studies (IHC)

Procedures of Paraffin Embedded Tumors IHC Staining: 8 to 12 µM sections of frozen tumor were and immediately fixed in pre cooled acetone −20° C. for 3 minutes. Slides were then cooled at room temperature for 30 minutes to 1 hour. After 2 washes in PBS the Endogenous peroxidase activity was blocked using Peroxidase Blocking Reagent (Dako K4007) for five minutes. Sections were washed with PBS and incubated in avidin/biotin blocking reagent (Dako X0590) just before saturation of the non specific sites in PBS-BSA 4% for 30 minutes at room temperature. Then, slides were incubated with the biotinylated h224G11 (50 to 10 ng/ml) or human biotinylated IgG1/kappa (50 to 10 ng/ml, the Binding Site) as negative control 2 hours at room temperature.

Sections were washed with PBS and incubated with Streptavidin-peroxydase complex universal (Dako K0679) for 30 to 45 minutes. 3-Amino-9-Ethylcarbazole was used for development of a red reaction product (Sigma). The slides were immersed in hematoxylin for 4 minutes to counterstain (Dako S3309).

Results are represented in FIG. 35.

h224G11 differentially stains the cell membrane of various tumor types. In this immunohistochemistry procedure, the red reaction product correlates to positive staining of the cell membrane and lack of red reaction product correlates to negative staining and no visualization of the cell membrane. The IgG control, human IgG1/kappa is an isotype matched control.

EXAMPLE 19

In Vivo Activity of Anti-c-Met Mabs on Three Cell Lines Amplified for c-Met and Xenografted in Mice Hs746T (ATCC) and MKN45 (JCRB), two stomach carcinoma cells, and, EBC-1 (JCRB), a lung squamous cell carcinoma, are 3 cell lines that over-express c-Met as shown by FACS analysis in FIGS. 36A, 37A and 38A. These cell lines are also described in the literature as amplified cell lines for c-Met. To confirm this latter point, c-Met gene amplification was determined by quantitative real-time PCR using ΔΔCt method. Fifty ng of genomic DNA from each indicated cell line, extracted using the QIAamp DNA midi kit (Qiagen, Les Ulis, FR) was used. The reference gene was DNA topoisomerase III alpha located on chromosome 17. Primers for c-Met gene were located on exon 14. The corresponding primers for both genes are those described by Smolen et al. (PNAS, 2006, 103:2316-2321) and yielded similar PCR efficiencies. The QPCR protocol consists in a 10 min cycle at 95° C., followed by 40 successive cycles of 15 sec at 95° C./45 sec at 95° C. Data were first normalized to the reference gene, and then each cell line was normalized to MCF-7 cells containing a single copy of c-Met gene per haploid genome. The results presented in FIGS. 36B, 37B and 38B demonstrate that the 3 cell lines display a significant amplification of c-Met ranking from 5 to 10-fold gene amplification.

As it has been described that such cells are constitutively activated for c-Met, a Western blot assay was performed to determine the level of c-Met phosphorylation of each cell line either in absence or in presence of HGF (50 ng/ml). For that purpose cells were cultured overnight in serum-free medium and then treated or not with 50 ng/ml of HGF for 2 min. Cells were lysed with lysis buffer supplemented with protease inhibitors. Cell lysates were incubated at 4° C. for 90 min, then centrifuged and supernatants were collected. Protein concentrations were determined using the BCA protein assay (Pierce) and samples were immunoblotted. Antibodies used include the anti-c-Met antibody, clone 25H2 from Cell Signaling and the anti-P-c-Met Y1230, 1234, 1235 from Biosource. Immunoblotting with the phospho-specific c-Met antibody against Y1230/1234/1235 showed strong baseline phosphorylation of the receptor in each amplified cell line (FIGS. 36C, 37C and 38C). No additional phosphorylation is observed when HGF was added to these cells. This last observation confirms that c-Met was activated in an HGF-independent way in Hs746T, MKN45 and EBC-1 cell lines.

In order to test our anti-c-Met antibodies in vivo on ligand-independent cell lines, Hs746T, MKN45 and EBC-1 cells were routinely cultured in complete DMEM, RPMI 1640 or EMEM medium respectively. Cells were split two days before engraftment so that they were in exponential phase of growth. Seven million cells were engrafted to either SCID (for Hs746T and EBC-1) or CD1 Swiss nude mice (for MKN45). Five to seven days after implantation, tumors were measurable and animals were divided into groups of 6 mice with comparable tumor size. Mice were treated i.p. with a loading dose of 2 mg of h224G11 Mab/mouse and then twice a week with 1 mg of antibody/mouse. Tumor volume was measured twice a week and calculated by the formula: $\pi/6\times$ length×width×height. Statistical analysis was performed at each measured time using a Mann-Whitney test.

This experiment demonstrates that h224G11 reduced significantly tumor growth of Hs746T, MKN45 and EBC1 (FIGS. 36D, 37D and 38D), indicating that the humanized antibody is able to inhibit tumor growth of gastric and lung ligand-independent cell lines. Before these results were obtained, it would not have been apparent how the presence of the modified hinge in this humanized antibody would affect its ligand-independent inactivation of c-Met, because the altered hinge also affected its agonist/antagonist properties.

EXAMPLE 20

Ex Vivo Analysis of h224G11 Activity on the Hs746T Xenograft Model in SCID Mice

In order to determine more precisely mechanisms of action that resulted in Hs746T tumor xenograft inhibition, the effect of 3 i. p. injections of h224G11 was evaluated on tumor mitotic index (Ki67), apoptosis (activated caspase 3) and c-Met expression using immunohistochemistry (IHC) methods. Three mice were analyzed for each condition. A significant down regulation of c-Met was observed on treated tumors compared to control one (FIGS. 39C and D respectively). Panel 39A and B corresponds to isotypes controls. In addition a significant decrease in Ki67 levels (FIGS. 39E and F) and an increase in activated caspase 3 staining (FIGS. 39G and H) was noticed on all treated tumors indicating that h224G11 was able to inhibit significantly cell proliferation and to induce cell apoptosis within the tumor.

The invention claimed is:

1. A method for inhibiting the growth and/or the proliferation of tumor cells with genic amplification of c-Met, the method comprising administering to a subject in need thereof an isolated anti-cMet antibody, or binding fragment thereof, that is capable to inhibit c-Met dimerization, wherein the antibody comprises:

a heavy chain comprising complementarity-determining region (CDR) CDR-H1, CDR-H2, and CDR-H3 comprising amino acid sequences SEQ ID Nos. 1, 2, and 3, respectively;

a light chain comprising CDR-L1, CDR-L2, and CDR-L3 comprising amino acid sequences SEQ ID Nos. 5, 6, and 7; and a modified hinge region comprising the amino acid sequence SEQ ID No. 56.

2. The method of claim 1, wherein the modified hinge region comprises the amino acid sequence SEQ ID No. 57.

3. The method of claim 1, wherein the modified hinge region comprises the amino acid sequence SEQ ID No. 21.

4. The method of claim 1, wherein the antibody comprises:

a heavy chain variable domain comprising the amino acid sequence SEQ ID No. 4; and a light chain variable domain comprising an amino acid sequence chosen from SEQ ID No. 8, 9, and 10.

5. The method of claim 1, wherein the antibody comprises:
a heavy chain variable domain comprising the amino acid sequence SEQ ID No. 4; and
a light chain variable domain comprising an amino acid sequence chosen from SEQ ID Nos. 8, 9, and 10; and
a modified hinge region comprising an amino acid sequence chosen from SEQ ID Nos. 22 to 28.

6. The method of claim 5, wherein the antibody comprises:
a heavy chain variable domain comprising the amino acid sequence SEQ ID No. 4; and
a light chain variable domain comprising SEQ ID No. 10; and
a modified hinge region comprising SEQ ID No. 28.

7. The method according to claim 1, wherein the tumor cells with genic amplification of c-Met comprise renal carcinoma cells or gastric cancer cells.

8. The method of claim 1, wherein the modified hinge region comprises the amino acid sequence SEQ ID No. 28.

9. A method for the treatment of a cancer with genic amplification of c-Met, the method comprising administering to a subject in need thereof an isolated anti-cMet antibody, or binding fragment thereof, that is capable to inhibit c-Met dimerization, wherein the antibody comprises:
a heavy chain comprising CDR-H1, CDR-H2, and CDR-H3 comprising amino acid sequences SEQ ID Nos. 1, 2, and 3, respectively;
a light chain comprising CDR-L1, CDR-L2, and CDR-L3 comprising amino acid sequences SEQ ID Nos. 5, 6, and 7; and
a modified hinge region comprising the amino acid sequence SEQ ID No. 56.

10. The method of claim 9, wherein the modified hinge region comprises the amino acid sequence SEQ ID No. 57.

11. The method of claim 9, wherein the modified hinge region comprises the amino acid sequence SEQ ID No. 21.

12. The method of claim 9, wherein the antibody comprises:
a heavy chain variable domain comprising the amino acid sequence SEQ ID No. 4; and
a light chain variable domain comprising an amino acid sequence chosen from SEQ ID No. 8, 9, and 10.

13. The method of claim 9, wherein the antibody comprises:
a heavy chain variable domain comprising the amino acid sequence SEQ ID No. 4; and
a light chain variable domain comprising an amino acid sequence chosen from SEQ ID Nos. 8, 9, and 10; and
a modified hinge region comprising an amino acid sequence chosen from SEQ ID Nos. 22 to 28.

14. The method of claim 13, wherein the antibody comprises:
a heavy chain variable domain comprising the amino acid sequence SEQ ID No. 4; and
a light chain variable domain comprising SEQ ID No. 10; and
a modified hinge region comprising SEQ ID No. 28.

15. The method according to claim 9, wherein the cancer with genic amplification of c-Met comprises a renal carcinoma or a gastric cancer.

16. A method for the treatment of a cancer with genic amplification of c-Met, the method comprising administering to a subject in need thereof an isolated anti-cMet antibody, or binding fragment thereof, that is capable to inhibit c-Met dimerization, in combination with an agent; wherein the antibody comprises:
a heavy chain comprising CDR-H1, CDR-H2, and CDR-H3 comprising amino acid sequences SEQ ID Nos. 1, 2, and 3, respectively;
a light chain comprising CDR-L1, CDR-L2, and CDR-L3 comprising amino acid sequences SEQ ID Nos. 5, 6, and 7; and
a modified hinge region comprising the amino acid sequence SEQ ID No. 56;
wherein the antibody, or binding fragment thereof, and the agent, are administered as a combination product for simultaneous, separate, or sequential use.

17. The method of claim 16, wherein the modified hinge region comprises the amino acid sequence SEQ ID No. 57.

18. The method of claim 16, wherein the modified hinge region comprises the amino acid sequence SEQ ID No. 21.

19. The method of claim 16, wherein the antibody comprises:
a heavy chain variable domain of sequence comprising the amino acid sequence SEQ ID No. 4; and
a light chain variable domain of sequence comprising an amino acid sequence chosen from SEQ ID No. 8, 9, and 10.

20. The method of claim 16, wherein the antibody comprises:
a heavy chain variable domain comprising the amino acid sequence SEQ ID No. 4; and
a light chain variable domain comprising an amino acid sequence chosen from SEQ ID Nos. 8, 9, and 10; and
a modified hinge region comprising an amino acid sequence chosen from SEQ ID Nos. 22 to 28.

21. The method of claim 17, wherein the antibody comprises:
a heavy chain variable domain comprising the amino acid sequence SEQ ID No. 4; and
a light chain variable domain comprising SEQ ID No. 10; and
a modified hinge region comprising SEQ ID No. 28.

22. The method according to claim 16, wherein the cancer with genic amplification of c-Met comprises a renal carcinoma or a gastric cancer.

23. The method of claim 16, wherein the agent is an anti-tumoral antibody.

24. The method of claim 16, wherein the agent is a cytotoxic/cytostatic agent.

25. The method of claim 16, wherein the modified hinge region comprises the amino acid sequence SEQ ID No. 28.

26. The method of claim 9, wherein the modified hinge region comprises the amino acid sequence SEQ ID No. 28.

27. The method of claim 9, wherein the cancer with genic amplification of c-Met comprises a gastric cancer.

28. The method of claim 14, wherein the cancer with genic amplification of c-Met comprises a gastric cancer.

29. The method of claim 21, wherein the cancer with genic amplification of c-Met comprises a gastric cancer.

30. The method of claim 24, wherein the agent is chosen from alkylating agents, anti-metabolites, anti-tumor antibiotics, mitotic inhibitors, chromatin function inhibitors, anti-angiogenesis agents, anti-estrogenic agents, anti-androgenic agents, and immunomodulators.

31. The method of claim 30, wherein the agent is a mitotic inhibitor.

32. The method of claim 21, wherein the agent is chosen from alkylating agents, anti-metabolites, anti-tumor antibiotics, mitotic inhibitors, chromatin function inhibitors, anti-angiogenesis agents, anti-estrogenic agents, anti-androgenic agents, and immunomodulators.

33. The method of claim 32, wherein the agent is a mitotic inhibitor.

* * * * *